(12) United States Patent
Khanna et al.

(10) Patent No.: US 7,220,770 B2
(45) Date of Patent: *May 22, 2007

(54) HETEROCYCLO-SUBSTITUTED IMIDAZOLES FOR THE TREATMENT OF INFLAMMATION

(76) Inventors: Ish K. Khanna, 149 Brandywine Ct., Vernon Hills, IL (US) 60061; Richard M. Weier, 240 Hickory Ct., Lake Bluff, IL (US) 60044; Paul W. Collins, 1557 Hawthorne Pl., Deerfield, IL (US) 60015; Yi Yu, 9065 Gross Point Rd., Skokie, IL (US) 60077; Xiangdong Xu, 855 Hinman Ave., Evanston, IL (US) 60077; Richard A. Partis, 2221 Noyes St., Evanston, IL (US) 60201; Francis J. Koszyk, 11 Wildwood Dr., South, Prospect Heights, IL (US) 60070; Renee M. Huff, 937 Lincoln Park, Park Ridge, IL (US) 60068

( * ) Notice: Subject to any disclaimer, the term of this patent is extended or adjusted under 35 U.S.C. 154(b) by 0 days.

This patent is subject to a terminal disclaimer.

(21) Appl. No.: 11/183,016

(22) Filed: Jul. 15, 2005

(65) Prior Publication Data

US 2005/0256120 A1 Nov. 17, 2005

Related U.S. Application Data

(63) Continuation of application No. 10/653,399, filed on Sep. 2, 2003, now abandoned, which is a continuation of application No. 10/004,944, filed on Dec. 5, 2001, now Pat. No. 6,613,789, which is a continuation of application No. 09/101,493, filed as application No. PCT/US97/00300 on Jan. 24, 1997, now abandoned, and a continuation-in-part of application No. PCT/US95/09506, filed on Jul. 27, 1995, which is a continuation-in-part of application No. 08/464,154, filed on Jun. 5, 1995, now Pat. No. 5,616,601, which is a continuation-in-part of application No. 08/282,395, filed on Jul. 28, 1994, now abandoned.

(51) Int. Cl.
  *A61K 31/44* (2006.01)
  *C07D 213/53* (2006.01)
  *C07D 401/04* (2006.01)

(52) U.S. Cl. ............... 514/397; 514/399; 544/139; 548/311.4; 548/323.5; 546/184; 546/334

(58) Field of Classification Search ............... 514/397, 514/399, 341, 400; 544/139; 548/311.4, 548/315.1, 323.5, 342.5; 546/184, 334
See application file for complete search history.

(56) References Cited

U.S. PATENT DOCUMENTS 3,487,087 A 12/1969 Sarett et al.
3,682,949 A 8/1972 Sarett et al.
3,719,759 A 3/1973 Sarett et al.
4,560,696 A 12/1985 Carenzi et al.
4,822,805 A 4/1989 Takasugi et al.
4,822,865 A 4/1989 De Martino et al.

(Continued)

FOREIGN PATENT DOCUMENTS

EP 257897 2/1968

(Continued)

OTHER PUBLICATIONS

Houben-Weyl: Methoden Der Organischen Chemie; Band E8C, "Hetarene III: Teil 3" (1994), Georg Thieme Verlag, Stuttgart, pp. 26-30, DE XP0022189377.

(Continued)

*Primary Examiner*—Taofiq Solola
(74) *Attorney, Agent, or Firm*—John H. Engelmann; Thomas A. Wootton; Charles Ashbrook

(57) ABSTRACT

A class of imidazolyl compounds is described for use in treating inflammation. Compounds of particular interest are defined by formula (V), wherein $R^3$ is a radical selected from hydrido, alkyl, haloalkyl, aralkyl, heterocycloalkyl, heteroaralkyl, acyl, cyano, alkoxy, alkylthio, alkylthioalkyl, alkylsulfonyl, cycloalkylthio, cycloalkylthioalkyl, cycloalkylsulfonyl, cycloalkylsulfonylalkyl, haloalkylsulfonyl, arylsulfonyl, halo, hydroxyalkyl, alkoxyalkyl, alkylcarbonyl, arylcarbonyl, aralkylcarbonyl, heterocyclocarbonyl, cyanoalkyl, aminoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, carboxyl, aminocarbonyl, alkylaminocarbonyl, alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroarylalkylthioalkyl, heteroaryloxy, heteroarylthio, arylthioalkyl, aryloxyalkyl, arylthio, aryloxy, aralkylthioalkyl, aralkoxyalkyl, aryl and heteroaryl; wherein $R^4$ is a radical selected from hydrido, alkyl and halo; and wherein $R^{13}$ and $R^{14}$ are independently selected from aryl and heterocyclo, wherein $R^{13}$ and $R^{14}$ are optionally substituted at a substitutable position with one or more radicals independently selected from alkylsulfonyl, aminosulfonyl, halo, alkylthio, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; provided at least one of $R^{13}$ and $R^{14}$ is aryl substituted with alkylsulfonyl or aminosulfonyl; or a pharmaceutically-acceptable salt thereof

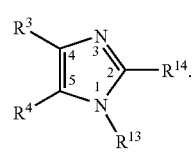

(V)

18 Claims, No Drawings

U.S. PATENT DOCUMENTS

| | | | |
|---|---|---|---|
| 5,112,532 | A | 5/1992 | Ninomiya et al. |
| 5,180,732 | A | 1/1993 | Tomioka et al. |
| 5,185,351 | A | 2/1993 | Finkelstein et al. |
| 5,207,820 | A | 5/1993 | Wriede et al. |
| 5,616,601 | A * | 4/1997 | Khanna et al. ............. 514/399 |
| 6,613,789 | B2 * | 9/2003 | Khanna et al. ............. 514/397 |

FOREIGN PATENT DOCUMENTS

| | | |
|---|---|---|
| EP | 516982 | 12/1992 |
| EP | 554829 | 11/1993 |
| FR | 1367746 | 6/1963 |
| JP | 5902887 | 1/1984 |
| JP | WO95/00501 | 1/1995 |
| WO | WO91/00277 | 1/1991 |
| WO | WO93/14802 | 8/1993 |
| WO | WO94/27980 | 12/1994 |
| WO | WO95/02591 | 1/1995 |
| WO | WO95/15315 | 6/1995 |
| WO | WO96/03388 | 2/1996 |

OTHER PUBLICATIONS

Gautier Jean-Albert et al., "Preparation d'amidines a partir de nitriles et d'amines aromatiques en solvant ammoniac liquide" Bulletin De La societe Chimique De France, No. 1:.

* cited by examiner

HETEROCYCLO-SUBSTITUTED IMIDAZOLES FOR THE TREATMENT OF INFLAMMATION

CROSS-REFERENCE TO RELATED APPLICATIONS

This is a continuation of application Ser. No. 10/653,399 filed on Sep. 2, 2003, now abandoned which is a continuation of application Ser. No. 10/004,944 filed on Dec. 5, 2001 now U.S. Pat. No. 6,613,789, which is a continuation of application Ser. No. 09/101,493 filed on Jun. 2, 1999 now abandoned, which is a national stage entry of International Application PCT/US97/00300 filed on Jan. 24, 1997, which is a continuation-in-part of International Application PCT/US95/09506 filed on Jul. 27, 1995, which is a continuation-in-part of application Ser. No. 08/464,154 filed on Jun. 5, 1995 now U.S. Pat. No. 5,616,601, which is a continuation-in-part of application Ser. No. 08/282,395 filed on Jul. 28, 1994 now abandoned. All of the aforementioned applications and patents are incorporated by reference.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel imidazoles disclosed herein are such safe and also effective antiinflammatory agents furthering such efforts. The invention compounds are found to show usefulness in vivo as antiinflammatory agents with minimal side effects. The substituted imidazoles disclosed herein preferably selectively inhibit cyclooxygenase-2 over cyclooxygenase-1.

Diaryl oxazoles have been described in WO patent publication WO94/27980 as having antiinflammatory activity. Substituted 4,5-diarylimidazoles have been described in WO95/00501 and in copending U.S. application Ser. No. 08/281,903.

2-Alkylimidazoles have been described as having angiotensin II activity. For example, see U.S. Pat. No. 5,185,351 and WO 91/00277.

U.S. Pat. No. 5,207,820 to Wriede et al. describes 1-arylimidazole carboxylic esters as herbicide safeners. Specifically, ethyl[1-[2,6-dinitro-4-(methylsulfonyl)phenyl]-2-methyl-1H-imidazol-3-yl]carboxylate is described.

WO 93/14082, published Jul. 22, 1993, describes 1-pyridyl-2-phenyl-imidazole derivatives for the treatment of interleukin-1 mediated diseases. 1-(4-Pyridyl)-2-(4-fluorophenyl)-4-methylimidazole is described. WO 95/02591, published Jan. 26, 1995, describe tri-substituted imidazoles for the treatment of cytokine mediated diseases.

U.S. Pat. No. 3,487,087, to Sarett et al., describes a method of nitration of imidazoles and specifically 1-methyl-2-[4-(methylsulfonyl)phenyl]-5-nitroimidazole.

U.S. Pat. No. 5,112,532, to Ninomiya et al., describes imidazoles as an organic non-linear optical material. Specifically, 4-(4-hydroxyphenyl)-2-[2-formyl-4-(methylsulfonyl)phenyl]imidazole is described.

U.S. Pat. Nos. 3,682,949 and 3,719,759, to Sarett et al., describe 2-aryl-nitroimidazoles as agents for the treatment of parasites and bacteria. Specifically, 1-(2-hydroxyethyl)-2-(4-sulfonamidophenyl)-5-nitroimidazole is described.

U.S. Pat. No. 4,822,805, to Takasugi et al., describes pyridylimidazoles as antiinflammatory agents. Specifically, 2-[2-methoxy-4-(methylsulfonyl)phenyl]-4-methyl-5-(3-pyridyl)imidazole is described.

The invention's imidazolyl compounds are found to show usefulness in vivo as antiinflammatory agents with minimal side effects.

DESCRIPTION OF THE INVENTION

A class of substituted imidazolyl compounds useful in treating inflammation-related disorders is defined by Formula I:

wherein $R^1$ and $R^2$ are independently selected from aryl, cycloalkyl, cycloalkenyl and heterocyclo, wherein $R^1$ and $R^2$ are optionally substituted at a substitutable position with one or more radicals independently selected from alkylsulfonyl, aminosulfonyl, haloalkylsulfonyl, halo, alkylthio, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro;

wherein $R^3$ is a radical selected from hydrido, alkyl, haloalkyl, aralkyl, heterocycloalkyl, acyl, cyano, alkoxy, alkylthio, alkylthioalkyl, alkylsulfonyl, cycloalkylthio, cycloalkylthioalkyl, cycloalkylsulfonyl, cycloalkylsulfonylalkyl, cycloalkyloxy, cycloalkyloxyalkyl, haloalkylsulfonyl, arylsulfonyl, halo, hydroxyalkyl, alkoxyalkyl, alkylcarbonyl, arylcarbonyl, aralkylcarbonyl, heterocycloalkylcarbonyl, cyanoalkyl, azidoalkyl, aminoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, carboxyl, aminocarbonyl, alkylaminocarbonyl, alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroarylalkylthioalkyl, heteroaryloxy, heteroarylthio, arylthioalkyl, aryloxyalkyl, arylthio, aryloxy, aralkylthioalkyl, aralkoxyalkyl, aryl and heterocyclo;

wherein $R^4$ is a radical selected from hydrido, alkyl and fluoro; wherein $R^5$ is selected from hydroxyl and alkoxy; and wherein $R^6$ is hydrido; or wherein $R^5$ and $R^6$ together form a double bond; provided at least one of $R^1$ and $R^2$ is substituted with alkylsulfonyl or aminosulfonyl; or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of the invention would be useful to treat arthritis, including but not limited to rheumatoid arthritis, spondyloarthopathies, gouty arthritis, osteoarthritis, systemic lupus erythematosus and juvenile arthritis. Such compounds of the invention would be useful in the treatment of asthma, bronchitis, menstrual cramps, tendinitis, bursitis, and skin-related conditions such as psoriasis, eczema, burns and dermatitis. Compounds of the invention also would be useful to treat gastrointestinal conditions such as inflammatory bowel disease, Crohn's disease, gastritis, irritable bowel syndrome and ulcerative colitis, and for the prevention or treatment of cancer, such as colorectal cancer. Compounds of the invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases such as retinitis, retinopathies, uveitis, conjunctivitis, and of acute injury to the eye tissue. The compounds would also be useful in the treatment of pulmonary inflammation, such as that associated with viral infections and cystic fibrosis. The compounds would also be useful for the treatment of certain central nervous system disorders such as cortical dementias including Alzheimers disease. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, atherosclerosis and central nervous system damage resulting from stroke, ischemia and trauma.

Besides being useful for human treatment, these compounds are also useful for veterinary treatment of mammals, including companion animals and farm animals, such as, but not limited to, horses, dogs, cats, cows, sheep and pigs.

The present compounds may also be used in co-therapies, partially or completely, in place of other conventional anti-inflammatories, such as together with steroids, NSAIDs, 5-lipoxygenase inhibitors, $LTB_4$ antagonists and $LTA_4$ hydrolase inhibitors.

Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, ONO compound ONO-LB457, Searle compound SC-53228, calcitrol, Lilly compounds LY-210073, LY223982, LY233469, and LY255283, ONO compound ONO-LB-448, Searle compounds SC-41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-615, Lilly compound LY-293111, Ono compound ONO-4057, and Terumo compound TMK-688.

Suitable 5-LO inhibitors include, among others, masoprocol, tenidap, zileuton, pranlukast, tepoxalin, rilopirox, flezelastine hydrochloride, enazadrem phosphate, and bunaprolast.

The present invention preferably includes compounds which selectively inhibit cyclooxygenase-2 over cyclooxygenase-1. Preferably, the compounds have a cyclooxygenase-2 $IC_{50}$ equal to or less than about 0.2 μM, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1.0 μM, and more preferably of greater than 10 μM. Such preferred selectivity may indicate an ability to reduce the incidence of common NSAID-induced side effects.

A preferred class of compounds consists of those compounds of Formula I wherein $R^1$ and $R^2$ are independently selected from phenyl, naphthyl, biphenyl, lower cycloalkyl, lower cycloalkenyl and heteroaryl, wherein $R^1$ and $R^2$ are optionally substituted at a substitutable position with one or more radicals independently selected from lower alkylsulfonyl, aminosulfonyl, lower haloalkylsulfonyl, halo, lower alkylthio, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; wherein $R^3$ is a radical selected from hydrido, lower alkyl, lower haloalkyl, lower aralkyl, lower heterocycloalkyl, acyl, cyano, lower alkoxy, lower alkylthio, lower alkylsulfonyl, lower cycloalkyloxy, lower cycloalkyloxyalkyl, lower cycloalkylthio, lower cycloalkylthioalkyl, lower cycloalkylsulfonyl, lower cycloalkylsulfonylalkyl, phenylsulfonyl, lower haloalkylsulfonyl, halo, lower hydroxyalkyl, lower alkoxyalkyl, lower alkylcarbonyl, lower azidoalkyl, lower haloalkylcarbonyl, phenylcarbonyl, lower aralkylcarbonyl, lower heterocycloalkylcarbonyl, lower cyanoalkyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower alkylthioalkyl, aminocarbonyl, lower alkylaminocarbonyl, lower alkylaminocarbonylalkyl, lower aralkoxy, lower aralkylthio, lower heteroaralkoxy, lower heteroaralkylthio, lower heteroarylalkoxyalkyl, lower heteroarylalkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, hydroxyl, lower alkoxy, lower hydroxyalkyl and lower haloalkoxy; wherein $R^4$ is a radical selected from hydrido, lower alkyl and fluoro; and wherein $R^5$ is selected from hydroxyl and lower alkoxy; wherein $R^6$ is hydrido; or wherein $R^5$ and $R^6$ together form a double bond; or a pharmaceutically-acceptable salt thereof.

A class of compounds of particular interest consists of those compounds of Formula I wherein $R^1$ and $R^2$ are independently selected from phenyl, naphthyl, biphenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, quinolinyl, isoquinolinyl, benzimidazolyl, pyrazinyl, indolyl, pyrazolyl and pyridyl, wherein $R^1$ and $R^2$ are optionally substituted at a substitutable position with one or more radicals independently selected from methylsulfonyl, aminosulfonyl, fluoromethylsulfonyl, difluoromethylsulfonyl, fluoro, chloro, bromo, methylthio, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-dimethylamino, phenylamino and nitro; wherein $R^3$ is a radical selected from hydrido, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinomethyl, pyrrolidinylmethyl, piperazinylmethyl, piperidinylmethyl, pyridylmethyl, thienylmethyl, formyl, cyano, methoxy, ethoxy, propoxy, n-butoxy, methylthio, ethylthio, isopropylthio, methylsulfonyl, phenylsulfonyl, trifluoromethylsulfonyl, fluoro, chloro, bromo, hydroxymethyl, hydroxyethyl, methoxymethyl, ethoxymethyl, methylthiomethyl, isopropylthiomethyl, cyclohexylthiomethyl, benzyloxy, benzylthio, methylcarbonyl, ethylcarbonyl, phenylcarbonyl, azidomethyl, trifluoromethylcarbonyl, difluoromethylcarbonyl, fluoromethylcarbonyl, benzylcarbonyl, cyanomethyl, cyanobutyl, aminomethyl, methylaminomethyl, N-phenylaminomethyl, N-methyl-N-phenylaminomethyl, acetyl, propanoyl, butanoyl, methoxycarbonylmethyl, ethoxycarbonylethyl, methoxycarbonyl, ethoxycarbonyl, isopropoxycarbonyl, tert-butoxycarbonyl, propoxycarbonyl, isobutoxycarbonyl, carboxymethyl, carboxypropyl, aminocarbonyl, methylaminocarbonyl, N,N-diethylaminocarbonyl, N-methylaminocarbonylmethyl, pyridyloxy, pyridylthio, phenyloxy, 4-chlorophenoxy, furylmethoxy, furylmethylthio, thienylmethoxy, quinolylmethoxy, pyridylmethoxy, 5-phenylpyridyl-2-methoxy, thienylmethylthio, pyridylmethylthio, benzylthiomethyl, quinolylmethoxymethyl, furylbutoxyethyl, pyridyloxymethyl, pyridylmethoxymethyl, thienyloxyhexyl, thienylthiomethyl, pyridylthiohexyl, furyloxymethyl, furylmethylthiomethyl, quinolylmethylthioethyl, phenylthiomethyl, 2-chlorophenylthiomethyl, 2,6-dichlorophenylthiomethyl, 4-methylphenylthiomethyl, 2-isopropylphenylthiomethyl, 2-methylphenylthiomethyl, phenyloxymethyl, 4-chlorophenyloxymethyl, 4-methylphenyloxymethyl, benzyloxymethyl, 4-methoxybenzyloxymethyl, naphthyl, phenyl, thienyl, furyl, pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; wherein $R^4$ is a radical selected from hydrido, methyl, ethyl, and fluoro; and wherein $R^5$ is selected from hydroxyl, methoxy, ethoxy, propoxy and n-butoxy; wherein $R^6$ is hydrido; or wherein $R^5$ and $R^6$ together form a double bond; or a pharmaceutically-acceptable salt thereof.

Within Formula I there is a subclass of compounds of high interest represented by Formula II:

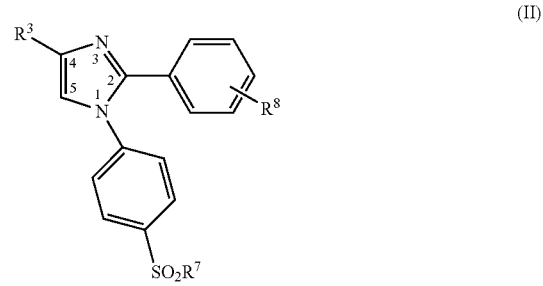

wherein $R^3$ is a radical selected from hydrido, alkyl, haloalkyl, aralkyl, heterocycloalkyl, acyl, cyano, alkoxy, alkylthio, alkylthioalkyl, alkylsulfonyl, cycloalkyloxy, cycloalkyloxyalkyl, cycloalkylthio, cycloalkylthioalkyl, cycloalkylsulfonyl, cycloalkylsulfonylalkyl, haloalkylsulfonyl, arylsulfonyl, halo, hydroxyalkyl, alkoxyalkyl, alkylcarbonyl, arylcarbonyl, aralkylcarbonyl, heterocycloalkylcarbonyl, cyanoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, aminocarbonyl, azidoalkyl, alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroaralkylthioalkyl, heteroaryloxy, heteroarylthio, arylthioalkyl, aryloxyalkyl, arylthio, aryloxy, aralkylthioalkyl, aralkoxyalkyl, aryl and heteroaryl, wherein the aryl and heteroaryl radicals are optionally substituted at a substitutable position with one or more radicals selected from halo, alkylthio, alkylsulfinyl, alkyl, cyano, haloalkyl, hydroxyl, alkoxy, hydroxyalkyl and haloalkoxy; wherein $R^7$ is a radical selected from alkyl, haloalkyl and amino; and wherein $R^8$ is one or more radicals selected from hydrido, halo, alkyl, haloalkyl, alkoxy, amino, haloalkoxy, cyano, carboxyl, hydroxyl, hydroxyalkyl, alkoxyalkyl, alkylamino, nitro and alkylthio; or a pharmaceutically-acceptable salt thereof.

A preferred class of compounds consists of those compounds of Formula II wherein $R^3$ is a radical selected from hydrido, lower alkyl, lower haloalkyl, lower aralkyl, lower heterocycloalkyl, acyl, cyano, lower alkoxy, lower alkylthio, lower alkylsulfonyl, phenylsulfonyl, lower haloalkylsulfonyl, lower cycloalkyloxy, lower cycloalkyloxyalkyl, lower cycloalkylthio, lower cycloalkylthioalkyl, lower cycloalkylsulfonyl, lower cycloalkylsulfonylalkyl, halo, lower hydroxyalkyl, lower alkoxyalkyl, lower alkylcarbonyl, lower haloalkylcarbonyl, phenylcarbonyl, lower aralkylcarbonyl, lower heterocycloalkylcarbonyl, lower cyanoalkyl, lower azidoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower alkylthioalkyl, aminocarbonyl, lower alkylaminocarbonylalkyl, lower aralkoxy, lower aralkylthio, lower heteroaralkoxy, lower heteroaralkylthio, lower heteroaralkoxyalkyl, lower heteroarylalkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, 5 or 6 membered heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, hydroxyl, lower alkoxy, lower hydroxyalkyl and lower haloalkoxy; wherein $R^7$ is a radical selected from lower alkyl, lower haloalkyl and amino; and wherein $R^8$ is a radical selected from hydrido, halo, lower alkyl, lower haloalkyl, lower alkoxy, amino, lower haloalkoxy, cyano, carboxyl, hydroxyl, lower hydroxyalkyl, lower alkoxyalkyl, lower alkylamino, nitro and lower alkylthio; or a pharmaceutically-acceptable salt thereof.

A class of compounds of particular interest consists of those compounds of Formula II wherein $R^3$ is a radical selected from hydrido, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinomethyl, pyrrolidinylmethyl, piperazinylmethyl, piperidinylmethyl, pyridylmethyl, thienylmethyl, formyl, cyano, methoxy, ethoxy, propoxy, n-butoxy, methylthio, ethylthio, isopropylthio, methylsulfonyl, phenylsulfonyl, trifluoromethylsulfonyl, fluoro, chloro, bromo, hydroxymethyl, hydroxyethyl, methoxymethyl, ethoxymethyl, methylthiomethyl, isopropylthiomethyl, cyclohexylthiomethyl, benzyloxy, benzylthio, methylcarbonyl, phenylcarbonyl, trifluoromethylcarbonyl, difluoromethylcarbonyl, fluoromethylcarbonyl, benzylcarbonyl, cyanomethyl, cyanobutyl, azidomethyl, methylaminomethyl, N-phenylaminomethyl, N-methyl-N-phenylaminomethyl, acetyl, propanoyl, butanoyl, methoxycarbonylmethyl, ethoxycarbonylethyl, methoxycarbonyl, ethoxycarbonyl, isopropoxycarbonyl, tert-butoxycarbonyl, propoxycarbonyl, carboxymethyl, carboxypropyl, aminocarbonyl, N-methylaminocarbonylmethyl, pyridyloxy, pyridylthio, phenyloxy, 4-chlorophenoxy, furylmethoxy, furylmethylthio, thienylmethoxy, quinolylmethoxy, pyridylmethoxy, 5-phenylpyridyl-2-methoxy, thienylmethylthio, pyridylmethylthio, benzylthiomethyl, quinolylmethoxymethyl, furylbutoxyethyl, pyridyloxymethyl, pyridylmethoxymethyl, thienyloxyhexyl, thienylthiomethyl, pyridylthiohexyl, furyloxymethyl, furylmethylthiomethyl, quinolylmethylthioethyl, phenylthiomethyl, 2-chlorophenylthiomethyl, 2,6-dichlorophenylthiomethyl, 4-methylphenylthiomethyl, 2-isopropylphenylthiomethyl, 2-methylphenylthiomethyl, phenyloxymethyl, 4-chlorophenyloxymethyl, 4-methylphenyloxymethyl, benzyloxymethyl, 4-methoxybenzyloxymethyl, naphthyl, phenyl, thienyl, furyl, pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; wherein $R^7$ is methyl or amino; and wherein $R^8$ is a radical selected from hydrido, methylsulfonyl, fluoro, chloro, bromo, methylthio, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-dimethylamino, phenylamino and nitro; or a pharmaceutically-acceptable salt thereof.

A family of specific compounds of particular interest within Formula II consists of compounds and pharmaceutically-acceptable salts thereof as follows:

2-(3,4-difluorophenyl)-1-[4-(methylsulfonyl)phenyl]-4-(trifluoromethyl)-1H-imidazole;

2-(4-chlorophenyl)-4-[(4-methylphenoxy)methyl]-1-[4-(methylsulfonyl)phenyl]-1H-imidazole;

2-(4-chlorophenyl)-1-[4-(methylsulfonyl)phenyl]-4-[(methylthio)methyl]-1H-imidazole;

1,2-bis[4-(methylsulfonyl)phenyl]-4-(trifluoromethyl)-1H-imidazole;

4-[2-(3,4-difluorophenyl)-4-(trifluoromethyl)-1H-imidazol-1-yl]benzenesulfonamide;

4-[2-(3-bromo-4-methoxyphenyl)-4-(trifluoromethyl)-1H-imidazol-1-yl]benzenesulfonamide;

2-(4-chlorophenyl)-1-[4-(methylsulfonyl)phenyl]-1H-imidazole-4-carboxaldehyde;

2-(4-chlorophenyl)-4-[[(4-methylphenyl)thiomethyl]-1-[4-(methylsulfonyl)phenyl]-1H-imidazole;

2-(3-methoxyphenyl)-1-[4-(methylsulfonyl)phenyl]-4-(trifluoromethyl)-1H-imidazole;

2-(4-chlorophenyl)-4-fluoromethyl-1-[4-(methylsulfonyl)phenyl]-1H-imidazole;

2-(2-fluorophenyl)-1-[4-(methylsulfonyl)phenyl]-4-(trifluoromethyl)-1H-imidazole;

2-(4-chlorophenyl)-1-[4-(methylsulfonyl)phenyl]-4-(phenylmethoxymethyl)-1H-imidazole;

4-[2-(2-fluorophenyl)-4-(trifluoromethyl)-1H-imidazol-1-yl]benzenesulfonamide;

N,N-dimethyl-4-[1-[4-(methylsulfonyl)phenyl]-4-(trifluoromethyl)-1H-imidazol-2-yl]benzenamine;

2-(4-chlorophenyl)-4-[[(1-methylethyl)thio]methyl]-1-[4-(methylsulfonyl)phenyl]-1H-imidazole;

2-(4-chlorophenyl)-4-[[(cyclohexyl)thio]methyl]-1-[4-(methylsulfonyl)phenyl-1H-imidazole;

1-[4-(methylsulfonyl)phenyl]-2-[3-(trifluoromethyl)phenyl]-4-(trifluoromethyl)-1H-imidazole;

2-[3-(methoxymethyl)phenyl]-1-[4-(methylsulfonyl)phenyl]-4-(trifluoromethyl)-1H-imidazole;

2-fluoro-N,N-dimethyl-4-[1-[4-(methylsulfonyl)phenyl]-4-(trifluoromethyl)-1H-imidazol-2-yl]benzenamine;

2-(3-bromophenyl)-1-[4-(methylsulfonyl)phenyl]-4-(trifluoromethyl)-1H-imidazole;

4-[4-(trifluoromethyl)-2-[3-(trifluoromethyl)phenyl]-1H-imidazol-1-yl]benzenesulfonamide;
2-(4-chlorophenyl)-4-[[(2-chlorophenyl)thio]methyl]-1-[4-(methylsulfonyl)phenyl]-1H-imidazole;
1-[4-(methylsulfonyl)phenyl]-2-(3-nitrophenyl)-4-(trifluoromethyl)-1H-imidazole;
2-(4-chlorophenyl)-4-[[(2-methylphenyl)thio]methyl]-1-[4-(methylsulfonyl)phenyl]-1H-imidazole;
N-methyl-4-[1-[4-(methylsulfonyl)phenyl]-4-(trifluoromethyl)-1H-imidazol-2-yl]benzenamine;
3-[1-[4-(methylsulfonyl)phenyl]-4-(trifluoromethyl)-1H-imidazol-2-yl]benzenamine;
N,N-dimethyl-3-[1-[4-(methylsulfonyl)phenyl]-4-(trifluoromethyl)-1H-imidazol-2-yl]benzenamine;
N-methyl-3-[1-[4-(methylsulfonyl)phenyl]-4-(trifluoromethyl)-1H-imidazol-2-yl]benzenamine;
2-fluoro-N-methyl-4-[1-[4-(methylsulfonyl)phenyl]-4-(trifluoromethyl)-1H-imidazol-2-yl]benzenamine;
2-(4-chlorophenyl)-4-[[(2,6-dichlorophenyl)thio]methyl]-1-[4-(methylsulfonyl)phenyl]-1H-imidazole;
2-(4-chlorophenyl)-4-[[(2-(1-methylethyl)phenyl]thio]methyl]-1-[4-(methylsulfonyl)phenyl]-1H-imidazole;
1-[2-(4-chlorophenyl)-1-[4-(methylsulfonyl)phenyl]-1H-imidazol-4-yl]ethanone;
1-[4-(methylsulfonyl)phenyl]-2-[3-(methylthio)phenyl]-4-(trifluoromethyl)-1H-imidazole;
4-[2-(3-bromophenyl)-4-(trifluoromethyl)-1H-imidazol-1-yl]benzenesulfonamide;
2-(3-chloro-5-methylphenyl)-1-[4-(methylsulfonyl)phenyl]-4-(trifluoromethyl)-1H-imidazole;
4-[2-(3-chloro-5-methylphenyl)-4-(trifluoromethyl)-1H-imidazol-1-yl]benzenesulfonamide;
2-(4-chlorophenyl)-1-[4-(methylsulfonyl)phenyl]-1H-imidazole-4-acetonitrile;
2-(3-fluoro-5-methylphenyl)-1-[4-(methylsulfonyl)phenyl]-4-(trifluoromethyl)-1H-imidazole;
2-(3-fluoro-5-methoxyphenyl)-1-[4-(methylsulfonyl)phenyl]-4-(trifluoromethyl)-1H-imidazole;
4-[2-(3-fluoro-5-methylphenyl)-4-(trifluoromethyl)-1H-imidazol-1-yl]benzenesulfonamide;
2-(4-chlorophenyl)-1-[4-(methylsulfonyl)phenyl]-1H-imidazole-4-acetic acid;
4-[2-(3-fluoro-5-methoxyphenyl)-4-(trifluoromethyl)-1H-imidazol-1-yl]benzenesulfonamide;
2-(4-chlorophenyl)-4-trifluoromethyl-1-[4-(methylsulfonyl)phenyl]-1H-imidazole;
2-(4-chlorophenyl)-4-difluoromethyl-1-[4-(methylsulfonyl)phenyl]-1H-imidazole;
2-(4-chlorophenyl)-4-methyl-1-[4-(methylsulfonyl)phenyl]-1H-imidazole;
2-(4-chlorophenyl)-4-ethyl-1-[4-(methylsulfonyl)phenyl]-1H-imidazole;
2-(4-chlorophenyl)-4-phenyl-1-[4-(methylsulfonyl)phenyl]-1H-imidazole;
2-(4-chlorophenyl)-4-(4-fluorophenyl)-1-[4-(methylsulfonyl)phenyl]-1H-imidazole;
2-(4-chlorophenyl)-4-(4-bromophenyl)-1-[4-(methylsulfonyl)phenyl]-1H-imidazole;
2-(4-chlorophenyl)-4-(4-chlorophenyl)-1-[4-(methylsulfonyl)phenyl]-1H-imidazole;
2-(4-chlorophenyl)-4-(2-naphthyl)-1-[4-(methylsulfonyl)phenyl]-1H-imidazole;
2-(4-chlorophenyl)-4-[4-(trifluoromethoxy)phenyl]-1-[4-(methylsulfonyl)phenyl]-1H-imidazole;
2-(4-chlorophenyl)-4-(3-chlorophenyl)-1-[4-(methylsulfonyl)phenyl]-1H-imidazole;
2-(4-chlorophenyl)-4-(3-fluorophenyl)-1-[4-(methylsulfonyl)phenyl]-1H-imidazole;
2-(4-chlorophenyl)-4-(4-methoxyphenyl)-1-[4-(methylsulfonyl)phenyl]-1H-imidazole;
2-(4-chlorophenyl)-4-phenoxymethyl-1-[4-(methylsulfonyl)phenyl]-1H-imidazole;
2-(4-chlorophenyl)-4-(4-chlorophenoxy)methyl-1-[4-(methylsulfonyl)phenyl]-1H-imidazole;
2-(4-chlorophenyl)-4-(4-fluorophenoxy)methyl-1-[4-(methylsulfonyl)phenyl]-1H-imidazole;
2-(4-chlorophenyl)-4-phenylthiomethyl-1-[4-(methylsulfonyl)phenyl]-1H-imidazole;
2-(4-chlorophenyl)-4-(N-phenyl-N-methylamino)methyl-1-[4-(methylsulfonyl)phenyl]-1H-imidazole;
2-(4-chlorophenyl)-4-(2-quinolyl)methoxymethyl-1-[4-(methylsulfonyl)phenyl]-1H-imidazole;
2-(4-chlorophenyl)-4-methoxymethyl-1-[4-(methylsulfonyl)phenyl]-1H-imidazole;
2-(4-chlorophenyl)-4-(4-methoxybenzyloxy)methyl-1-[4-(methylsulfonyl)phenyl]-1H-imidazole;
2-(4-chlorophenyl)-1-[4-(methylsulfonyl)phenyl]-1H-imidazole-4-methanol;
2-(4-chlorophenyl)-4-formyl-1-[4-(methylsulfonyl)phenyl]-1H-imidazole;
2-(4-chlorophenyl)-1-[4-(methylsulfonyl)phenyl]-1H-imidazole-4-carbonitrile;
2-(4-chlorophenyl)-4-benzyl-1-[4-(methylsulfonyl)phenyl]-1H-imidazole;
2-(4-chlorophenyl)-4-phenylethyl-1-[4-(methylsulfonyl)phenyl]-1H-imidazole;
2-(4-chlorophenyl)-4-hexyl-1-[4-(methylsulfonyl)phenyl]-1H-imidazole;
2-(4-chlorophenyl)-4-hexylcarbonyl-1-[4-(methylsulfonyl)phenyl]-1H-imidazole;
2-(4-chlorophenyl)-4-phenylcarbonyl-1-[4-(methylsulfonyl)phenyl]-1H-imidazole;
2-(4-chlorophenyl)-4-benzylcarbonyl-1-[4-(methylsulfonyl)phenyl]-1H-imidazole;
2-(4-chlorophenyl)-4-(1-hydroxy-1-phenyl-methyl)-1-[4-(methylsulfonyl)phenyl]-1H-imidazole;
2-(4-chlorophenyl)-4-(1-hexanol)-1-[4-(methylsulfonyl)phenyl]-1H-imidazole;
2-(4-chlorophenyl)-1-[(methylsulfonyl)phenyl]-1H-imidazole;
2-(4-chlorophenyl)-4-octyl-1-[4-(methylsulfonyl)phenyl]-1H-imidazole;
2-(4-chlorophenyl)-4-methoxy-1-[4-(methylsulfonyl)phenyl]-1H-imidazole;
2-(4-chlorophenyl)-4-butoxy-1-[4-(methylsulfonyl)phenyl]-1H-imidazole;
2-(4-chlorophenyl)-4-methylthio-1-[4-(methylsulfonyl)phenyl]-1H-imidazole;
2-(4-chlorophenyl)-1-[4-(methylsulfonyl)phenyl]-4-trifluoromethylsulfonyl-1H-imidazole;
2-(4-chlorophenyl)-1-[4-(methylsulfonyl)phenyl]-4-trifluoromethylcarbonyl-1H-imidazole;
2-(4-chlorophenyl)-4-(2-thienyl)-1-[4-(methylsulfonyl)phenyl]-1H-imidazole;
2-(4-chlorophenyl)-4-(3-furyl)-1-[4-(methylsulfonyl)phenyl]-1H-imidazole;
2-(4-chlorophenyl)-4-(4-pyridyl)-1-[4-(methylsulfonyl)phenyl]-1H-imidazole;
2-(4-chlorophenyl)-4-chloro-1-[4-(methylsulfonyl)phenyl]-1H-imidazole;
2-(4-chlorophenyl)-4-fluoro-1-[4-(methylsulfonyl)phenyl]-1H-imidazole;

methyl[2-(4-chlorophenyl)-1-[4-(methylsulfonyl)phenyl]-1H-imidazol-4-yl]carboxylate;

[2-(4-chlorophenyl)-1-[4-(methylsulfonyl)phenyl]-1H-imidazol-4-yl]carboxamide;

methyl[2-(4-chlorophenyl)-1-[4-(methylsulfonyl)phenyl]-1H-imidazol-4-yl]carboxamide;

4-[2-(4-chlorophenyl)-4-trifluoromethyl-1H-imidazol-1-yl]benzenesulfonamide;

4-[2-(4-chlorophenyl)-4-difluoromethyl-1H-imidazol-1-yl]benzenesulfonamide;

4-[2-(4-chlorophenyl)-4-methyl-1H-imidazol-1-yl]benzenesulfonamide;

4-[2-(4-chlorophenyl)-4-ethyl-1H-imidazol-1-yl]benzenesulfonamide;

4-[2-(4-chlorophenyl)-4-phenyl-1H-imidazol-1-yl]benzenesulfonamide;

4-[2-(4-chlorophenyl)-4-(4-fluorophenyl)-1H-imidazol-1-yl]benzenesulfonamide;

4-[2-(4-chlorophenyl)-4-(4-bromophenyl)-1H-imidazol-1-yl]benzenesulfonamide;

4-[2-(4-chlorophenyl)-4-(4-chlorophenyl)-1H-imidazol-1-yl]benzenesulfonamide;

4-[2-(4-chlorophenyl)-4-(2-naphthyl)-1H-imidazol-1-yl]benzenesulfonamide;

4-[2-(4-chlorophenyl)-4-[4-(trifluoromethoxy)phenyl]-1H-imidazol-1-yl]benzenesulfonamide;

4-[2-(4-chlorophenyl)-4-(3-chlorophenyl)-1H-imidazol-1-yl]benzenesulfonamide;

4-[2-(4-chlorophenyl)-4-(3-fluorophenyl)-1H-imidazol-1-yl]benzenesulfonamide;

4-[2-(4-chlorophenyl)-4-(4-methoxyphenyl)-1H-imidazol-1-yl]benzenesulfonamide;

4-[2-(4-chlorophenyl)-4-phenoxymethyl-1H-imidazol-1-yl]benzenesulfonamide;

4-[2-(4-chlorophenyl)-4-(4-chlorophenoxy)methyl-1H-imidazol-1-yl]benzenesulfonamide;

4-[2-(4-chlorophenyl)-4-(4-fluorophenoxy)methyl-1H-imidazol-1-yl]benzenesulfonamide;

4-[2-(4-chlorophenyl)-4-phenylthiomethyl-1H-imidazol-1-yl]benzenesulfonamide;

4-[2-(4-chlorophenyl)-4-(N-phenyl-N-methylamino)methyl-1H-imidazol-1-yl]benzenesulfonamide;

4-[2-(4-chlorophenyl)-4-(2-quinolyl)methoxymethyl-1H-imidazol-1-yl]benzenesulfonamide;

4-[2-(4-chlorophenyl)-4-methoxymethyl-1H-imidazol-1-yl]benzenesulfonamide;

4-[2-(4-chlorophenyl)-4-(4-methoxybenzyloxy)methyl-1H-imidazol-1-yl]benzenesulfonamide;

4-[2-(4-chlorophenyl)-4-hydroxymethyl-1H-imidazol-1-yl]benzenesulfonamide;

4-[2-(4-chlorophenyl)-4-formyl-1H-imidazol-1-yl]benzenesulfonamide;

4-[2-(4-chlorophenyl)-4-cyano-1H-imidazol-1-yl]benzenesulfonamide;

4-[2-(4-chlorophenyl)-4-benzyl-1H-imidazol-1-yl]benzenesulfonamide;

4-[2-(4-chlorophenyl)-4-phenylethyl-1H-imidazol-1-yl]benzenesulfonamide;

4-[2-(4-chlorophenyl)-4-hexyl-1H-imidazol-1-yl]benzenesulfonamide;

4-[2-(4-chlorophenyl)-4-hexylcarbonyl-1H-imidazol-1-yl]benzenesulfonamide;

4-[2-(4-chlorophenyl)-4-phenylcarbonyl-1H-imidazol-1-yl]benzenesulfonamide;

4-[2-(4-chlorophenyl)-4-benzylcarbonyl-1H-imidazol-1-yl]benzenesulfonamide;

4-[2-(4-chlorophenyl)-4-(1-hydroxy-1-phenyl-methyl)-1H-imidazol-1-yl]benzenesulfonamide;

4-[2-(4-chlorophenyl)-4-(1-hexanol)-1H-imidazol-1-yl]benzenesulfonamide;

4-[2-(4-chlorophenyl)-1H-imidazol-1-yl]benzenesulfonamide;

4-[2-(4-chlorophenyl)-4-octyl-1H-imidazol-1-yl]benzenesulfonamide;

4-[2-(4-chlorophenyl)-4-methoxy-1H-imidazol-1-yl]benzenesulfonamide;

4-[2-(4-chlorophenyl)-4-butoxy-1H-imidazol-1-yl]benzenesulfonamide;

4-[2-(4-chlorophenyl)-4-methylthio-1H-imidazol-1-yl]benzenesulfonamide;

4-[2-(4-chlorophenyl)-4-(2-thienyl)-1H-imidazol-1-yl]benzenesulfonamide;

4-[2-(4-chlorophenyl)-4-(3-furyl)-1H-imidazol-1-yl]benzenesulfonamide;

4-[2-(4-chlorophenyl)-4-(4-pyridyl)-1H-imidazol-1-yl]benzenesulfonamide;

4-[2-(4-chlorophenyl)-4-chloro-1H-imidazol-1-yl]benzenesulfonamide;

4-[2-(4-chlorophenyl)-4-fluoro-1H-imidazol-1-yl]benzenesulfonamide;

[2-(4-chlorophenyl)-1-[4-(aminosulfonyl)phenyl)-1H-imidazol-4-yl]carboxylic acid;

methyl[2-(4-chlorophenyl)-1-[4-(aminosulfonyl)phenyl)-1H-imidazol-4-yl]carboxylate;

[2-(4-chlorophenyl)-1-[4-(aminosulfonyl)phenyl)-1H-imidazol-4-yl]carboxamide;

methyl[2-(4-chlorophenyl)-1-[4-(aminosulfonyl)phenyl)-1H-imidazol-4-yl]carboxamide;

2-(3-methylphenyl)-1-[4-(methylsulfonyl)phenyl]-4-trifluoromethyl-1H-imidazole;

2-(2-methylphenyl)-1-[4-(methylsulfonyl)phenyl]-4-trifluoromethyl-1H-imidazole;

2-(4-fluoro-3-methylphenyl)-1-[4-(methylsulfonyl)phenyl]-4-trifluoromethyl-1H-imidazole;

2-(4-chloro-3-methylphenyl)-1-[4-(methylsulfonyl)phenyl]-4-trifluoromethyl-1H-imidazole;

2-(4-fluoro-3-methoxyphenyl)-1-[4-(methylsulfonyl)phenyl]-4-trifluoromethyl-1H-imidazole;

2-(4-chloro-3-methoxyphenyl)-1-[4-(methylsulfonyl)phenyl]-4-trifluoromethyl-1H-imidazole;

2-(3-fluoro-4-methylphenyl)-1-[4-(methylsulfonyl)phenyl]-4-trifluoromethyl-1H-imidazole;

2-(3-chloro-4-methylphenyl)-1-[4-(methylsulfonyl)phenyl]-4-trifluoromethyl-1H-imidazole;

2-(3-fluoro-4-methylthiophenyl)-1-[4-(methylsulfonyl)phenyl]-4-trifluoromethyl-1H-imidazole;

2-(3-chloro-4-methylthiophenyl)-1-[4-(methylsulfonyl)phenyl]-4-trifluoromethyl-1H-imidazole;

2-(4-fluoro-3-methylthiophenyl)-1-[4-(methylsulfonyl)phenyl]-4-trifluoromethyl-1H-imidazole;

2-(4-chloro-3-methylthiophenyl)-1-[4-(methylsulfonyl)phenyl]-4-trifluoromethyl-1H-imidazole;

2-(3,5-dimethyl-4-methoxyphenyl)-1-[4-(methylsulfonyl)phenyl]-4-trifluoromethyl-1H-imidazole;

2-(3,5-dichloro-4-methoxyphenyl)-1-[4-(methylsulfonyl)phenyl]-4-trifluoromethyl-1H-imidazole;

2-(3,5-difluoro-4-methoxyphenyl)-1-[4-(methylsulfonyl)phenyl]-4-trifluoromethyl-1H-imidazole;

2-(3,4-dimethylphenyl)-1-[4-(methylsulfonyl)phenyl]-4-trifluoromethyl-1H-imidazole;

2-(3,5-dichlorophenyl)-1-[4-(methylsulfonyl)phenyl]-4-trifluoromethyl-1H-imidazole;

4-[2-(3-methylphenyl)-4-trifluoromethyl-1H-imidazol-1-yl]benzenesulfonamide;
4-[2-(2-methylphenyl)-4-trifluoromethyl-1H-imidazol-1-yl]benzenesulfonamide;
4-[2-(4-fluoro-3-methylphenyl)-4-trifluoromethyl-1H-imidazol-1-yl]benzenesulfonamide;
4-[2-(4-chloro-3-methylphenyl)-4-trifluoromethyl-1H-imidazol-1-yl]benzenesulfonamide;
4-[2-(4-fluoro-3-methoxyphenyl)-4-trifluoromethyl-1H-imidazol-1-yl]benzenesulfonamide;
4-[2-(4-chloro-3-methoxyphenyl)-4-trifluoromethyl-1H-imidazol-1-yl]benzenesulfonamide;
4-[2-(3-fluoro-4-methylphenyl)-4-trifluoromethyl-1H-imidazol-1-yl]benzenesulfonamide;
4-[2-(3-chloro-4-methylthiophenyl)-4-trifluoromethyl-1H-imidazol-1-yl]benzenesulfonamide;
4-[2-(3-fluoro-4-methylthiophenyl)-4-trifluoromethyl-1H-imidazol-1-yl]benzenesulfonamide;
4-[2-(4-fluoro-3-methylthiophenyl)-4-trifluoromethyl-1H-imidazol-1-yl]benzenesulfonamide;
4-[2-(4-chloro-4-methylthiophenyl)-4-trifluoromethyl-1H-imidazol-1-yl]benzenesulfonamide;
4-[2-(3,5-dimethyl-4-methoxyphenyl)-4-trifluoromethyl-1H-imidazol-1-yl]benzenesulfonamide;
4-[2-(3,5-dichloro-4-methoxyphenyl)-4-trifluoromethyl-1H-imidazol-1-yl]benzenesulfonamide;
4-[2-(3,5-difluoro-4-methoxyphenyl)-4-trifluoromethyl-1H-imidazol-1-yl]benzenesulfonamide;
4-[2-(3,4-dimethylphenyl)-4-trifluoromethyl-1H-imidazol-1-yl]benzenesulfonamide;
4-[2-(3,5-dichlorophenyl)-4-trifluoromethyl-1H-imidazol-1-yl]benzenesulfonamide;
ethyl[2-(4-chlorophenyl)-1-[4-(methylsulfonyl)phenyl]-1H-imidazol-4-yl]carboxylate;
ethyl[1-[4-(aminosulfonyl)phenyl]-2-(4-chlorophenyl)-1H-imidazol-4-yl]carboxylate;
1-[4-(methylsulfonyl)phenyl]-2-(4-methylphenyl)-4-trifluoromethyl-1H-imidazole;
1-[4-(methylsulfonyl)phenyl]-2-(3-chlorophenyl)-4-trifluoromethyl-1H-imidazole;
1-[4-(methylsulfonyl)phenyl]-2-(4-methyl-3-chlorophenyl)-4-trifluoromethyl-1H-imidazole;
5-[1-[4-(methylsulfonyl)phenyl]-4-trifluoromethyl-1H-imidazol-2-yl]-1,3-benzodioxole;
1-[4-(methylsulfonyl)phenyl]-2-(4-methoxyphenyl)-4-trifluoromethyl-1H-imidazole;
1-[4-(methylsulfonyl)phenyl]-2-(3-fluorophenyl)-4-trifluoromethyl-1H-imidazole;
1-[4-(methylsulfonyl)phenyl]-2-(4-fluorophenyl)-4-trifluoromethyl-1H-imidazole;
1-[4-(methylsulfonyl)phenyl]-2-(4-methoxy-3-fluorophenyl)-4-trifluoromethyl-1H-imidazole;
1-[4-(methylsulfonyl)phenyl]-2-phenyl-4-trifluoromethyl-1H-imidazole;
1-[4-(methylsulfonyl)phenyl]-2-(4-methoxy-3-chlorophenyl)-4-trifluoromethyl-1H-imidazole;
1-[4-(methylsulfonyl)phenyl]-2-[4-(trifluoromethyl)phenyl]-4-trifluoromethyl-1H-imidazole;
1-[4-(methylsulfonyl)phenyl]-2-(4-bromophenyl)-4-trifluoromethyl-1H-imidazole;
1-[4-(methylsulfonyl)phenyl]-2-(2-chlorophenyl)-4-trifluoromethyl-1H-imidazole;
1-[4-(methylsulfonyl)phenyl]-2-(4-ethylphenyl)-4-trifluoromethyl-1H-imidazole;
1-[4-(methylsulfonyl)phenyl]-2-(4-butylphenyl)-4-trifluoromethyl-1H-imidazole;
1-[4-(methylsulfonyl)phenyl]-2-[4-(difluoromethyl)phenyl]-4-trifluoromethyl-1H-imidazole;
1-[4-(methylsulfonyl)phenyl]-2-(4-butoxyphenyl)-4-trifluoromethyl-1H-imidazole;
1-[4-(methylsulfonyl)phenyl]-2-[4-(methylthio)phenyl]-4-trifluoromethyl-1H-imidazole;
1-[4-(methylsulfonyl)phenyl]-2-(4-methoxy-3,5-dichlorophenyl)-4-trifluoromethyl-1H-imidazole;
1-[4-(methylsulfonyl)phenyl]-2-(4-methyl-3,5-difluorophenyl)-4-trifluoromethyl-1H-imidazole;
1-[4-(methylsulfonyl)phenyl]-2-(2,4-dichlorophenyl)-4-trifluoromethyl-1H-imidazole;
1-[4-(methylsulfonyl)phenyl]-2-(3,4-dichlorophenyl)-4-trifluoromethyl-1H-imidazole;
1-[4-(methylsulfonyl)phenyl]-2-[4-(trifluoromethyl)phenyl]-4-trifluoromethoxy-1H-imidazole;
1-[4-(methylsulfonyl)phenyl]-2-(3,5-dimethyl-4-methoxyphenyl)-4-trifluoromethyl-1H-imidazole;
1-[4-(methylsulfonyl)phenyl]-2-(3,4-dimethylphenyl)-4-trifluoromethyl-1H-imidazole;
1-[4-(methylsulfonyl)phenyl]-2-(4-aminophenyl)-4-trifluoromethyl-1H-imidazole;
4-[2-(4-methylphenyl)-4-trifluoromethyl-1H-imidazol-1-yl]benzenesulfonamide;
4-[2-(3-chlorophenyl)-4-trifluoromethyl-1H-imidazol-1-yl]benzenesulfonamide;
4-[2-(4-methyl-3-chlorophenyl)-4-trifluoromethyl-1H-imidazol-1-yl]benzenesulfonamide;
5-[1-[4-(aminosulfonyl)phenyl]-4-trifluoromethyl-1H-imidazol-2-yl]-1,3-benzodioxole;
4-[2-(4-methoxyphenyl)-4-trifluoromethyl-1H-imidazol-1-yl]benzenesulfonamide;
4-[2-(3-fluorophenyl)-4-trifluoromethyl-1H-imidazol-1-yl]benzenesulfonamide;
4-[2-(4-fluorophenyl)-4-trifluoromethyl-1H-imidazol-1-yl]benzenesulfonamide;
4-[2-(4-methoxy-3-fluorophenyl)-4-trifluoromethyl-1H-imidazol-1-yl]benzenesulfonamide;
4-[2-phenyl-4-trifluoromethyl-1H-imidazol-1-yl]benzenesulfonamide;
4-[2-(4-methoxy-3-chlorophenyl)-4-trifluoromethyl-1H-imidazol-1-yl]benzenesulfonamide;
4-[2-[4-(trifluoromethyl)phenyl]-4-trifluoromethyl-1H-imidazol-1-yl]benzenesulfonamide;
4-[2-(4-bromophenyl)-4-trifluoromethyl-1H-imidazol-1-yl]benzenesulfonamide;
4-[2-(2-chlorophenyl)-4-trifluoromethyl-1H-imidazol-1-yl]benzenesulfonamide;
4-[2-(4-ethylphenyl)-4-trifluoromethyl-1H-imidazol-1-yl]benzenesulfonamide;
4-[2-(4-butylphenyl)-4-trifluoromethyl-1H-imidazol-1-yl]benzenesulfonamide;
4-[2-[4-(difluoromethyl)phenyl]-4-trifluoromethyl-1H-imidazol-1-yl]benzenesulfonamide;
4-[2-(4-butoxyphenyl)-4-trifluoromethyl-1H-imidazol-1-yl]benzenesulfonamide;
4-[2-[4-(methylthio)phenyl]-4-trifluoromethyl-1H-imidazol-1-yl]benzenesulfonamide;
4-[2-(4-methoxy-3,5-dichloro-phenyl)-4-trifluoromethyl-1H-imidazol-1-yl]benzenesulfonamide;
4-[2-(4-methyl-3,5-difluorophenyl)-4-trifluoromethyl-1H-imidazol-1-yl]benzenesulfonamide;
4-[2-(2,4-dichlorophenyl)-4-trifluoromethyl-1H-imidazol-1-yl]benzenesulfonamide;
4-[2-(3,4-dichlorophenyl)-4-trifluoromethyl-1H-imidazol-1-yl]benzenesulfonamide;

4-[2-[4-(trifluoromethoxy)phenyl]-4-trifluoromethyl-1H-imidazol-1-yl]benzenesulfonamide;

4-[2-(3,5-dimethyl-4-methoxy-phenyl)-4-trifluoromethyl-1H-imidazol-1-yl]benzenesulfonamide;

4-[2-(3,4-dimethylphenyl)-4-trifluoromethyl-1H-imidazol-1-yl]benzenesulfonamide; and 4-[2-(4-aminophenyl)-4-trifluoromethyl-1H-imidazol-1-yl]benzenesulfonamide.

Within Formula I there is a second subclass of compounds of high interest represented by Formula III:

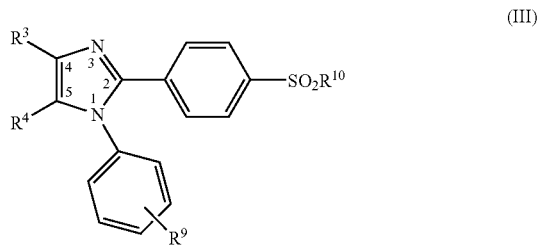

(III)

wherein $R^3$ is a radical selected from hydrido, alkyl, haloalkyl, aralkyl, heterocycloalkyl, acyl, cyano, alkoxy, alkylthio, alkylthioalkyl, alkylsulfonyl, cycloalkylthio, cycloalkylthioalkyl, cycloalkylsulfonyl, cycloalkylsulfonylalkyl, cycloalkyloxy, cycloalkyloxyalkyl, haloalkylsulfonyl, arylsulfonyl, halo, hydroxyalkyl, alkoxyalkyl, alkylcarbonyl, arylcarbonyl, aralkylcarbonyl, heterocycloalkylcarbonyl, cyanoalkyl, azidoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, aminocarbonyl, N-alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroarylalkylthioalkyl, heteroaryloxy, heteroarylthio, arylthioalkyl, aryloxyalkyl, arylthio, aryloxy, aralkylthioalkyl, aralkoxyalkyl, aryl and heteroaryl; wherein the aryl and heteroaryl radicals are optionally substituted at a substitutable position with one or more radicals selected from halo, alkylthio, alkylsulfinyl, alkyl, cyano, haloalkyl, hydroxyl, alkoxy, hydroxyalkyl and haloalkoxy; wherein $R^4$ is a radical selected from hydrido, alkyl and fluoro; wherein $R^9$ is one or more radicals selected from hydrido, halo, alkyl, haloalkyl, alkoxy, amino, haloalkoxy, cyano, carboxyl, hydroxyl, hydroxyalkyl, alkoxyalkyl, alkylamino, nitro and alkylthio; and wherein $R^{10}$ is a radical selected from alkyl, haloalkyl and amino; or a pharmaceutically-acceptable salt thereof.

A preferred class of compounds consists of those compounds of Formula III wherein $R^3$ is a radical selected from hydrido, lower alkyl, lower haloalkyl, lower aralkyl, lower heterocycloalkyl, lower heteroaralkyl, acyl, cyano, lower alkoxy, lower alkylthio, lower alkylsulfonyl, phenylsulfonyl, lower haloalkylsulfonyl, halo, lower hydroxyalkyl, lower alkoxyalkyl, lower alkylcarbonyl, lower haloalkylcarbonyl, phenylcarbonyl, lower aralkylcarbonyl, lower cyanoalkyl, lower azidoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower alkylthioalkyl, aminocarbonyl, lower alkylaminocarbonylalkyl, lower aralkylthio, lower aralkythio, lower heteroaralkoxy, lower heteroaralkylthio, lower heteroaralkoxyalkyl, lower heteroaralkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, 5 or 6 membered heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, hydroxyl, lower alkoxy, lower hydroxyalkyl and lower haloalkoxy; wherein $R^4$ is a radical selected from hydrido, lower alkyl and fluoro; wherein $R^9$ is a radical selected from hydrido, halo, lower alkyl, lower haloalkyl, lower alkoxy, amino, lower haloalkoxy, cyano, carboxyl, hydroxyl, lower hydroxyalkyl, lower alkoxyalkyl, lower alkylamino, nitro and lower alkylthio; and wherein $R^{10}$ is a radical selected from lower alkyl, lower haloalkyl and amino; or a pharmaceutically-acceptable salt thereof.

A class of compounds of particular interest consists of those compounds of Formula III wherein $R^3$ is a radical selected from hydrido, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinomethyl, pyrrolidinylmethyl, piperazinylmethyl, piperidinylmethyl, pyridylmethyl, thienylmethyl, formyl, cyano, methoxy, ethoxy, propoxy, n-butoxy, methylthio, ethylthio, methylsulfonyl, phenylsulfonyl, trifluoromethylsulfonyl, fluoro, chloro, bromo, hydroxymethyl, hydroxyethyl, methoxymethyl, ethoxymethyl, methylthiomethyl, benzyloxy, benzylthio, methylcarbonyl, phenylcarbonyl, trifluoromethylcarbonyl, difluoromethylcarbonyl, fluoromethylcarbonyl, benzylcarbonyl, cyanomethyl, cyanobutyl, azidomethyl, methylaminomethyl, N-phenylaminomethyl, N-methyl-N-phenylaminomethyl, acetyl, propanoyl, butanoyl, methoxycarbonylmethyl, ethoxycarbonylethyl, methoxycarbonyl, ethoxycarbonyl, isopropoxycarbonyl, tert-butoxycarbonyl, propoxycarbonyl, aminocarbonyl, methylaminocarbonylmethyl, pyridyloxy, pyridylthio, phenyloxy, 4-chlorophenoxy, furylmethoxy, furylmethylthio, thienylmethoxy, quinolylmethoxy, pyridylmethoxy, 5-phenylpyridyl-2-methoxy, thienylmethylthio, pyridylmethylthio, quinolylmethoxymethyl, furylbutoxyethyl, pyridyloxymethyl, pyridylmethoxymethyl, thienyloxyhexyl, thienylthiomethyl, pyridylthiohexyl, furyloxymethyl, furylmethylthiomethyl, quinolylmethylthioethyl, phenylthiomethyl, phenyloxymethyl, 4-chlorophenyloxymethyl, benzyloxymethyl, 4-methoxybenzyloxymethyl, naphthyl, phenyl, thienyl, furyl, pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; wherein $R^4$ is a radical selected from hydrido, methyl, ethyl and fluoro; wherein $R^9$ is a radical selected from hydrido, fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, isopropoxy, tert-butoxy, propoxy, butoxy, isobutoxy, pentoxy, methylenedioxy, amino, trifluoromethoxy, cyano, carboxyl, hydroxyl, nitro, hydroxymethyl, methoxymethyl, ethoxymethyl, methylamino, methylthio, ethylthio, propylthio and butylthio; and wherein $R^{10}$ is methyl, fluoromethyl or amino, or a pharmaceutically-acceptable salt thereof.

A family of specific compounds of particular interest within Formula III consists of compounds and pharmaceutically-acceptable salts thereof as follows:

1-(4-chlorophenyl)-4-trifluoromethyl-2-[4-(methylsulfonyl)phenyl]-1H-imidazole;
1-(4-chlorophenyl)-4-difluoromethyl-2-[4-(methylsulfonyl)phenyl]-1H-imidazole;
1-(4-chlorophenyl)-4-methyl-2-[4-(methylsulfonyl)phenyl]-1H-imidazole;
1-(4-chlorophenyl)-4-ethyl-2-[4-(methylsulfonyl)phenyl]-1H-imidazole;
1-(4-chlorophenyl)-4-phenyl-2-[4-(methylsulfonyl)phenyl]-1H-imidazole;
1-(4-chlorophenyl)-4-(4-fluorophenyl)-2-[4-(methylsulfonyl)phenyl]-1H-imidazole;
1-(4-chlorophenyl)-4-(4-bromophenyl)-2-[4-(methylsulfonyl)phenyl]-1H-imidazole;
1-(4-chlorophenyl)-4-(4-chlorophenyl)-2-[4-(methylsulfonyl)phenyl]-1H-imidazole;
1-(4-chlorophenyl)-4-(2-naphthyl)-2-[4-(methylsulfonyl)phenyl]-1H-imidazole;
1-(4-chlorophenyl)-4-[4-(trifluoromethoxy)phenyl]-2-[4-(methylsulfonyl)phenyl]-1H-imidazole;
1-(4-chlorophenyl)-4-(3-chlorophenyl)-2-[4-(methylsulfonyl)phenyl]-1H-imidazole;
1-(4-chlorophenyl)-4-(3-fluorophenyl)-2-[4-(methylsulfonyl)phenyl]-1H-imidazole;
1-(4-chlorophenyl)-4-(4-methoxyphenyl)-2-[4-(methylsulfonyl)phenyl]-1H-imidazole;
1-(4-chlorophenyl)-4-phenoxymethyl-2-[4-(methylsulfonyl)phenyl]-1H-imidazole;
1-(4-chlorophenyl)-4-(4-chlorophenoxy)methyl-2-[4-(methylsulfonyl)phenyl]-1H-imidazole;
1-(4-chlorophenyl)-4-(4-fluorophenoxy)methyl-2-[4-(methylsulfonyl)phenyl]-1H-imidazole;
1-(4-chlorophenyl)-4-phenylthiomethyl-2-[4-(methylsulfonyl)phenyl]-1H-imidazole;
1-(4-chlorophenyl)-4-(N-phenyl-N-methylamino)methyl-2-[4-(methylsulfonyl)phenyl]-1H-imidazole;
1-(4-chlorophenyl)-4-(2-quinolyl)methoxymethyl-2-[4-(methylsulfonyl)phenyl]-1H-imidazole;
1-(4-chlorophenyl)-4-methoxymethyl-2-[4-(methylsulfonyl)phenyl]-1H-imidazole;
1-(4-chlorophenyl)-4-(4-methoxybenzyloxy)methyl-2-[4-(methylsulfonyl)phenyl]-1H-imidazole;
1-(4-chlorophenyl)-4-hydroxymethyl-2-[4-(methylsulfonyl)phenyl]-1H-imidazole;
1-(4-chlorophenyl)-4-formyl-2-[4-(methylsulfonyl)phenyl]-1H-imidazole;
1-(4-chlorophenyl)-4-cyano-2-[4-(methylsulfonyl)phenyl]-1H-imidazole;
1-(4-chlorophenyl)-4-benzyl-2-[4-(methylsulfonyl)phenyl]-1H-imidazole;
1-(4-chlorophenyl)-4-phenylethyl-2-[4-(methylsulfonyl)phenyl]-1H-imidazole;
1-(4-chlorophenyl)-4-hexyl-2-[4-(methylsulfonyl)phenyl]-1H-imidazole;
1-(4-chlorophenyl)-4-hexylcarbonyl-2-[4-(methylsulfonyl)phenyl]-1H-imidazole;
1-(4-chlorophenyl)-4-phenylcarbonyl-2-[4-(methylsulfonyl)phenyl]-1H-imidazole;
1-(4-chlorophenyl)-4-benzylcarbonyl-2-[4-(methylsulfonyl)phenyl]-1H-imidazole;
1-(4-chlorophenyl)-4-(1-hydroxy-2-phenyl-methyl)-2-[4-(methylsulfonyl)phenyl]-1H-imidazole;
1-(4-chlorophenyl)-4-(1-hexanol)-2-[4-(methylsulfonyl)phenyl]-1H-imidazole;
1-(4-chlorophenyl)-2-[(methylsulfonyl)phenyl]-1H-imidazole;
1-(4-chlorophenyl)-4-octyl-2-[4-(methylsulfonyl)phenyl]-1H-imidazole;
1-(4-chlorophenyl)-4-methoxy-2-[4-(methylsulfonyl)phenyl]-1H-imidazole;
1-(4-chlorophenyl)-4-butoxy-2-[4-(methylsulfonyl)phenyl]-1H-imidazole;
1-(4-chlorophenyl)-4-methylthio-2-[4-(methylsulfonyl)phenyl]-1H-imidazole;
1-(4-chlorophenyl)-4-(2-thienyl)-2-[4-(methylsulfonyl)phenyl]-1H-imidazole;
1-(4-chlorophenyl)-4-(3-furyl)-2-[4-(methylsulfonyl)phenyl]-1H-imidazole;
1-(4-chlorophenyl)-4-(4-pyridyl)-2-[4-(methylsulfonyl)phenyl]-1H-imidazole;
1-(4-chlorophenyl)-4-chloro-2-[4-(methylsulfonyl)phenyl]-1H-imidazole;
1-(4-chlorophenyl)-4-fluoro-2-[4-(methylsulfonyl)phenyl]-1H-imidazole;
[1-(4-chlorophenyl)-2-[4-(methylsulfonyl)phenyl)-1H-imidazol-4-yl]carboxylic acid;
methyl[1-(4-chlorophenyl)-2-[4-(methylsulfonyl)phenyl)-1H-imidazol-4-yl]carboxylate;
[1-(4-chlorophenyl)-2-[4-(methylsulfonyl)phenyl)-1H-imidazol-4-yl]carboxamide;
methyl[1-(4-chlorophenyl)-2-[4-(methylsulfonyl)phenyl)-1H-imidazol-4-yl]carboxamide;
4-[1-(4-chlorophenyl)-4-trifluoromethyl-1H-imidazol-2-yl]benzenesulfonamide;
4-[1-(4-chlorophenyl)-4-difluoromethyl-1H-imidazol-2-yl]benzenesulfonamide;
4-[1-(4-chlorophenyl)-4-methyl-1H-imidazol-2-yl]benzenesulfonamide;
4-[1-(4-chlorophenyl)-4-ethyl-1H-imidazol-2-yl]benzenesulfonamide;
4-[1-(4-chlorophenyl)-4-phenyl-1H-imidazol-2-yl]benzenesulfonamide;
4-[1-(4-chlorophenyl)-4-(4-fluorophenyl)-1H-imidazol-2-yl]benzenesulfonamide;
4-[1-(4-chlorophenyl)-4-(4-bromophenyl)-1H-imidazol-2-yl]benzenesulfonamide;
4-[1-(4-chlorophenyl)-4-(4-chlorophenyl)-1H-imidazol-2-yl]benzenesulfonamide;
4-[1-(4-chlorophenyl)-4-(2-naphthyl)-1H-imidazol-2-yl]benzenesulfonamide;
4-[1-(4-chlorophenyl)-4-[4-(trifluoromethoxy)phenyl]-1H-imidazol-2-yl]benzenesulfonamide;
4-[1-(4-chlorophenyl)-4-(3-chlorophenyl)-1H-imidazol-2-yl]benzenesulfonamide;
4-[1-(4-chlorophenyl)-4-(3-fluorophenyl)-1H-imidazol-2-yl]benzenesulfonamide;
4-[1-(4-chlorophenyl)-4-(4-methoxyphenyl)-1H-imidazol-2-yl]benzenesulfonamide;
4-[1-(4-chlorophenyl)-4-phenoxymethyl-1H-imidazol-2-yl]benzenesulfonamide;
4-[1-(4-chlorophenyl)-4-(4-chlorophenoxy)methyl-1H-imidazol-2-yl]benzenesulfonamide;

4-[1-(4-chlorophenyl)-4-(4-fluorophenoxy)methyl-1H-imidazol-2-yl]benzenesulfonamide;
4-[1-(4-chlorophenyl)-4-phenylthiomethyl-1H-imidazol-2-yl]benzenesulfonamide;
4-[1-(4-chlorophenyl)-4-(N-phenyl-N-methylamino)methyl-1H-imidazol-2-yl]benzenesulfonamide;
4-[1-(4-chlorophenyl)-4-(2-quinolyl)methoxymethyl-1H-imidazol-2-yl]benzenesulfonamide;
4-[1-(4-chlorophenyl)-4-methoxymethyl-1H-imidazol-2-yl]benzenesulfonamide;
4-[1-(4-chlorophenyl)-4-(4-methoxybenzyloxy)methyl-1H-imidazol-2-yl]benzenesulfonamide;
4-[1-(4-chlorophenyl)-4-hydroxymethyl-1H-imidazol-2-yl]benzenesulfonamide;
4-[1-(4-chlorophenyl)-4-formyl-1H-imidazol-2-yl]benzenesulfonamide;
4-[1-(4-chlorophenyl)-4-cyano-1H-imidazol-2-yl]benzenesulfonamide;
4-[1-(4-chlorophenyl)-4-benzyl-1H-imidazol-2-yl]benzenesulfonamide;
4-[1-(4-chlorophenyl)-4-phenylethyl-1H-imidazol-2-yl]benzenesulfonamide;
4-[1-(4-chlorophenyl)-4-hexyl-1H-imidazol-2-yl]benzenesulfonamide;
4-[1-(4-chlorophenyl)-4-hexylcarbonyl-1H-imidazol-2-yl]benzenesulfonamide;
4-[1-(4-chlorophenyl)-4-phenylcarbonyl-1H-imidazol-2-yl]benzenesulfonamide;
4-[1-(4-chlorophenyl)-4-benzylcarbonyl-1H-imidazol-2-yl]benzenesulfonamide;
4-[1-(4-chlorophenyl)-4-(1-hydroxy-2-phenyl-methyl)-1H-imidazol-2-yl]benzenesulfonamide;
4-[1-(4-chlorophenyl)-4-(1-hexanol)-1H-imidazol-2-yl]benzenesulfonamide;
4-[1-(4-chlorophenyl)-1H-imidazol-2-yl]benzenesulfonamide;
4-[1-(4-chlorophenyl)-4-octyl-1H-imidazol-2-yl]benzenesulfonamide;
4-[1-(4-chlorophenyl)-4-methoxy-1H-imidazol-2-yl]benzenesulfonamide;
4-[1-(4-chlorophenyl)-4-butoxy-1H-imidazol-2-yl]benzenesulfonamide;
4-[1-(4-chlorophenyl)-4-methylthio-1H-imidazol-2-yl]benzenesulfonamide;
4-[1-(4-chlorophenyl)-4-(3-thienyl)-1H-imidazol-2-yl]benzenesulfonamide;
4-[1-(4-chlorophenyl)-4-(2-furyl)-1H-imidazol-2-yl]benzenesulfonamide;
4-[1-(4-chlorophenyl)-4-(3-pyridyl)-1H-imidazol-2-yl]benzenesulfonamide;
4-[1-(4-chlorophenyl)-4-chloro-1H-imidazol-2-yl]benzenesulfonamide;
4-[1-(4-chlorophenyl)-4-fluoro-1H-imidazol-2-yl]benzenesulfonamide;
[1-(4-chlorophenyl)-2-[4-(aminosulfonyl)phenyl)-1H-imidazol-4-yl]carboxylic acid;
methyl[1-(4-chlorophenyl)-2-[4-(aminosulfonyl)phenyl)-1H-imidazol-4-yl]carboxylate;
[1-(4-chlorophenyl)-2-[4-(aminosulfonyl)phenyl)-1H-imidazol-4-yl]carboxamide;
methyl[1-(4-chlorophenyl)-2-[4-(aminosulfonyl)phenyl)-1H-imidazol-4-yl]carboxamide;
2-[4-(methylsulfonyl)phenyl]-1-(4-methylphenyl)-4-trifluoromethyl-1H-imidazole;
2-[4-(methylsulfonyl)phenyl]-1-(3-chlorophenyl)-4-trifluoromethyl-1H-imidazole;
2-[4-(methylsulfonyl)phenyl]-2-(4-methyl-3-chlorophenyl)-4-trifluoromethyl-1H-imidazole;
5-[2-[4-(methylsulfonyl)phenyl]-4-trifluoromethyl-1H-imidazol-1-yl]-1,3-benzodioxole;
2-[4-(methylsulfonyl)phenyl]-2-(4-methoxyphenyl)-4-trifluoromethyl-1H-imidazole;
2-[4-(methylsulfonyl)phenyl]-1-(3-fluorophenyl)-4-trifluoromethyl-1H-imidazole;
2-[4-(methylsulfonyl)phenyl]-1-(4-fluorophenyl)-4-trifluoromethyl-1H-imidazole;
2-[4-(methylsulfonyl)phenyl]-1-(4-methoxy-3-fluorophenyl)-4-trifluoromethyl-1H-imidazole;
2-[4-(methylsulfonyl)phenyl]-1-phenyl-4-trifluoromethyl-1H-imidazole;
2-[4-(methylsulfonyl)phenyl]-1-(4-methoxy-3-chlorophenyl)-4-trifluoromethyl-1H-imidazole;
2-[4-(methylsulfonyl)phenyl]-1-[4-(trifluoromethyl)phenyl]-4-trifluoromethyl-1H-imidazole;
2-[4-(methylsulfonyl)phenyl]-1-(4-bromophenyl)-4-trifluoromethyl-1H-imidazole;
2-[4-(methylsulfonyl)phenyl]-1-(2-chlorophenyl)-4-trifluoromethyl-1H-imidazole;
2-[4-(methylsulfonyl)phenyl]-1-(4-ethylphenyl)-4-trifluoromethyl-1H-imidazole;
2-[4-(methylsulfonyl)phenyl]-1-(4-butylphenyl)-4-trifluoromethyl-1H-imidazole;
2-[4-(methylsulfonyl)phenyl]-1-[4-(difluoromethyl)phenyl]-4-trifluoromethyl-1H-imidazole;
2-[4-(methylsulfonyl)phenyl]-1-(4-butoxyphenyl)-4-trifluoromethyl-1H-imidazole;
2-[4-(methylsulfonyl)phenyl]-1-[4-(methylthio)phenyl]-4-trifluoromethyl-1H-imidazole;
2-[4-(methylsulfonyl)phenyl]-1-(4-methoxy-3,5-dichlorophenyl)-4-trifluoromethyl-1H-imidazole;
2-[4-(methylsulfonyl)phenyl]-1-(4-methyl-3,5-difluorophenyl)-4-trifluoromethyl-1H-imidazole;
2-[4-(methylsulfonyl)phenyl]-1-(2,4-dichlorophenyl)-4-trifluoromethyl-1H-imidazole;
2-[4-(methylsulfonyl)phenyl]-1-(3,4-dichlorophenyl)-4-trifluoromethyl-1H-imidazole;
2-[4-(methylsulfonyl)phenyl]-1-[4-(trifluoromethyl)phenyl]-4-trifluoromethoxy-1H-imidazole;
2-[4-(methylsulfonyl)phenyl]-1-(3,5-dimethyl-4-methoxyphenyl)-4-trifluoromethyl-1H-imidazole;
2-[4-(methylsulfonyl)phenyl]-1-(3,4-dimethylphenyl)-4-trifluoromethyl-1H-imidazole;
2-[4-(methylsulfonyl)phenyl]-1-(4-aminophenyl)-4-trifluoromethyl-1H-imidazole;
4-[1-(4-methylphenyl)-4-trifluoromethyl-1H-imidazol-2-yl]benzenesulfonamide;
4-[1-(3-chlorophenyl)-4-trifluoromethyl-1H-imidazol-2-yl]benzenesulfonamide;
4-[1-(4-methyl-3-chlorophenyl)-4-trifluoromethyl-1H-imidazol-2-yl]benzenesulfonamide;
5-[2-[4-(aminosulfonyl)phenyl]-4-trifluoromethyl-1H-imidazol-1-yl]-1,3-benzodioxole;
4-[1-(3-fluorophenyl)-4-trifluoromethyl-1H-imidazol-2-yl]benzenesulfonamide;
4-[1-(4-fluorophenyl)-4-trifluoromethyl-1H-imidazol-2-yl]benzenesulfonamide;
4-[1-(4-methoxy-3-fluorophenyl)-4-trifluoromethyl-1H-imidazol-2-yl]benzenesulfonamide;
4-[1-phenyl-4-trifluoromethyl-1H-imidazol-2-yl]benzenesulfonamide;
4-[1-(4-methoxy-3-chlorophenyl)-4-trifluoromethyl-1H-imidazol-2-yl]benzenesulfonamide;

4-[1-[4-(trifluoromethyl)phenyl]-4-trifluoromethyl-1H-imidazol-2-yl]benzenesulfonamide;
4-[1-(4-bromophenyl)-4-trifluoromethyl-1H-imidazol-2-yl]benzenesulfonamide;
4-[1-(2-chlorophenyl)-4-trifluoromethyl-1H-imidazol-2-yl]benzenesulfonamide;
4-[1-(4-ethylphenyl)-4-trifluoromethyl-1H-imidazol-2-yl]benzenesulfonamide;
4-[1-(4-butylphenyl)-4-trifluoromethyl-1H-imidazol-2-yl]benzenesulfonamide;
4-[1-[4-(difluoromethyl)phenyl]-4-trifluoromethyl-1H-imidazol-2-yl]benzenesulfonamide;
4-[1-(4-butoxyphenyl)-4-trifluoromethyl-1H-imidazol-2-yl]benzenesulfonamide;
4-[1-[4-(methylthio)phenyl]-4-trifluoromethyl-1H-imidazol-2-yl]benzenesulfonamide;
4-[1-(4-methoxy-3,5-dichloro-phenyl)-4-trifluoromethyl-1H-imidazol-2-yl]benzenesulfonamide;
4-[1-(4-methyl-3,5-difluorophenyl)-4-trifluoromethyl-1H-imidazol-2-yl]benzenesulfonamide;
4-[1-(2,4-dichlorophenyl)-4-trifluoromethyl-1H-imidazol-2-yl]benzenesulfonamide;
4-[1-(3,4-dichlorophenyl)-4-trifluoromethyl-1H-imidazol-2-yl]benzenesulfonamide;
4-[1-[4-(trifluoromethoxy)phenyl]-4-trifluoromethyl-1H-imidazol-2-yl]benzenesulfonamide;
4-[1-(3,5-dimethyl-4-methoxy-phenyl)-4-trifluoromethyl-1H-imidazol-2-yl]benzenesulfonamide;
4-[1-(3,4-dimethylphenyl)-4-trifluoromethyl-1H-imidazol-2-yl]benzenesulfonamide; and
4-[1-(4-aminophenyl)-4-trifluoromethyl-1H-imidazol-2-yl]benzenesulfonamide.

Within Formula I there is a third subclass of compounds of high interest represented by Formula IV:

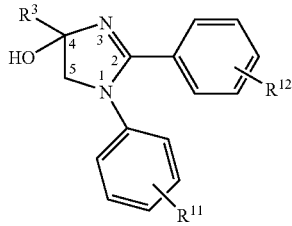

(IV)

wherein $R^3$ is selected from alkyl, haloalkyl, alkylsulfonylalkyl, cycloalkylthioalkyl, alkoxycarbonyl, aralkoxyalkyl, aryloxyalkyl, arylthioalkyl, N-aryl-N-alkylaminoalkyl, heteroarylalkoxyalkyl, heterocyclocarbonyl, heteroaryloxyalkyl, N-alkoxy-N-alkylaminocarbonyl, heteroaralkylthioalkyl, heteroarylthioalkyl and aryl optionally substituted at a substitutable position with halo, alkoxy and haloalkoxy; and wherein $R^{11}$ and $R^{12}$ are independently selected from hydrido, halo, alkyl, haloalkyl, alkoxy, alkylsulfonyl, haloalkylsulfonyl and sulfamyl; or a pharmaceutically-acceptable salt thereof.

A preferred class of compounds consists of those compounds of Formula IV wherein $R^3$ is selected from lower alkyl, lower haloalkyl, lower aralkoxyalkyl, lower aryloxyalkyl, lower alkoxycarbonyl, lower arylthioalkyl, lower heteroaralkylthioalkyl, lower heteroarylthioalkyl, lower N-aryl-N-alkylaminoalkyl, lower heteroarylalkoxyalkyl and aryl selected from naphthyl, phenyl and biphenyl, wherein the aryl radical is optionally substituted at a substitutable position with halo, lower alkoxy and lower haloalkoxy; and wherein $R^{11}$ and $R^{12}$ are independently selected from hydrido, halo, lower alkyl, lower haloalkyl, lower alkoxy, lower alkylsulfonyl, lower haloalkylsulfonyl and sulfamyl; or a pharmaceutically-acceptable salt thereof.

A class of compounds of particular interest consists of those compounds of Formula IV wherein $R^3$ is selected from methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethoxycarbonyl, methoxycarbonyl, benzyloxymethyl, phenylthiomethyl, pyridylthiomethyl, pyridylmethylthiomethyl, phenyloxymethyl, 4-chlorophenyloxymethyl, N-phenyl-N-methylaminomethyl, quinolyloxymethyl and aryl selected from naphthyl and phenyl, wherein the aryl radical is optionally substituted at a substitutable position with fluoro, chloro, bromo, iodo, methoxy, ethoxy, isopropoxy, tert-butoxy, propoxy, butoxy, isobutoxy, pentoxy, methylenedioxy and trifluoromethoxy; and wherein $R^{11}$ and $R^{12}$ are independently selected from hydrido, fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, isopropoxy, tert-butoxy, propoxy, butoxy, isobutoxy, pentoxy, methylenedioxy, methylsulfonyl, fluoromethylsulfonyl and sulfamyl; or a pharmaceutically-acceptable salt thereof.

A family of specific compounds of particular interest within Formula IV consists of compounds and pharmaceutically-acceptable salts thereof as follows:

2-[4-(dimethylamino)-3-fluorophenyl]-4,5-dihydro-4-hydroxy-1-[4-(methylsulfonyl)phenyl]-4-(trifluoromethyl)-1H-imidazole;
2-(4-chlorophenyl)-4-trifluoromethyl-1-[4-(methylsulfonyl)phenyl]-4-hydroxy-4,5-dihydro-1H-imidazole;
2-(4-chlorophenyl)-4-difluoromethyl-1-[4-(methylsulfonyl)phenyl]-4-hydroxy-4,5-dihydro-1H-imidazole;
2-(4-chlorophenyl)-4-methyl-1-[4-(methylsulfonyl)phenyl]-4-hydroxy-4,5-dihydro-1H-imidazole;
2-(4-chlorophenyl)-4-ethyl-1-[4-(methylsulfonyl)phenyl]-4-hydroxy-4,5-dihydro-1H-imidazole;
2-(4-chlorophenyl)-4-phenyl-1-[4-(methylsulfonyl)phenyl]-4-hydroxy-4,5-dihydro-1H-imidazole;
2-(4-chlorophenyl)-4-(4-fluorophenyl)-1-[4-(methylsulfonyl)phenyl]-4-hydroxy-4,5-dihydro-1H-imidazole;
2-(4-chlorophenyl)-4-(4-bromophenyl)-1-[4-(methylsulfonyl)phenyl]-4-hydroxy-4,5-dihydro-1H-imidazole;
2-(4-chlorophenyl)-4-(4-chlorophenyl)-1-[4-(methylsulfonyl)phenyl]-4-hydroxy-4,5-dihydro-1H-imidazole;
2-(4-chlorophenyl)-4-(2-naphthyl)-1-[4-(methylsulfonyl)phenyl]-4-hydroxy-4,5-dihydro-1H-imidazole;
2-(4-chlorophenyl)-4-[4-(trifluoromethoxy)phenyl]-1-[4-(methylsulfonyl)phenyl]-4-hydroxy-4,5-dihydro-1H-imidazole;
2-(4-chlorophenyl)-4-(3-fluorophenyl)-1-[4-(methylsulfonyl)phenyl]-4-hydroxy-4,5-dihydro-1H-imidazole;
2-(4-chlorophenyl)-4-(3-chlorophenyl)-1-[4-(methylsulfonyl)phenyl]-4-hydroxy-4,5-dihydro-1H-imidazole;
2-(4-chlorophenyl)-4-(4-methoxyphenyl)-1-[4-(methylsulfonyl)phenyl]-4-hydroxy-4,5-dihydro-1H-imidazole;
2-(4-chlorophenyl)-4-phenoxymethyl-1-[4-(methylsulfonyl)phenyl]-4-hydroxy-4,5-dihydro-1H-imidazole;

2-(4-chlorophenyl)-4-(4-chlorophenoxy)methyl-1-[4-(methylsulfonyl)phenyl]-4-hydroxy-4,5-dihydro-1H-imidazole;

2-(4-chlorophenyl)-4-(4-fluorophenoxy)methyl-1-[4-(methylsulfonyl)phenyl]-4-hydroxy-4,5-dihydro-1H-imidazole;

2-(4-chlorophenyl)-4-phenylthiomethyl-1-[4-(methylsulfonyl)phenyl]-4-hydroxy-4,5-dihydro-1H-imidazole;

2-(4-chlorophenyl)-4-(N-phenyl-N-methylamino)methyl-1-[4-(methylsulfonyl)phenyl]-4-hydroxy-4,5-dihydro-1H-imidazole;

2-(4-chlorophenyl)-4-(2-quinolyl)methoxymethyl-1-[4-(methylsulfonyl)phenyl]-4-hydroxy-4,5-dihydro-1H-imidazole;

2-(4-chlorophenyl)-4-methoxymethyl-1-[4-(methylsulfonyl)phenyl]-4-hydroxy-4,5-dihydro-1H-imidazole;

2-(4-chlorophenyl)-4-(4-methoxybenzyloxy)methyl-1-[4-(methylsulfonyl)phenyl]-4-hydroxy-4,5-dihydro-1H-imidazole;

2-(4-chlorophenyl)-4-hydroxymethyl-1-[4-(methylsulfonyl)phenyl]-4-hydroxy-4,5-dihydro-1H-imidazole;

2-(4-chlorophenyl)-4-formyl-1-[4-(methylsulfonyl)phenyl]-4-hydroxy-4,5-dihydro-1H-imidazole;

2-(4-chlorophenyl)-4-cyano-1-[4-(methylsulfonyl)phenyl]-4-hydroxy-4,5-dihydro-1H-imidazole;

2-(4-chlorophenyl)-4-benzyl-1-[4-(methylsulfonyl)phenyl]-4-hydroxy-4,5-dihydro-1H-imidazole;

2-(4-chlorophenyl)-4-phenylethyl-1-[4-(methylsulfonyl)phenyl]-4-hydroxy-4,5-dihydro-1H-imidazole;

2-(4-chlorophenyl)-4-hexyl-1-[4-(methylsulfonyl)phenyl]-4-hydroxy-4,5-dihydro-1H-imidazole;

2-(4-chlorophenyl)-4-hexylcarbonyl-1-[4-(methylsulfonyl)phenyl]-4-hydroxy-4,5-dihydro-1H-imidazole;

2-(4-chlorophenyl)-4-phenylcarbonyl-1-[4-(methylsulfonyl)phenyl]-4-hydroxy-4,5-dihydro-1H-imidazole;

2-(4-chlorophenyl)-4-benzylcarbonyl-1-[4-(methylsulfonyl)phenyl]-4-hydroxy-4,5-dihydro-1H-imidazole;

2-(4-chlorophenyl)-4-(1-hydroxy-1-phenyl-methyl)-1-[4-(methylsulfonyl)phenyl]-4-hydroxy-4,5-dihydro-1H-imidazole;

2-(4-chlorophenyl)-4-(1-hexanol)-1-[4-(methylsulfonyl)phenyl]-4-hydroxy-4,5-dihydro-1H-imidazole;

2-(4-chlorophenyl)-1-[(methylsulfonyl)phenyl]-4-hydroxy-4,5-dihydro-1H-imidazole;

2-(4-chlorophenyl)-4-octyl-1-[4-(methylsulfonyl)phenyl]-4-hydroxy-4,5-dihydro-1H-imidazole;

2-(4-chlorophenyl)-4-methoxy-1-[4-(methylsulfonyl)phenyl]-4-hydroxy-4,5-dihydro-1H-imidazole;

2-(4-chlorophenyl)-4-butoxy-1-[4-(methylsulfonyl)phenyl]-4-hydroxy-4,5-dihydro-1H-imidazole;

2-(4-chlorophenyl)-4-methylthio-1-[4-(methylsulfonyl)phenyl]-4-hydroxy-4,5-dihydro-1H-imidazole;

2-(4-chlorophenyl)-4-(2-thienyl)-1-[4-(methylsulfonyl)phenyl]-4-hydroxy-4,5-dihydro-1H-imidazole;

2-(4-chlorophenyl)-4-(2-furyl)-1-[4-(methylsulfonyl)phenyl]-4-hydroxy-4,5-dihydro-1H-imidazole;

2-(4-chlorophenyl)-1-[4-(methylsulfonyl)phenyl]-4-(4-pyridyl)-4-hydroxy-4,5-dihydro-1H-imidazole;

2-(4-chlorophenyl)-4-chloro-1-[4-(methylsulfonyl)phenyl]-4-hydroxy-4,5-dihydro-1H-imidazole;

2-(4-chlorophenyl)-4-fluoro-1-[4-(methylsulfonyl)phenyl]-4-hydroxy-4,5-dihydro-1H-imidazole;

[2-(4-chlorophenyl)-1-[4-(methylsulfonyl)phenyl]-4-hydroxy-4,5-dihydro-1H-imidazol-4-yl]carboxylic acid;

methyl[2-(4-chlorophenyl)-1-[4-(methylsulfonyl)phenyl]-4-hydroxy-4,5-dihydro-1H-imidazol-4-yl]carboxylate;

[2-(4-chlorophenyl)-1-[4-(methylsulfonyl)phenyl]-4-hydroxy-4,5-dihydro-1H-imidazol-4-yl]carboxamide;

methyl[2-(4-chlorophenyl)-1-[4-(methylsulfonyl)phenyl]-4-hydroxy-4,5-dihydro-1H-imidazol-4-yl]carboxamide;

4-[2-(4-chlorophenyl)-4-trifluoromethyl-4-hydroxy-4,5-dihydro-1H-imidazol-1-yl]benzenesulfonamide;

4-[2-(4-chlorophenyl)-4-difluoromethyl-4-hydroxy-4,5-dihydro-1H-imidazol-1-yl]benzenesulfonamide;

4-[2-(4-chlorophenyl)-4-methyl-4-hydroxy-4,5-dihydro-1H-imidazol-1-yl]benzenesulfonamide;

4-[2-(4-chlorophenyl)-4-ethyl-4-hydroxy-4,5-dihydro-1H-imidazol-1-yl]benzenesulfonamide;

4-[2-(4-chlorophenyl)-4-phenyl-4-hydroxy-4,5-dihydro-1H-imidazol-1-yl]benzenesulfonamide;

4-[2-(4-chlorophenyl)-4-(4-fluorophenyl)-4-hydroxy-4,5-dihydro-1H-imidazol-1-yl]benzenesulfonamide;

4-[2-(4-chlorophenyl)-4-(4-bromophenyl)-4-hydroxy-4,5-dihydro-1H-imidazol-1-yl]benzenesulfonamide;

4-[2-(4-chlorophenyl)-4-(4-chlorophenyl)-4-hydroxy-4,5-dihydro-1H-imidazol-1-yl]benzenesulfonamide;

4-[2-(4-chlorophenyl)-4-(2-naphthyl)-4-hydroxy-4,5-dihydro-1H-imidazol-1-yl]benzenesulfonamide;

4-[2-(4-chlorophenyl)-4-(4-(trifluoromethoxy)phenyl)-4-hydroxy-4,5-dihydro-1H-imidazol-1-yl]benzenesulfonamide;

4-[2-(4-chlorophenyl)-4-(3-chlorophenyl)-4-hydroxy-4,5-dihydro-1H-imidazol-1-yl]benzenesulfonamide;

4-[2-(4-chlorophenyl)-4-(3-fluorophenyl)-4-hydroxy-4,5-dihydro-1H-imidazol-1-yl]benzenesulfonamide;

4-[2-(4-chlorophenyl)-4-(4-methoxyphenyl)-4-hydroxy-4,5-dihydro-1H-imidazol-1-yl]benzenesulfonamide;

4-[2-(4-chlorophenyl)-4-phenoxymethyl-4-hydroxy-4,5-dihydro-1H-imidazol-1-yl]benzenesulfonamide;

4-[2-(4-chlorophenyl)-4-(4-chlorophenoxy)methyl-4-hydroxy-4,5-dihydro-1H-imidazol-1-yl]benzenesulfonamide;

4-[2-(4-chlorophenyl)-4-(4-fluorophenoxy)methyl-4-hydroxy-4,5-dihydro-1H-imidazol-1-yl]benzenesulfonamide;

4-[2-(4-chlorophenyl)-4-phenylthiomethyl-4-hydroxy-4,5-dihydro-1H-imidazol-1-yl]benzenesulfonamide;

4-[2-(4-chlorophenyl)-4-(N-phenyl-N-methylamino)methyl-4-hydroxy-4,5-dihydro-1H-imidazol-1-yl]benzenesulfonamide;

4-[2-(4-chlorophenyl)-4-(2-quinolyl)methoxymethyl-4-hydroxy-4,5-dihydro-1H-imidazol-1-yl]benzenesulfonamide;

4-[2-(4-chlorophenyl)-4-methoxymethyl-4-hydroxy-4,5-dihydro-1H-imidazol-1-yl]benzenesulfonamide;

4-[2-(4-chlorophenyl)-4-(4-methoxybenzyloxy)methyl-4-hydroxy-4,5-dihydro-1H-imidazol-1-yl]benzenesulfonamide;

4-[2-(4-chlorophenyl)-4-hydroxymethyl-4-hydroxy-4,5-dihydro-1H-imidazol-1-yl]benzenesulfonamide;

4-[2-(4-chlorophenyl)-4-formyl-4-hydroxy-4,5-dihydro-1H-imidazol-1-yl]benzenesulfonamide;

4-[2-(4-chlorophenyl)-4-cyano-4-hydroxy-4,5-dihydro-1H-imidazol-1-yl]benzenesulfonamide;

4-[2-(4-chlorophenyl)-4-benzyl-4-hydroxy-4,5-dihydro-1H-imidazol-1-yl]benzenesulfonamide;

4-[2-(4-chlorophenyl)-4-phenylethyl-4-hydroxy-4,5-dihydro-1H-imidazol-1-yl]benzenesulfonamide;

4-[2-(4-chlorophenyl)-4-hexyl-4-hydroxy-4,5-dihydro-1H-imidazol-1-yl]benzenesulfonamide;

4-[2-(4-chlorophenyl)-4-hexylcarbonyl-4-hydroxy-4,5-dihydro-1H-imidazol-1-yl]benzenesulfonamide;

4-[2-(4-chlorophenyl)-4-phenylcarbonyl-4-hydroxy-4,5-dihydro-1H-imidazol-1-yl]benzenesulfonamide;
4-[2-(4-chlorophenyl)-4-benzylcarbonyl-4-hydroxy-4,5-dihydro-1H-imidazol-1-yl]benzenesulfonamide;
4-[2-(4-chlorophenyl)-4-(1-hydroxy-1-phenyl-methyl)-4-hydroxy-4,5-dihydro-1H-imidazol-1-yl]benzenesulfonamide;
4-[2-(4-chlorophenyl)-4-(1-hexanol)-4-hydroxy-4,5-dihydro-1H-imidazol-1-yl]benzenesulfonamide;
4-[2-(4-chlorophenyl)-4-hydroxy-4,5-dihydro-1H-imidazol-1-yl]benzenesulfonamide;
4-[2-(4-chlorophenyl)-4-octyl-4-hydroxy-4,5-dihydro-1H-imidazol-1-yl]benzenesulfonamide;
4-[2-(4-chlorophenyl)-4-methoxy-4-hydroxy-4,5-dihydro-1H-imidazol-1-yl]benzenesulfonamide;
4-[2-(4-chlorophenyl)-4-butoxy-4-hydroxy-4,5-dihydro-1H-imidazol-1-yl]benzenesulfonamide;
4-[2-(4-chlorophenyl)-4-methylthio-4-hydroxy-4,5-dihydro-1H-imidazol-1-yl]benzenesulfonamide;
4-[2-(4-chlorophenyl)-4-(3-thienyl)-4-hydroxy-4,5-dihydro-1H-imidazol-1-yl]benzenesulfonamide;
4-[2-(4-chlorophenyl)-4-(2-furyl)-4-hydroxy-4,5-dihydro-1H-imidazol-1-yl]benzenesulfonamide;
4-[2-(4-chlorophenyl)-4-(4-pyridyl)-4-hydroxy-4,5-dihydro-1H-imidazol-1-yl]benzenesulfonamide;
4-[2-(4-chlorophenyl)-4-chloro-4-hydroxy-4,5-dihydro-1H-imidazol-1-yl]benzenesulfonamide;
4-[2-(4-chlorophenyl)-4-fluoro-4-hydroxy-4,5-dihydro-1H-imidazol-1-yl]benzenesulfonamide;
[2-(4-chlorophenyl)-1-[4-(aminosulfonyl)phenyl)-4-hydroxy-4,5-dihydro-1H-imidazol-4-yl]carboxylic acid;
methyl[2-(4-chlorophenyl)-1-[4-(aminosulfonyl)phenyl)-4-hydroxy-4,5-dihydro-1H-imidazol-4-yl]carboxylate;
[2-(4-chlorophenyl)-1-[4-(aminosulfonyl)phenyl)-4-hydroxy-4,5-dihydro-1H-imidazol-4-yl]carboxamide;
methyl[2-(4-chlorophenyl)-1-[4-(aminosulfonyl)phenyl)-4-hydroxy-4,5-dihydro-1H-imidazol-4-yl]carboxamide;
2-[4-(methylsulfonyl)phenyl]-1-(4-methylphenyl)-4-trifluoromethyl-4-hydroxy-4,5-dihydro-1H-imidazole;
2-[4-(methylsulfonyl)phenyl]-1-(3-chlorophenyl)-4-trifluoromethyl-4-hydroxy-4,5-dihydro-1H-imidazole;
1-[4-(methylsulfonyl)phenyl]-2-(4-methyl-3-chlorophenyl)-4-trifluoromethyl-4-hydroxy-4,5-dihydro-1H-imidazole;
5-[1-[4-(methylsulfonyl)phenyl]-4-hydroxy-4-trifluoromethyl-4,5-dihydro-1H-imidazol-2-yl]-1,3-benzodioxole;
1-[4-(methylsulfonyl)phenyl]-2-(4-methoxyphenyl)-4-trifluoromethyl-4-hydroxy-4,5-dihydro-1H-imidazole;
1-[4-(methylsulfonyl)phenyl]-2-(3-fluorophenyl)-4-trifluoromethyl-4-hydroxy-4,5-dihydro-1H-imidazole;
1-[4-(methylsulfonyl)phenyl]-2-(4-fluorophenyl)-4-trifluoromethyl-4-hydroxy-4,5-dihydro-1H-imidazole;
1-[4-(methylsulfonyl)phenyl]-2-(4-methoxy-3-fluorophenyl)-4-trifluoromethyl-4-hydroxy-4,5-dihydro-1H-imidazole;
1-[4-(methylsulfonyl)phenyl]-2-phenyl-4-trifluoromethyl-4-hydroxy-4,5-dihydro-1H-imidazole;
1-[4-(methylsulfonyl)phenyl]-2-(4-methoxy-3-chlorophenyl)-4-trifluoromethyl-4-hydroxy-4,5-dihydro-1H-imidazole;
1-[4-(methylsulfonyl)phenyl]-2-[4-(trifluoromethyl)phenyl]-4-trifluoromethyl-4-hydroxy-4,5-dihydro-1H-imidazole;
1-[4-(methylsulfonyl)phenyl]-2-(4-bromophenyl)-4-trifluoromethyl-4-hydroxy-4,5-dihydro-1H-imidazole;
1-[4-(methylsulfonyl)phenyl]-2-(4-ethylphenyl)-4-trifluoromethyl-4-hydroxy-4,5-dihydro-1H-imidazole;
1-[4-(methylsulfonyl)phenyl]-2-(4-butylphenyl)-4-trifluoromethyl-4-hydroxy-4,5-dihydro-1H-imidazole;
1-[4-(methylsulfonyl)phenyl]-2-[4-(difluoromethyl)phenyl]-4-trifluoromethyl-4-hydroxy-4,5-dihydro-1H-imidazole;
1-[4-(methylsulfonyl)phenyl]-2-(4-butoxyphenyl)-4-trifluoromethyl-4-hydroxy-4,5-dihydro-1H-imidazole;
1-[4-(methylsulfonyl)phenyl]-2-[4-(methylthio)phenyl]-4-trifluoromethyl-4-hydroxy-4,5-dihydro-1H-imidazole;
1-[4-(methylsulfonyl)phenyl]-2-(4-methoxy-3,5-dichlorophenyl)-4-trifluoromethyl-4-hydroxy-4,5-dihydro-1H-imidazole;
1-[4-(methylsulfonyl)phenyl]-2-(4-methyl-3,5-difluorophenyl)-4-trifluoromethyl-4-hydroxy-4,5-dihydro-1H-imidazole;
1-[4-(methylsulfonyl)phenyl]-2-(2,4-dichlorophenyl)-4-trifluoromethyl-4-hydroxy-4,5-dihydro-1H-imidazole;
1-[4-(methylsulfonyl)phenyl]-2-(3,4-dichlorophenyl)-4-trifluoromethyl-4-hydroxy-4,5-dihydro-1H-imidazole;
1-[4-(methylsulfonyl)phenyl]-2-[4-(trifluoromethyl)phenyl]-4-trifluoromethoxy-4-hydroxy-4,5-dihydro-1H-imidazole;
2-(3,5-dimethyl-4-methoxy-phenyl)-1-[4-(methylsulfonyl)phenyl]-4-trifluoromethyl-4-hydroxy-4,5-dihydro-1H-imidazole;
2-(3,4-dimethylphenyl)-1-[4-(methylsulfonyl)phenyl]-4-trifluoromethyl-4-hydroxy-4,5-dihydro-1H-imidazole;
2-(4-aminophenyl)-1-[4-(methylsulfonyl)phenyl]-4-trifluoromethyl-4-hydroxy-4,5-dihydro-1H-imidazole;
4-[2-(4-methylphenyl)-4-trifluoromethyl-4-hydroxy-4,5-dihydro-1H-imidazol-1-yl]benzenesulfonamide;
4-[2-(3-chlorophenyl)-4-trifluoromethyl-4-hydroxy-4,5-dihydro-1H-imidazol-1-yl]benzenesulfonamide;
4-[2-(4-methyl-3-chlorophenyl)-4-trifluoromethyl-4-hydroxy-4,5-dihydro-1H-imidazol-1-yl]benzenesulfonamide;
5-[1-[4-(aminosulfonyl)phenyl]-4-hydroxy-4-trifluoromethyl-4,5-dihydro-1H-imidazol-2-yl]-1,3-benzodioxole;
4-[2-(4-methoxyphenyl)-4-trifluoromethyl-4-hydroxy-4,5-dihydro-1H-imidazol-1-yl]benzenesulfonamide;
4-[2-(3-fluorophenyl)-4-trifluoromethyl-4-hydroxy-4,5-dihydro-1H-imidazol-1-yl]benzenesulfonamide;
4-[2-(4-fluorophenyl)-4-trifluoromethyl-4-hydroxy-4,5-dihydro-1H-imidazol-1-yl]benzenesulfonamide;
4-[2-(4-methoxy-3-fluorophenyl)-4-trifluoromethyl-4-hydroxy-4,5-dihydro-1H-imidazol-1-yl]benzenesulfonamide;
4-[2-phenyl-4-trifluoromethyl-4-hydroxy-4,5-dihydro-1H-imidazol-1-yl]benzenesulfonamide;
4-[2-(4-methoxy-3-chlorophenyl)-4-trifluoromethyl-4-hydroxy-4,5-dihydro-1H-imidazol-1-yl]benzenesulfonamide;
4-[2-[4-(trifluoromethyl)phenyl]-4-trifluoromethyl-4-hydroxy-4,5-dihydro-1H-imidazol-1-yl]benzenesulfonamide;
4-[2-(4-bromophenyl)-4-trifluoromethyl-4-hydroxy-4,5-dihydro-1H-imidazol-1-yl]benzenesulfonamide;
4-[2-(2-chlorophenyl)-4-trifluoromethyl-4-hydroxy-4,5-dihydro-1H-imidazol-1-yl]benzenesulfonamide;
4-[2-(4-ethylphenyl)-4-trifluoromethyl-4-hydroxy-4,5-dihydro-1H-imidazol-1-yl]benzenesulfonamide;
4-[2-(4-butylphenyl)-4-trifluoromethyl-4-hydroxy-4,5-dihydro-1H-imidazol-1-yl]benzenesulfonamide;
4-[2-[4-(difluoromethyl)phenyl]-4-trifluoromethyl-4-hydroxy-4,5-dihydro-1H-imidazol-1-yl]benzenesulfonamide;

4-[2-(4-butoxyphenyl)-4-trifluoromethyl-4-hydroxy-4,5-dihydro-1H-imidazol-1-yl]benzenesulfonamide;
4-[2-[4-(methylthio)phenyl]-4-trifluoromethyl-4-hydroxy-4,5-dihydro-1H-imidazol-1-yl]benzenesulfonamide;
4-[2-(4-methoxy-3,5-dichloro-phenyl)-4-trifluoromethyl-4-hydroxy-4,5-dihydro-1H-imidazol-1-yl]benzenesulfonamide;
4-[2-(4-methyl-3,5-difluorophenyl)-4-trifluoromethyl-4-hydroxy-4,5-dihydro-1H-imidazol-1-yl]benzenesulfonamide;
4-[2-(2,4-dichlorophenyl)-4-trifluoromethyl-4-hydroxy-4,5-dihydro-1H-imidazol-1-yl]benzenesulfonamide;
4-[2-(3,4-dichlorophenyl)-4-trifluoromethyl-4-hydroxy-4,5-dihydro-1H-imidazol-1-yl]benzenesulfonamide;
4-[2-[4-(trifluoromethoxy)phenyl]-4-trifluoromethyl-4-hydroxy-4,5-dihydro-1H-imidazol-1-yl]benzenesulfonamide;
4-[2-(3,5-dimethyl-4-methoxy-phenyl)-4-trifluoromethyl-4-hydroxy-4,5-dihydro-1H-imidazol-1-yl]benzenesulfonamide;
4-[2-(3,4-dimethylphenyl)-4-trifluoromethyl-4-hydroxy-4,5-dihydro-1H-imidazol-1-yl]benzenesulfonamide;
4-[2-(4-aminophenyl)-4-trifluoromethyl-4-hydroxy-4,5-dihydro-1H-imidazol-1-yl]benzenesulfonamide;
1-(4-chlorophenyl)-4-trifluoromethyl-2-[4-(methylsulfonyl)phenyl]-4-hydroxy-4,5-dihydro-1H-imidazole;
1-(4-chlorophenyl)-4-difluoromethyl-2-[4-(methylsulfonyl)phenyl]-4-hydroxy-4,5-dihydro-1H-imidazole;
1-(4-chlorophenyl)-4-methyl-2-[4-(methylsulfonyl)phenyl]-4-hydroxy-4,5-dihydro-1H-imidazole;
1-(4-chlorophenyl)-4-ethyl-2-[4-(methylsulfonyl)phenyl]-4-hydroxy-4,5-dihydro-1H-imidazole;
1-(4-chlorophenyl)-4-phenyl-2-[4-(methylsulfonyl)phenyl]-4-hydroxy-4,5-dihydro-1H-imidazole;
1-(4-chlorophenyl)-4-(4-fluorophenyl)-2-[4-(methylsulfonyl)phenyl]-4-hydroxy-4,5-dihydro-1H-imidazole;
4-(4-bromophenyl)-1-(4-chlorophenyl)-2-[4-(methylsulfonyl)phenyl]-4-hydroxy-4,5-dihydro-1H-imidazole;
1-(4-chlorophenyl)-4-(3-chlorophenyl)-2-[4-(methylsulfonyl)phenyl]-4-hydroxy-4,5-dihydro-1H-imidazole;
1-(4-chlorophenyl)-4-(3-fluorophenyl)-2-[4-(methylsulfonyl)phenyl]-4-hydroxy-4,5-dihydro-1H-imidazole;
1-(4-chlorophenyl)-4-(4-methoxyphenyl)-2-[4-(methylsulfonyl)phenyl]-4-hydroxy-4,5-dihydro-1H-imidazole;
1,4-bis(4-chlorophenyl)-2-[4-(methylsulfonyl)phenyl]-4-hydroxy-4,5-dihydro-1H-imidazole;
1-(4-chlorophenyl)-4-(2-naphthyl)-2-[4-(methylsulfonyl)phenyl]-4-hydroxy-4,5-dihydro-1H-imidazole;
1-(4-chlorophenyl)-4-[4-(trifluoromethoxy)phenyl]-2-[4-(methylsulfonyl)phenyl]-4-hydroxy-4,5-dihydro-1H-imidazole;
1-(4-chlorophenyl)-4-phenoxymethyl-2-[4-(methylsulfonyl)phenyl]-4-hydroxy-4,5-dihydro-1H-imidazole;
1-(4-chlorophenyl)-4-(4-chlorophenoxy)methyl-2-[4-(methylsulfonyl)phenyl]-4-hydroxy-4,5-dihydro-1H-imidazole;
1-(4-chlorophenyl)-4-(4-fluorophenoxy)methyl-2-[4-(methylsulfonyl)phenyl]-4-hydroxy-4,5-dihydro-1H-imidazole;
1-(4-chlorophenyl)-4-phenylthiomethyl-2-[4-(methylsulfonyl)phenyl]-4-hydroxy-4,5-dihydro-1H-imidazole;
1-(4-chlorophenyl)-4-(N-phenyl-N-methylamino)methyl-2-[4-(methylsulfonyl)phenyl]-4-hydroxy-4,5-dihydro-1H-imidazole;
1-(4-chlorophenyl)-4-(2-quinolyl)methoxymethyl-2-[4-(methylsulfonyl)phenyl]-4-hydroxy-4,5-dihydro-1H-imidazole;
1-(4-chlorophenyl)-4-methoxymethyl-2-[4-(methylsulfonyl)phenyl]-4-hydroxy-4,5-dihydro-1H-imidazole;
1-(4-chlorophenyl)-4-(4-methoxybenzyloxy)methyl-2-[4-(methylsulfonyl)phenyl]-4-hydroxy-4,5-dihydro-1H-imidazole;
1-(4-chlorophenyl)-4-hydroxymethyl-2-[4-(methylsulfonyl)phenyl]-4-hydroxy-4,5-dihydro-1H-imidazole;
1-(4-chlorophenyl)-4-formyl-2-[4-(methylsulfonyl)phenyl]-4-hydroxy-4,5-dihydro-1H-imidazole;
1-(4-chlorophenyl)-4-cyano-2-[4-(methylsulfonyl)phenyl]-4-hydroxy-4,5-dihydro-1H-imidazole;
1-(4-chlorophenyl)-4-benzyl-2-[4-(methylsulfonyl)phenyl]-4-hydroxy-4,5-dihydro-1H-imidazole;
1-(4-chlorophenyl)-4-phenylethyl-2-[4-(methylsulfonyl)phenyl]-4-hydroxy-4,5-dihydro-1H-imidazole;
1-(4-chlorophenyl)-4-hexyl-2-[4-(methylsulfonyl)phenyl]-4-hydroxy-4,5-dihydro-1H-imidazole;
1-(4-chlorophenyl)-4-hexylcarbonyl-2-[4-(methylsulfonyl)phenyl]-4-hydroxy-4,5-dihydro-1H-imidazole;
1-(4-chlorophenyl)-4-phenylcarbonyl-2-[4-(methylsulfonyl)phenyl]-4-hydroxy-4,5-dihydro-1H-imidazole;
1-(4-chlorophenyl)-4-benzylcarbonyl-2-[4-(methylsulfonyl)phenyl]-4-hydroxy-4,5-dihydro-1H-imidazole;
1-(4-chlorophenyl)-4-(1-hydroxy-2-phenyl-methyl)-2-[4-(methylsulfonyl)phenyl]-4-hydroxy-4,5-dihydro-1H-imidazole;
1-(4-chlorophenyl)-4-(1-hexanol)-2-[4-(methylsulfonyl)phenyl]-4-hydroxy-4,5-dihydro-1H-imidazole;
1-(4-chlorophenyl)-2-[(methylsulfonyl)phenyl]-4-hydroxy-4,5-dihydro-1H-imidazole;
1-(4-chlorophenyl)-4-octyl-2-[4-(methylsulfonyl)phenyl]-4-hydroxy-4,5-dihydro-1H-imidazole;
1-(4-chlorophenyl)-4-methoxy-2-[4-(methylsulfonyl)phenyl]-4-hydroxy-4,5-dihydro-1H-imidazole;
1-(4-chlorophenyl)-4-butoxy-2-[4-(methylsulfonyl)phenyl]-4-hydroxy-4,5-dihydro-1H-imidazole;
1-(4-chlorophenyl)-4-methylthio-2-[4-(methylsulfonyl)phenyl]-4-hydroxy-4,5-dihydro-1H-imidazole;
1-(4-chlorophenyl)-4-(2-thienyl)-2-[4-(methylsulfonyl)phenyl]-4-hydroxy-4,5-dihydro-1H-imidazole;
1-(4-chlorophenyl)-4-(2-furyl)-2-[4-(methylsulfonyl)phenyl]-4-hydroxy-4,5-dihydro-1H-imidazole;
1-(4-chlorophenyl)-4-(4-pyridyl)-2-[4-(methylsulfonyl)phenyl]-4-hydroxy-4,5-dihydro-1H-imidazole;
1-(4-chlorophenyl)-4-chloro-2-[4-(methylsulfonyl)phenyl]-4-hydroxy-4,5-dihydro-1H-imidazole;
1-(4-chlorophenyl)-4-fluoro-2-[4-(methylsulfonyl)phenyl]-4-hydroxy-4,5-dihydro-1H-imidazole;
[1-(4-chlorophenyl)-2-[4-(methylsulfonyl)phenyl]-4-hydroxy-4,5-dihydro-1H-imidazol-4-yl]carboxylic acid;
methyl[1-(4-chlorophenyl)-2-[4-(methylsulfonyl)phenyl]-4-hydroxy-4,5-dihydro-1H-imidazol-4-yl]carboxylate;
[1-(4-chlorophenyl)-2-[4-(methylsulfonyl)phenyl]-4-hydroxy-4,5-dihydro-1H-imidazol-4-yl]carboxamide;
methyl[1-(4-chlorophenyl)-2-[4-(methylsulfonyl)phenyl]-4-hydroxy-4,5-dihydro-1H-imidazol-4-yl]carboxamide;
4-[1-(4-chlorophenyl)-4-trifluoromethyl-4-hydroxy-4,5-dihydro-1H-imidazol-2-yl]benzenesulfonamide;
4-[1-(4-chlorophenyl)-4-difluoromethyl-4-hydroxy-4,5-dihydro-1H-imidazol-2-yl]benzenesulfonamide;
4-[1-(4-chlorophenyl)-4-methyl-4-hydroxy-4,5-dihydro-1H-imidazol-2-yl]benzenesulfonamide;
4-[1-(4-chlorophenyl)-4-ethyl-4-hydroxy-4,5-dihydro-1H-imidazol-2-yl]benzenesulfonamide;
4-[1-(4-chlorophenyl)-4-phenyl-4-hydroxy-4,5-dihydro-1H-imidazol-2-yl]benzenesulfonamide;

4-[1-(4-chlorophenyl)-4-(4-fluorophenyl)-4-hydroxy-4,5-dihydro-1H-imidazol-2-yl]benzenesulfonamide;
4-[1-(4-chlorophenyl)-4-(4-bromophenyl)-4-hydroxy-4,5-dihydro-1H-imidazol-2-yl]benzenesulfonamide;
4-[1-(4-chlorophenyl)-4-(4-chlorophenyl)-4-hydroxy-4,5-dihydro-1H-imidazol-2-yl]benzenesulfonamide;
4-[1-(4-chlorophenyl)-4-(2-naphthyl)-4-hydroxy-4,5-dihydro-1H-imidazol-2-yl]benzenesulfonamide;
4-[1-(4-chlorophenyl)-4-[4-(trifluoromethoxy)phenyl]-4-hydroxy-4,5-dihydro-1H-imidazol-2-yl]benzenesulfonamide;
4-[1-(4-chlorophenyl)-4-(3-chlorophenyl)-4-hydroxy-4,5-dihydro-1H-imidazol-2-yl]benzenesulfonamide;
4-[1-(4-chlorophenyl)-4-(3-fluorophenyl)-4-hydroxy-4,5-dihydro-1H-imidazol-2-yl]benzenesulfonamide;
4-[1-(4-chlorophenyl)-4-(4-methoxyphenyl)-4-hydroxy-4,5-dihydro-1H-imidazol-2-yl]benzenesulfonamide;
4-[1-(4-chlorophenyl)-4-phenoxymethyl-4-hydroxy-4,5-dihydro-1H-imidazol-2-yl]benzenesulfonamide;
4-[1-(4-chlorophenyl)-4-(4-chlorophenoxy)methyl-4-hydroxy-4,5-dihydro-1H-imidazol-2-yl]benzenesulfonamide;
4-[1-(4-chlorophenyl)-4-(4-fluorophenoxy)methyl-4-hydroxy-4,5-dihydro-1H-imidazol-2-yl]benzenesulfonamide;
4-[1-(4-chlorophenyl)-4-phenylthiomethyl-4-hydroxy-4,5-dihydro-1H-imidazol-2-yl]benzenesulfonamide;
4-[1-(4-chlorophenyl)-4-(N-phenyl-N-methylamino)methyl-4-hydroxy-4,5-dihydro-1H-imidazol-2-yl]benzenesulfonamide;
4-[1-(4-chlorophenyl)-4-(2-quinolyl)methoxymethyl-4-hydroxy-4,5-dihydro-1H-imidazol-2-yl]benzenesulfonamide;
4-[1-(4-chlorophenyl)-4-methoxymethyl-4-hydroxy-4,5-dihydro-1H-imidazol-2-yl]benzenesulfonamide;
4-[1-(4-chlorophenyl)-4-(4-methoxybenzyloxy)methyl-4-hydroxy-4,5-dihydro-1H-imidazol-2-yl]benzenesulfonamide;
4-[1-(4-chlorophenyl)-4-hydroxymethyl-4-hydroxy-4,5-dihydro-1H-imidazol-2-yl]benzenesulfonamide;
4-[1-(4-chlorophenyl)-4-formyl-4-hydroxy-4,5-dihydro-1H-imidazol-2-yl]benzenesulfonamide;
4-[1-(4-chlorophenyl)-4-cyano-4-hydroxy-4,5-dihydro-1H-imidazol-2-yl]benzenesulfonamide;
4-[1-(4-chlorophenyl)-4-benzyl-4-hydroxy-4,5-dihydro-1H-imidazol-2-yl]benzenesulfonamide;
4-[1-(4-chlorophenyl)-4-phenylethyl-4-hydroxy-4,5-dihydro-1H-imidazol-2-yl]benzenesulfonamide;
4-[1-(4-chlorophenyl)-4-hexyl-4-hydroxy-4,5-dihydro-1H-imidazol-2-yl]benzenesulfonamide;
4-[1-(4-chlorophenyl)-4-hexylcarbonyl-4-hydroxy-4,5-dihydro-1H-imidazol-2-yl]benzenesulfonamide;
4-[1-(4-chlorophenyl)-4-phenylcarbonyl-4-hydroxy-4,5-dihydro-1H-imidazol-2-yl]benzenesulfonamide;
4-[1-(4-chlorophenyl)-4-benzylcarbonyl-4-hydroxy-4,5-dihydro-1H-imidazol-2-yl]benzenesulfonamide;
4-[1-(4-chlorophenyl)-4-(1-hydroxy-2-phenyl-methyl)-4-hydroxy-4,5-dihydro-1H-imidazol-2-yl]benzenesulfonamide;
4-[1-(4-chlorophenyl)-4-(1-hexanol)-4-hydroxy-4,5-dihydro-1H-imidazol-2-yl]benzenesulfonamide;
4-[1-(4-chlorophenyl)-4-hydroxy-4,5-dihydro-1H-imidazol-2-yl]benzenesulfonamide;
4-[1-(4-chlorophenyl)-4-octyl-4-hydroxy-4,5-dihydro-1H-imidazol-2-yl]benzenesulfonamide;
4-[1-(4-chlorophenyl)-4-methoxy-4-hydroxy-4,5-dihydro-1H-imidazol-2-yl]benzenesulfonamide;
4-[1-(4-chlorophenyl)-4-butoxy-4-hydroxy-4,5-dihydro-1H-imidazol-2-yl]benzenesulfonamide;
4-[1-(4-chlorophenyl)-4-methylthio-4-hydroxy-4,5-dihydro-1H-imidazol-2-yl]benzenesulfonamide;
4-[1-(4-chlorophenyl)-4-(2-thienyl)-4-hydroxy-4,5-dihydro-1H-imidazol-2-yl]benzenesulfonamide;
4-[1-(4-chlorophenyl)-4-(2-furyl)-4-hydroxy-4,5-dihydro-1H-imidazol-2-yl]benzenesulfonamide;
4-[1-(4-chlorophenyl)-4-(3-pyridyl)-4-hydroxy-4,5-dihydro-1H-imidazol-2-yl]benzenesulfonamide;
4-[1-(4-chlorophenyl)-4-chloro-4-hydroxy-4,5-dihydro-1H-imidazol-2-yl]benzenesulfonamide;
4-[1-(4-chlorophenyl)-4-fluoro-4-hydroxy-4,5-dihydro-1H-imidazol-2-yl]benzenesulfonamide;
[1-(4-chlorophenyl)-2-[4-(aminosulfonyl)phenyl]-4-hydroxy-4,5-dihydro-1H-imidazo-4-yl]carboxylic acid;
methyl[1-(4-chlorophenyl)-2-[4-(aminosulfonyl)phenyl]-4-hydroxy-4,5-dihydro-1H-imidazol-4-yl]carboxylate;
[1-(4-chlorophenyl)-2-[4-(aminosulfonyl)phenyl]-4-hydroxy-4,5-dihydro-1H-imidazol-4-yl]carboxamide;
methyl[1-(4-chlorophenyl)-2-[4-(aminosulfonyl)phenyl]-4-hydroxy-4,5-dihydro-1H-imidazol-4-yl]carboxamide;
2-[4-(methylsulfonyl)phenyl]-1-(4-methylphenyl)-4-trifluoromethyl-4-hydroxy-4,5-dihydro-1H-imidazole;
2-[4-(methylsulfonyl)phenyl]-1-(3-chlorophenyl)-4-trifluoromethyl-4-hydroxy-4,5-dihydro-1H-imidazole;
2-[4-(methylsulfonyl)phenyl]-1-(4-methyl-3-chlorophenyl)-4-trifluoromethyl-4-hydroxy-4,5-dihydro-1H-imidazole;
5-[2-[4-(methylsulfonyl)phenyl]-4-hydroxy-4-trifluoromethyl-4,5-dihydro-1H-imidazol-1-yl]-1,3-benzodioxole;
2-[4-(methylsulfonyl)phenyl]-1-(4-methoxyphenyl)-4-trifluoromethyl-4-hydroxy-4,5-dihydro-1H-imidazole;
2-[4-(methylsulfonyl)phenyl]-1-(3-fluorophenyl)-4-trifluoromethyl-4-hydroxy-4,5-dihydro-1H-imidazole;
2-[4-(methylsulfonyl)phenyl]-1-(4-fluorophenyl)-4-trifluoromethyl-4-hydroxy-4,5-dihydro-1H-imidazole;
2-[4-(methylsulfonyl)phenyl]-1-(4-methoxy-3-fluorophenyl)-4-trifluoromethyl-4-hydroxy-4 5-dihydro-1H-imidazole;
2-[4-(methylsulfonyl)phenyl]-1-phenyl-4-trifluoromethyl-4-hydroxy-4,5-dihydro-1H-imidazole;
2-[4-(methylsulfonyl)phenyl]-1-(4-methoxy-3-chlorophenyl)-4-trifluoromethyl-4-hydroxy-4,5-dihydro-1H-imidazole;
2-[4-(methylsulfonyl)phenyl]-1-[4-(trifluoromethyl)phenyl]-4-trifluoromethyl-4-hydroxy-4,5-dihydro-1H-imidazole;
2-[4-(methylsulfonyl)phenyl]-1-(4-bromophenyl)-4-trifluoromethyl-4-hydroxy-4,5-dihydro-1H-imidazole;
2-[4-(methylsulfonyl)phenyl]-1-(1-chlorophenyl)-4-trifluoromethyl-4-hydroxy-4,5-dihydro-1H-imidazole;
2-[4-(methylsulfonyl)phenyl]-1-(4-ethylphenyl)-4-trifluoromethyl-4-hydroxy-4,5-dihydro-1H-imidazole;
2-[4-(methylsulfonyl)phenyl]-1-(4-butylphenyl)-4-trifluoromethyl-4-hydroxy-4,5-dihydro-1H-imidazole;
2-[4-(methylsulfonyl)phenyl]-1-[4-(difluoromethyl)phenyl]-4-trifluoromethyl-4-hydroxy-4,5-dihydro-1H-imidazole;
2-[4-(methylsulfonyl)phenyl]-1-(4-butoxyphenyl)-4-trifluoromethyl-4-hydroxy-4,5-dihydro-1H-imidazole;
2-[4-(methylsulfonyl)phenyl]-1-[4-(methylthio)phenyl]-4-trifluoromethyl-4-hydroxy-4,5-dihydro-1H-imidazole;
2-[4-(methylsulfonyl)phenyl]-1-(4-methoxy-3,5-dichlorophenyl)-4-trifluoromethyl-4-hydroxy-4,5-dihydro-1H-imidazole;

2-[4-(methylsulfonyl)phenyl]-1-(4-methyl-3,5-difluorophenyl)-4-trifluoromethyl-4-hydroxy-4,5-dihydro-1H-imidazole;
2-[4-(methylsulfonyl)phenyl]-1-(2,4-dichlorophenyl)-4-trifluoromethyl-4-hydroxy-4,5-dihydro-1H-imidazole;
2-[4-(methylsulfonyl)phenyl]-1-(3,4-dichlorophenyl)-4-trifluoromethyl-4-hydroxy-4,5-dihydro-1H-imidazole;
2-[4-(methylsulfonyl)phenyl]-1-[4-(trifluoromethyl)phenyl]-4-trifluoromethoxy-hydroxy-4,5-dihydro-1H-imidazole;
2-[4-(methylsulfonyl)phenyl]-1-(3,5-dimethyl-4-methoxyphenyl)-4-trifluoromethyl-4-hydroxy-4,5-dihydro-1H-imidazole;
2-[4-(methylsulfonyl)phenyl]-1-(3,4-dimethylphenyl)-4-trifluoromethyl-4-hydroxy-4,5-dihydro-1H-imidazole;
2-[4-(methylsulfonyl)phenyl]-1-(4-aminophenyl)-4-trifluoromethyl-4-hydroxy-4,5-dihydro-1H-imidazole;
4-[1-(4-methylphenyl)-4-trifluoromethyl-4-hydroxy-4,5-dihydro-1H-imidazol-2-yl]benzenesulfonamide;
4-[1-(3-chlorophenyl)-4-trifluoromethyl-4-hydroxy-4,5-dihydro-1H-imidazol-2-yl]benzenesulfonamide;
4-[1-(4-methyl-3-chlorophenyl)-4-trifluoromethyl-4-hydroxy-4,5-dihydro-1H-imidazol-2-yl]benzenesulfonamide;
5-[2-[4-(aminosulfonyl)phenyl]-4-hydroxy-4,5-dihydro-4-trifluoromethyl-1H-imidazol-1-yl]-1,3-benzodioxole;
4-[1-(3-fluorophenyl)-4-trifluoromethyl-4-hydroxy-4,5-dihydro-1H-imidazol-2-yl]benzenesulfonamide;
4-[1-(4-fluorophenyl)-4-trifluoromethyl-4-hydroxy-4,5-dihydro-1H-imidazol-2-yl]benzenesulfonamide;
4-[1-(4-methoxy-3-fluorophenyl)-4-trifluoromethyl-4-hydroxy-4,5-dihydro-1H-imidazol-2-yl]benzenesulfonamide;
4-[1-phenyl-4-trifluoromethyl-4-hydroxy-4,5-dihydro-1H-imidazol-2-yl]benzenesulfonamide;
4-[1-(4-methoxy-3-chlorophenyl)-4-trifluoromethyl-4-hydroxy-4,5-dihydro-1H-imidazol-2-yl]benzenesulfonamide;
4-[1-[4-(trifluoromethyl)phenyl]-4-trifluoromethyl-4-hydroxy-4,5-dihydro-1H-imidazol-2-yl]benzenesulfonamide;
4-[1-(4-bromophenyl)-4-trifluoromethyl-4-hydroxy-4,5-dihydro-1H-imidazol-2-yl]benzenesulfonamide;
4-[1-(1-chlorophenyl)-4-trifluoromethyl-4-hydroxy-4,5-dihydro-1H-imidazol-2-yl]benzenesulfonamide;
4-[1-(4-ethylphenyl)-4-trifluoromethyl-4-hydroxy-4,5-dihydro-1H-imidazol-2-yl]benzenesulfonamide;
4-[1-(4-butylphenyl)-4-trifluoromethyl-4-hydroxy-4,5-dihydro-1H-imidazol-2-yl]benzenesulfonamide;
4-[1-[4-(difluoromethyl)phenyl]-4-trifluoromethyl-4-hydroxy-4,5-dihydro-1H-imidazol-2-yl]benzenesulfonamide;
4-[1-(4-butoxyphenyl)-4-trifluoromethyl-4-hydroxy-4,5-dihydro-1H-imidazol-2-yl]benzenesulfonamide;
4-[1-[4-(methylthio)phenyl]-4-trifluoromethyl-4-hydroxy-4,5-dihydro-1H-imidazol-2-yl]benzenesulfonamide;
4-[1-(4-methoxy-3,5-dichloro-phenyl)-4-trifluoromethyl-4-hydroxy-4,5-dihydro-1H-imidazol-2-yl]benzenesulfonamide;
4-[1-(4-methyl-3,5-difluorophenyl)-4-trifluoromethyl-4-hydroxy-4,5-dihydro-1H-imidazol-2-yl]benzenesulfonamide;
4-[1-(2,4-dichlorophenyl)-4-trifluoromethyl-4-hydroxy-4,5-dihydro-1H-imidazol-2-yl]benzenesulfonamide;
4-[1-(3,4-dichlorophenyl)-4-trifluoromethyl-4-hydroxy-4,5-dihydro-1H-imidazol-2-yl]benzenesulfonamide;
4-[1-[4-(trifluoromethoxy)phenyl]-4-trifluoromethyl-4-hydroxy-4,5-dihydro-1H-imidazol-2-yl]benzenesulfonamide;
4-[1-(3,5-dimethyl-4-methoxy-phenyl)-4-trifluoromethyl-4-hydroxy-4,5-dihydro-1H-imidazol-2-yl]benzenesulfonamide;
4-[1-(3,4-dimethylphenyl)-4-trifluoromethyl-4-hydroxy-4,5-dihydro-1H-imidazol-2-yl]benzenesulfonamide; and
4-[1-(4-aminophenyl)-4-trifluoromethyl-4-hydroxy-4,5-dihydro-1H-imidazol-2-yl]benzenesulfonamide.

Within Formula I there is a fourth subclass of compounds of high interest represented by Formula V:

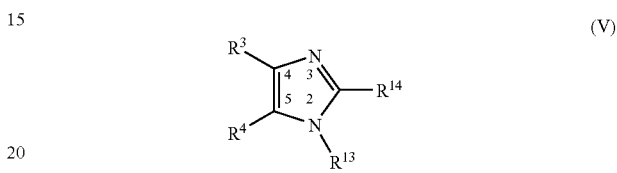

wherein $R^3$ is a radical selected from hydrido, alkyl, haloalkyl, aralkyl, heterocycloalkyl, heteroaralkyl, acyl, cyano, alkoxy, alkylthio, alkylthioalkyl, alkylsulfonyl, cycloalkylthio, cycloalkylthioalkyl, cycloalkylsulfonyl, cycloalkylsulfonylalkyl, haloalkylsulfonyl, arylsulfonyl, halo, hydroxyalkyl, alkoxyalkyl, alkylcarbonyl, arylcarbonyl, aralkylcarbonyl, heterocyclocarbonyl, cyanoalkyl, aminoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, carboxyl, aminocarbonyl, alkylaminocarbonyl, alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroarylalkylthioalkyl, heteroaryloxy, heteroarylthio, arylthioalkyl, aryloxyalkyl, arylthio, aryloxy, aralkylthioalkyl, aralkoxyalkyl, aryl and heteroaryl; wherein $R^4$ is a radical selected from hydrido, alkyl and halo; and wherein $R^{13}$ and $R^{14}$ are independently selected from aryl and heterocyclo, wherein $R^{13}$ and $R^{14}$ are optionally substituted at a substitutable position with one or more radicals independently selected from alkylsulfonyl, aminosulfonyl, halo, alkylthio, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; provided at least one of $R^{13}$ and $R^{14}$ is aryl substituted with alkylsulfonyl or aminosulfonyl; or a pharmaceutically-acceptable salt thereof.

A preferred class of compounds consists of those compounds of Formula V wherein $R^3$ is a radical selected from hydrido, lower alkyl, lower haloalkyl, lower aralkyl, lower heterocycloalkyl, lower heteroaralkyl, acyl, cyano, lower alkoxy, lower alkylthio, lower alkylsulfonyl, phenylsulfonyl, lower haloalkylsulfonyl, halo, lower hydroxyalkyl, lower alkoxyalkyl, lower alkylcarbonyl, lower haloalkylcarbonyl, phenylcarbonyl, lower aralkylcarbonyl, lower cyanoalkyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, carboxyl, lower alkylthioalkyl, aminocarbonyl, lower alkylaminocarbonyl, lower alkylaminocarbonylalkyl, lower aralkoxy, lower aralkylthio, lower heteroaralkoxy, lower heteroaralkylthio, lower heteroarylalkoxyalkyl, lower heteroarylalkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, 5 or 6 membered heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, hydroxyl, lower alkoxy, lower hydroxyalkyl and lower haloalkoxy; wherein $R^4$ is a radical selected from hydrido, lower alkyl and halo; and wherein $R^{13}$ and $R^{14}$ are independently selected from phenyl and heteroaryl, wherein $R^{13}$ and $R^{14}$ are optionally substituted at a substitutable position with one or more radicals independently selected from lower methylsulfonyl, aminosulfonyl, lower alkylthio, lower alkyl, lower haloalkyl, lower alkoxy, lower hydroxyalkyl, lower alkoxyalkyl, and lower haloalkoxy; or a pharmaceutically-acceptable salt thereof.

A class of compounds of particular interest consists of those compounds of Formula V wherein $R^3$ is a radical selected from hydrido, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinomethyl, pyrrolidinylmethyl, piperazinylmethyl, piperidinylmethyl, pyridylmethyl, thienylmethyl, formyl, cyano, methoxy, ethoxy, propoxy, n-butoxy, methylthio, ethylthio, isopropylthio, methylsulfonyl, phenylsulfonyl, trifluoromethylsulfonyl, fluoro, chloro, bromo, hydroxymethyl, hydroxyethyl, methoxymethyl, ethoxymethyl, methylthiomethyl, isopropylthiomethyl, cyclohexylthiomethyl, benzyloxy, benzylthio, methylcarbonyl, ethylcarbonyl, phenylcarbonyl, trifluoromethylcarbonyl, difluoromethylcarbonyl, fluoromethylcarbonyl, benzylcarbonyl, pyrrolidinylcarbonyl, cyanomethyl, cyanobutyl, aminomethyl, methylaminomethyl, N-phenylaminomethyl, N-methyl-N-phenylaminomethyl, acetyl, propanoyl, butanoyl, methoxycarbonylmethyl, ethoxycarbonylethyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, carboxyl, carboxymethyl, carboxypropyl, aminocarbonyl, methylaminocarbonyl, N,N-diethylaminocarbonyl, N-methoxy-N-methylaminocarbonyl, methylaminocarbonylmethyl, pyridyloxy, pyridylthio, phenyloxy, 4-chlorophenoxy, furylmethoxy, furylmethylthio, thienylmethoxy, quinolylmethoxy, pyridylmethoxy, 5-phenylpyridyl-2-methoxy, thienylmethylthio, pyridylmethylthio, quinolylmethoxymethyl, furylbutoxyethyl, pyridyloxymethyl, pyridylmethoxymethyl, thienyloxyhexyl, thienylthiomethyl, pyridylthiohexyl, furyloxymethyl, furylmethylthiomethyl, quinolylmethylthioethyl, phenylthiomethyl, 2-chlorophenylthiomethyl, 2,6-dichlorophenylthiomethyl, 4-methylphenylthiomethyl, 2-isopropylphenylthiomethyl, 2-methylphenylthiomethyl, phenyloxymethyl, 4-chlorophenyloxymethyl, 4-methylphenyloxymethyl, benzyloxymethyl, 4-methoxybenzyloxymethyl, naphthyl, phenyl, thienyl, furyl, pyridyl, wherein the thienyl, furyl, pyridyl and phenyl radicals are optionally substituted at a substitutable position with one or more radicals selected from fluoro, chloro, bromo, methylthio, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl and trifluoromethoxy; wherein $R^4$ is a radical selected from hydrido, methyl, ethyl, fluoro, chloro and bromo; and wherein $R^{13}$ and $R^{14}$ are independently selected from phenyl, imidazolyl, thienyl, thiazolyl, pyrrolyl, oxazolyl, isoxazolyl, triazolyl, pyrazinyl, pyrimidinyl, quinolinyl, isoquinolinyl, indolyl, benzimidazolyl, pyrazolyl and pyridyl, wherein $R^{13}$ and $R^{14}$ are optionally substituted at a substitutable position with one or more radicals independently selected from methylsulfonyl, aminosulfonyl, fluoromethylsulfonyl, difluoromethylsulfonyl, fluoro, chloro, bromo, methylthio, methylsulfinyl, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-diethylamino, phenylamino and nitro; or a pharmaceutically-acceptable salt thereof.

A class of compounds of even more particular interest consists of those compounds of Formula V wherein $R^3$ is a radical selected from hydrido, cyano, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and 2-methylphenylthiomethyl; wherein $R^4$ is hydrido; wherein $R^{13}$ is phenyl substituted with methylsulfonyl or aminosulfonyl; and wherein $R^{14}$ is selected from imidazolyl, thienyl, thiazolyl, pyrrolyl, oxazolyl, isoxazolyl, triazolyl, pyrimidinyl, quinolinyl, indolyl, benzimidazolyl, pyrazolyl and pyridyl, wherein $R^{14}$ is optionally substituted at a substitutable position with one or more radicals independently selected from methylthio, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl, methoxymethyl, ethoxymethyl, and trifluoromethoxy; or a pharmaceutically-acceptable salt thereof.

A family of specific compounds of particular interest within Formula V consists of compounds and pharmaceutically-acceptable salts thereof as follows:

3-[4-[[(methylphenyl)thio]methyl]-1-[4-(methylsulfonyl)phenyl]-1H-imidazol-2-yl]pyridine;

4-[2-(pyrindin-3-yl)-4-[[(methylphenyl)thio]methyl]-1H-imidazol-1-yl]benzenesulfonamide;

3-[4-methyl-1-[4-(methylsulfonyl)phenyl]-1H-imidazol-2-yl]pyridine;

4-[2-(6-methylpyrindin-2-yl)-4-trifluoromethyl-1H-imidazol-1-yl]benzenesulfonamide;

4-methyl-3-[1-[4-(methylsulfonyl)phenyl]-4-trifluoromethyl-1H-imidazol-2-yl]pyridine;

4-[2-(4-methylpyrindin-3-yl)-4-trifluoromethyl-1H-imidazol-1-yl]benzenesulfonamide:

3-methyl-2-[1-[4-(methylsulfonyl)phenyl]-4-trifluoromethyl-1H-imidazol-2-yl]pyridine;

1-[1-[4-(methylsulfonyl)phenyl]-4-trifluoromethyl-1H-imidazol-2-yl]isoquinoline;

4-[2-(3-methylpyrindin-2-yl)-4-trifluoromethyl-1H-imidazol-1-yl]benzenesulfonamide;
3-[1-[4-(methylsulfonyl)phenyl]-4-trifluoromethyl-1H-imidazol-2-yl]quinoline;
4-[2-(2-thienyl)-4-trifluoromethyl-1H-imidazol-1-yl]benzenesulfonamide;
3-bromo-5-[1-[4-(methylsulfonyl)phenyl]-4-trifluoromethyl-1H-imidazol-2-yl]pyridine;
1-[4-(methylsulfonyl)phenyl]-2-(3-pyridinyl)-1H-imidazole-4-carbonitrile;
2-(2-methyloxazol-4-yl)-1-[4-(methylsulfonyl)phenyl]-4-trifluoromethyl-1H-imidazole;
4-[2-(5-bromopyrindin-3-yl)-4-trifluoromethyl-1H-imidazol-1-yl]benzenesulfonamide;
2-(5-methylpyridin-3-yl)-1-[4-(methylsulfonyl)phenyl]-1H-imidazole-4-carbonitrile;
3-[4-difluoromethyl-1-[4-(methylsulfonyl)phenyl]-1H-imidazol-2-yl]pyridine;
4-[4-difluoromethyl-2-(pyrindin-3-yl)-1H-imidazol-1-yl]benzenesulfonamide;
4-[4-cyano-2-(pyrindin-3-yl)-1H-imidazol-1-yl]benzenesulfonamide;
4-[4-cyano-2-(5-methylpyrindin-3-yl)-1H-imidazol-1-yl]benzenesulfonamide;
4-[2-(2-quinolinyl)-4-trifluoromethyl-1H-imidazol-1-yl]benzenesulfonamide;
1-methyl-4-[1-[4-(methylsulfonyl)phenyl]-4-trifluoromethyl-1H-imidazol-2-yl]-1H-pyrazole;
4-[2-(1-methyl-1H-pyrazol-4-yl)-4-trifluoromethyl-1H-imidazol-1-yl]benzenesulfonamide;
2-(1-methyl-1H-imidazol-4-yl)-1-[4-(methylsulfonyl)phenyl]-4-trifluoromethyl-1H-imidazole;
4-[2-(1-methyl-1H-imidazol-4-yl)-4-trifluoromethyl-1H-imidazol-1-yl]benzenesulfonamide;
2-(1-methyl-1H-imidazol-5-yl)-1-[4-(methylsulfonyl)phenyl]-4-trifluoromethyl-1H-imidazole;
4-[2-(1-methyl-1H-imidazol-5-yl)-4-trifluoromethyl-1H-imidazol-1-yl]benzenesulfonamide;
2-(1-methyl-1H-imidazol-2-yl)-1-[4-(methylsulfonyl)phenyl]-4-trifluoromethyl-1H-imidazole;
4-[2-(1-methyl-1H-imidazol-2-yl)-4-trifluoromethyl-1H-imidazol-1-yl]benzenesulfonamide;
1-[4-(methylsulfonyl)phenyl]-2-(4-methylthiazol-2-yl)-4-trifluoromethyl-1H-imidazole;
4-[2-(4-methylthiazol-2-yl)-4-trifluoromethyl-1H-imidazol-1-yl]benzenesulfonamide;
1-[4-(methylsulfonyl)phenyl]-2-(2-methylthiazol-5-yl)-4-trifluoromethyl-1H-imidazole;
4-[2-(2-methylthiazol-5-yl)-4-trifluoromethyl-1H-imidazo-1-yl]benzenesulfonamide;
5-methyl-3-[1-[4-(methylsulfonyl)phenyl]-4-trifluoromethyl-1H-imidazol-2-yl]isoxazole;
4-[2-(5-methylisoxazol-3-yl)-4-trifluoromethyl-1H-imidazol-1-yl]benzenesulfonamide;
5-[1-[4-(methylsulfonyl)phenyl]-4-trifluoromethyl-1H-imidazol-2-yl]pyrimidine;
4-[2-(5-pyrimidinyl)-4-trifluoromethyl-1H-imidazol-1-yl]benzenesulfonamide;
4-[2-(pyrazin-2-yl)-4-(trifluoromethyl)-1H-imidazol-1-yl]benzenesulfonamide;
4-[2-(quinol-3-yl)-4-(trifluoromethyl)-1H-imidazol-1-yl]benzenesulfonamide;
1-methyl-3-[1-[4-(methylsulfonyl)phenyl]-4-trifluoromethyl-1H-imidazol-2-yl]-1H-indole;
4-[2-(1-methylindol-3-yl)-4-(trifluoromethyl)-1H-imidazol-1-yl]benzenesulfonamide;
4-[2-(isoquinol-2-yl)-4-(trifluoromethyl)-1H-imidazol-1-yl]benzenesulfonamide;
4-[2-(2-methyloxazol-4-yl)-4-(trifluoromethyl)-1H-imidazol-1-yl]benzenesulfonamide;
4-[2-(2-methylthiazol-4-yl)-4-(trifluoromethyl)-1H-imidazol-1-yl]benzenesulfonamide;
4-[2-(oxazol-4-yl)-4-(trifluoromethyl)-1H-imidazol-1-yl]benzenesulfonamide;
4-[2-(1-methylpyrazol-3-yl)-4-(trifluoromethyl)-1H-imidazol-1-yl]benzenesulfonamide;
4-[2-(5-methylisoxazol-3-yl)-4-(trifluoromethyl)-1H-imidazol-1-yl]benzenesulfonamide;
4-[2-(4-methylpyridin-2-yl)-4-(trifluoromethyl)-1H-imidazol-1-yl]benzenesulfonamide;
2-[1-[4-(methylsulfonyl)phenyl]-4-(trifluoromethyl)-1H-imidazol-2-yl]thiophene;
3-[1-[4-(methylsulfonyl)phenyl]-4-(trifluoromethyl)-1H-imidazol-2-yl]thiophene;
4-[2-(5-methylpyridin-3-yl)-4-(trifluoromethyl)-1H-imidazol-1-yl]benzenesulfonamide;
2-methyl-3-[1-[4-(methylsulfonyl)phenyl]-4-(trifluoromethyl)-1H-imidazol-2-yl]pyridine;
4-[2-(2-methylpyridin-3-yl)-4-(trifluoromethyl)-1H-imidazol-1-yl]benzenesulfonamide;
4-[2-(pyridin-3-yl)-4-(trifluoromethyl)-1H-imidazol-1-yl]benzenesulfonamide;
3-fluoro-5-[1-[4-(methylsulfonyl)phenyl]-4-(trifluoromethyl)-1H-imidazol-2-yl]pyridine;
3-chloro-5-[1-[4-(methylsulfonyl)phenyl]-4-(trifluoromethyl)-1H-imidazol-2-yl]pyridine;
4-[2-(5-fluoropyridin-3-yl)-4-(trifluoromethyl)-1H-imidazol-1-yl]benzenesulfonamide;
4-[2-(5-chloropyridin-3-yl)-4-(trifluoromethyl)-1H-imidazol-1-yl]benzenesulfonamide;
5-methyl-2-[1-[4-(methylsulfonyl)phenyl]-4-(trifluoromethyl)-1H-imidazol-2-yl]pyridine;
4-methyl-2-[1-[4-(methylsulfonyl)phenyl]-4-(trifluoromethyl)-1H-imidazol-2-yl]pyridine;
2-methoxy-6-[1-[4-(methylsulfonyl)phenyl]-4-(trifluoromethyl)-1H-imidazol-2-yl]pyridine;
5-methoxy-2-[1-[4-(methylsulfonyl)phenyl]-4-(trifluoromethyl)-1H-imidazol-2-yl]pyridine;
4-methoxy-2-[1-[4-(methylsulfonyl)phenyl]-4-(trifluoromethyl)-1H-imidazol-2-yl]pyridine;
2-chloro-6-[1-[4-(methylsulfonyl)phenyl]-4-(trifluoromethyl)-1H-imidazol-2-yl]pyridine;
5-chloro-2-[1-[4-(methylsulfonyl)phenyl]-4-(trifluoromethyl)-1H-imidazol-2-yl]pyridine;
4-chloro-2-[1-[4-(methylsulfonyl)phenyl]-4-(trifluoromethyl)-1H-imidazol-2-yl]pyridine;
2-fluoro-6-[1-[4-(methylsulfonyl)phenyl]-4-(trifluoromethyl)-1H-imidazol-2-yl]pyridine;
4-fluoro-2-[1-[4-(methylsulfonyl)phenyl]-4-(trifluoromethyl)-1H-imidazol-2-yl]pyridine;
4-fluoro-2-[1-[4-(methylsulfonyl)phenyl]-4-(trifluoromethyl)-1H-imidazol-2-yl]pyridine;
4-[2-(5-methylpyridin-2-yl)-4-(trifluoromethyl)-1H-imidazol-1-yl]benzenesulfonamide;
4-[2-(4-methylpyridin-2-yl)-4-(trifluoromethyl)-1H-imidazol-1-yl]benzenesulfonamide;
4-[2-(6-methoxypyridin-2-yl)-4-(trifluoromethyl)-1H-imidazol-1-yl]benzenesulfonamide;
4-[2-(5-methoxypyridin-2-yl)-4-(trifluoromethyl)-1H-imidazol-1-yl]benzenesulfonamide;
4-[2-(4-methoxypyridin-2-yl)-4-(trifluoromethyl)-1H-imidazol-1-yl]benzenesulfonamide;

4-[2-(6-chloropyridin-2-yl)-4-(trifluoromethyl)-1H-imidazol-1-yl]benzenesulfonamide;
4-[2-(5-chloropyridin-2-yl)-4-(trifluoromethyl)-1H-imidazol-1-yl]benzenesulfonamide;
4-[2-(4-chloropyridin-2-yl)-4-(trifluoromethyl)-1H-imidazol-1-yl]benzenesulfonamide;
4-[2-(6-fluoropyridin-2-yl)-4-(trifluoromethyl)-1H-imidazol-1-yl]benzenesulfonamide;
4-[2-(5-fluoropyridin-2-yl)-4-(trifluoromethyl)-1H-imidazol-1-yl]benzenesulfonamide;
4-[2-(4-fluoropyridin-2-yl)-4-(trifluoromethyl)-1H-imidazol-1-yl]benzenesulfonamide;
3-methoxy-5-[1-[4-(methylsulfonyl)phenyl]-4-(trifluoromethyl)-1H-imidazol-2-yl]pyridine;
4-methyl-3-[1-[4-(methylsulfonyl)phenyl]-4-(trifluoromethyl)-1H-imidazol-2-yl]pyridine;
3-[1-[4-(methylsulfonyl)phenyl]-4-(trifluoromethyl)-1H-imidazol-2-yl]pyridine-1-oxide;
3-[4-(4-fluorophenyl)-1-[4-(methylsulfonyl)phenyl]-1H-imidazol-2-yl]pyridine;
5-[1-[4-(methylsulfonyl)phenyl]-4-(trifluoromethyl)-1H-imidazol-2-yl]-2-(methylthio)pyridine;
3-[4-(difluoromethyl)-1-[4-(methylsulfonyl)phenyl]-1H-imidazol-2-yl]pyridine;
4-[2-(5-methoxypyridin-3-yl)-4-(trifluoromethyl)-1H-imidazol-1-yl]benzenesulfonamide;
4-[4-methyl-2-(3-pyridinyl)-1H-imidazol-1-yl]benzenesulfonamide;
4-[2-(3-pyridinyl)-4-(trifluoromethyl)-1H-imidazol-1-yl]benzenesulfonamide-1-oxide;
4-[4-(4-fluorophenyl)-2-(3-pyridinyl)-1H-imidazol-1-yl]benzenesulfonamide;
4-[2-(3-pyridinyl)-4-(trifluoromethyl)-1H-imidazol-1-yl]benzenesulfonamide 1-oxide;
4-[4-(4-fluorophenyl)-2-(3-pyridinyl)-1H-imidazol-1-yl]benzenesulfonamide;
4-[2-[6-(methylthio)pyridin-3-yl]-4-trifluoromethyl)-1H-imidazol-1-yl]benzenesulfonamide;
4-[4-(difluoromethyl)-2-(3-pyridinyl)-1H-imidazol-1-yl]benzenesulfonamide;
3-[1-[4-(methylsulfonyl)phenyl]-4-(trifluoromethyl)-1H-imidazol-2-yl]pyridine;
2-[1-[4-(methylsulfonyl)phenyl]-4-(trifluoromethyl)-1H-imidazol-2-yl]pyridine;
2-methyl-4-[1-[4-(methylsulfonyl)phenyl]-4-(trifluoromethyl)-1H-imidazol-2-yl]pyridine;
4-[1-[4-(methylsulfonyl)phenyl]-4-(trifluoromethyl)-1H-imidazol-2-yl]pyridine;
2-methyl-6-[1-[4-(methylsulfonyl)phenyl]-4-(trifluoromethyl)-1H-imidazol-2-yl]pyridine;
4-[2-(6-methylpyridin-3-yl)-4-(trifluoromethyl)-1H-imidazol-1-yl]benzenesulfonamide;
1-methyl-3-[1-[4-(methylsulfonyl)phenyl]-4-(trifluoromethyl)-1H-imidazol-2-yl]pyridinium iodide;
2-methyl-5-[1-[4-(methylsulfonyl)phenyl]-4-(trifluoromethyl)-1H-imidazol-2-yl]pyridine 1-oxide;
3-methyl-5-(1-[4-(methylsulfonyl)phenyl]-4-(trifluoromethyl)-1H-imidazol-2-yl]pyridine;
2-methoxy-5-[1-[4-(methylsulfonyl)phenyl]-4-(trifluoromethyl)-1H-imidazol-2-yl]pyridine;
2-[4-(4-fluorophenyl-1-[4-(methylsulfonyl)phenyl]-4-(trifluoromethyl)-1H-imidazol-2-yl]pyridine;
3-methyl-5-[1-[4-(methylsulfonyl)phenyl]-4-(trifluoromethyl)-1H-imidazol-2-yl]pyridine 1-oxide;
3-methoxy-5-[1-[4-(methylsulfonyl)phenyl]-4-(trifluoromethyl)-1H-imidazol-2-yl]pyridine;
4-[2-(3-methoxypyridin-5-yl)-4-(trifluoromethyl)-1H-imidazol-1-yl]benzenesulfonamide;
2-[1-[4-(methylsulfonyl)phenyl]-4-(trifluoromethyl)-1H-imidazol-2-yl]quinoline;
2-[1-[4-(methylsulfonyl)phenyl]-4-(trifluoromethyl)-1H-imidazol-2-yl]pyrazine;
2-methyl-4-[1-[4-(methylsulfonyl)phenyl]-4-(trifluoromethyl)-1H-imidazol-2-yl]thiazole; and
4-[2-(5-methylpyridin-2-yl)-4-(trifluoromethyl)-1H-imidazol-1-yl]benzenesulfonamide.

Compounds of Formula V, especially where $R^{14}$ is pyridyl, may form N-oxides, which may be active forms or prodrugs which would be converted to compounds of Formula V in vivo.

Compounds of Formula V would also be capable of inhibiting cytokines, such as TNF, IL-1, IL-6, and IL-8. As such, the compounds can be used in the manufacture of a medicament or in a method for the treatment for the prophylactic or therapeutic treatment of diseases mediated by cytokines, such as TNF, IL-1, IL-6, and IL-8.

The term "hydrido" denotes a single hydrogen atom (H). This hydrido radical may be attached, for example, to an oxygen atom to form a hydroxyl radical, or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl", radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl", radicals may be further substituted with one or more halo atoms, such as fluoro, chloro or bromo, to provide "haloalkoxy" or "haloalkoxyalkyl" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cyanoalkyl" embraces radicals having a cyano or nitrile (—CN) radical attached to an alkyl radical as described above. More preferred cyanoalkyl radicals are "lower cyanoalkyl" radicals having one to six carbon atoms. Examples of such lower cyanoalkyl radicals include cyanomethyl, cyanopropyl, cyanoethyl and cyanobutyl. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces unsaturated cyclic radicals having three to ten carbon atoms. More preferred cycloalkenyl radicals are "lower cycloalkenyl", radicals having about five to about eight carbon atoms. Examples of such radicals include cyclobutenyl, cyclopentenyl, cyclohexenyl and cycloheptenyl. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Such aryl radicals may be substituted at a substitutable position with one or more substituents selected from halo, alkylthio, alkylsulfinyl, alkyl, cyano, haloalkyl, hydroxyl, alkoxy, hydroxyalkyl and haloalkoxy. The terms "heterocyclic" and "heterocyclo" embraces saturated, partially saturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms [e.g. morpholinyl, etc.]; and saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of "heteroaryl" radicals include unsaturated 3 to 6 membered heteromonocyclic group containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2, 3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl (quinolinyl), isoquinolyl (isoquinolinyl), indazolyl, benzotriazolyl, tetrazolopyridazinyl [e.g., tetrazolo [1,5-b] pyridazinyl, etc.], etc.; unsaturated 3 to 6-membered heteromonocyclic group containing an oxygen atom, for example, pyranyl, 2-furyl, 3-furyl, etc.; unsaturated 3 to 6-membered heteromonocyclic group containing a sulfur atom, for example, 2-thienyl, 3-thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.) etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3, 4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuran, benzothiophene, and the like. Said heterocyclo may be substituted at a substitutable position with one or more substituents selected from halo, alkylthio, alkylsulfinyl, alkyl, cyano, haloalkyl, hydroxyl, alkoxy, hydroxyalkyl and haloalkoxy. More preferred heteroaryl radicals include five to six membered heteroaryl radicals. The term "heterocycloalkyl" embraces heterocyclic-substituted alkyl radicals. More preferred heterocycloalkyl radicals are "lower heterocycloalkyl" radicals having one to six carbon atoms and a heterocyclic radical. Examples include such radicals as pyrrolidinylmethyl. The term "heteroarylalkyl" embraces heteroaryl-substituted alkyl radicals. More preferred heteroarylalkyl radicals are "lower heteroarylalkyl" radicals having one to six carbon atoms and a heteroaryl radical. Examples include such heteroarylalkyl radicals such as pyridylmethyl and thienylmethyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "arylthioalkyl" embraces arylthio radicals attached to an alkyl radical. More preferred arylthioalkyl radicals are "lower arylthioalkyl" radicals having alkyl radicals of one to six carbon atoms and an arylthio radical as described above. Examples of such radicals include phenylthiomethyl, where the phenyl radical may be substituted as described above. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" denotes $NH_2O_2S$—. The term "acyl" denotes a radical provided by the residue after removal of hydroxyl from an organic acid. Examples of such acyl radicals include formyl, alkanoyl and aroyl radicals. The alkanoyl radicals may be substituted or unsubstituted, such as formyl, acetyl, propanoyl, butanoyl, isobutanoyl, valeryl, isovaleryl, pivaloyl, hexanoyl or the like. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such phenylalkyl radicals include benzyl, diphenylmethyl, triphenylmethyl, phenylethyl and diphenylethyl. The aryl in said aralkyl radicals may be substituted at a substitutable position with one or more substituents selected from halo, alkylthio, alkylsulfinyl, alkyl, cyano, haloalkyl, hydroxyl, alkoxy, hydroxyalkyl and haloalkoxy. The terms benzyl and phenylmethyl are interchangeable. The terms "alkylcarbonyl", "arylcarbonyl" and "aralkylcarbonyl" include radicals having alkyl, aryl and aralkyl radicals, respectively, as defined above, attached to a carbonyl radical. More preferred alkylcarbonyl radicals are "lower alkylcarbonyl" radicals having one to six carbon atoms. Examples of such radicals include methylcarbonyl and ethylcarbonyl. More preferred aralkylcarbonyl radicals are "lower aralkylcarbonyl" radicals having aryl radicals attached to alkyl radicals having one to six carbon atoms. Examples of such aralkylcarbonyl radicals include benzylcarbonyl. An example of an arylcarbonyl radical is phenylcarbonyl. The term "alkoxycarbonylalkyl" embraces radicals having "alkoxycarbonyl", as defined above attached to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The term "carboxyalkyl" embraces radicals having a carboxy radical as defined above, attached to an alkyl radical. More preferred carboxyalkyl radicals are "lower carboxyalkyl" radicals having one or more carboxy radicals attached to an alkyl radical having one to six carbon atoms. The term "heteroaralkyl" embraces heteroaryl-substituted alkyl radicals. More preferred heteroaralkyl radicals are "lower heteroaralkyl" radicals having five to six membered heteroaryl radicals attached to one to six carbon atoms. Examples of such radicals include pyridylmethyl, quinolylmethyl, thienylmethyl, furylethyl and quinolylethyl. The heteroaryl in said heteroaralkyl may be additionally substituted with halo, alkyl, alkoxy, halkoalkyl and haloalkoxy. The term "aryloxy" embraces aryl radicals, as defined above, attached to an oxygen atom. Examples of such radicals include phenoxy. The term "heteroaryloxy" embraces heteroaryl radicals as defined above attached to an oxygen radical. More preferred heteroaryloxy radicals are "lower heteroaryloxy" radicals having five to six membered heteroaryl radicals. The term "aralkoxy" embraces oxy-containing aralkyl radicals attached through the oxygen atom to other radicals. The term "aralkoxyalkyl" embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl. The term "cycloalkylthio" embraces radicals containing a cycloalkyl radical, of three to about ten carbon atoms attached to a divalent sulfur atom. More preferred cycloalkylthio radicals are "lower cycloalkylthio" radicals having cycloalkyl radicals of four to six carbon atoms. Examples of such lower cycloalkylthio radicals are cyclobutylthio, cyclopentylthio and cyclohexylthio. The term "cycloalkylthioalkyl" embraces radicals containing a cycloalkylthio radical, as described above, attached to an alkyl radical. More preferred cycloalkylthioalkyl radicals are "lower cycloalkylthioalkyl" radicals having cycloalkyl radicals of four to six carbon atoms and alkyl radicals of one to six carbons. The term "cycloalkylsulfony" embraces radicals containing a cycloalkyl radical, of three to about ten carbon atoms attached to a divalent sulfonyl radical. More preferred cycloalkylsulfonyl radicals are "lower cycloalkylsulfonyl" radicals having cycloalkyl radicals of four to six carbon atoms. Examples of such lower cycloalkylsulfonyl radicals are cyclobutylsulfonyl, cyclopentylsulfonyl and cyclohexylsulfonyl. The term "cycloalkylsulfonylalkyl" embraces radicals containing a cycloalkylsulfonyl radical, as described above, attached to an alkyl radical. More preferred cycloalkylsulfonylalkyl radicals are "lower cycloalkylsulfonylalkyl" radicals having cycloalkyl radicals of four to six carbon atoms and alkyl radicals of one to six carbons. The term "cycloalkyloxy" embraces radicals containing a cycloalkyl radical, of three to about ten carbon atoms attached to a divalent oxygen atom. More preferred cycloalkyloxy radicals are "lower cycloalkyloxy" radicals having cycloalkyl radicals of four to six carbon atoms. Examples of such lower cycloalkyloxy radicals are cyclobutyloxy, cyclopentyloxy and cyclohexyloxy. The term "cycloalkyloxyalkyl" embraces radicals containing a cycloalkyloxy radical, as described above, attached to an alkyl radical. More preferred cycloalkyloxyalkyl radicals are "lower cycloalkyloxyalkyl" radicals having cycloalkyl radicals of four to six carbon atoms and alkyl radicals of one to six carbons. The term "heteroarylthio" embraces radicals having heteroaryl radicals attached to a sulfur radical. More preferred heteroarylthio radicals are "lower heteroarylthio" radicals having five to six membered heteroaryl radicals. Examples of such radicals include 2-furylthio, 2-thienylthio, 3-thienylthio, 4-pyridylthio and 3-pyridylthio. The term "heteroarylalkylthio" denotes radicals having an heteroaryl radical attached to an alkylthio radical. More preferred heteroarylalkylthio radicals are "lower heteroarylalkylthio" radicals having heteroaryl radicals attached to lower alkylthio radicals as described above. Examples of such radicals include furylmethylthio and quinolylmethylthio. The term "heteroarylalkylthioalkyl" denotes radicals having an heteroaryl radical attached to an alkylthio radical further attached through the sulfur atom to an alkyl radical. More preferred heteroarylalkylthioalkyl are "lower heteroarylalkylthioalkyl" radicals having lower heteroarylalkyl radicals as described above. Examples of such radicals include furylmethylthiomethyl and quinolylmethylthioethyl. The term "heteroarylthioalkyl" denotes radicals having an heteroaryl radical attached to a sulfur atom further attached through the sulfur atom to an alkyl radical. More prefered heteroarylthioalkyl radicals are "lower heteroarylthioalkyl" having lower heteroarylthio radicals as described above. Examples of such radicals include thienylthiomethyl and pyridylthiohexyl. The term "aralkylthio" embraces radicals having aralkyl radicals attached to a bridging sulfur atom. More preferred aralkylthio radicals are "lower aralkylthio" radicals having the aryl radicals attached to one to six carbon atoms. Examples of such radicals include benzylthio and phenylethylthio. The term "aralkylthioalkyl" embraces radicals having aralkyl radicals attached to alkyl radicals through a bridging sulfur atom. More preferred aralkylthioalkyl radicals are "lower aralkylthioalkyl" radicals having the aralkylthio radicals attached to one to six carbon atoms. Examples of such radicals include benzylthiomethyl and phenylethylthiomethyl. The term "heteroaryloxyalkyl" denotes radicals having an heteroaryl radical attached to an oxygen atom further attached through the oxygen atom to an alkyl radical. More preferred heteroaryloxyalkyl radicals are "lower heteroaryloxyalkyl" radicals having five to six membered heteroaryl radicals. Examples of such radicals include furyloxyethyl, pyridyloxymethyl and thienyloxyhexyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. The term "alkylamino" denotes amino groups which have been substituted with one or two alkyl radicals. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino and the like. The term "aminocarbonyl" denotes an amide group of the formula —C(=O)NH$_2$. The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylaminocarbonyl. The term "arylamino" denotes amino groups which have been substituted with one or two aryl radicals, such as N-phenylamino. The "arylamino" radicals may be further substituted on the aryl ring portion of the radical. The terms "N-arylaminoalkyl" and "N-aryl-N-alkylaminoalkyl" denote amino groups which have been substituted with one aryl radical or one aryl and one alkyl radical respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The term "alkylaminocarbonylalkyl" denotes an alkylaminocarbonyl group which is attached to an alkyl radical. More preferred are "lower alkylaminocarbonylalkyl" having lower alkylaminocarbonyl radicals as described above attached to one to six carbon atoms. The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl. The term "heteroarylalkoxy" embraces radicals having one or more heteroaryl radicals attached to an alkoxy radical. More preferred heteroarylalkoxy radicals are "lower heteroarylalkoxy" radicals having five to six membered heteroaryl radicals. Examples of such radicals include 2-thienylmethoxy, 3-thienylmethoxy, 2-furylmethoxy, 3-furylmethoxy and 2-pyridylmethoxy, 3-pyridylmethoxy, 4-pyridylmethoxy. The term "heteroarylalkoxyalkyl" embraces alkyl radicals having one or more heteroaryl radicals attached to an alkoxy radical, further attached to the alkyl radical. More preferred heteroarylalkoxyalkyl radicals are "lower heteroarylalkoxyalkyl" radicals having five to six membered heteroaryl radicals. Examples of such radicals include 2-thienylmethoxymethyl. The term "azidoalkyl" denotes alkyl radicals substituted with azido groups (—N$_3$). More preferred azidoalkyl radicals are "lower azidoalkyl" having one to six carbon atoms. Examples include azidomethyl, azidoethyl and aminopropyl.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising treating the subject having or susceptible to such inflammation or disorder with a therapeutically-effective amount of a compound of Formula I.

Also included in the family of compounds of Formula I are the stereoisomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Racemic alcohol containing compounds may be resolved to their single enantiomers by the following procedure. Treatment of the racemic alcohols with an acetylating agent, such as vinyl acetate or isopropenyl acetate, in the presence of an appropriate enzyme results in the selective acetylation of one of the constituent enantiomeric alcohols, leading to a crude product consisting of essentially enantiomerically pure alcohol. Appropriate enzymes include, but are not limited to, lipases (such as AMANO Lipase PS30), cholinesterases and proteases. The reaction may be monitored to complete acetylation of one of the enantiomers using HPLC. The enantiomerically pure alcohol may be separated from enantiomerically pure acetate by column chromatography. Saponification of the acetate using aqueous base provides the other enantiomerically pure alcohol.

Alternatively, alcohols can be resolved via procedures outlined in E. Eliel and S. Wilen, *Stereochemistry of Organic compounds*, 337–340 (1994).

GENERAL SYNTHETIC PROCEDURES

The compounds of the invention can be synthesized according to the following procedures of Schemes I–XV, wherein the $R^1$–$R^{14}$ substituents are as defined for Formula I–V, above, except where further noted.

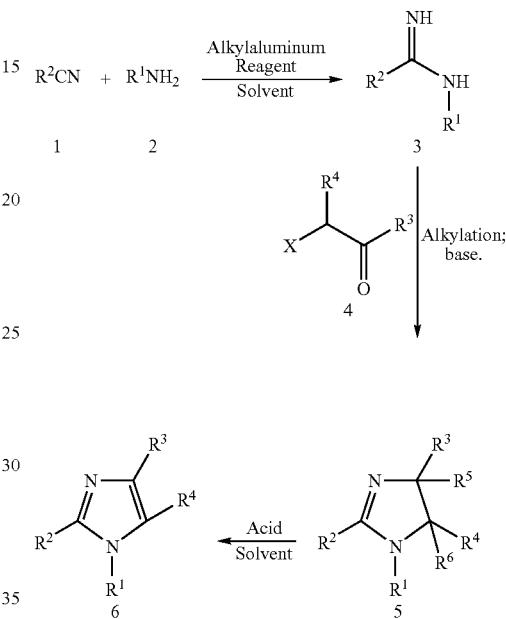

Scheme I shows the three step preparation of the 4,5-dihydro-imidazoles 5 and substituted imidazoles 6 of the present invention. In step 1, the reaction of substituted nitriles ($R^2CN$) 1 with primary amines ($R^1NH_2$) 2 in the presence of alkylaluminum reagents such as trimethylaluminum, triethylaluminum, dimethylaluminum chloride, diethylaluminum chloride in the presence of inert solvents such as toluene, benzene and xylene, gives amidines 3. In step 2, the reaction of amidine 3 with 2-halo-ketones 4 (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 5 (where $R^5$ is hydroxyl and $R^6$ is hydrido). Some of the suitable solvents for this reaction are isopropanol, acetone and dimethylformamide. The reaction may be carried out at temperatures of about 20° C. to about 90° C. In step 3, the 4,5-dihydroimidazoles 5 may be dehydrated in the presence of an acid catalyst such as 4-toluenesulfonic acid or mineral acids to form the 1,2-disubstituted imidazoles 6 of the invention. Suitable solvents for this dehydration step are e.g., toluene, xylene and benzene. Trifluoroacetic acid can be used as solvent and catalyst for this dehydration step.

In some cases (e.g., where $R^3$=methyl or phenyl) the intermediate 5 may not be readily isolable. The reaction, under the conditions described above, proceeds to give the targeted imidazoles directly.

Scheme II

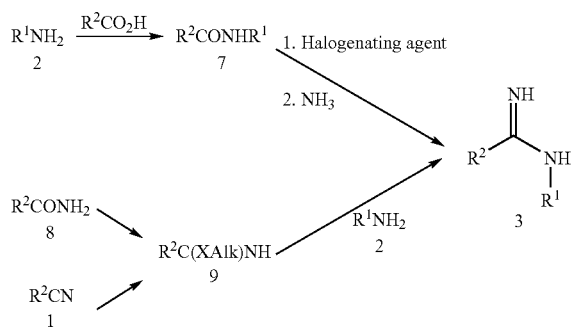

Scheme II shows alternative methods of forming amidines 3. Amidines 3 are also available by the two step conversion of amide 7 ($R^2CONHR^1$ formed by the conversion of primary amine 2). In Step 1, the amide 7 is converted to the corresponding imidoyl chloride by treatment with a halogenating agent such as phosphorus oxychloride. In step two, treatment of the imidoyl chloride with ammonia forms the desired amidine 3. In addition, amidines 3 may also be obtained by conversion of primary amides 8 (e.g., $R^2CONH_2$) or nitriles 1 ($R^2CN$) to their corresponding iminothioethers or iminoethers 9 (where X is sulfur and oxygen, respectively) followed by reaction with amine 2.

Scheme III

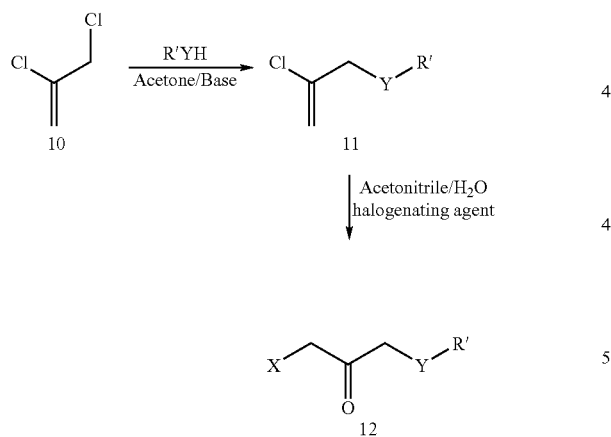

Scheme III shows the two step method of preparing certain. 2-halo-ketones 12 (compound 4 from Scheme I where X is bromo or chloro, $R^3$ is —$CH_2YR'$ [Y is oxygen, sulfur or —NH] and $R^4$ is hydrido) which are not commercially available, from 1,2-dihalopropenes 10. In step 1, 2,3-dichloro-1-propene 10 is added to a mixture of alcohol, amine or mercaptan (R'YH) and base, such as potassium carbonate in acetone, to form the 2-chloropropene 11, where R' is an alkyl or aryl group and Y is an oxygen, nitrogen or sulfur atom. In step 2, the 2-chloropropene 11 is converted to 2-haloketones 12 via a method as described by H. E. Morton and M. R. Leanna (*Tet. Letters*, 34, 4481 (1993)).

Scheme IV

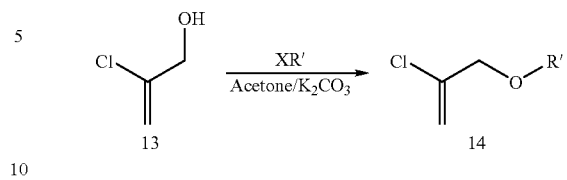

Scheme IV shows a method of forming 2-chloropropenes 14 (compound 11 in Scheme III where Y is oxygen). The 2-chloro-2-propen-1-ol 13 is added to a mixture of an alkyl, aralkyl or heteroaralkyl halide (XR') and base, such as potassium carbonate in acetone, to form the 2-chloropropene 14.

Alternatively, 2-chloropropenes 14 can be formed from the corresponding 2,3-dichloro-1-propenes 10 (Scheme III) by reaction with a metal alkoxide in an appropriate solvent. Sodium methoxide in methanol is an example of one such alkoxide and solvent.

Scheme V

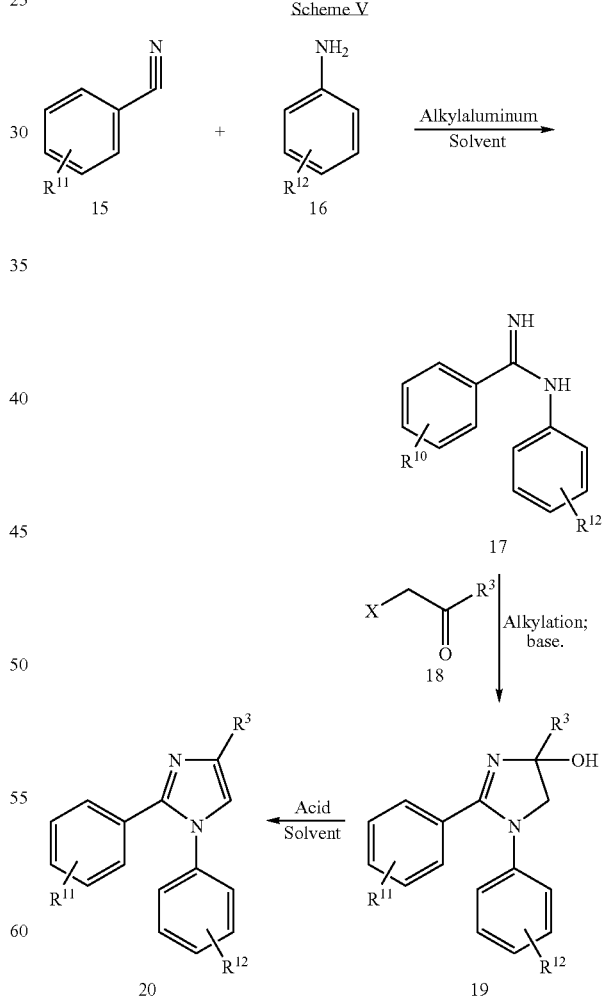

Scheme V shows the three step preparation of 1,2-diarylimidazoles 20 of the present invention. In step 1, the reaction of substituted benzonitriles 15 with substituted anilines 16 in the presence of alkylaluminum reagents such as trimethylaluminum, triethylaluminum, dimethylaluminum chloride, diethylaluminum chloride gives amidines 17. In step 2, the reaction of amidines 17 with haloketones 18 (compound 4 in Scheme I where X is Br or Cl and $R^4$ is hydrido) in the presence of bases, such as sodium bicarbonate, potassium carbonate, sodium carbonate, potassium bicarbonate or hindered tertiary amines such as N,N'-diisopropylethylamine, gives the 1,2-diaryl-4,5-dihydro-imidazoles 19. Some bf the suitable solvents for this reaction are isopropanol, acetone and dimethylformamide. The reaction may be carried out at a temperature between about 20° C. to about 90° C. In step 3, the 1,2-diaryl-4,5-dihydro-imidazoles 19 may be dehydrated in the presence of an acid catalyst such as 4-toluenesulfonic acid to form the 1,2-diarylimidazoles 20 of the present invention. Suitable solvents for this dehydration step are, for example, toluene, xylene and benzene. Trifluoroacetic acid can be used as solvent and catalyst for this dehydration step.

In some cases (e.g., where $R^3$ is methyl or phenyl), the intermediate 19 may not be readily isolable. The reaction, under the conditions described above, proceeds to give the targeted imidazoles 20 directly.

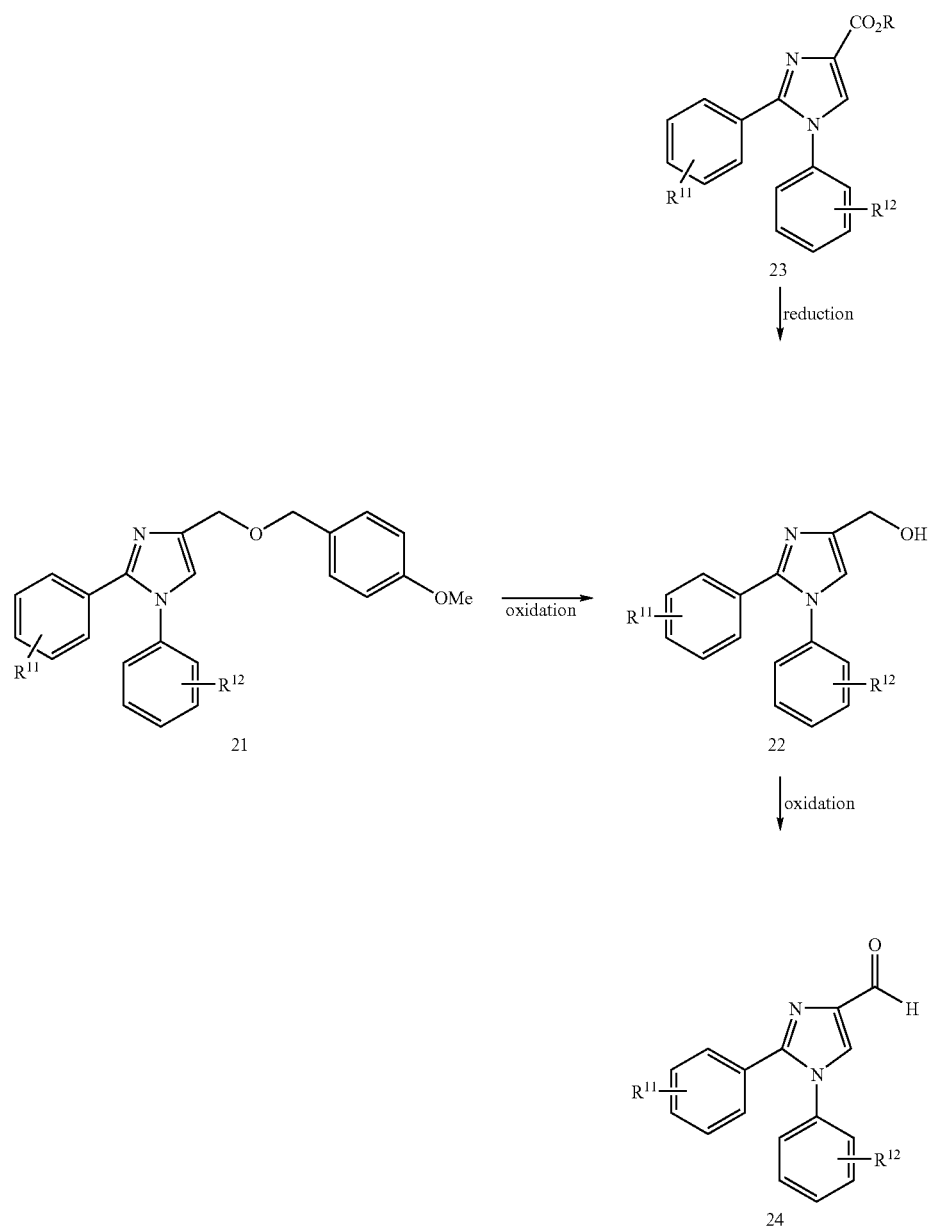

Scheme VI shows the formation of 4-hydroxymethyl imidazoles 22 and 4-formyl-imidazoles 23 from benzyloxy-protected imidazoles 21 and from 4-carboalkoxy imidazoles 23. In step 1, the oxidative deprotection of 4-methoxybenzyl group in 21, such as with ceric ammonium nitrate, gives the hydroxymethyl imidazoles 22. Alternatively, the alkoxycarbonyl group of 23 may be reduced to the hydroxymethyl group. Suitable reducing agents include lithium borohydride. In step 2, the hydroxymethyl imidazoles 22 are oxidized, for example, with pyridinium chlorcchromate, to give the 4-formyl-imidazoles 24.

Scheme VII shows the formation of 4-difluoromethyl-imidazoles 25 from 4-formyl-imidazoles 24. The 4-formyl-imidazoles 24 are converted to desired 4-difluoromethyl-imidazoles 25 by direct fluorination using the known reagents such as $SF_4$ or diethylaminosulfur trifluoride (DAST). For discussion of the reaction and the representative procedures, see e.g., *Organic Reactions*, 34, 319 (1987), *Organic Reactions*, 35, 513 (1988), *Organic Reactions*, 21, 319 (1974) and *Chem. Soc. Reviews*, 16, 381 (1987), Alternatively, the imidazoles 25 can be synthesized by reaction of hydrazones of 24 with N-bromosuccinimide/pyridinium poly(hydrogen fluoride). This transformation has been developed by Olah and co-workers (see, *Synlett*, 594 (1990)].

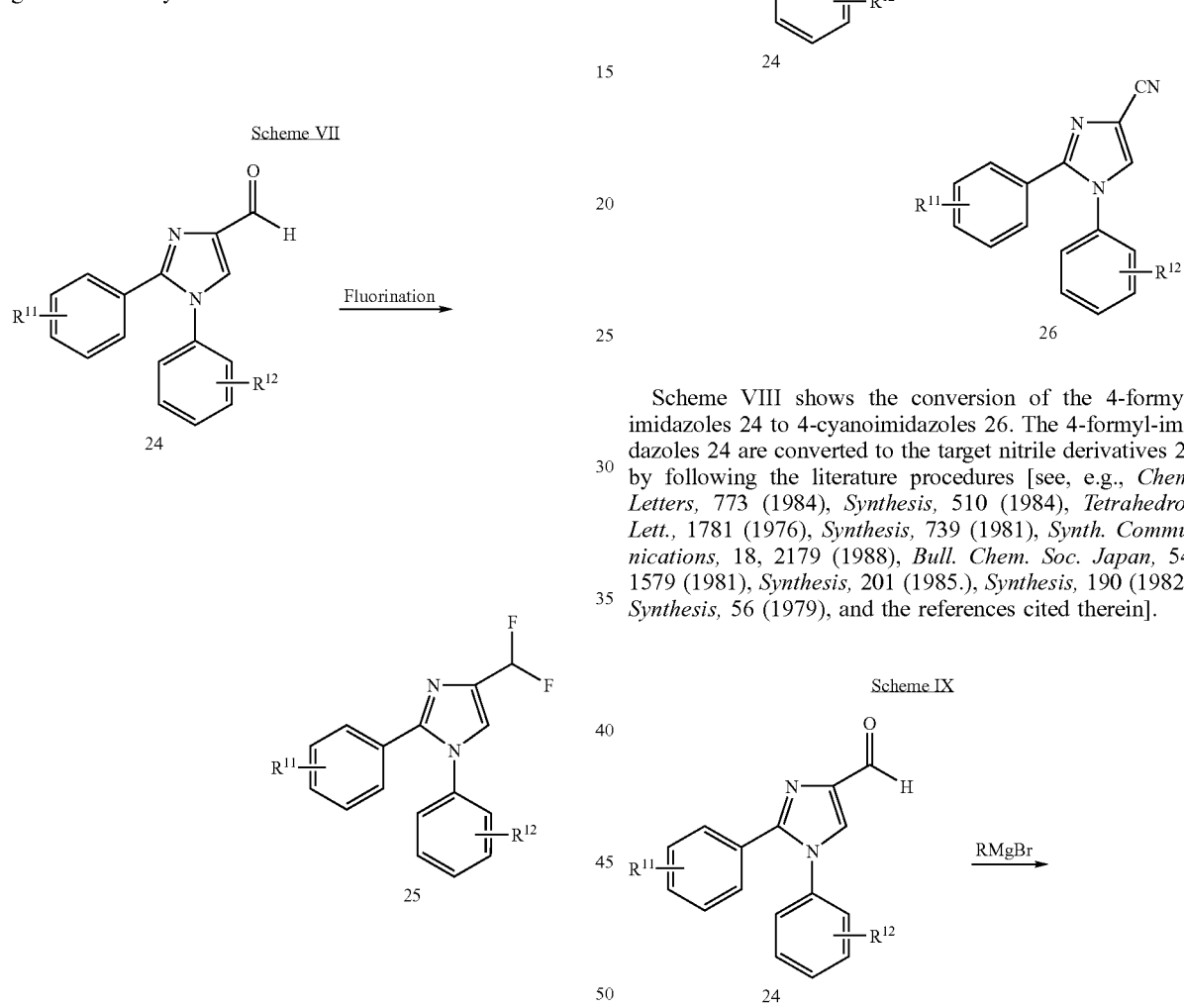

Scheme VIII shows the conversion of the 4-formyl-imidazoles 24 to 4-cyanoimidazoles 26. The 4-formyl-imidazoles 24 are converted to the target nitrile derivatives 26 by following the literature procedures [see, e.g., *Chem. Letters*, 773 (1984), *Synthesis*, 510 (1984), *Tetrahedron Lett.*, 1781 (1976), *Synthesis*, 739 (1981), *Synth. Communications*, 18, 2179 (1988), *Bull. Chem. Soc. Japan*, 54, 1579 (1981), *Synthesis*, 201 (1985.), *Synthesis*, 190 (1982), *Synthesis*, 56 (1979), and the references cited therein].

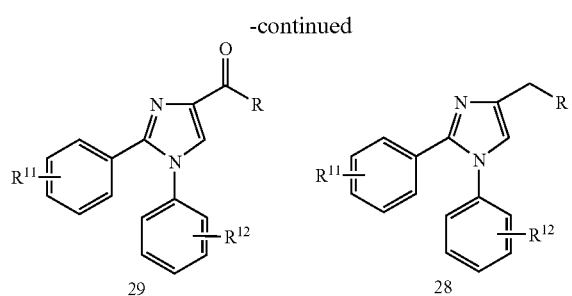

Scheme IX shows other 1,2-diarylimidazoles that can be synthesized from the 4-formyl-imidazoles 24 in two steps. In step 1, the 4-formyl-imidazoles 24 are converted to carbinol derivatives (where R is aralkyl or alkyl) by addition of Grignard reagents (RMgBr). In step 2, the hydroxy derivatives 27 are reduced by catalytic hydrogenation (using e.g., Pd/C or Pt/C), preferably in the presence of a small amount of acid (e.g., acetic acid or aqueous HCl) to form the alkyl or aralkyl derivatives 28. Alternatively, the ketones 29 are-synthesized by oxidation (e.g., using pyridinium chlorochromate) of the hydroxy derivatives 27.

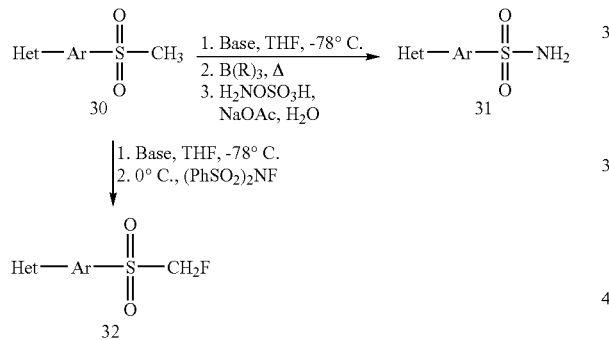

Synthetic Scheme X shows the three step procedure used to prepare sulfonamide antiinflammatory agents 31 and the two step procedure used to prepare fluoromethyl sulfone antiinflammatory agents 32 from their corresponding methyl sulfones 30. In step one, THF solutions of the methyl sulfones 30 at −78° C. are treated with a base such as alkyllithium reagents, lithioamides and Grignard reagents. Examples of such bases include n-butyllithium, methyllithium, lithium diisopropylamide (LDA), butylmagnesium chloride, phenylmagnesium bromide and methylmagnesium chloride. In step two, the anions generated in step one are treated with an organoborane, e.g., triethylborane, tributylborane, etc., at −78° C. then warmed to ambient temperature prior to stirring at reflux. An alternative to the boron chemistry involves room temperature alkylation, such as with haloalkltrialkylsilanes, followed by treatment with silyalky-elimination agents. Examples of such haloalkltrialkyl-silanes include trimethylsilylmethylhalides such as (iodomethyl)trimethylsilane and (chloromethyl)trimethylsilane. Suitable silylalkyl-elimination agents include compounds which produce a fluoride ion. Examples of such compounds include alkylammonium fluorides and cesium fluoride. Tetrabutylammonium fluoride (1M in THF) is preferred. The deprotonation of sulfone is conveniently carried out in the temperature range of about −70° C. to about 25° C., preferably at about 0° C. The formation of silylalkylsulfone is conveniently carried out in the temperature range of about 0° C. to about 35° C., preferably at about 20° C. In step three, an aqueous solution of sodium acetate and hydroxylamine-O-sulfonic acid is added to provide the corresponding sulfonamide antiinflammatory agents 31 of this invention. Alternatively, the anion solutions generated in step one may be warmed to 0° C. and treated with N-fluorodibenzene-sulfonamide to provide the corresponding fluoromethyl sulfone antiinflammatory agents 32 of this invention.

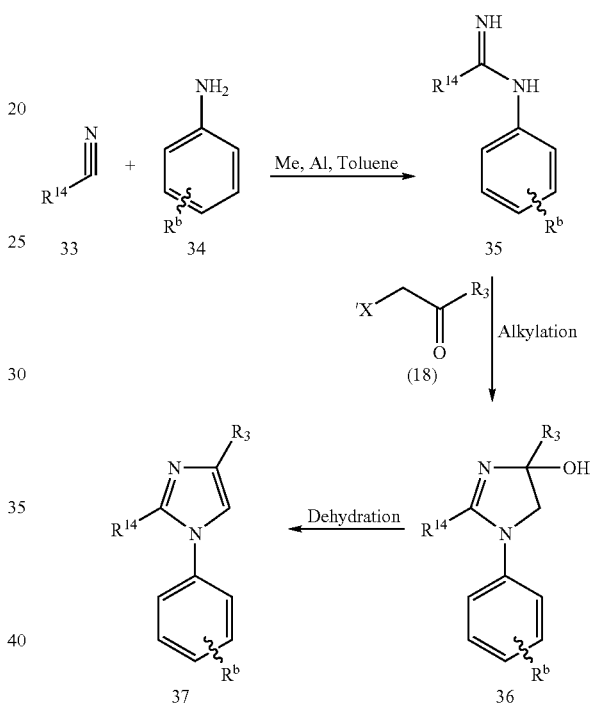

1-Phenyl-2-heterocycloimidazoles of the current invention 37 are synthesized by following the generic synthesis shown in Scheme XI. The reaction of a substituted heterocyclonitrile 33 with substituted anilines 34 (where $R^b$ is as defined above for aryl and heteroaryl radicals) in the presence of alkylaluminum reagents such as trimethylaluminum, triethylaluminum, dimethylaluminum chloride, diethylaluminum chloride gives the amidine 35. The reaction of amidine 35 with a 2-halo-ketone derivative 18 (X'=Br or Cl) in the presence of bases such as sodium bicarbonate, potassium carbonate, sodium carbonate, potassium bicarbonate or N,N'-diisopropylethylamine gives the alkylated product 36. Some of the suitable solvents for this reaction are isopropanol, acetone and dimethylformamide. The reaction may be carried out at 20 to 90° C. The intermediate 36 may be dehydrated in the presence of an acid catalyst such as 4-toluenesulfonic acid to give the targeted 1,2-diarylimidazoles 37. Suitable solvents for this dehydration step are e.g., toluene, xylene and benzene. Alternatively, trifluoroacetic acid may be used both as solvent and catalyst in this dehydration step.

Scheme XII

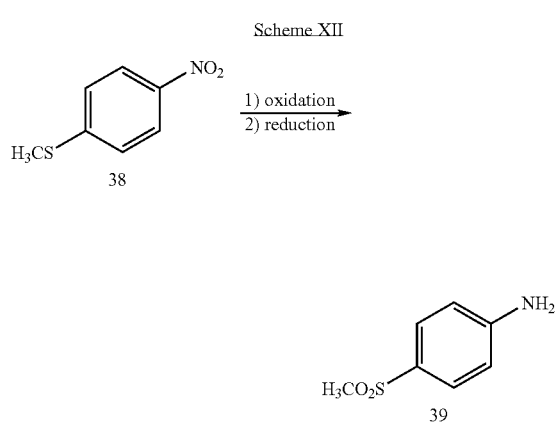

Scheme XII shows a two step method of forming sulfonyl anilines 39 from nitro compounds 38. In step one, the 4-methylthio-nitrobenzene 38 is oxidized to the sulfone with an oxidizing reagent such as hydrogen peroxide, potassium peroxymonosulfate (Oxone®) or 3-chloroperoxybenzoic acid (MCPBA). In step 2, the 4-methylsulfonyl-nitrobenzene is reduced to the corresponding aniline 39.

Scheme XIII

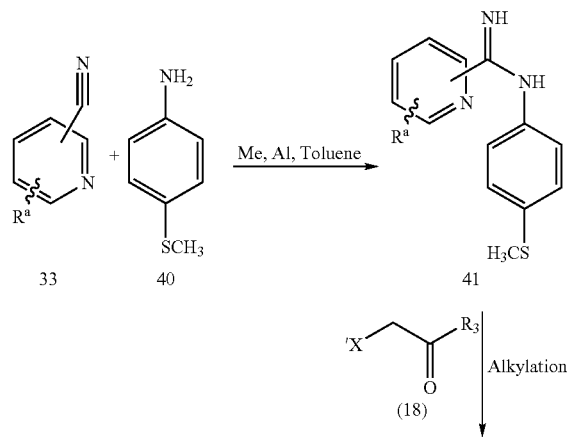

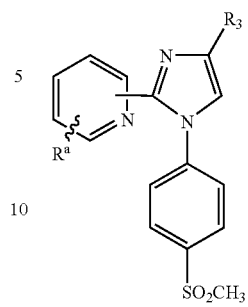

Synthetic Scheme XIII describes an alternative method of forming 1-aryl-2-pyridyl-imidazoles 44 from 4-alkylthioanilines 40. The reaction of a substituted cyanopyridine 33 (where $R^a$ is as defined above for aryl and heteroaryl radicals) with substituted anilines 40 in the presence of alkylaluminum reagents such as trimethylaluminum, triethylaluminum, dimethylaluminum chloride, diethylaluminum chloride gives the amidine 41. Alternatively, amidine 41 may be synthesized by reaction of aniline 40 first with a suitable base, and then with nitrile 33. Examples of suitable bases include sodium hydride, sodium methoxide, n-butyllithium and lithium diisopropylamide. These reactions may be run in solvents such as dimethyl sulfoxide, tetrahydrofuran, dimethoxyethane and methanol or the like. The reaction of amidine 41 with a 2-halo-ketone derivative 18 (X'=Br or Cl) in the presence of bases such as sodium bicarbonate, potassium carbonate, sodium carbonate, potassium bicarbonate or N,N'-diisopropylethylamine gives the alkylated product 42. Some of the suitable solvents for this reaction are isopropanol, acetone and dimethylformamide. The reaction may be carried out at 20 to 90° C. The intermediate 42 is dehydrated in the presence of an acid catalyst such as 4-toluenesulfonic acid to give the 1-(4-alkylthio)aryl-2-pyridylimidazoles 43. Suitable solvents for this dehydration step are e.g., toluene, xylene and benzene. Oxidation of the alkylthio 43, with an oxidizing reagent such as hydrogen peroxide, Oxone® or MCPBA, yields the sulfones 44.

Scheme XIV

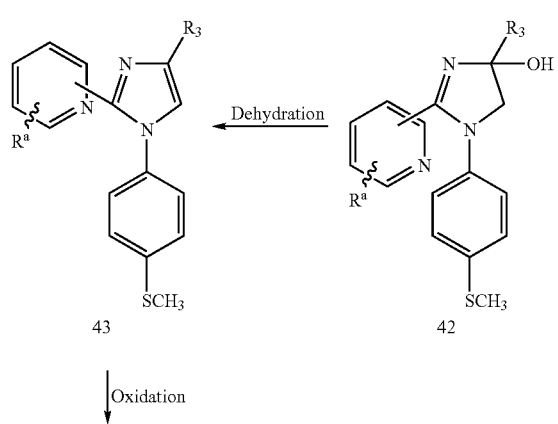

Scheme XIV shows a method of forming sulfones and sulfonamides 46 from the corresponding 1-phenylimidazoles 45, where X is a leaving group such as halo. Treatment of 45 with base, such as butyl lithium, followed by addition of sulfur dioxide and a substituted alkyl or amine yields the corresponding sulfone or sulfonamide 46 (where $R^a$ is alkyl or amino).

Synthetic Scheme XV describes an alternative method of forming 1-aryl-2-pyridyl-imidazoles 53 from 4-nitrobenzenesulfonamide 47. Protection of 4-nitrobenzenesulfonamide 47, such as by reaction with acetonylacetone with p-toluenesulfonic acid as catalyst in a solvent such as toluene, forms the protected pyrrolylsulfonyl 48. A preferred protecting agent is 2,5-lower alkyl pyrrole, and more preferred is 2,5-dimethyl pyrrole. Reduction of the nitro compound 48, such as by Raney Nickel-catalyzed hydrogenation, Scheme XV

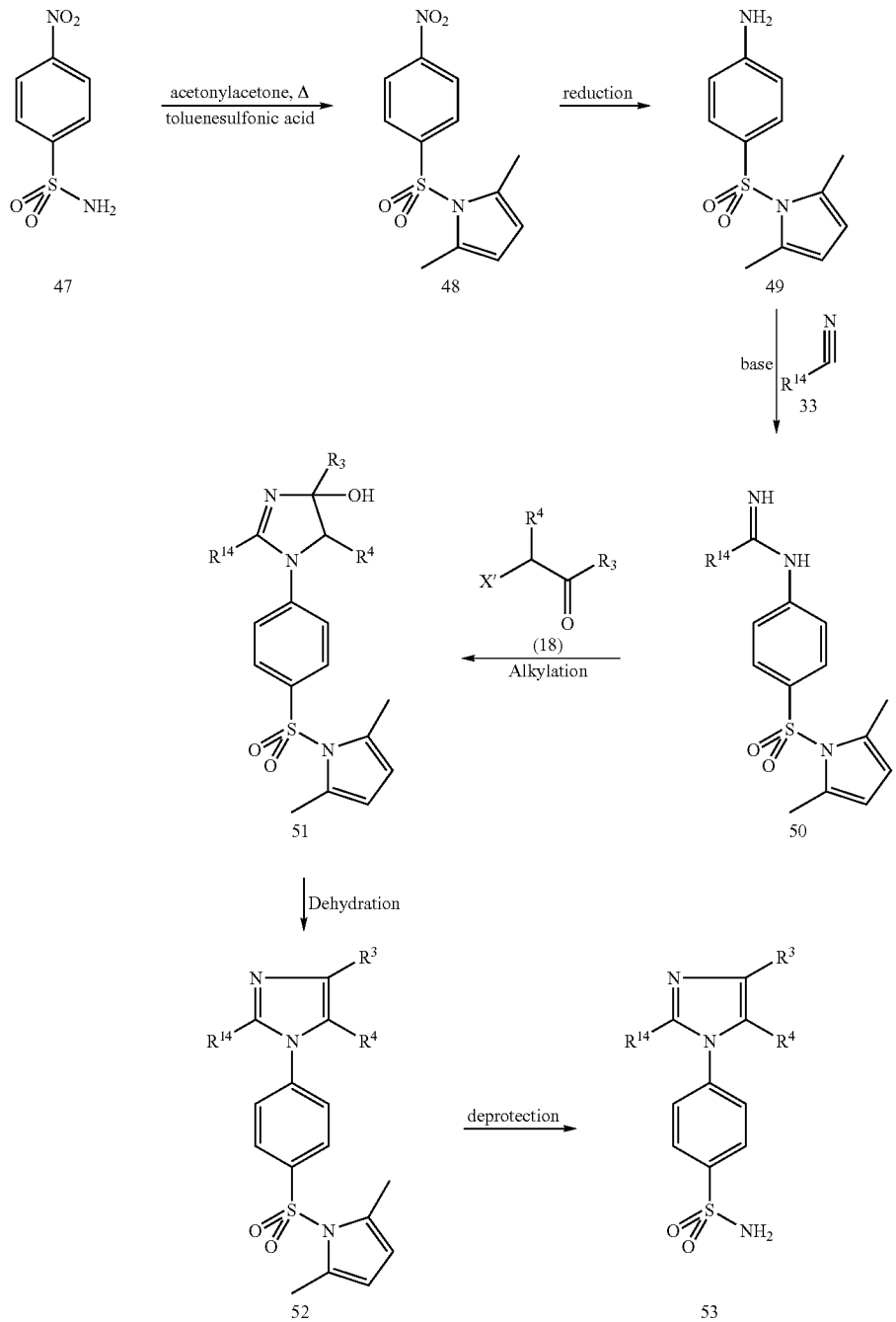

yields the protected benzenamine 49. Amidine 50 is synthesized by reaction of benzenamine 49 first with a suitable base, and then with nitrile 33. Examples of suitable bases include sodium bis(trimethylsilyl)amide, sodium hydride, sodium methoxide, n-butyllithium and lithium diisopropylamide. This reaction may be run in solvents such as dimethyl sulfoxide, tetrahydrofuran, dimethoxyethane, methanol, or the like. The reaction of amidine 50 with a 2-halo-ketone derivative 18 (X'=Br or Cl) in the presence of bases such as sodium bicarbonate, potassium carbonate, sodium carbonate, potassium bicarbonate or N,N'-diisopropylethylamine gives the hydroxyimidazole 51. Some of the suitable solvents for this reaction are isopropanol, acetone and dimethylformamide. The reaction may be carried out at 20 to 90° C. The intermediate 51 is dehydrated in the presence of an acid catalyst such as 4-toluenesulfonic acid to give the protected 1-(4-sulfonyl)aryl-imidazoles 52. Suitable solvents for this dehydration step are e.g., toluene, xylene and benzene. Acid deprotection of 52 such as with aqueous trifluoroacetic acid (TFA) at reflux temperature produces the sulfonamides 53.

The following currently pending applications are incorporated by reference: International Application PCT/US95/09506, patent application Ser. No. 08/464,154, and patent application Ser. No. 08/282,395.

The following examples contain detailed descriptions of the methods of preparation of compounds of Formula I–V. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures. In some cases, the assigned structures were confirmed by nuclear Overhauser effect (NOE) experiments.

EXAMPLE 1

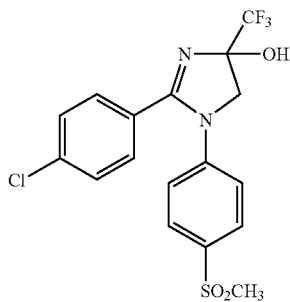

2-(4-Chlorophenyl)-4-hydroxy-1-[4-(methylsulfonyl)phenyl]-4-(trifluoromethyl)-4,5-dihydro-1H-imidazole Step 1: Preparation of 4-chloro-N-[4-(methylsulfonyl)phenyl]benzenecarboximidamide To a suspension of 4-(methylsulfonyl)aniline (7 g, 41 mmol) in toluene (400 mL), trimethylaluminum (2M solution in toluene, 30.5 mL, 61 mmol) was added over 15 minutes. The reaction mixture was warmed to room temperature and stirred for 2.5 hours. A solution of 4-chlorobenzonitrile (11.3 g, 82 mmol) in toluene (200 mL) was added over 10 minutes and the reaction mixture was heated to 80–85° C. After 16 hours, the reaction mixture was cooled to room temperature and poured over a slurry of silica gel in chloroform. After filtration, the residue was washed with a mixture of methylene chloride/methanol. The combined filtrates were concentrated in vacuo and the resulting yellowish solid was stirred with a mixture of hexane/ether (2/1, 1000 mL). The intermediate was filtered and washed with more of hexane/ether (2/1). The pale yellow solid 4-chloro-N-[4-(methylsulfonyl)phenyl] benzenecarboximidamide (10.93 g, 86%) was used in the next reaction without further purification: mp (DSC) 191° C. Anal. Calc'd. for $C_{14}H_{13}N_2SO_2Cl$: C, 54.46; H, 4.24; N, 9.07; Found: C, 54.42; H. 4.30; N, 9.07.

Step 2: Preparation of 2-(4-chlorophenyl)-4-hydroxy-1-[4-(methylsulfonyl)phenyl]-4-(trifluoromethyl)-4,5-dihydro-1H-imidazole To a mixture of 4-chloro-N-[4-(methylsulfonyl)phenyl) benzenecarboximidamide from Step 1 (8 g, 26 mmol) and sodium bicarbonate (4.36 g, 52 mmol) in isopropanol (240 mL), 3-bromo-1,1,1-trifluoroacetone (5.4 mL, 52 mmol) was added. After heating the reaction mixture at 75–80° C. for 24 hours, the solvent was removed. The residue was redissolved in methylene chloride and washed with water. The organic fractions were combined, dried over sodium sulfate, filtered and concentrated in vacuo. The crude product (16.2 g) was purified by chromatography (silica gel, hexane/ethyl acetate, 55/45) to give pure 2-(4-chlorophenyl)-4-hydroxy-1-[4-(methylsulfonyl)phenyl]-4-(trifluoromethyl)-4,5-dihydro-1H-imidazole (6.7 g, 62%) as a white solid: Anal. Calc'd. for $C_{17}H_{14}N_2SO_3ClF_3$: C, 48.75; H, 3.37; N, 6.69. Found: C, 48.56; H, 3.22; N, 6.51.

EXAMPLE 2

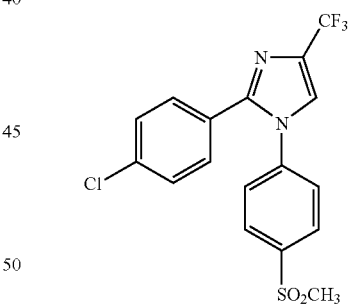

2-(4-Chlorophenyl)-1-[4-(methylsulfonyl)phenyl]-4-(trifluoromethyl)-1H-imidazole A mixture of 2-(4-chlorophenyl)-4-hydroxy-1-[4-(methylsulfonyl)phenyl]-4-(trifluoromethyl)-4,5-dihydro-1H-imidazole from Example 1 (6.2 g, 15.4 mmol) and p-toluenesulfonic acid monohydrate (0.9 g, 4.7 mmol) in toluene (300 mL) was heated to reflux for 84 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentrating in vacuo, the crude mixture was purified by chromatography on silica gel using hexane/ethyl acetate (1/1) to give pure 2-(4-chlorophenyl)-1-[4-(methylsulfonyl)phenyl]-4-(trifluoromethyl)-1H-imidazole (4.21 g, 71%) as a white solid: mp (DSC) 183° C. Anal. Calc'd. for $C_{17}H_{12}N_2SO_2F_3Cl$: C, 50.94; H, 3.02; N, 6.99. Found: C, 50.64; H, 3.03; N, 6.85.

EXAMPLE 3

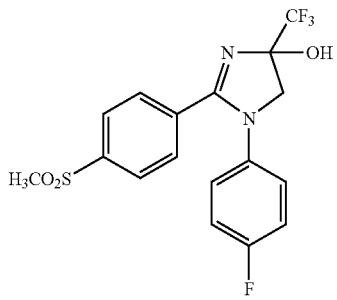

1-(4-Fluorophenyl)-4-hydroxy-2-[4-(methyloulfonyl)phenyl]-4-(trifluoromethyl)-4,5-dihydro-1H-imidazole Step 1: Preparation of 4-methylsulfonyl-N-[4-chlorophenyl]benzenecarboximidamide To a suspension of 4-fluoroaniline (4 mL, 40 mmol) in toluene (120 mL), trimethylaluminum (2M solution in toluene, 21 mL, 42 mmol) was added over 15 minutes. The reaction mixture was warmed to room temperature and stirred for 3 hours. A solution of 4-(methylsulfonyl)benzonitrile (7.65 g, 40 mmol) in methylene chloride (100 mL) was added over 10 minutes and the reaction mixture was heated to 70–75° C. After 48 hours, the reaction mixture was cooled to room temperature and poured over a slurry of silica gel in chloroform. After filtration, the residue was washed with a mixture of methylene chloride/methanol. The combined filtrates were concentrated in vacuo and the resulting crude intermediate (7.7 g) was purified by chromatography [silica gel, hexane/ethyl acetate, 25/75] to give 4-methylsulfonyl-N-[4-chlorophenyl]benzenecarboximidamide (4.1 g, 35%) as a white solid: mp (DSC) 182° C. Anal. Calc'd. for $C_{14}H_{13}N_2SO_2F$: C, 57.52; H, 4.48; N, 9.58; S, 10.97. Found: C, 57.37; H, 4.69; N, 9.21; S, 10.69.

Step2: Preparation of 1-(4-fluorophenyl)-4-hydroxy-2-[4-(methylsulfonyl)phenyl]-4-(trifluoromethyl)-4,5-dihydro-1H-imidazole To a mixture of 4-methylsulfonyl-N-[4-chlorophenyl]benzenecarboximidamide from Step 1 (1 g, 3.42 mmol) and sodium bicarbonate (575 mg, 6.85 mmol) in isopropanol (30 mL), 3-bromo-1,1,1-trifluoroacetone (5.0 g, 25 mmol) was added. After heating the reaction mixture at 80–90° C. for 24 hours, the solvent was removed. The residue was redissolved in methylene chloride and washed with water. The organic fractions were combined, dried over sodium sulfate, filtered and concentrated in vacuo. The crude product (2.34 g) was purified by chromatography (silica gel, hexane/ethyl acetate, 1/1] to give 1-(4-fluorophenyl)-4-hydroxy-2-[4-(methylsulfonyl)phenyl]-4-(trifluoromethyl)-4,5-dihydro-1H-imidazole (650 mg, 47%) as a white solid: mp (DSC) 209° C. Anal. Calc'd. for $C_{17}H_{14}N_2SO_3F_4$: C, 50.75; H, 3.51; N, 6.96. Found: C, 51.11; H, 3.86; N, 6.57.

EXAMPLE 4

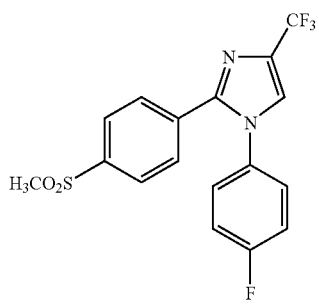

1-(4-Fluorophenyl)-2-[4-(methylsulfonyl)phenyl]-4-(trifluoromethyl)-1H-imidazole A mixture of 1-(4-fluorophenyl)-4-hydroxy-2-[4-(methylsulfonyl)phenyl]-4-(trifluoromethyl)-4,5-dihydro-1H-imidazole (Example 3) (770 mg, 1.9 mmol) and p-toluenesulfonic acid monohydrate (88 mg) in toluene (80 mL) was heated to reflux for 20 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture (520 mg) was purified by chromatography on silica gel using hexane/ethyl acetate (1/1) to give pure 1-(4-fluorophenyl)-2-[4-(methylsulfonyl)phenyl]-4-(trifluoromethyl)-1H-imidazole (328 mg, 44%) as a white solid: mp (DSC) 183° C. Anal. Calc'd. for $C_{17}H_{12}N_2SO_2F_4$: C, 53.13; H, 3.15; N, 7.29. Found: C, 53.20; H, 3.22; N, 7.18.

EXAMPLE 5

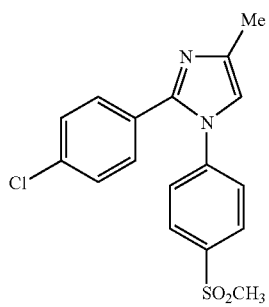

2-(4-Chlorophenyl)-1-[4-(methylsulfonyl)phenyl]-4-methyl-1H-imidazole

To a mixture of 4-chloro-N-[4-(methylsulfonyl)phenyl)benzenecarboximidamide (Example 1, Step 1) (240 mg, 0.78 mmol) and sodium bicarbonate (131 mg, 1.56 mmol) in isopropanol (20 mL), excess chloroacetone (1.5 mL) was added. After heating to reflux, the reaction mixture for 72 hours, the solvent was removed. The residue was redissolved in methylene chloride and washed with aqueous sodium bicarbonate and water. The organic fractions were combined, dried over sodium sulfate, filtered and concentrated in vacuo. The crude product (370 mg) was purified by chromatography (silica gel, hexane/ethyl acetate, 25/75) to give pure 2-(4-chlorophenyl)-1-(4-(methylsulfonyl)phenyl]-4-methyl-1H-imidazole (160 mg, 67%): mp (DSC) 166° C. Anal Calc'd. for $C_{17}H_{15}N_2SO_2Cl$ C, 58.87; H, 4.36; N, 8.08; Found: C, 58.78; H, 4.62; N, 7.99.

EXAMPLE 6

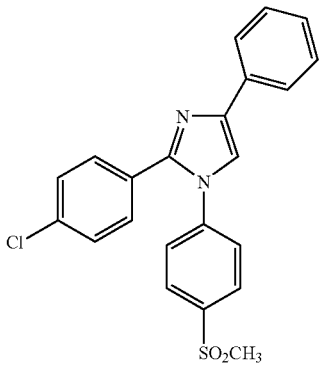

2-(4-Chlorophenyl)-1-4-(methylsulfonyl)phenyl]-4-phenyl-1H-imidazole

To a mixture of 4-chloro-N-[4-(methylsulfonyl)phenyl] benzenecarboximidamide (Example 1, Step 1) (400 mg, 1.29 mmol) and sodium bicarbonate (216 mg, 2.59 mmol) in isopropanol (25 mL), 2-bromoacetophenone (780 mg, 3.87 mmol) was added. After heating the reaction mixture at 55° C. for 20 hours, the solvent was removed. The residue was redissolved in methylene chloride and washed with aqueous sodium bicarbonate and water. The organic fractions were combined, dried over sodium sulfate, filtered and concentrated in vacuo. The crude product (1.2 g) was purified by chromatography on silica gel with toluene/ethyl acetate (75/25) to give pure 2-(4-chlorophenyl)-1-[4-(methylsulfonyl)phenyl]-4-phenyl-1H-imidazole (300 mg, 57%) as a white solid: mp (DSC) 202° C. Anal. Calc'd. for $C_{22}H_{17}N_2SO_2Cl$: C, 63.78; H, 4.28; N, 6.76; S, 7.74. Found: C, 63.69; H, 4.11; N, 6.68; S, 7.65.

EXAMPLE 7

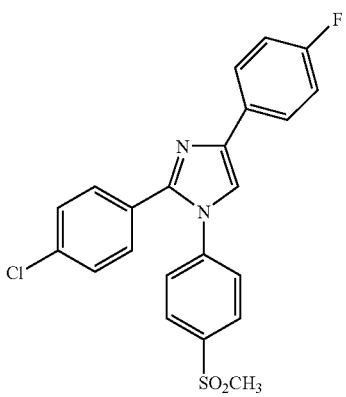

2-(4-Chlorophenyl)-4-(4-fluorophenyl)-1-[4-(methyloulfonyl)phenyl]-1H-imidazole

To a mixture of 4-chloro-N-[4-(methylsulfonyl)phenyl] benzenecarboximidamide (Example 1, Step 1) (400 mg, 1.29 mmol) and sodium bicarbonate (216 mg, 2.59 mmol) in isopropanol (25 mL), 2-chloro-4'-fluotoacetophenone (670 mg, 3.87 mmol) was added. After heating the reaction mixture at 80–85° C. for 48 hours, the solvent was removed. The residue was redissolved in methylene chloride and washed with aqueous sodium bicarbonate and water. The organic fractions were combined, dried over sodium sulfate, filtered and concentrated in vacuo. The crude product (800 mg) was purified by chromatography (silica gel, hexane/ ethyl acetate, 1/1) to give 2-(4-chlorophenyl)-4-(4-fluorophenyl)-1-[4-(methylsulfonyl)phenyl]-1H-imidazole (200 mg, 36%) as a pale yellow solid: mp (DSC) 180° C. Anal. Calc'd. for $C_{22}H_{16}N_2SO_2FCl$: C, 61.90; H, 3.78; N, 6.56; S, 7.51. Found: C, 61.92; H, 3.74; N, 6.43; S, 7.62.

EXAMPLE 8

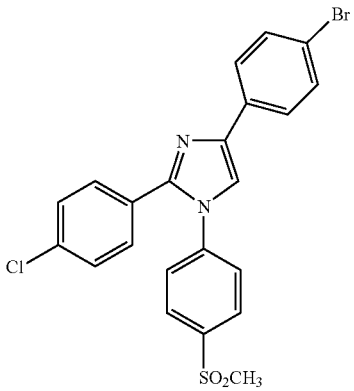

4-(4-Bromophenyl)-2-(4-chlorophenyl)-1-[4-(methylsulfonyl)phenyl]-1H-imidazole

To a mixture of 4-chloro-N-[4-(methylsulfonyl)phenyl] benzenecarboximidamide (Example 1, Step 1) (400 mg, 1.29 mmol) and sodium bicarbonate (216 mg, 2.59 mmol) in isopropanol (30 mL), 2,4'-dibromoacetophenone (720 mg, 2.58 mmol) was added. After heating the reaction mixture at 80–85° C. for 18 hours, the solvent was removed. The residue was redissolved in methylene chloride and washed with aqueous sodium bicarbonate and water. The organic fractions were combined, dried over sodium sulfate, filtered and concentrated in vacuo. The crude product (810 mg) was purified by chromatography (silica gel, hexane/ethyl acetate, 6/4) to give 4-(4-bromophenyl)-2-(4-chlorophenyl)-1-[4-(methylsulfonyl)phenyl]-1H-imidazole (400 mg, 64%) as a pale yellow solid: mp 145–48° C. Anal. Calc'd. for $C_{22}H_{16}N_2SO_2BrCl$: C, 54.17; H, 3.31; N, 5.74; S, 6.57. Found: C, 54.41; H, 3.33; N, 5.50; S, 6.52.

EXAMPLE 9

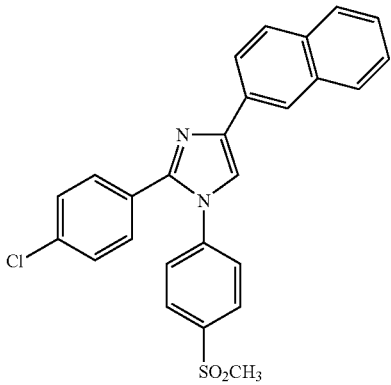

2-(4-Chlorophenyl)-1-[4-(methylsulfonyl)phenyl]-4-(2-naphthyl)-1H-imidazole

To a mixture of 4-chloro-N-(4-(methylsulfonyl)phenyl] benzenecarboximidamide (Example 1, Step 1) (400 mg, 1.29 mmol) and sodium bicarbonate (216 mg, 2.59 mmol) in isopropanol (30 mL), 2-bromo-2'-acetonaphthone (970 mg, 3.89 mmol) was added. After heating the reaction mixture at 80–85° C. for 20 hours, the solvent was removed. The residue was redissolved in methylene chloride and washed with aqueous sodium bicarbonate and water. The organic fractions were combined, dried over sodium sulfate, filtered and concentrated in vacuo. The crude product (1.2 g) was purified by chromatography (silica gel, hexane/ethyl acetate, 6/4) to give 2-(4-chlorophenyl)-1-(4-(methylsulfonyl)phenyl]-4-(2-naphthyl)-1H-imidazole (318 mg, 54%) as a pale yellow solid: mp 204–206° C. Anal Calc'd. for $C_{26}H_{19}N_2SO_2Cl$: C, 68.04; H, 4.17; N, 6.10; S, 6.99. Found: C, 67.65; H, 4.19; N, 5.96; S, 7.10.

EXAMPLE 10

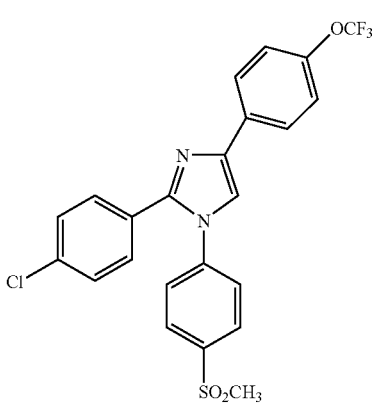

2-(4-Chlorophenyl)-1-[4-(methylsulfonyl)phenyl]-4-[4-(trifluoromethoxy)phenyl]-1H-imidazole To a mixture of 4-chloro-N-[4-(methylsulfonyl)phenyl] benzenecarboximidamide (Example 1, step 1) (700 mg, 2.24 mmol) and sodium bicarbonate (376 mg, 4.48-mmol) in isopropanol (25 mL), 4-(trifluoromethoxy)phenacyl bromide (950 mg, 3.36 mmol) was added. After heating the reaction mixture at 80–85° C. for 22 hours, the solvent was removed. The residue was redissolved in methylene chloride and washed with aqueous sodium bicarbonate and water. The organic fractions were combined, dried over sodium sulfate, filtered and concentrated in vacuo. The crude product was purified by chromatography (silica gel, hexane/ethyl acetate, 6/4) to give 2-(4-chlorophenyl)-1-[4-(methylsulfonyl)phenyl]-E4-(trifluoromethoxy)phenyl]-1H-imidazole (467 mg, 42%) as a pale yellow solid: mp 95–97° C. Anal. Calc'd. for $C_{23}H_{16}N_2SO_3F_3Cl$: C, 56.05; H, 3.27; N, 5.68; S, 6.51. Found: C, 55.90; H, 3.04; N, 5.62; S, 6.74.

EXAMPLE 11

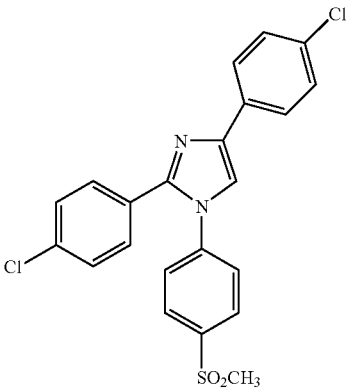

2,4-Bis(4-chlorophenyl)-1-[4-(methyloulfonyl)phenyl]-1H-imidazole

To a mixture of 4-chloro-N-(4-(methylsulfonyl)phenyl] benzenecarboximidamide (Example 1, Step 1) (700 mg, 2.24 mmol) and sodium bicarbonate (376 mg, 4.48 mmol) in isopropanol (30 mL), 4-chlorophenacyl bromide (1.05 g, 4.48 mmol) was added. After heating the reaction mixture at 80–85° C. for 18 hours, the solvent was removed. The residue was redissolved in methylene chloride and washed with aqueous sodium bicarbonate and water. The organic fractions were combined, dried over sodium sulfate, filtered and concentrated in vacuo. The crude product was purified by chromatography (silica gel, hexane/ethyl acetate, 6/4) to give 2,4-bis-(4-chlorophenyl)-1-[4-(methylsulfonyl)phenyl]-1H-imidazole (545 mg, 55%) as a pale yellow solid: mp 169–171° C. Anal. Calc'd. for $C_{22}H_{16}N_2SO_2Cl_2$: C, 59.60; H, 3.64; N, 6.32; S, 7.23. Found: C, 59.86; H, 3.80; N, 6.10; S, 7.27.

EXAMPLE 12

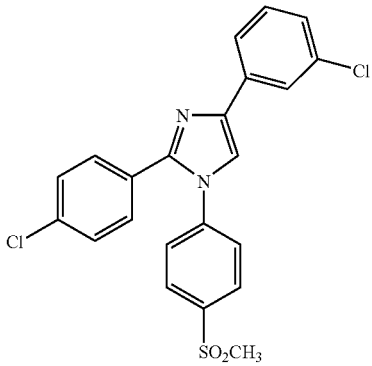

2-(4-Chlorophenyl)-4-(3-chlorophenyl)-1-[4-(methyloulfonyl)phenyl]-1H-imidazole

To a mixture of 4-chloro-N-[4-(methylsulfonyl)phenyl] benzenecarboximidamide (Example 1, Step 1) (700 mg, 2.24 mmol) and sodium bicarbonate (376 mg, 4.48 mmol) in isopropanol (35 mL), 3-chlorophenacyl bromide (1.05 g, 4.48 mmol) was added. After heating the reaction mixture at 80–85° C. for 18 hours, the solvent was removed. The residue was redissolved in methylene chloride and washed with aqueous sodium bicarbonate and water. The organic. fractions were combined, dried over sodium sulfate, filtered and concentrated in vacuo. The crude product was purified by chromatography (silica gel, hexane/ethyl acetate, 6/4) to give 2-(4-chlorophenyl)-4-(3-chlorophenyl)-1-[4-(methylsulfonyl)phenyl]-1H-imidazole (525 mg, 53%) as a pale yellow solid: mp 156–159° C. Anal Calc'd. for $C_{22}H_{16}N_2SO_2Cl_2$: C, 59.60; H, 3.69; N, 6.32; S, 7.23. Found: C, 59.43; H, 3.59; N, 6.15; S, 7.16.

EXAMPLE 13

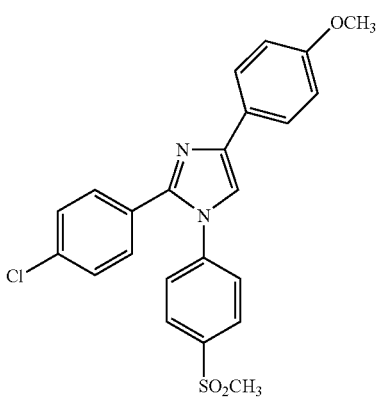

2-(4-Chlorophenyl)-4-(4-methoxyphenyl)-1-[4-(methylsulfonyl)phenyl]-1H-imidazole To a mixture of 4-chloro-N-[4-(methylsulfonyl)phenyl] benzenecarboximidamide (Example 1, Step 1) (700 mg, 2.24 mmol) and sodium bicarbonate (376 mg, 4.48 mmol) in isopropanol (50 mL), 4-methoxyphenacyl bromide (1.03 g, 4.48 mmol) was added. After, heating the reaction mixture at 75–80° C. for 20 hours, the solvent was removed. The residue was redissolved in methylene chloride and washed with aqueous sodium bicarbonate and water. The organic fractions were combined, dried over sodium sulfate, filtered and concentrated in vacuo. The crude product was purified by chromatography (silica gel, hexane/ethyl acetate, 6/4) to give 2-(4-chlorophenyl)-4-(4-methoxyphenyl)-1-[4-(methylsulfonyl)phenyl]-4-(4-methoxyphenyl)-1H-imidazole (695 mg, 71%) as a white solid: mp 110–113° C. Anal Calc'd. for $C_{23}H_{19}N_2SO_3Cl$: C, 62.94; H, 4.36; N, 6.38; S, 7.30. Found: C, 62.54; H, 4.43; N, 6.17; S, 7.15.

EXAMPLE 14

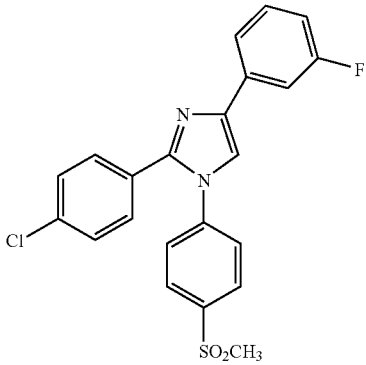

2-(4-Chlorophenyl)-4-(3-fluorophenyl)-1-[4-(methylsulfonyl)phenyl]-1H-imidazole

To a mixture of 4-chloro-N-[4-(methylsulfonyl)phenyl] benzenecarboximidamide (Example 1, Step 1) (700 mg, 2.24 mmol) and sodium bicarbonate (376 mg, 4.48 mmol) in isopropanol (30 mL), 3-fluorophenacyl bromide (0.97 g, 4.48 mmol) was added. After heating the reaction mixture at 75–80° C. for 18 hours, the solvent was removed. The residue was redissolved in methylene chloride and washed with aqueous sodium bicarbonate and water. The organic fractions were combined, dried over sodium sulfate, filtered and concentrated in vacuo. The crude product was purified by chromatography (silica gel, hexane/ethyl acetate, 6/4) to give 2-(4-chlorophenyl)-4-(3-fluorophenyl)-1-[4-(methylsulfonyl)phenyl)-1H-imidazole (481 mg, 50%) as a white solid: mp 194–196° C. Anal. Calc'd. for $C_{22}H_{16}N_2SO_2FCl$: C, 61.90; H, 3.78; N, 6.56; S, 7.51. Found: C, 61.71; H, 3.59; N, 6.42; S, 7.69.

EXAMPLE 15

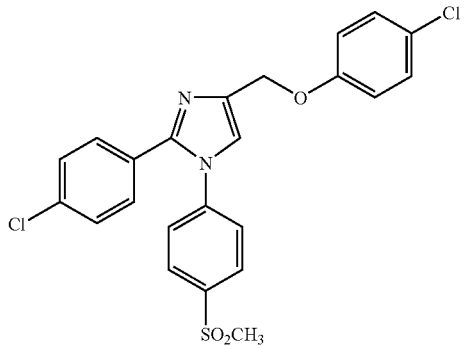

2-(4-Chlorophenyl)-4-[(4-chlorophenoxy)methyl]-1-[4-(methylsulfonyl)phenyl]-1H-imidazole Step 1: Preparation of 1-(4-chlorophenoxy)-2-chloro-2-propene To a mixture of 4-chlorophenol (6.1 g, 47.4 mmol) and potassium carbonate (13.1 g, 94.7 mmol) in acetone (200 mL), 2,3-dichloropropane (6.6 mL, 71 mmol) was added. After heating to reflux the reaction mixture for 48 hours, the reaction mixture was cooled and filtered. The residue was washed with more acetone and the combined filtrates were concentrated in vacuo. The crude pale brown liquid (11.5 g) was purified by chromatography (silica gel, hexane/ethyl acetate, 85/15) to give 1-(4-chlorophenoxy)-2-chloro-2-propene (8.9 g, 98%) as a white liquid: Anal. Calc'd for $C_9H_8OCl_2$: C, 53.23; H, 3.97. Found: C, 53.09; H, 3.95.

Step 2: Preparation of 1-bromo-3-[(4-chlorophenoxy)phenyl]-2-propanone

To a turbid solution of 1-(4-chlorophenoxy)-2-chloro-2-propene from Step 1 (3 g, 15.7 mmol) in acetonitrile/water (4/1, 100 mL), N-bromosuccinimide (4.84 g, 31.4 mmol) was added in one lot. A catalytic amount of 48% HBr (40 μl) was added to the reaction and the yellowish orange mixture was stirred at room temperature. After 24 hours, the reaction mixture was diluted with ether and washed with 5% w/v of sodium thiosulfate. The organic layer was separated and washed with saturated sodium bicarbonate and brine. After drying ($MgSO_4$), filtration and concentration in vacuo, the crude liquid (4.8 g) was purified by chromatography (silica gel, hexane/ethyl acetate, 80/20) to give crude 1-bromo-3-[(4-chlorophenoxy)phenyl]-2-propanone (2.3 g, 54%) which was used in the next step without further purification.

Step 3. Preparation of 2-(4-chlorophenyl)-4-hydroxy-1-[4-(methylsulfonyl)phenyl]-4-[(4-chlorophenoxy)methyl]-4,5-dihydro-1H-imidazole To a mixture of 4-chloro-N-[4-(methylsulfonyl)phenyl]benzenecarboximidamide (Example 1, Step 1) (1 g, 3.24 mmol) and sodium bicarbonate (550 mg, 6.5 mmol) in acetone (100 mL), 1-bromo-3-[(4-chlorophenoxy)phenyl]-2-propanone from Step 2 (1.5 g, 5.8 mmol) was added. After heating to reflux for 24 hours, the reaction mixture was filtered, washed with acetone and concentrated in vacuo. The crude mixture (2.5 g) was purified by chromatography (silica gel, toluene/ethyl acetate, 1/1) to give 2-(4-chlorophenyl)-4-hydroxy-1-[4-(methylsulfonyl)phenyl]-4-((4-chlorophenoxy)methyl]-4,5-dihydro-1H-imidazole (565 mg, 35%) as a white solid.

Step 4: Preparation of 2-(4-chlorophenyl)-1-[4-(methylsulfonyl)phenyl]-4-[(4-chlorophenoxy)methyl]-1H-imidazole A mixture of 2-(4-chlorophenyl)-4-hydroxy-1-[4-(methylsulfonyl)phenyl]-4-[(4-chlorophenoxy)methyl]-4,5-dihydro-1H-imidazole from Step 3 (750 mg, 1.5 mmol) and p-toluenesulfonic acid monohydrate (135 mg) in toluene (100 mL) was heated to reflux for 48 hours. The reaction mixture was cooled and the solvent removed under reduced pressure. The crude residue was redissolved in methylene chloride and washed with water, aqueous sodium bicarbonate and brine. After drying (Na2SO4), filtration and concentration in vacuo, the crude mixture was purified by chromatography on silica gel using hexane/ethyl acetate (1/1) to give 2-(4-chlorophenyl)-1-[4-(methylsulfonyl)phenyl]-4-[(4-chlorophenoxy)methyl]-1H-imidazole as a white solid: mp (DSC) 173° C. Anal. Calc'd for $C_{23}H_{18}N_2Cl_2SO_3 \cdot 0.25 H_2O$: C, 57.81; H, 3.90; N, 5.86; Cl, 14.84. Found: C, 57.67; H, 3.83; N, 5.52; Cl, 15.17.

EXAMPLE 16

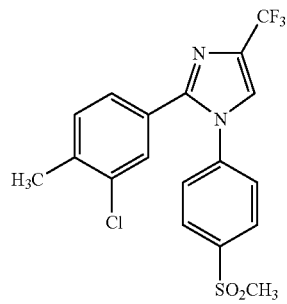

2-(3-Chloro-4-methylphenyl)-1-[4-(methylsulfonyl)phenyl]-4-(trifluoromethyl)-1H-imidazole Step 1: Preparation of 3-chloro-4-methyl-N-[4-(methylsulfonyl)phenyl]benzenecarboximidamide To a suspension of 4-(methylsulfonyl)aniline (2.82 g, 16.5 mmol) in toluene (150 mL), trimethylaluminum (2M solution in toluene, 12.5 mL, 24.7 mmol) was added over 15 minutes. The reaction mixture was warmed to room temperature and stirred for 2.5 hours. A solution of 3-chloro-4-methylbenzonitrile (5 g, 33 mmol) in toluene (100 mL) was added over 10 minutes and the reaction mixture was heated to 90–95° C. After 20 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the resulting yellowish solid was stirred with a mixture of hexane/ether (2/1, 700 mL). The intermediate was filtered and washed with more of hexane/ether (2/1). The pale yellow solid 3-chloro-4-methyl-N-[4-(methylsulfonyl)phenyl]benzenecarboximidamide (4.7 g, 88%) was used in the next reaction without further purification: mp (DSC) 179° C. Anal. Calc'd. for $C_{15}H_{15}N_2SO_2Cl$: C, 55.81; H, 4.68; N, 8.68. Found: C, 55.65; H. 4.63; N, 8.59.

Step 2: Preparation of 2-(3-chloro-4-methylphenyl)-4-hydroxy-1-[4-(methylsulfonyl)phenyl]-4-(trifluoromethyl)-4,5-dihydro-1H-imidazole To a mixture of 3-chloro-4-methyl-N-[4-(methylsulfonyl)phenyl]benzenecarboximidamide from Step 1 (2.35 g, 7.3 mmol) and sodium bicarbonate (1.23 g, 14.6 mmol) in isopropanol (100 mL), 3-bromo-1,1,1-trifluoroacetone (5.4 mL, 52 mmol) was added. After heating to reflux the reaction mixture for 24 hours, the solvent was removed. The residue was redissolved in methylene chloride and washed with water. The organic fractions were combined, dried over sodium sulfate, filtered and concentrated in vacuo. The crude mixture (7.3 g) was purified by chromatography (silica gel, toluene/ethyl acetate, 1/1) to give 2-(3-chloro-4-methylphenyl)-4-hydroxy-1-[4-(methylsulfonyl)phenyl]-4-(trifluoromethyl)-4,5-dihydro-1H-imidazole (0.79 g, 25%) as a white solid: mp 201° C. Anal. Calc'd. for $C_{18}H_{16}N_2SO_3F_3Cl·0.5$ $PhCH_3$: C, 53.92; H, 4.21; N, 5.81. Found: C, 54.20; H, 4.19; N, 5.67.

Step 3: Preparation of 2-(3-chloro-4-methylphenyl)-1-[4-(methylsulfonyl)phenyl]-4-(trifluoromethyl)-1H-imidazole A mixture of 2-(3-chloro-4-methylphenyl)-4-hydroxy-1-[4-(methylsulfonyl)phenyl]-4-(trifluoromethyl)-4,5-dihydro-1H-imidazole from Step 2 (725 mg, 1.7 mmol) and p-toluenesulfonic acid monohydrate (150 mg) in toluene (40 mL) was heated to reflux for 48 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture (860 mg) was purified by chromatography on silica gel using toluene/ethyl acetate 1/1 to give pure 2-(3-chloro-4-methylphenyl)-1-[4-(methylsulfonyl)phenyl]-4-(trifluoromethyl)-1H-imidazole (660 mg, 95%) as a white solid: mp(DSC) 206° C. Anal. Calc'd. for $C_{18}H_{14}N_2SO_2F_3Cl$: C, 52.12; H, 3.40; N, 6.75; S, 7.73. Found: C, 52.24; H, 3.45; N, 6.64; S, 7.83.

EXAMPLE 17

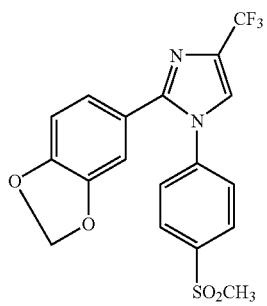

5-[1-[4-(Methylsulfonyl)phenyl]-4-(trifluoromethyl)-1H-imidazol-2-yl]-1,3-benzodioxole Step 1: Preparation of 3,4-methylenedioxy-N-[4-(methylsulfonyl)phenyl]benzenecarboximidamide To a suspension of (4-methylsulfonyl)aniline (2.82 g, 16.5 mmol) in toluene (150 mL), trimethylaluminum (2M solution in toluene, 12.5 mL, 24.7 mmol) was added over 15 minutes. The reaction mixture was warmed to room temperature and stirred for 2.5 hours. A solution of piperonylonitrile (4.85 g, 33 mmol) in toluene (100 mL) was added over 10 minutes and the reaction mixture was heated to 90–95° C. After 20 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the resulting yellowish solid was stirred with a mixture of hexane/ether (2/1, 1000 mL). The product was filtered and washed with more of hexane/ether (2/1). The pale yellow solid 3,4-methylenedioxy-N-[4-(methylsulfonyl)phenyl]benzenecarboximidamide (4.8 g, 91%) was used in the next reaction without further purification: mp (DSC) 214° C. Anal. Calc'd. for $C_{15}H_{14}N_2SO_4$: C, 56.59; H, 4.43; N, 8.80. Found: C, 56.33; H, 4.28; N, 8.66.

Step 2: Preparation of 5-[1-[4-(methylsulfonyl)phenyl]-4-hydroxy-4-(trifluoromethyl)-4,5-dihydro-1H-imidazol-2-yl]-1,3-benzodioxole To a mixture of 3,4-methylenedioxy-N-[4-(methylsulfonyl)phenyl]benzenecarboximidamide from Step 1 (2.32 g, 7.3 mmol) and sodium bicarbonate (1.23 g, 14.6 mmol) in isopropanol (100 mL), 3-bromo-1,1,1-trifluoroacetone (5.4 mL, 52 mmol) was added. After heating the reaction mixture to reflux for 24 hours, the solvent was removed. The residue was redissolved in methylene chloride and washed with water. The organic fractions were combined, dried over sodium sulfate, filtered and concentrated in vacuo. The crude mixture (7.1 g) was purified by chromatography (silica gel, toluene/ethyl acetate, 1/1) to give 5-[1-[4-(methylsulfonyl)phenyl]-4-hydroxy-4-(trifluoromethyl)-4,5-dihydro-1H-imidazol-2-yl]-1,3-benzodioxole (1.46 g, 47%) as a white solid: mp 200–202° C. Anal. Calc'd. for $C_{18}H_{15}N_2SO_5F_3·0.25$ $PhCH_3$: C, 52.55; H, 3.80; N, 6.21. Found: C, 52.73; H, 3.78; N, 6.01.

Step 3: Preparation of 5-[1-[4-(methylsulfonyl)phenyl]-4-(trifluoromethyl)-1H-imidazol-2-yl]-1.3-benzodioxole A mixture of 5-[1-[4-(methylsulfonyl)phenyl]-4-hydroxy-4-(trifluoromethyl)-4,5-dihydro-1H-imidazol-2-yl]-1,3-benzodioxole from Step 2 (1.26 g, 2.9 mmol) and p-toluenesulfonic acid monohydrate (200 mg) in toluene (50 mL) was heated to reflux for 72 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture (1.34 g) was purified by chromatography on silica gel using toluene/ethyl acetate 1/1 to give pure 5-(1-(4-(methylsulfonyl)phenyl)-4-(trifluoromethyl)-1H-imidazol-2-yl]-1,3-benzodioxole (940 mg, 80%) as a white solid: mp (DSC) 165° C. Anal Calc'd. for $C_{18}H_{13}N_2SO_4F_3$: C, 52.68; H, 3.19; No 6.83. Found: C, 53.05; H, 3.19; N, 6.65.

EXAMPLE 18

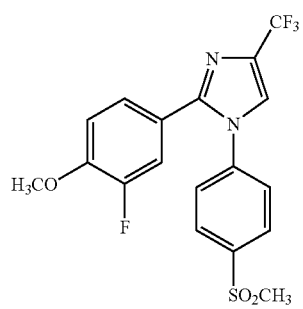

2-(3-Fluoro-4-methoxyphenyl)-1-[4-(methyloulfo-
nyl)phenyl]-4-(trifluoromethyl)-1H-imidazole Step 1 Preparation of 3-fluoro-4-methoxy-N-[4-(methylsulfonyl)phenyl]benzenecarboximidamide To a suspension of 4-(methylsulfonyl)aniline, (2.82 g, 16.5 mmol) in toluene (150 mL), trimethylaluminum (2M solution in toluene, 12.5 mL, 24.7 mmol) was added over 15 minutes. The reaction mixture was warmed to room temperature and stirred for 2.5 hours. A solution of 3-fluoro-4-methoxybenzonitrile (5 g, 33 mmol) in toluene (100 mL) was added over 10 minutes and the reaction mixture was heated to 80–85° C. After 20 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the resulting yellowish solid was stirred with a mixture of hexane/ether (2/1, 1000 mL). The intermediate was filtered and washed with more hexane/ether (2/1). The pale yellow solid 3-fluoro-4-methoxy-N-[4-(methylsulfonyl)phenyl]benzenecarboximidamide (3.95 g, 74%) was used in the next reaction without further purification: mp (DSC) 195° C. Anal. Calc'd. for $C_{15}H_{15}N_2SO_3F$: C, 55.89; H, 4.69; N, 8.69. Found: C, 55.92; H, 4.74; N, 8.53.

Step 2: Preparation of 2-(3-fluoro-4-methoxyphenyl)-4-hydroxy-1-[4-(methylsulfonyl)phenyl]-4-(trifluoromethyl)-4,5-dihydro-1H-imidazole To a mixture of 3-fluoro-4-methoxy-N-[4-(methylsulfonyl)phenyl]benzenecarboximidamide from Step 1 (4.15 g, 12.9 mmol) and sodium bicarbonate (2.16 g, 25.8 mmol) in isopropanol (150 mL), 3-bromo-1,1,1-trifluoroacetone (4.8 mL, 45 mmol) was added. After heating the reaction mixture at 70–75° C. for 20 hours, the solvent was removed. The residue was redissolved in methylene chloride and washed with water. The organic fractions were combined, dried over sodium sulfate, filtered and concentrated in vacuo. The crude mixture (7.8 g) was purified by chromatography (silica gel, toluene/ethyl acetate, 7/3) to give 2-(3-fluoro-4-methoxyphenyl)-4-hydroxy-1-[4-(methylsulfonyl)phenyl]-4-(trifluoromethyl)-4,5-dihydro-1H-imidazole (3.54 g, 64%) as a white solid: mp (DSC) 210° C. Anal. Calc'd. for $C_{18}H_{16}N_2SO_4F_4 \cdot 0.1\ PhCH_3$: C, 50.86; H, 3.83; N, 6.34. Found: C, 50.61; H. 3.64; N, 6.16.

Step 3: Preparation of 2-(3-fluoro-4-methoxyphenyl)-1-[4-(methylsulfonyl)phenyl-4-(trifluoromethyl)-1H-imidazole A mixture of 2-(3-fluoro-4-methoxyphenyl)-4-hydroxy-1-[4-(methylsulfonyl)phenyl]-4-(trifluoromethyl)-4,5-dihydro-1H-imidazole from Step 2 (3.4 g, 7.9 mmol) and p-toluenesulfonic acid monohydrate (700 mg) in toluene (200 mL) was heated to reflux for 72 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture (3.6 g) was purified by chromatography on silica gel using toluene/ethyl acetate (8/2) to give pure 2-(3-fluoro-4-methoxyphenyl)-1-[4-(methylsulfonyl)phenyl]-4-(trifluoromethyl)-1H-imidazole (2.12 g, 65%) as a white solid: mp (DSC) 182° C. Anal. Calc'd. for $C_{18}H_{14}N_2SO_3F_4$: C, 52.17; H, 3.41; N, 6.76; S, 7.74. Found: C, 52.56; H, 3.65; N, 6.53; S, 8.01.

EXAMPLE 19

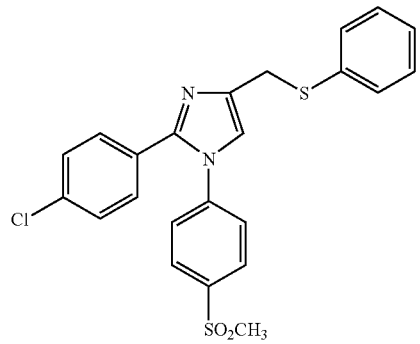

2-(4-Chlorophenyl)-4-[(phenylthio)methyl]-1-[4-(methylsulfonyl)phenyl]-1H-imidazole Step 1: Preparation of 1-bromo-3-phenylthio-2-propanone 1-Bromo-3-phenylthio-2-propanone is synthesized by reaction of thiophenol with 2,3-dichloropropene followed by treatment of the resulting product with aqueous NBS as described for Example 15.

Step 2: Preparation of 2-(4-chlorophenyl)-4-hydroxy-1-[4-(methylsulfonyl)phenyl]-4-[(phenylthio)methyl]-4,5-dihydro-1H-imidazole To a mixture of 4-chloro-N-(4-(methylsulfonyl)phenyl]benzenecarboximidamide (Example 1, Step 1) (1 mmol) and sodium bicarbonate (2 mmol) in acetone (20 mL), 1-bromo-3-phenylthio-2-propanone (1.5 mmol) is added. After heating to reflux for 24 hours, the reaction mixture is filtered, washed with acetone and concentrated in vacuo. The crude product is purified by chromatography (silica gel, toluene/ethyl acetate) to give 2-(4-chlorophenyl)-4-hydroxy-1-[4-(methylsulfonyl) phenyl]-4-[(phenylthio)methyl]-4,5-dihydro-1H-imidazole.

Step 3: Preparation of 2-(4-chlorophenyl)-4-[(phenylthio)methyl]-1-[4-(methylsulfonyl)phenyl]-1H-imidazole A mixture of 2-(4-chlorophenyl)-4-hydroxy-1-[4-(methylsulfonyl)phenyl]-4-[(phenylthio)methyl]-4,5-dihydro-1H-imidazole (1 mmol) and p-toluenesulfonic acid monohydrate (100 mg) in toluene (70 mL) is heated to reflux for 48 hours. The reaction mixture is cooled and the solvent removed under reduced pressure. The crude residue is redissolved in methylene chloride and washed with water, aqueous sodium bicarbonate and brine. After drying ($Na_2SO_4$), filtration and concentration in vacuo, the crude mixture is purified by chromatography on silica gel using hexane/ethyl acetate to give 2-(4-chlorophenyl)-4-[(phenylthio) methyl)-1-[4-(methylsulfonyl)phenyl]-1H-imidazole.

EXAMPLE 20

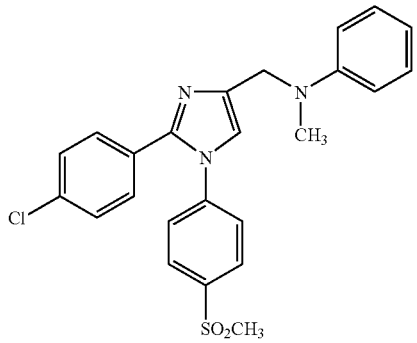

2-(4-Chlorophenyl)-4-[(N-methyl-N-phenylamino)methyl]-1-[4-(methylsulfonyl)phenyl]-1H-imidazole Step 1: Preparation of 1-bromo-3-(N-methyl-N-phenylamine)-2-propanone 1-Bromo-3-(N-methyl-N-phenylamine)-2-propanone is synthesized by reaction of N-methylaniline with 2,3-dichloropropene followed by treatment of the resulting product with aqueous NBS as described for Example 15.

Step 2: Preparation of 2-(4-chlorophenyl)-4-hydroxy-4-[(N-methyl-N-phenylamino)methyl]-1-[4-(methylsulfonyl)phenyl]-4,5-dihydro-1H-imidazole To a mixture of 4-chloro-N-[4-(methylsulfonyl)phenyl]benzenecarboximidamide (Example 1, step 1) (1 mmol) and sodium bicarbonate (2 mmol) in acetone (20 mL), 1-bromo-3-(N-methyl-N-phenylamine)-2-propanone from Step 1 (1.5 mmol) is added. After heating to reflux for 24 hours, the reaction mixture is filtered, washed with acetone and concentrated in vacuo. The crude product is purified by chromatography (silica gel, toluene/ethyl acetate) to give 2-(4-chlorophenyl)-4-hydroxy-4-[(N-methyl-N-phenylamine)methyl]-1-(4-(methylsulfonyl)phenyl]-4,5-dihydro-1H-imidazole.

Step 3: Preparation of 2-(4-chlorophenyl)-4-[(N-methyl-N-phenylamino)methyl]-1-[4-(methylsulfonyl)phenyl]-1H-imidazole A mixture of 2-(4-chlorophenyl)-4-hydroxy-4-[(N-methyl-N-phenylamine)methyl]-1-[4-(methylsulfonyl)phenyl]-4,5-dihydro-1H-imidazole (1 mmol) and p-toluenesulfonic acid monohydrate (100 mg) in toluene (70 mL) is heated to reflux for 48 hours. The reaction mixture is cooled and the solvent removed under reduced pressure. The crude residue is redissolved in methylene chloride and washed with water, aqueous sodium bicarbonate and brine. After drying (Na$_2$SO$_4$), filtration and concentration in vacuo, the crude mixture is purified by chromatography on silica gel using hexane/ethyl acetate to give 2-(4-chlorophenyl)-4-[(N-methyl-N-phenylamine)methyl]-1-[(4-(methylsulfonyl)phenyl]-1H-imidazole.

EXAMPLE 21

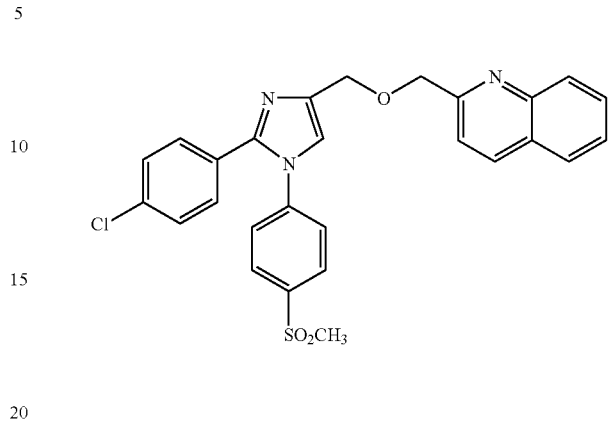

2-(4-Chlorophenyl)-4-[2-quinolyl)methoxymethyl]-1-[4-(methylsulfonyl)phenyl]-1H-imidazole Step 1: Preparation of 1-bromo-3-(2-quinolylmethoxy)-2-propanone The compound 1-bromo-3-(2-quinolylmethoxy)-2-propanone is synthesized by reaction of 2-chloromethylquinoline with 2-chloro-2-propen-1-ol followed by treatment of the resulting quinolylether with aqueous NBS.

Step 2: Preparation of 2-(4-chlorophenyl)-4-hydroxy-1-[4-(methylsulfonyl)phenyl]-4-[(2-quinolylmethoxy)methyl]-4,5-dihydro-1H-imidazole To a mixture of 4-chloro-N-[4-(methylsulfonyl)phenyl] benzenecarboximidamide (Example 1, Step 1) (1 mmol) and sodium bicarbonate (2 mmol) in acetone (20 mL), 1-bromo-3-(2-quinolylmethoxy)-2-propanone from Step 1 (1.5 mmol) is added. After heating to reflux for 24 hours, the reaction mixture is filtered, washed with acetone and concentrated in vacuo. The crude product is purified by chromatography (silica gel, toluene/ethyl acetate) to give 2-(4-chlorophenyl)-4-hydroxy-1-[4-(methylsulfonyl)phenyl]-4-[(2-quinolylmethoxy)methyl]-4,5-dihydro-1H-imidazole.

Step 3: Preparation of 2-(4-chlorophenyl)-1-[4-(methylsulfonyl)phenyl]-4-[(2-quinolylmethoxy)methyl]-1H-imidazole A mixture of 2-(4-chlorophenyl)-4-hydroxy-1-[4-(methylsulfonyl)phenyl]-4-[(2-quinolylmethoxy)methyl]-4,5-dihydro-1H-imidazole (1 mmol) and p-toluenesulfonic acid monohydrate (100 mg) in toluene (70 mL) is heated to reflux for 48 hours. The reaction mixture is cooled and the solvent removed under reduced pressure. The crude residue is redissolved in methylene chloride and washed with water, aqueous sodium bicarbonate and brine. After drying (Na$_2$SO$_4$), filtration and concentration in vacuo, the crude mixture is purified by chromatography on silica gel using hexane/ethyl acetate to give 2-(4-chlorophenyl)-1-(4-(methylsulfonyl)phenyl)-4-[(2-quinolylmethoxy)methyl)-1H-imidazole.

EXAMPLE 22

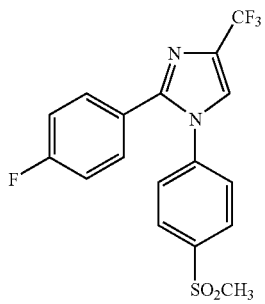

2-(4-Fluorophenyl)-1-[4-(methylsulfonyl)phenyl]-4-trifluoromethyl-1H-imidazole Step 1: Preparation of 4-fluoro-N-[4-(methylsulfonyl)phenyl]benzenecarboximidamide To a suspension of 4-(methylsulfonyl)aniline (3.53 g, 20.2 mmol) in toluene (100 mL), trimethylaluminum (15.2 ml, 2M solution in toluene, 30.2 mmol) was added over 15 minutes. The reaction mixture was warmed to room temperature and stirred for 2.5 hours. A solution of 4-fluorobenzonitrile (5 g, 40.3 mmol) in toluene (100 mL) was added over 10 minutes and the reaction mixture heated to 80–85° C. After 20 hours, the reaction mixture was cooled to room temperature and poured over a slurry of silica gel in chloroform. After filtration, the residue was washed with a mixture of methylene chloride/methanol (2/1). The combined filtrates were concentrated in vacuo and the resulting yellowish solid stirred with a mixture of hexane/ether (2/1, 1000 mL). The intermediate was filtered and concentrated. The pale yellow solid 4-fluoro-N-[4-(methylsulfonyl)phenyl]benzenecarboximidamide (5.25 g, 87%) was used in the next reaction without further purification: mp (DSC) 206.2° C. Anal. Calc'd for $C_{14}H_{13}N_2FSO_3 \cdot 1.25\ H_2O$: C, 53.41; H, 4.91; N, 8.90. Found: C, 53.08; H, 4.50; N, 8.61.

Step 2: Preparation of 2-(4-fluorophenyl)-4-hydroxy-1-[4-(methylsulfonyl)phenyl]-4-trifluoromethyl-4,5-dihydro-1H-imidazole To a mixture of 4-fluoro-N-[4-(methylsulfonyl)phenyl]benzenecarboximidamide (Step 1) (4.5 g. 15.4 mmol) and sodium bicarbonate (2.59 g, 30.8 mmol) in isopropanol (200 mL), 3-bromo-1,1,1-trifluoroacetone (3.2 mL) was added. After heating the reaction mixture at 75–80° C. for 22 hours, the solvent was removed. The residue was redissolved in methylene chloride and washed with water. The organic fractions were combined, dried over sodium sulfate, filtered and concentrated in vacuo. The crude mixture (7.2 g) was purified by chromatography (silica gel, toluene/ethyl acetate, 1/1) to give 2-(4-fluorophenyl)-4-hydroxy-1-[4-(methylsulfonyl)phenyl]-4-trifluoromethyl-4,5-dihydro-1H-imidazole (3.28 g, 53%) as a white solid: mp (DSC) 203° C. Anal. Calc'd for $C_{17}H_{14}N_2F_4SO_3$: C, 50.75; H, 3.51; N, 6.96. Found: C, 51.16; H, 3.69; N, 6.54.

Step 3: Preparation of 2-(4-fluorophenyl)-1-[4-(methylsulfonyl)phenyl]-4-trifluoromethyl-1H-imidazole A mixture of 2-(4-fluorophenyl)-4-hydroxy-1-[4-(methylsulfonyl)phenyl]-4-trifluoromethyl-4,5-dihydro-1H-imidazole (Step 2) (2.8 g, 7 mmol) and p-toluenesulfonic acid monohydrate (300 mg) in toluene (200 mL) was heated to reflux for 72 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture (3.2 g) was purified by chromatography on silica gel using toluene/ethyl acetate (1/1) to give pure 2-(4-fluorophenyl)-1-(4-(methylsulfonyl)phenyl]-4-trifluoromethyl-1H-imidazole (1.38 g, 52%) as a white solid: mp (DSC) 205.5° C. Anal. Calc'd for $C_{17}H_{12}N_2F_4SO_2$: C, 53.13; H, 3.15; N, 7.29; S, 8.34. Found: C, 53.18; H. 3.17; N, 7.26; S, 8.57.

EXAMPLE 23

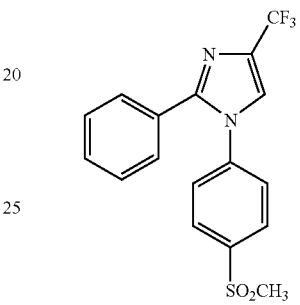

1-[4-(methylsulfonyl)phenyl]-2-phenyl-4-trifluoromethyl-1H-imidazole

Step 1: Preparation of N-[4-(methylsulfonyl)phenyl]benzenecarboximidamide

To a suspension of 4-(methylsulfonyl)aniline (12 g, 70 mmol) in toluene (400 mL), trimethylaluminum (52.5 ml, 2M solution in toluene, 0.1 mol) was added over 15 minutes. The reaction mixture was warmed to room temperature and stirred for 3.5 hours. A solution of benzonitrile (14.5 g, 0.14 mol) in toluene (300 mL) was added over 10 minutes and the reaction mixture heated to 70–75° C. After 17 hours, the reaction mixture was cooled to room temperature and poured over a slurry of silica gel in chloroform. After filtration, the residue is washed with a mixture of methylene chloride/methanol (2/1). The combined filtrates are concentrated in vacuo and the resulting yellowish solid is stirred with a mixture of hexane/ether (2/1, 1000 mL). The intermediate is filtered and washed with more of hexane/ether (2/1). The yellowish solid N-[4-(methylsulfonyl)phenyl]benzenecarboximidamide (16.7 g, 87%) was used in the next reaction without further purification.

Step 2: Preparation of 4-hydroxy-1-[4-(methylsulfonyl)phenyl]-2-phenyl-4-trifluoromethyl-4,5-dihydro-1H-imidazole To a mixture of N-[4-(methylsulfonyl)phenyl]benzenecarboximidamide (Step 1) (16.5 g, 60.1 mmol) and sodium bicarbonate (10.1 g, 0.12 mol) in isopropanol (900 mL), 3-bromo-1,1,1-trifluoroacetone (8.7 ml, 84 mmol) was added. After heating the reaction mixture at 75–80° C. for 20 hours, the solvent was removed. The residue was redissolved in methylene chloride and washed with water. The organic fractions were combined, dried over sodium sulfate, filtered and concentrated in vacuo. The crude mixture was purified by chromatography (silica gel, hexane/ethyl acetate, 45/55) to give 4-hydroxy-1-[4-(methylsulfonyl)phenyl]-2- phenyl-4-trifluoromethyl-4,5-dihydro-1H-imidazole (13.6 g, 59%) as awhite solid: mp 189–190° C. Anal. Calc'd for $C_{17}H_{15}N_2F_3SO_3$: C, 53.12; H, 3.93; N, 7.29; S, 8.34. Found: C, 53.05; H, 3.90; N, 7.14; S, 8.38.

Step 3: Preparation of 1-[4-(methylsulfonyl)phenyl]-2-phenyl-4-trifluoromethyl-1H-imidazole A mixture of 4-hydroxy-1-[4-(methylsulfonyl)phenyl]-2-phenyl-4-trifluoromethyl-4,5-dihydro-1H-imidazole (step 2) (5.43 g, 14.1 mmol) and p-toluenesulfonic acid monohydrate (1.63 g) in toluene (500 mL) was heated to reflux for 96 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture was purified by chromatography on silica gel using hexane/ethyl acetate (65/35) to give pure 1-[4-(methylsulfonyl)phenyl]-2-phenyl-4-trifluoromethyl-1H-imidazole (3.12 g, 60%) as a white solid: mp (DSC) 233° C. Anal. Calc'd for $C_{17}H_{13}N_2F_3SO_2$: C, 55.73; H, 3.58; N, 7.65; S, 8.75. Found: C, 55.49; H, 3.47; N, 7.46; S, 8.95.

EXAMPLE 24

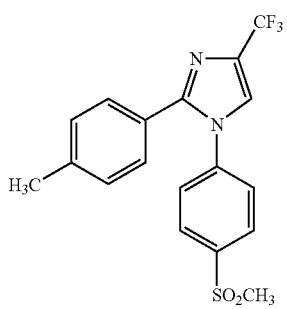

2-(4-Methylphenyl)-1-[4-(methyloulfonyl)phenyl]-4-trifluoromethyl-1H-imidazole

Step 1: Preparation of 4-methyl-N-[4-(methylsulfonyl)phenyl]benzenecarboximidamide To a suspension of 4-(methylsulfonyl)aniline (3.57 g, 20.9 mmol) in toluene (150 mL), trimethylaluminum (15.6 ml, 2M solution in toluene, 31.4 mmol) was added over 15 minutes. The reaction mixture was warmed to room temperature and stirred for 2.5 hours. A solution of 4-methylbenzonitrile (5 ml, 41.8 mmol) in toluene (100 mL) was added over 10 minutes and the reaction mixture heated to 80–85° C. After 20 hours, the reaction mixture was cooled to room temperature and poured over a slurry of silica gel in chloroform. After filtration, the residue was washed with a mixture of methylene chloride/methanol (2/1). The combined filtrates are concentrated in vacuo and the resulting yellowish solid was stirred with a mixture of hexane/ether (2/1, 600 mL). The intermediate was filtered and washed with more of hexane/ether (2/1). The pale yellow solid 4-methyl-N-[4-(methylsulfonyl)phenyl]benzenecarboximidamide (5.3 g, 88%) was used in the next reaction without further purification: mp (DSC) 213° C. Anal. Calc'd for $C_{15}H_{16}N_2SO_2$: C, 62.48; H, 5.59; N, 9.71. Found: C, 62.00; H, 5.52; N, 9.60.

Step 2: Preparatioan of 2-(4-methylphenyl)-4-hydroxy-1-[4-(methylsulfonyl)phenyl]-4-trifluoromethyl-4,5-dihydro-1H-imidazole To a mixture of 4-methyl-N-[4-(methylsulfonyl)phenyl]benzenecarboximidamide (step 1) (5 g, 17.4 mmol) and sodium bicarbonate (2.9 g, 34.7 mmol) in isopropanol (200 mL), 3-bromo-1,1,1-trifluoroacetone (3.6 ml, 34.7 mmol) was added. After heating the reaction mixture at 75–80° C. for 20 hours, the solvent was removed. The residue was redissolved in methylene chloride and washed with water. The organic fractions were combined, dried over sodium sulfate, filtered and concentrated in vacuo. The crude mixture (8.9 g) was purified by chromatography (silica gel, toluene/ethyl acetate 6/4) to give 2-(4-methylphenyl)-4-hydroxy-1-[4-(methylsulfonyl)phenyl]-4-trifluoromethyl-4,5-dihydro-1H-imidazole (3.28 g, 47%) as a white solid: mp 198–199° C. Anal. Calc'd for $C_{18}H_{17}N_2F_3SO_3 \cdot 0.3$ PhMe C, 56.67; H, 4.59; N, 6.58. Found: C, 56.95; H, 4.68; N, 6.13.

Step 3: Preparation of 2-(4-methylphenyl)-1-[4-(methylsulfonyl)phenyl]-4-trifluoromethyl-1H-imidazole A mixture of 2-(4-methylphenyl)-4-hydroxy-1-[4-(methylsulfonyl)phenyl]-4-trifluoromethyl-4,5-dihydro-1H-imidazole (Step 2) (0.9 g, 2.3 mmol) and p-toluenesulfonic acid monohydrate (150 mg) in toluene (100 mL) was heated to reflux for 72 hours. The reaction mixture was cooled and the solvent removed under reduced pressure. The crude residue was redissolved in methylene chloride and washed with water, aqueous sodium bicarbonate and brine. After drying ($Na_2SO_4$), filtration and concentration in vacuo, the crude mixture was purified by chromatography on silica gel using toluene/ethyl acetate (1/1) to give pure 2-(4-methylphenyl)-1-[4-(methylsulfonyl)phenyl]-4-trifluoromethyl-1H-imidazole (462. mg, 54%) as a white solid: mp (DSC) 190° C. Anal. Calc'd for $C_{18}H_{15}N_2F_3SO_2$: C, 56.84; H, 3.97; N, 7.36; S, 8.43. Found: C, 56.66; H, 3.82; N, 7.23; S, 8.45.

EXAMPLE 25

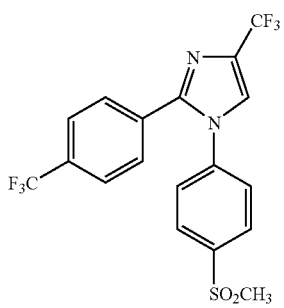

1-[4-(Methyloulfonyl)phenyl]-2-(4-trifluoromethylphenyl)-4-trifluoromethyl-1H-imidazole Step 1: Preparation of 4-(trifluoromethyl)-N-[4-(methylsulfonyl)phenyl]benzenecarboximidamide To a suspension of 4-(methylsulfonyl)aniline (10 mmol) in toluene (100 mL), trimethylaluminum (2M solution in toluene, 15 mmol) is added over 15 minutes. The reaction mixture is warmed to room temperature and stirred for 2.5 hours. A solution of 4-trifluoromethylbenzonitrile (20 mmol) in toluene (50 mL) is added over 10 minutes and the reaction mixture is heated to 80–85° C. After 20 hours, the reaction mixture is cooled to room temperature and poured over a slurry of silica gel in chloroform. After filtration, the residue is washed with a mixture of methylene chloride/methanol (2/1). The combined filtrates are concentrated in vacuo and the resulting yellowish solid is stirred with a mixture of hexane/ether (2/1, 1000 mL). The intermediate is filtered and washed with more of hexane/ether (2/1). The pale yellow solid 4-(trifluoromethyl)-N-[4-(methylsulfonyl)phenyl]benzenecarboximidamide is used in the next reaction without further purification.

Step 2: Preparation of 4-hydroxy-1-[4-(methylsulfonyl)phenyl]-2-(4-trifluoromethylphenyl)-4-trifluoromethyl-4,5-dihydro-1H-imidazole To a mixture of 4-(trifluoromethyl)-N-[4-(methylsulfonyl)phenyl]benzenecarboximidamide (10 mmol) and sodium bicarbonate (20 mmol) in isopropanol (100 mL), 3-bromo-1,1,1-trifluoroacetone (20 mmol) is added. After heating the reaction mixture at 70–75° C. for 20 hours, the solvent is removed. The residue is redissolved in methylene chloride and washed with water. The organic fractions are combined, dried over sodium sulfate, filtered and concentrated in vacuo. The crude product is purified by chromatography (silica gel, toluene/ethyl acetate, 7/3) to give 4-hydroxy-1-[4-(methylsulfonyl)phenyl]-2-(4-trifluoromethylphenyl)-4-trifluoromethyl-4,5-dihydro-1H-imidazole.

Step 3: Preparation of 1-[4-(methylsulfonyl)phenyl]-2-(4-trifluoromethylphenyl)-4-trifluoromethyl-1H-imidazole A mixture of 4-hydroxy-1-[4-(methylsulfonyl)phenyl]-2-(4-trifluoromethylphenyl)-4-trifluoromethyl-4,5-dihydro-1H-imidazole (10 mmol) and p-toluenesulfonic acid monohydrate (1 mmol) in toluene (100 mL) is heated to reflux for 72 hours. The reaction mixture is cooled and the solvent removed under reduced pressure. The crude residue is redissolved in methylene chloride and washed with water, aqueous sodium bicarbonate and brine. After drying (Na$_2$SO$_4$), filtration and concentration in vacuo, the crude mixture is purified by chromatography on silica gel using toluene/ethyl acetate to give pure 1-[4-(methylsulfonyl)phenyl]-2-(4-trifluoromethylphenyl)-4-trifluoromethyl-1H-imidazole.

EXAMPLE 26

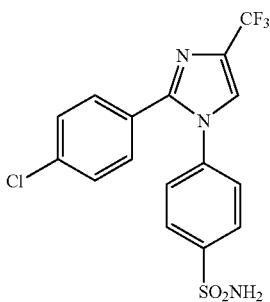

4-[2-(4-Chlorophenyl)-4-(trifluoromethyl)-1H-imidazol-1-yl]benzenesulfonamide

To a clear solution of 2-(4-chlorophenyl)-1-[4-(methylsulfonyl)phenyl]-4-(trifluoromethyl)-1H-imidazole from Example 2 (40,0 mg, 1 mmol) in tetrahydrofuran (THF) (8 mL) at 0° C., n-BuMgCl (2M solution in THF, 2 mL, 4 mmol) was added over 10 minutes. After stirring for additional 10 minutes, ice bath was removed and solution stirred for 1 hour. The reaction mixture was re-cooled to 0° C. and triethylborane (1M solution in THF, 5 mL, 5 mmol) was added. After stirring for 2 hours, the reaction was heated to reflux for 48 hours. The reaction mixture was cooled to room temperature and treated with aqueous sodium acetate (1 g in 4 mL water). After stirring for 5 minutes, solid hydroxylamine-O-sulfonic acid (1 g) was added and the mixture stirred for 20 hours. The reaction mixture was diluted with water and extracted with ether (2×250).The ethereal layer was dried over sodium sulfate, filtered and concentrated in vacuo. The crude solid (568 mg) was purified by chromatography [silica gel, ethyl acetate/toluene (3/7)] to give 4-[2-(4-chlorophenyl)-4-(trifluoromethyl)-1H-imidazol-1-yl]benzenesulfonamide (260 mg, 65%): mp (DSC) 225° C. Anal. Calc'd. for C$_{16}$H$_{11}$N$_3$SO$_2$F$_3$Cl: C, 47.83; H, 2.76; N, 10.46; S, 7.98. Found: C, 48.00; H, 2.83; N, 10.14; S, 7.94.

EXAMPLE 27

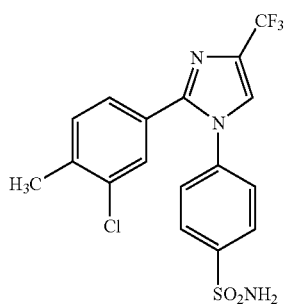

4-[2-(3-Chloro-4-methylphenyl)-4-(trifluoromethyl)-1H-imidazol-1-yl]benzenesulfonamide To a clear solution of 2-(3-chloro-4-methylphenyl)-1-[4-(methylsulfonyl)phenyl]-4-(trifluoromethyl)-1H-imidazole (Example 16) (500 mg, 1.2 mmol) in tetrahydrofuran (10 mL) at 0° C., n-BuMgCl (2M solution in THF, 2.4 mL, 4.8 mmol) was added over 10 minutes. After stirring for additional 10 minutes, ice bath was removed and solution stirred for 1 hour. The reaction mixture was re-cooled to 0° C. and triethylborane (1M solution in THF, 6 ML, 6 mmol) was added. After stirring for 2 hours, the reaction was heated to reflux for 72 hours. The reaction mixture was cooled to room temperature and treated with aqueous sodium acetate (1 g in 4 mL water). After stirring for 5 minutes, solid hydroxylamine-O-sulfonic acid (1 g) was added and the mixture stirred for 20 hours. The reaction mixture was diluted with water and extracted with ether (2×250). The ethereal layer was dried over sodium sulfate, filtered and concentrated in vacuo. The crude product (710 mg) was purified by chromatography (silica gel, ethyl acetate/toluene 3/7) to give pure 4-[2-(3-chloro-4-methylphenyl)-4-(trifluoromethyl)-1H-imidazol-1-yl]benzenesulfonamide (180 mg, 36%) as a white solid: mp (DSC) 222° C. Anal. Calc'd. for C$_{17}$H$_{13}$N$_3$SO$_2$F$_3$Cl: C, 49.10; H, 3.15; N, 10.11. Found: C, 49.42; H, 3.19; N, 9.75.

EXAMPLE 28

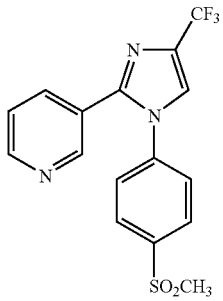

3-[1-[4-(Methylsulfonyl)phenyl]-4-trifluoromethyl-1H-imidazol-2-yl]pyridine

Step 1: Preparation of N-[4-(methylsulfonyl)phenyl]-3-pyridinecarboximidamide

To a suspension of 4-(methylsulfonyl)aniline hydrochloride (6 g, 28.8 mmol) in toluene (150 ml) at 0° C., trimethylaluminum (2M solution in toluene, 21.6 ml, 43.2 mmol) was added over 15 minutes. The reaction mixture was warmed to room temperature and stirred for 2.5 hours. A solution of 3-cyanopyridine (6 g, 57.6 mmol) in toluene (150 ml) was added over 10 minutes and the reaction mixture was heated to 90–95° C. After 24 hours, the reaction mixture was cooled to room temperature and poured over a slurry of silica gel in chloroform. After filtration, the residue was washed with a mixture of methylene chloride/methanol and later methanol. The combined filtrates were concentrated and the resulting yellowish solid was stirred with ethyl acetate (1000 ml) and filtered. The pale yellow amidine (4.5 g, 34%) was used in the next reaction without further purification: mp (DSC) 265° C. Anal Calc'd. for $C_{13}H_{14}N_3SO_2Cl·0.5\ H_2O$: C, 48.67; H, 4.71; N, 13.10. Found: C, 48.34; H, 4.26; N, 12.77.

Step 2: Preparation of 3-[4-hydroxy-1-[4-(methylsulfonyl)phenyl]-4-(trifluoromethyl)-4,5-dihydro-1H-imidazol-2-yl]pyridine To a mixture of the amidine of Step 1 (4.4 g, 16 mmol) and sodium bicarbonate (2.68 g, 32 mmol) in isopropanol (400 ml), 3-bromo-1,1,1-trifluoroacetone (2.5 ml, 24 mmol) was added. After heating at 60–65° C. for 36 hours, the reaction mixture was cooled and filtered. The residue was washed with methylene chloride and the combined organic fractions were dried over sodium sulfate, filtered and concentrated. The crude mixture (16.2 g) was purified by chromatography [silica gel, ethyl acetate/acetone (98:2)] to give the compound (3.7 g, 60%) as a white solid. Anal Calc'd. for $C_{16}H_{14}N_3SO_3F_3·0.5\ H_2O$: C, 48.18; H, 3.92; N, 10.53. Found: C, 48.52; H, 3.61; N, 9.79.

Step 3: Preparation of 3-[1-[4-(methylsulfonyl)phenyl]-4-trifluoromethyl-1H-imidazol-2-yl]pyridine A mixture of the compound of step 2 (3.6 g, 9.35 mmol) and p-toluenesulfonic acid monohydrate (0.52 g, 2.7 mmol) in toluene (280 ml) was heated to reflux for 24 hours. The reaction mixture was cooled and the solvent removed under reduced pressure. The crude mixture was purified by chromatography on silica gel using ethyl acetate/acetone (98/2) to give pure 3-[1-[4-(methylsulfonyl)phenyl]-4-trifluoromethyl-1H-imidazol-2-yl]pyridine (790 mg, 23%) as a white solid: mp (DSC) 193° C. Anal Calc'd. for $C_{16}H_{12}N_3SO_2F_3$: C, 52.30; H, 3.29; N, 11.44; S, 8.73. Found: C, 52.38; H, 3.26; N, 11.30; S, 8.76.

EXAMPLE 29

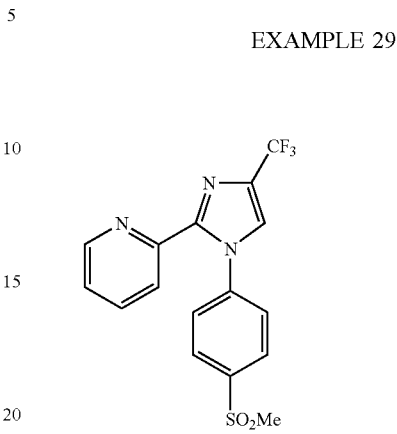

2-[1-[4-(Methylsulfonyl)phenyl]-4-trifluoromethyl-1H-imidazol-2-yl]pyridine

Step 1: Preparation of N-[4-(methylsulfonyl)phenyl]-2-pyridinecarboximidamide

To a suspension of 4-(methylsulfonyl)aniline hydrochloride (6 g, 28.8 mmol) in toluene (150 ml) at 0° C., trimethylaluminum (2M solution in toluene, 21.6 ml, 43.2 mmol) was added over 15 minutes. The reaction mixture was warmed to room temperature and stirred for 2.5 hours. A solution of 2-cyanopyridine (6 g, 57.6 mmol) in toluene (150 ml) was added over 10 minutes and the reaction mixture was heated to 85–90° C. After 24 hours, the reaction mixture was cooled to room, temperature and poured over a slurry of silica gel in chloroform. After filtration, the residue was washed with a mixture of methylene chloride/methanol and later methanol. The combined filtrates were concentrated and the resulting yellowish solid was stirred with ethyl acetate (1500 ml) and filtered. The pale yellow solid (5.2 g, 66%) was used in the next reaction without further purification.

Step 2: Preparation of 2-[4-hydroxy-1-[4-(methylsulfonyl)phenyl]-4-(trifluoromethyl)-4,5-dihydro-1H-imidazol-2-yl]pyridine To a mixture of the amidine of step 1 (4.4 g, 16 mmol) and sodium bicarbonate (2.7 g, 32 mmol) in isopropanol (400 ml), 3-bromo-1,1,1-trifluoroacetone (2.5 ml, 24 mmol) was added. After heating at 75–80° C. for 24 hours, the reaction mixture was cooled and filtered. The residue was washed with methylene chloride and the combined organic fractions were dried over sodium sulfate, filtered and concentrated. The crude product (16.2 g) was purified by chromatography (silica gel, ethyl acetate/toluene 1/1) to give 2-[4-hydroxy-1-[4-(methylsulfonyl)phenyl]-4-(trifluoromethyl)-4,5-dihydro-1H-imidazol-2-yl]pyridine (1.1 g, 18%) as a white solid: mp 195–198° C. Anal. Calc'd. for $C_{16}H_{14}N_3SO_3F_3$: C, 49.87; H, 3.66; N, 10.90. Found: C, 50.13; H, 3.66; N, 10.30.

Step 3: Preparation of 2-[1-[4-(methylsulfonyl)phenyl]-4-trifluoromethyl-1H-imidazol-2-yl]pyridine A mixture of 2-[4-hydroxy-1-[4-(methylsulfonyl)phenyl]-4-(trifluoromethyl)-4,5-dihydro-1H-imidazol-2-yl]pyridine from step 2 (1.0 g, 2.6 mmol) and p-toluenesulfonic acid monohydrate (0.2 g, 2.7 mmol) in toluene (100 ml) was heated to reflux for 24 hours. The reaction mixture was cooled and the solvent removed under reduced pressure. The crude mixture (1.2 g) was purified by chromatography on silica gel using ethyl acetate/toluene (1/1) to give pure 2-[1-[4-(methylsulfonyl)phenyl]-4-trifluoromethyl-1H-imidazol-2-yl]pyridine (620 mg, 65%) as a white solid: mp (DSC) 184° C. Anal. Calc'd. for $C_{16}H_{12}N_3SO_2F_3$: C, 52.30; H, 3.29; N, 11.44. Found: C, 52.23; H, 3.23; N, 11.19.

EXAMPLE 30

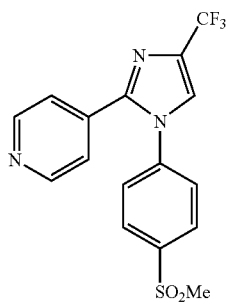

4-[1-[4-(Methyloulfonyl)phenyl]-4-trifluoromethyl-1H-imidazol-2-yl]pyridine

Step 1: Preparation of N-[4-(methylsulfonyl)phenyl]-4-pyridinecarboximidamide

To a suspension of 4-(methylsulfonyl)aniline hydrochloride (10 g, 48.1 mmol) in toluene (250 ml) at 0° C., trimethylaluminum (2M solution in toluene, 36.1 ml, 72.2 mmol) was added over 10 minutes. The reaction mixture was warmed to room temperature and stirred for 2.5 hours. A solution of 4-cyanopyridine (10 g, 96.2 mmol) in toluene (250 ml) was added over 10 minutes and the mixture was heated to 70° C. After 24 hours, the reaction mixture was cooled to room temperature and poured over a slurry of silica gel in chloroform. After filtration, the residue was washed with a mixture of methylene chloride/methanol and later with methanol. The combined filtrates were concentrated and the resulting yellowish solid was stirred with ethyl acetate and filtered. The pale yellow solid (4.8 g, 36%) was used in the next reaction without further purification. Anal. Calc'd. for $C_{13}H_{14}N_3SClO_2H_2O$: C, 47.34; H, 4.89; N, 12.74; S, 9.72. Found C, 47.69; H, 4.35; N, 12.77; S, 9.74.

Step 2: Preparation of 4-[4-hydroxy-1-[4-(methylsulfonyl)phenyl]-4-(trifluoromethyl)-4,5-dihydro-1H-imidazol-2-yl]pyridine To a mixture of the amidine of step 1 (4.75 g, 16 mmol) and sodium bicarbonate (2.86 g, 34.4 mmol) in isopropanol (400 ml), 3-bromo-1,1,1-trifluoroacetone (2.7 ml, 26 mmol) was added. After heating at 75–80° C. for 24 hours, the reaction mixture was cooled and filtered. The residue was washed with methylene chloride and the combined organic fractions were dried over sodium sulfate, filtered and concentrated. The crude product (16.2 g) was purified by chromatography (silica gel, ethyl acetate/isopropanol (95/5)) to give 4-[4-hydroxy-1-[4-(methylsulfonyl)phenyl]-4-(trifluoromethyl)-4,5-dihydro-1H-imidazol-2-yl]pyridine (1.55 g, 23%) as a white solid: mp 219° C., Anal. Calc'd. for $C_{16}H_{14}N_3SO_3F_3$C, 49.87; H, 3.661; N, 10.90; S, 8.32. Found: C, 49.93; H, 3.51; N, 10.79; S, 8.66.

Step 3: Preparation of 4-[1-[4-(methylsulfonyl)phenyl]-4-trifluoromethyl-1H-imidazol-2-yl]pyridine A mixture of the 4,5-dihydro-imidazole of step 2 (0.85 g, 2.2 mmol) and p-toluenesulfonic acid monohydrate (0.12 g) in toluene (150 ml) was heated to reflux for 24 hours. The reaction mixture was cooled and the solvent removed under reduced pressure. The crude mixture was purified by chromatography on silica gel using ethyl acetate/acetone (96/4) to give pure 4-[1-[4-(methylsulfonyl)phenyl]-4-trifluoromethyl-1H-imidazol-2-yl]pyridine (330 mg, 41%) as a white solid: mp (DSC) 197° C. Anal. Calc'd. for $C_{16}H_{12}N_3SO_2F_3$: C, 52.30; H, 3.29; N, 11.44; S, 8.73. Found: C, 52.19; H, 3.26; N, 11.25; S, 8.99.

EXAMPLE 31

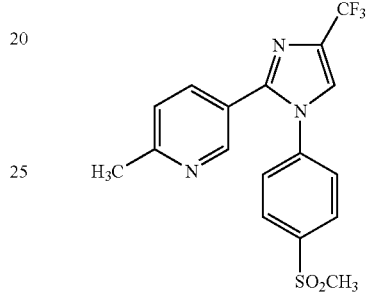

2-Methyl-5-[1-[4-(methylsulfonyl)phenyl]-4-trifluoromethyl-1H-imidazol-2-yl]pyridine Step 1: Preparation of 2-methyl-N-[4-(methylsulfonyl)phenyl]-5-pyridinecarboximidamide To a suspension of 4-(methylsulfonyl)aniline hydrochloride (8.8 g, 42.3 mmol) in toluene (150 ml) at 0° C., trimethylaluminum (2M solution in toluene, 42.3 ml, 84.6 mmol) was added over 10 minutes. The reaction mixture was warmed to room temperature and stirred for 2.5 hours. A solution of 6-methyl-4-cyanopyridine (10 g, 84.6 mmol) in toluene (150 ml) was added over 10 minutes and the mixture was heated to 80–85° C. After 24 hours, the reaction mixture was cooled to room temperature and poured over a slurry of silica gel in chloroform. After filtration, the residue was washed with a mixture of methylene chloride/methanol and later with methanol. The combined filtrates were concentrated and the resulting yellowish solid was stirred with ethyl acetate and filtered. The pale yellow solid (9.8 g, 80%) was used in the next reaction without further purification. Anal Calc'd. for $C_{14}H_{15}N_3SO_2.H_2O$: C, 54.71; H, 5.57; N, 13.67. Found: C, 54.62; H, 5.24; N, 13.67.

Step 2: Preparation of 2-methyl-5-[4-hydroxy-1-[4-(methylsulfonyl)phenyl]-4-(trifluoromethyl)-4,5-dihydro-1H-imidazol-2-yl]pyridine To a mixture of the amidine of Step 1 (9.8 g, 33.9 mmol) and sodium bicarbonate (5.7 g, 67.8 mmol) in isopropanol (700 ml), 3-bromo-1,1,1-trifluoroacetone (5.3 ml, 50.8 mmol) was added. After heating at 80–85° C. for 24 hours, the reaction mixture was cooled and filtered. The residue was washed with methylene chloride and the combined organic fractions were dried over sodium sulfate, filtered and concentrated. The crude material (25.7 g) was purified by chromatography (silica gel, ethyl acetate/acetone, 98/2) to give 2-methyl-5-[4-hydroxy-1-[4-(methylsulfonyl)phenyl]-4-(trifluoromethyl)-4,5-dihydro-1H-imidazol-2-yl]pyridine (6.3 g, 46%) as a white solid: Anal. Calc'd. for $C_{17}H_{16}N_3SO_3F_3$: C, 50.55; H, 4.12; N, 10.40. Found: C, 50.51; H, 3.91; N, 10.25.

Step 3: Preparation of 2-methyl-5-[1-[4-(methylsulfonyl)phenyl]-4-trifluoromethyl-1H-imidazol-2-yl]pyridine A mixture of the 4,5-dihydro-imidazole of step 2 (6.2 g, 15.5 mmol) and p-toluenesulfonic acid monohydrate (1.6 g, 8.4 mmol) in toluene (550 ml) was heated to reflux for 24 hours. The reaction mixture was cooled and the solvent removed under reduced pressure. The crude mixture (8.2 g) was purified by chromatography on silica gel using ethyl acetate/acetone (98/2) to give pure 2-methyl-5-[1-[4-(methylsulfonyl)phenyl]-4-trifluoromethyl-1H-imidazol-2-yl]pyridine (3.9 g, 66%) as a white solid: mp (DSC) 163° C. Anal Calc'd. for $C_{17}H_{14}N_3SO_2F_3$: C, 53.54; H, 3.70; N, 11.02; S, 8.41. Found: C, 53.12; H, 3.56; N, 11.00; S, 8.50.

EXAMPLE 32

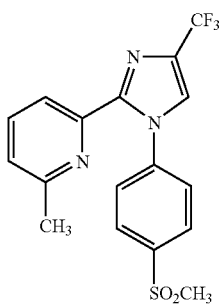

2-Methyl-6-[1-[4-(methylsulfonyl)phenyl]-4-trifluoromethyl-1H-imidazol-2-yl]pyridine Step 1: Preparation of 2-methyl-N-[4-(methylsulfonyl)phenyl]-6-pyridinecarboximidamide To a suspension of 4-(methylsulfonyl)aniline hydrochloride (4.2 g, 20.3 mmol) in toluene (100 ml) at 0° C., was added trimethylaluminum (2M solution in toluene, 12 ml, 24 mmol) over 10 minutes. The reaction mixture was warmed to room temperature and stirred for 2 hours. A solution of 6-methyl-2-cyanopyridine (3.6 g, 30.5 mmol) in toluene (100 ml) was added over 10 minutes and the mixture was heated to 85–90° C. After 24 hours, the reaction mixture was cooled to room temperature and poured over a slurry of silica gel in chloroform. After filtration, the residue was washed with a mixture of methylene chloride/methanol and later with methanol. The combined filtrates were concentrated and the resulting yellowish solid was stirred with hexane and ethyl acetate (1000 ml) and filtered. The white solid (5.1 g, 87%) was used in the next reaction without further purification. Anal. Calc'd. for $C_{14}H_{16}N_3SClO_2 0.2H_2O$: C, 51.05; H, 5.02; N, 12.76. Found: C, 50.97; H, 4.78; N, 12.80.

Step 2: Preparation of 2-methyl-6-[4-hydroxy-1-[4-(methylsulfonyl)phenyl]-4-(trifluoromethyl)-4,5-dihydro-1H-imidazol-2-yl]pyridine To a mixture of the amidine of Step 1 (4.9 g, 16.95 mmol) and sodium bicarbonate (2.85 g, 33.9 mmol) in isopropanol (300 ml), 3-bromo-1,1,1-trifluoroacetone (2.65 ml, 25.4 mmol) was added. After heating at 80–85° C. for 24 hours, the reaction mixture was cooled and filtered. The residue was washed with methylene chloride and the combined organic fractions were dried over sodium sulfate, filtered and concentrated. The crude mixture (9 g) was purified by chromatography (silica gel, ethyl acetate/isopropanol/ammonium hydroxide 95/5/0.5) to give 2-methyl-6-[4-hydroxy-1-[4-(methylsulfonyl)phenyl]-4-(trifluoromethyl)-4,5-dihydro-1H-imidazol-2-yl]pyridine (1.4 g, 21%) as a white solid: Anal. Calc'd. for $C_{17}H_{16}N_3SO_3F_3$: C, 51.12; H, 4.02; N, 10.52. Found: C, 51.43; H, 3.96; N, 10.06.

Step 3: Preparation of 2-methyl-6-[1-[4-(methylsulfonyl)phenyl]-4-trifluoromethyl-1H-imidazol-2-yl]pyridine A mixture of the 4,5-dihydro-imidazole of step 2 (1.3 g, 3.26 mmol) and p-toluenesulfonic acid monohydrate (0.26 g, 1.36 mmol) in toluene (200 ml) was heated to reflux for 24 hours. The reaction mixture was cooled and the solvent removed under reduced pressure. The crude mixture (1.56 g) was purified by chromatography on silica gel using ethyl acetate/acetone (98/2) to give pure 2-methyl-6-[1-[4-(methylsulfonyl)phenyl]-4-trifluoromethyl-1H-imidazol-2-yl]pyridine (0.48 g, 38%) as a white solid: mp (DSC) 205° C. Anal. Calc'd. for $C_{17}H_{14}N_3SO_2F_3 0.25H_2O$: C, 52.91; H, 3.79; N, 10.89; S, 8.31. Found: C, 52.67; H, 3.55; N, 10.64; S, 8.68.

EXAMPLE 33

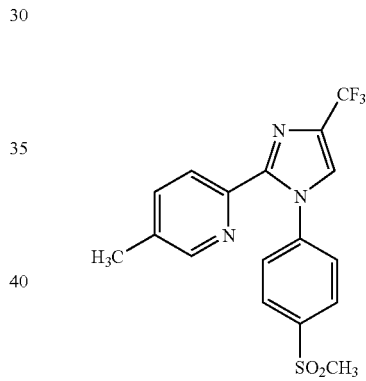

5-Methyl-2-[1-[4-(methylsulfonyl)phenyl]-4-trifluoromethyl-1H-imidazol-2-yl]pyridine Step 1: Preparation of 5-methyl-2-cyanopyridine To a solution of 2-fluoro-5-methylpyridine (39 g; 351.5 mmol) in 141 ml of dimethylsulfoxide was added 17.23 g of sodium cyanide (351.5 mmol). After stirring for 3 days at 150° C., an additional 3 g of sodium cyanide was added and heating was continued for 5 hours. The reaction mixture was cooled to 25° C. then poured into 525 ml of ice water. The solution was filtered through a coarse fritted funnel and a dark brown solid was collected. The solid was air dried to give 17 g of the desired cyanopyridine: Anal Calc'd. for $C_7H_6N_2$: C, 71.17; H, 5.12; N, 23.71. Found: C, 69.91; H, 5.24; N, 23.26.

Step 2: Preparation of 5-methyl-N-[4-(methylthio)phenyl]-2-pyridinecarboximidamide To a solution of 4-thiomethylaniline (8.25 g; 59 mmol) in 1,2-dichloroethane (164 ml) at 0° C., triethylaluminum (1.9M solution in toluene, 31.2 ml, 59 mmol) was added over 10 minutes. The reaction mixture was warmed to room temperature and stirred for 1.5 hours. A solution of 5-methyl-2-cyanopyridine (Step 1) (59 mmol) in 1,2-dichloroethane (62 ml) was added over 10 minutes and the mixture was heated to reflux. After 12 hours, the reaction mixture was cooled to room temperature and 50 g of silica gel were added. The suspension was stirred for 1–2 hours at 25° C. and 12 ml of methanol was added and stirred at 25° C. After filtration through celite®, the residue was washed with a mixture of methylene chloride/methanol and later with methanol. The combined filtrates were concentrated and the resulting solid stirred with hexane/ethyl acetate (1000 ml) and filtered. The solid obtained (7 g) was used in the next reaction without further purification: Anal Calc'd. for $C_{14}H_{15}N_3.0.3\ H_2O$: C, 63.99; H, 5.98; N, 15.99. Found: C, 64.05; H, 6.06; N, 16.11.

Step 3: Preparation of 5-methyl-2-[4-hydroxy-1-[4-(methylthio)phenyl]-4-(trifluoromethyl)-4,5-dihydro-1H-imidazol-2-yl]pyridine To a mixture of the amidine of step 2 (10 g, 52.41 mmol) and sodium bicarbonate (8.6 g, 103 mmol) in isopropanol (1200 ml), 3-bromo-1,1,1-trifluoroacetone (10 g, 52 mmol) was added. After heating at reflux for 22 hours, the reaction mixture was cooled and filtered. The residue was dissolved in methylene chloride and washed water than brine. The organic extracts were dried (MgSO$_4$), filtered and concentrated. The crude mixture was purified by chromatography (silica gel, 100% ethyl acetate) to give. the desired dihydroimidazole (5.1 g): Anal Calc'd. for $C_{17}H_{16}N_3SOF_3$: C, 55.58; H, 4.39; N, 11.44. Found: C, 55.54; H, 4.35; N, 11.20.

Step 4: Preparation of 5-methyl-2-[1-[4-(methylthio)phenyl]-4-trifluoromethyl-1H-imidazol-2-yl]pyridine A mixture of the dihydro-imidazole of step 3 (3. 95 g, 13.9 mmol) and p-toluenesulfonic acid monohydrate (785 mg, 4 mmol) in toluene (500 ml) was heated to reflux for 4–5 hours. The reaction mixture was cooled and 10 ml of triethylamine was added and the solvent removed-under reduced pressure. The crude mixture was purified by chromatography on silica gel using ethyl acetate to give the desired product which was used in the next reaction without further purification.

Step 5: Preparation of 5-methyl-2-[1-[4-(methylsulfonyl)phenyl]-4-trifluoromethyl-1H-imidazol-2-yl]pyridine To solution of the methylthio compound from step 4 (3.95 g, 11.5 mmol) in 45 ml of methanol was added an aqueous solution of Oxone® (6.94 g dissolved in 28 ml of water). After stirring at 25° C. for 4–5 hours, the solvent was removed under reduced pressure, redissolved in 50 ml of methylene chloride and extracted with 50 ml of an aqueous solution of sodium bicarbonate. The organic extracts were dried (MgSO$_4$), filtered and concentrated. The crude material was purified by chromatography (silica gel; 50% ethyl acetate/toluene) to provide 1.6 g of the desired product: mp 196° C. Anal Calc'd. for $C_{17}H_{14}N_3SO_2F_3$: C, 53.54; H, 3.70; N, 11.02; S, 8.41. Found: C, 53.09; H, 3.43; N, 10.75; S, 8.69.

EXAMPLE 34

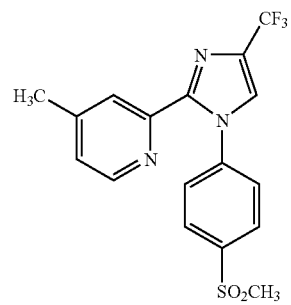

4-Methyl-2-[1-[4-(methyloulfonyl)phenyl]-4-trifluoromethyl-1H-imidazol-2-yl]pyridine Step 1: Preparation of 2-cyano-4-methylpyridine To a suspension of 4-picoline N-oxide (13.64 g, 0.124 mole) in 82 ml of THF, under an inert atmosphere, was added trimethylsilyl cyanide (20.1 ml, 0.15 mole) followed by 1,8-diazabicyclo[5.4.0]undec-7-ene (DBU) (4.4 ml, 0.028 mole). After stirring at 25° C. for 12 hours, the reaction mixture was heated to reflux. After 4.5 hours, the solvent was removed under reduced pressure and the crude sample was eluted with methylene chloride through a pad of Florisil®. The solvent was removed under reduced pressure to provide (8.7 g, 60%) of 2-cyano-4-methyl pyridine, a white crystalline solid: mp 88–89° C. Anal. Calc'd. for $C_7H_6N_2$: C, 71.17; H, 5.12; N, 23.71. Found: C, 70.17; H, 5.12; N, 23.44.

Step 2: Preparation of 4-methyl-N-[4-(methylsulfonyl)phenyl]-2-pyridinecarboximidamide To a solution of 4-methylsulfonyl aniline (7.62 g, 44.5 mmol) in 40 ml of 1,2-dichloroethane, was added 23.4 ml of a 1.9 M solution of triethylaluminum in toluene. After stirring for 1.5 hours at 0° C., 2-cyano-4-methyl-pyridine from step 1 (5.26 g, 44.5 mmol) was added. The reaction mixture was heated to reflux for 20 hours and poured onto a pad of silica gel, in a fritted filter funnel, pre-wetted and washed with 50% methanol/methylene chloride. The filtrates were evaporated under reduced pressure to provide 11.05 g (85%) of the desired amidine as a light brown solid: mp 180–184° C. Anal. Calc'd. for $C_{14}H_{15}N_3O_2S$: C, 58.11; H, 5.23; N, 14.52. Found: C, 57.56; H, 5.15; N, 14.35.

Step 3: Preparation of 4-methyl-2-[4-hydroxy-1-[4-(methylsulfonyl)phenyl]-4-(trifluoromethyl)-4,5-dihydro-1H-imidazol-2-yl]pyridine To the amidine of step 2 (12.9 g, 44.67 mmol) and sodium bicarbonate (7.15 g, 85.1 mmol) in 1 L of isopropanol, 3-bromo-1,1,1-trifluoro-acetone (12.3 g, 64.4 mmol) was added. The mixture was heated to reflux. After 24 hours, the solvent was removed under reduced pressure and the resulting residue was partitioned between methylene chloride and brine. The organic extracts were dried (MgSO$_4$), filtered and the solvent was removed under reduced pressure to provide a dark brown oil which was purified by flash chromatography (SiO$_2$, 5% isopropanol/methylene chloride) to provide 3.81 g (24%) of the 4,5-dihydro-imidazole as a brown solid.

Step 4: Preparation of 4-methyl-2-[1-[4-(methylsulfonyl)phenyl]-4-trifluoromethyl-1H-imidazol-2-yl]pyridine To a suspension of the 4,5-dihydro-imidazole of step 3 (3.82 g, 10.78 mmol) in 700 ml of toluene was added 0.62 g of p-toluenesulfonic acid. After heating at reflux for 12 hours, an additional 0.3 g of p-toluenesulfonic acid was added. After 12 hours, 2.7 ml of triethylamine was added and the solvent was removed under reduced pressure to provide 5.17 g of crude compound. Crude compound was purified by chromatography twice (SiO$_2$; 30% heptane/ethyl acetate) by HPLC to provide 263 mg of the targeted compound. Impure fractions containing the desired product were recombined and repurified by chromatography using HPLC (SiO$_2$; 50% ethyl acetate/toluene) to provide an additional 639.5 mg of the desired compound: mp (DSC) 195° C. Anal. Calc'd. for $C_{17}H_{14}F_3N_3O_2S$: C, 53.54; H, 3.70; N, 11.02; S, 8.41. Found: C, 53.21; H, 3.71; N, 10.77; S, 8.63.

EXAMPLE 35

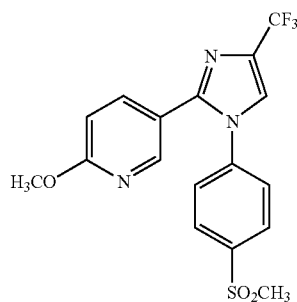

2-Methoxy-5-[1-[4-(methylsulfonyl)phenyl]-4-trifluoromethyl-1H-imidazol-2-yl]pyridine Step 1: Preparation of 2-methoxy-N-[4-(methylsulfonyl)phenyl]-5-pyridinecarboximidamide To a suspension of 4-(methylsulfonyl)aniline hydrochloride (1.8 g, 8.7 mmol) in toluene (50 ml) at 0° C., trimethylaluminum (2M solution in toluene, 5.2 ml, 10.4 mmol) was added over 10 minutes. The reaction mixture was warmed to room temperature and stirred for 2 hours. A solution of 6-methoxy-3-cyanopyridine (1.75 g, 13 mmol) in toluene (100 ml) was added over 10 minutes and the mixture was heated to 85–90° C. After 24 hours, the reaction mixture was cooled to room temperature and poured over a slurry of silica gel in chloroform. After filtration, the residue was washed with a mixture of methylene chloride and methanol and later with methanol. The combined filtrates were concentrated and the resulting yellowish solid was stirred with ethyl acetate (1000 ml) and filtered. The white solid (2 g, 75%) was used in the next reaction without further purification. Anal. Calc'd. for $C_{14}H_{16}N_3SClO_3 \cdot 0.5H_2O$: C, 47.93; H, 4.88; N, 11.98. Found: C, 48.01; H, 4.82; N, 11.32.

Step 2: Preparation of 2-methoxy-5-[4-hydroxy-1-[4-(methylsulfonyl)phenyl]-4-(trifluoromethyl)-4,5-dihydro-1H-imidazol-2-yl]pyridine To a mixture of the amidine of step 1 (1.9 g, 6.23 mmol) and sodium bicarbonate (1.05 g, 12.46 mmol) in isopropanol (150 ml), 3-bromo-1,1,1-trifluoroacetone (0.97 ml, 9.34 mmol) was added. After heating at 85–90° C for 48 hours, the reaction mixture was cooled and filtered. The residue was washed with methylene chloride and the combined organic fractions were dried over sodium sulfate, filtered and concentrated. The crude mixture (4.25 g) was purified by chromatography (silica gel, methylene chloride/methanol/ammonium hydroxide, 95/5/0.5) to give the 4,5-dihydro-imidazole (1.1 g, 42%) as a white solid: Anal. Calcld. for $C_{17}H_{16}N_3SO_4F_3 \cdot 0.5$ EtOAc: C, 49.67, H, 4.39, N, 9.15. Found: C, 49.80, H, 4.06, N. 9.33.

Step 3: Preparation of 2-methoxy-5-[1-[4-(methylsulfonyl)phenyl]-4-trifluoromethyl-1H-imidazol-2-yl]pyridine A mixture of the 4,5-dihydro-imidazole of step 2 (0.8 g, 1.93 mmol) and p-toluenesulfonic acid monohydrate (0.2 g, 1.04 mmol) in toluene (150 ml) was heated to reflux for 24 hours. The reaction mixture was cooled and the solvent removed under reduced pressure. The crude mixture (1.1 g) was purified by chromatography on silica gel using ethyl acetate/toluene (1/1) to give pure 2-methoxy-5-[1-[4-(methylsulfonyl)phenyl]-4-trifluoromethyl-1H-imidazol-2-yl]pyridine (0.38 g, 49%) as a white solid: mp (DSC) 166° C. Anal. Calc'd. for $C_{17}H_{14}N_3SO_3F_3$: C, 51.38, H, 3.55, N, 10.57. Found: C, 51.38, H, 3.25, N, 10.41.

EXAMPLE 36

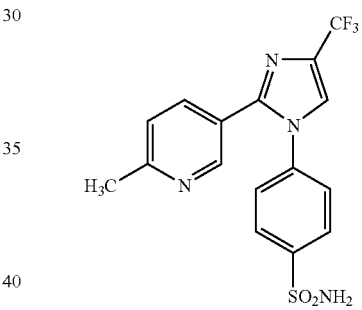

4-[2-(6-Methylpyridin-3-yl)-4-(trifluoromethyl)-1H-imidazol-1-yl]benzenesulfonamide To a clear solution of Example 31 (2.4 g, 6.3 mmol) in tetrahydrofuran (60 ml) at 0° C., n-BuMgCl (2M solution in THF, 15.7 ml, 31.5 mmol) was added over 10 minutes. After stirring for additional 20 minutes, the ice bath was removed and the solution was stirred for 2 hours. The reaction mixture was recooled to 0° C. and triethylborane (1M solution in THF, 38 ml, 38 mmol) was added. After stirring for 1 hour, the reaction was heated to reflux for 72 hours. The reaction mixture was cooled to room temperature and treated with aqueous sodium acetate (5.5 g in 22 ml water). After stirring for 5 minutes, solid hydroxylamine-O-sulfonic acid (5.5 g) was added and the mixture stirred for 24 hours. The reaction mixture was diluted with water and extracted with ether. The ethereal layer was dried over sodium sulfate, filtered and concentrated. The crude solid (13.3 g) was purified by chromatography (silica gel, hexane/isopropanol, 7/3) to give 4-[2-(6-methylpyridin-3-yl)-4-(trifluoromethyl)-1H-imidazol-1-yl]benzenesulfonamide (298 mg, 12%): mp (DSC) 203° C. Anal. Calc'd. for $C_{16}H_{13}N_4SO_2F_3 \cdot 0.25$ H$_2$O: C, 49.68, H, 3.52 N, 14.48, S, 8.29. Found: C, 49.88, H, 3.39, N, 13.94, S, 8.47.

EXAMPLE 37

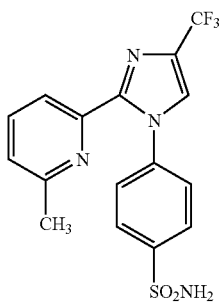

4-[2-(6-Methylpyridin-2-yl)-4-(trifluoromethyl)-1H-imidazol-1-yl]benzenesulfonamide To a clear solution of Example 32 (10 mmol) in tetrahydrofuran (60 ml) at 0° C., n-BuMgCl (2M solution in THF, 25 ml, 50 mmol) is added over 10 minutes. After stirring for an additional 20 minutes, the ice bath is removed and the solution is stirred for 2 hours. The reaction mixture is recooled to 0° C. and triethylborane (1M solution in THF, 60 ml, 60 mmol) is added. After stirring for 1 hour, the reaction is heated to reflux for 72 hours. The reaction mixture is cooled to room temperature and treated with aqueous sodium acetate (5.5 g in 22 ml water). After stirring for 5 minutes, solid hydroxylamine-O-sulfonic acid (5.5 g) is added and the mixture stirred for 24 hours. The reaction mixture is diluted with water and extracted with ether. The ethereal layer is dried over sodium sulfate, filtered and concentrated. The crude solid is purified by chromatography on silica gel using mixtures of hexane and isopropanol to give the desired product.

EXAMPLE 38

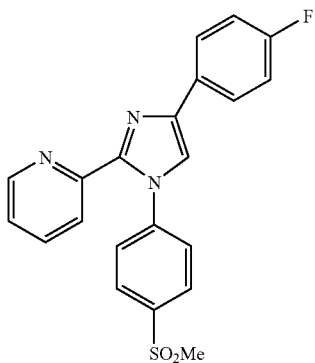

2-[4-(4-Fluorophenyl)-1-[4-(methylsulfonyl)phenyl]-1H-imidazol-2-yl]pyridine

Step 1: Preparation of N-[4-(methylsulfonyl)phenyl]-2-pyridinecarboximidamide

To a suspension of 5.00 g (24.0 mmol) of 4-methylsulfonylaniline hydrochloride in 150 ml of toluene stirring in an ice bath under nitrogen, was added dropwise 18.0 ml (containing 36.0 mmol) of a 2M solution of trimethylaluminum in toluene. After stirring for 30 minutes, a solution of 3.75 g (36.0 mmol) of 2-cyanopyridine in 20 ml of toluene. The resulting solution was stirred overnight at room temperature, and then at 85° for four hours. After cooling, the toluene was decanted and evaporated. The residue was taken up in 150 ml of methylene chloride and added back to the reaction flask. Methanol (150 ml) was cautiously added, and the mixture was filtered through a bed of silica gel using 50–50 methanol/methylene chloride as eluent. Evaporation of the solvent gave the amidine (6.85 g) as a yellow solid, which was used in the next reaction without further purification.

Step 2: Preparation of 2-[4-(4-fluorophenyl)-1-[4-(methylsulfonyl)phenyl]-1H-imidazol-2-yl]pyridine A mixture of the amidine of Step 1 (2.00 g, 7.27 mmol), 2-bromo-4'-fluoroacetophenone (3.16 g, 14.5 mmol) and sodium bicarbonate (1.22 g, 14.5 mmol) in isopropanol (70 ml) was stirred at reflux for two days. After cooling, the solvent was evaporated. The residue was partitioned between methylene chloride and aqueous sodium chloride, and the aqueous layer further extracted with methylene chloride. The combined organic extracts were dried over sodium sulfate, filtered, and evaporated. Chromatography of the residue over silica gel using 40% ethyl acetate/toluene followed by a second chromatography over silica gel using 40% ethyl acetate/methylene chloride as eluant gave 2-[4-(4-fluorophenyl)-1-[4-(methylsulfonyl)phenyl]-1H-imidazol-2-yl]pyridine (190 mg) as a light tan solid: m.p. 88–91° C. Anal. Calc'd for $C_{21}H_{16}FN_3O_2S$ (M.W. 393.44): C, 64.11;, H, 4.10, N, 10.68. Found: C, 63.80; H. 4.16, N, 10.23.

EXAMPLE 39

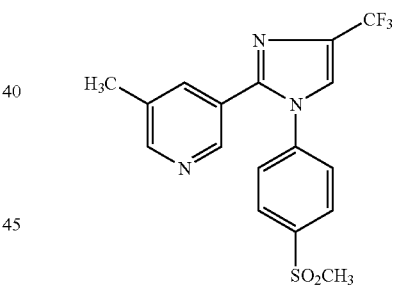

3-Methyl-5-[1-[4-(methyloulfonyl)phenyl]-4-(trifluoromethyl)-1H-imidazol-2-yl]pyridine Step 1: Preparation of 5-methylnicotinic acid:

The 5-methylnicotinic acid was prepared by the method of E. P. Kyba et al., *J. Org. Chem.*, 53, 3513–3521 (1988)]. To a solution of KMnO$_4$ in water (1.1 L) was added lutidine (25.0 g, 0.233 mol) and the mixture was stirred mechanically at 45° C. overnight. The reaction mixture was cooled and filtered through Celite® to remove MnO$_2$. The filtrate was concentrated to about 150 mL and acidified with a 2N HCl solution. White solid precipitated and was removed by filtration and washed with water (2×50 mL). The filtrate and washings were evaporated to dryness. The residue was boiled with ethanol (200 mL) and filtered repeatedly. The combined filtrate was concentrated to give of 5-methylnicotinic acid as a white solid (14.8 g, 46%): mp 213–215° C.

Step 2: Preparation of 5-methylpyridinylcarboxamide

A solution of 5-methylnicotinic acid from step 1 (14.5 g, 0.106 mol) in 125 mL of thionyl chloride was heated to reflux for 5 hours. Excess thionyl chloride was removed by distillation and the residue was suspended in 75 mL of dichloroethane. Ammonia was bubbled into the mixture at −30° C. for half hour and the mixture was stirred at room temperature overnight. Solvent was evaporated and the residue was treated with methanol and filtered. The filtrate was concentrated and the residue was extracted with boiling hot ethyl acetate (3×150 mL) to separate product from ammonium chloride. The extracts were filtered and concentrated to afford 10.6 g of 5-methylpyridinylcarboxamide as a brown solid (73%): mp 160–163° C.

Step 3: Preparation of 3-cyano-5-methylpyridine

To a suspension of 5-methylpyridinylcarboxamide from step 2 (10.5 g, 0.077 mol) in triethylamine (23.3 g, 0.23 mol) and 400 mL of methylene chloride was added trifluoroacetic anhydride (21.0 g, 0.100 mol) rapidly at 0° C. The reaction was completed after a few minutes. Water was added and the aqueous layer was extracted with methylene chloride. The combined organic layers were washed with water, brine and dried over magnesium sulfate. After filtration, the filtrate was concentrated to give 9.18 g of 3-cyano-5-methylpyridine crude, which 10 was used in the next step without purification.

Step 4: Preparation of 3-methyl-5-[4-hydroxy-1-[4-(methylsulfonyl)phenyl]-4-(trifluoromethyl)-4,5-dihydro-1H-imidazol-2-yl]pyridine To a suspension of 4-(methylsulfonyl)aniline hydrochloride (10.5 g, 0.051 mol) in toluene (500 mL) was added trimethylaluminum (2M solution in toluene, 75.0 mL, 0.150 mol) over 15 minutes at 0° C. The reaction mixture was warmed up to room temperature and stirred for 2 hours. A solution of 3-cyano-5-methylpyridine from step 3 in 90 mL of toluene was added over 10 minutes and the mixture was stirred at 85–90° C. for 16 hours. The reaction mixture was cooled to room temperature and filtered through a slurry of silica gel. After filtration, the residue was washed with methanol (800 mL). The combined filtrate was concentrated under reduced pressure and the residue was treated with a mixture of ether and hexane (2/1, 1000 mL). The brownish solid was filtered and washed with more ether and hexane to give 11.8 g of N-[4-(methylsulfonyl)phenyl]-5-methylnicotinamidine (80%). To a mixture of the above crude amidine (11.3 g, 0.039 mol) and sodium bicarbonate (9.83 g, 0.12 mol) in isopropanol (400 mL) was added 3-bromo-1,1,1-trifluoroacetone (11.2 g, 0.059 mol) quickly at room temperature. After heating the reaction mixture at 75–80° C. for 16 hours, the solvent was removed and the residue was partitioned between water and methylene chloride. The organic layers were washed with brine, dried over anhydrous magnesium sulfate, filtered and concentrated under reduced pressure. The crude was purified by chromatography on silica gel (ethyl acetate/acetone, 98:2) to give pure 3-methyl-5-[4-hydroxy-1-[4-(methylsulfonyl)phenyl]-4-(trifluoromethyl)-4,5-dihydro-1H-imidazol-2-yl]pyridine as a yellow solid (3.85 g, 25%): mp (DSC) 237–239° C.; Anal. Calc'd. for $C_{17}H_{16}F_3N_3O_3S$: C, 51.12, H, 4.04, N, 10.52,. S, 8.03. Found: C, 51.02, H, 3.94, N, 10.19, S, 8.11.

Step 5. Preparation of 3-methyl-5-[1-[4-(methylsulfonyl)phenyl]-4-(trifluoromethyl)-1H-imidazol-2-yl]pyridine A mixture of 3-methyl-5-[4-hydroxy-1-[4-(methylsulfonyl)phenyl]-4-(trifluoromethyl)-4,5-dihydro-1H-imidazol-2-yl]pyridine from step 4 (3.8 g, 9.5 mmol) and p-toluenesulfonic acid monohydrate (0.91 g, 4.8 mmol) in 150 mL of toluene was heated to reflux for 24 hours. The reaction mixture was cooled and the solvent was removed under reduced pressure. The residue was partitioned between water and methylene chloride. The organic layer was washed with water, saturated sodium bicarbonate solution and brine, dried over magnesium sulfate and filtered. The filtrate was evaporated in vacuo and the crude product was purified by flash chromatography on silica gel (ethyl acetate/acetone, 98:2) to give 3-methyl-5-(1-[4-(methylsulfonyl)phenyl]-4-(trifluoromethyl)-1H-imidazol-2-yl]pyridine as a yellow solid (1.7 g, 47%): mp (DSC) 196–198° C.; Anal. Calc'd. for $C_{17}H_{14}F_3N_3P_2S$: C, 53.54, H, 3.70, N, 11.02, S, 8.41. Found: C, 53.50, H, 3.65, N, 10.82, S, 8.55.

EXAMPLE 40

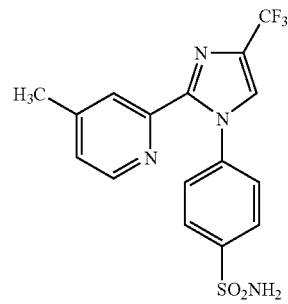

4-[2-(4-Methylpyridin-2-yl)-4-(trifluoromethyl)-1H-imidazol-1-yl]benzenesulfonamide To a stirred solution of the product of Example 34 (294.5 mg, 0.77 mmol) in 11 ml of freshly distilled THF at 0° C. was added 1.54 ml of butyl magnesium chloride (2.0 M solution in THF) over a period of 6 minutes. After stirring at 25° C. for 2.5 hours, the reaction was cooled to 0° C. and 3.85 ml of triethylborane (1.0 M solution in THF) was added over 30 minutes. The reaction mixture was stirred at 25° C. for 1.5 hours and heated to reflux. After 72 hours, the reaction mixture was diluted with 50 ml of ethyl acetate and washed with aqueous sodium bicarbonate (2×50 ml). The organic extracts were dried (MgSO₄), filtered and the solvent removed under reduced pressure to provide 359 of an orange solid, which was purified by chromatography (SiO₂; 40% toluene/ethyl acetate) to provide 68.1 mg of a light yellow solid. Preparative thin layer chromatography (SiO₂; 50% ethyl acetate/toluene) of 22 mg of this material yielded 14 mg of 4-[2-(4-methylpyridin-2-yl)-4-(trifluoromethyl)-1H-imidazol-1-yl]benzenesulfonamide: mp (DSC) 283° C. Anal. Calc'd. for $C_{16}H_{13}F_3N_4O_2S$: C, 50.26; H, 3.43; N, 14.65; S, 8.50. Found: C, 50.41; H, 3.37; N, 14.18; S., 8.51.

EXAMPLE 41

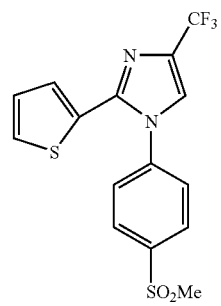

2-[1-[4-(Methyloulfonyl)phenyl]-4-(trifluoromethyl)-1H-imidazol-2-yl]thiophene Step 1: Preparation of N-[4-(methylsulfonyl) phenyl]-2-thiophenecarboximidamide To a suspension of 4-(methylsulfonyl)aniline (10.4 g, 61.1 mmol) in toluene (400 ml) at 0° C., trimethylaluminum (2M solution in toluene, 46.8 ml, 91.6 mmol) was added over 15 minutes. The reaction mixture was warmed to room temperature and stirred for 2 hours. A solution of 2-thiophenecarbonitrile (10.0 g, 91.6 mmol) in toluene (200 ml) was added over 10 minutes and the mixture was heated to 80–85° C. After 16 hours, the reaction mixture was cooled to room temperature and poured over a slurry of silica gel in chloroform. After filtration, the residue was washed with a mixture of methylene chloride/methanol and later with methanol. The combined filtrates were concentrated and the resulting yellow solid was stirred with ethyl acetate and filtered. The pale yellow solid (9.8 g, 57%) was used in the next reaction without further purification: m.p. (DSC) 182° C. Anal. Calcld. for $C_{12}H_{12}N_2S_2O_2$: C, 51.41, H. 4.31, N, 9.99, S, 22.87. Found: C, 51.02, H, 4.37, N, 9.80, S, 22.93.

Step 2: Preparation of 2-[4-hydroxy-1-[4-(methylsulfonyl)phenyl]-4-(trifluoromethyl)-4,5-dihydro-1H-imidazol-2-yl]thiophene To a mixture of the amidine of step 1 (2.0 g, 7.1 mmol) and sodium bicarbonate (1.2 g, 14.3 mmol) in isopropanol (200 ml), 3-bromo-1,1,1-trifluoroacetone 1.1 ml, 10.7 mmol) was added. After heating at 80–85° C. for 16 hours, the reaction mixture was cooled and filtered. The residue was washed with methylene chloride and the combined organic fractions were dried over sodium sulfate, filtered and concentrated. The crude mixture (25.7 g) was purified by chromatography (silica gel, ethyl acetate/hexane 55/45) to give the 4,5-dihydro-imidazole (1.1 g, 38%) as a white solid: mp (DSC) 214° C. Anal. Calcld. for $C_{15}H_{13}N_2S_2O_3F_3$: C, 46.15, H, 3.36, N, 7.18, S, 16.43. Found: C, 46.09, H, 3.26, N, 7.07, S, 16.71.

Step 3: Preparation of 2-[1-[4-(methylsulfonyl)phenyl]-4-(trifluoromethyl)-1H-imidazol-2-yl]thiorhene A mixture of the 4,5-dihydro-imidazole of step 2 (0.60 g, 1.54 mmol) and p-toluenesulfonic acid monohydrate (0.12 g, 0.63 mmol) in toluene (100 ml) was heated to reflux for 4.5 hours. The reaction mixture was cooled and the solvent removed under reduced pressure. The crude mixture (1.2 g) was purified by chromatography on silica gel using ethyl acetate/hexane 50/50 to give pure 2-[1-[4-(methylsulfonyl)phenyl]-4-(trifluoromethyl)-1H-imidazol-2-yl]thiophene (0.47 g, 82%) as a white solid: mp (DSC) 182° C. Anal. Calced. for $C_{15}H_{11}N_2S_2O_2F_3$ C, 48.38, H, 2.98, N, 7.52, S, 17.22. Found: C, 48.36, H, 3.02, N, 7.42, S, 17.47.

EXAMPLE 42

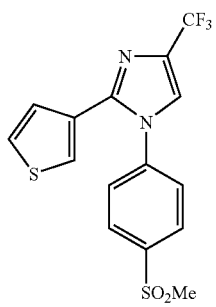

3-1-[4-(Methylsulfonyl)phenyl]-4-(trifluoromethyl)-1H-imidazol-2-yl]thiophene Step 1: Preparation of N-[4-(methylsulfonyl)phenyl]-2-thiorhenecarboximidamide To a suspension of 4-(methylsulfonyl)aniline (3.3 g, 19.5 mmol) in toluene (200 ml) at 0° C., trimethylaluminum (2M solution in toluene, 14.7 ml, 29.3 mmol) was added over 15 minutes. The reaction mixture was warmed to room temperature and stirred for 2 hours. A solution of 3-thiophenecarbonitrile (3.2 g, 29.3 mmol) in toluene (50 ml) was added over 10 minutes and the mixture was heated to 80–85° C. After 16 hours, the reaction mixture was cooled to room temperature and poured over a slurry of silica gel in chloroform. After filtration, the residue was washed with a mixture of methylene chloride/methanol and later with methanol. The combined filtrates were concentrated and the resulting yellow solid was stirred with ethyl acetate and filtered. The pale yellow solid (2.7 g, 49%) was used in the next reaction without further purification: mp (DSC) 213° C., Anal. Calcld. for $C_{12}H_{12}N_2S_2O_2$: C, 51.41, H, 4.31, N, 9.99, S, 22.87. Found: C, 51.28, H, 4.06, N, 9.86, S, 23.14.

Step 2: Preparation of 3-[4-hydroxy-1-[4-(methylsulfonyl)phenyl]-4-(trifluoromethyl)-4,5-dihydro-1H-imidazol-2-yl]thiophene To a mixture of the amidine of step 1 (3.5 g, 12.5 mmol) and sodium bicarbonate (2.1 g, 25.0 mmol) in isopropanol (200 ml), 3-bromo-1,1,1-trifluoroacetone (1.96 ml, 18.7 mmol) was added. After heating at 80–85° C. for 16 hours, the reaction mixture was cooled and filtered. The residue was washed with methylene chloride and the combined organic fractions were dried over sodium sulfate, filtered and concentrated. The crude material was purified by chromatography (silica gel, ethyl acetate/toluene (6/4)) to give 3-[4-hydroxy-1-[4-(methylsulfonyl)phenyl]-4-(trifluoromethyl)-4,5-dihydro-1H-imidazol-2-yl]thiophene (1.7 g, 35%) as a white solid: mp (DSC) 226° C. Anal. Calc'd. for $C_{15}H_{13}N_2S_2O_3F_3$: C, 46.15, H, 3.36, N,.7.18, S, 16.43. Found: C, 46.56, H, 3.39, N, 7.01, S, 16.88.

Step 3: Preparation of 3-[1-[4-(methylsulfonyl)phenyl]-4-(trifluoromethyl)-1H-imidazol-2-yl]thiophene A mixture of the 4,5-dihydro-imidazole of step 2 (1.5 g, 3.8 mmol) and p-toluenesulfonic acid monohydrate (0.30 g, 1.5 mmol) in toluene (250 ml) was heated to reflux for 40 hours. An additional p-toluenesulfonic acid monohydrate (0.15.g, 0.78 mmol) was added. The reaction mixture was heated to reflux for 18 hours. The reaction mixture was cooled and the solvent removed under reduced pressure. The crude mixture (3.5 g) was purified by chromatography on silica gel using ethyl acetate/toluene (55/45) to give pure 3-[1-[4-(methylsulfonyl)phenyl]-4-(trifluoromethyl)-1H-imidazol-2-yl]thiophene (0.90 g, 64%) as a white solid: mp 194–197° C. Anal. Calc'd. for $C_{15}H_{11}N_2S_2O_2F_3$: C, 48.38, H, 2.98, N, 7.52, S, 17.22. Found: C, 48.74, H, 2.98, N, 7.56, S. 17.45

EXAMPLE 43

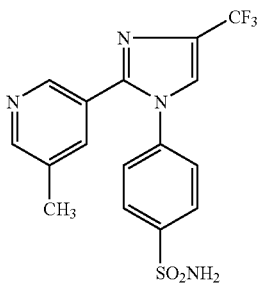

4-[2-(5-Methylpyridin-3-yl)-4-(trifluoromethyl)-1H-imidazol-1-yl]benzenesulfonamide To a solution of 3-methyl-5-(1-[4-(methylsulfonyl)phenyl]-4-(trifluoromethyl)-1H-imidazol-2-yl]pyridine (Example 39) (1.9 mmol) in 25 mL of dry THF was added n-BuMgCl (3.8 mL of 2.0 M THF solution, 7.5 mmol) slowly at 0° C. After stirring for additional 15 minutes, the solution was stirred at room temperature for 2 hours. The reaction mixture was re-cooled to 0° C. and triethylborane (9.5 mL of 1.0 M THF solution, 9.5 mmol) was added. After stirring at for 2 hours, the mixture was heated to reflux for 72 hours. The reaction mixture was cooled to room temperature and treated with a solution of sodium acetate (2.3 g) in 10 mL of water. After stirring for 5 minutes, hydroxylamine-O-sulfonic acid (2.3 g) was added and the mixture was stirred for 20 hours. The reaction mixture was extracted with ether (2×100 mL). The ethereal layer was dried over $MgSO_4$, filtered and concentrated in vacuo. The crude product was purified by chromatography on silica gel (isopropanol/toluene, 5:95) to give 0.07 g of 4-[2-(5-methylpyridin-3-yl)-4-(trifluoromethyl)-1H-imidazol-1-yl]benzenesulfonamide as a colorless solid (8%): mp 242–243° C. Anal. Calc'd. For $C_{16}H_{13}F_3N_4O_2S$: C, 50.26, H, 3.43, N, 14.65, S, 8.39. Found: C, 50.02, H, 3.63, N, 14.26, S, 8.41.

EXAMPLE 44

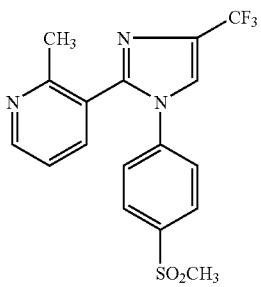

2-Methyl-3-[1-[4-(methyloulfonyl)phenyl]-4-(trifluoromethyl)-1H-imidazol-2-yl]pyridine Step 1: Preparation of 2-methylnicotinamide:

To a stirred mixture of 2-methylnicotinic acid (15.0 g, 0.111 mol) and 1,1-carbonyldiimidazole (36.0 g, 0.222 mol) was added 300 mL of methylene chloride dropwise. The reaction mixture was stirred at room temperature overnight. Ammonia gas was distilled into the reaction mixture for 30 minutes using a dry ice condenser and the mixture was stirred at room temperature for an additional hour. Solvent was removed under vacuum and the residue was dissolved with 500 mL of acetonitrile. The solution was concentrated to half volume at low temperature and the product precipitated out as white solid. The crude mixture was recrystallized from ethanol/ether to give 11.5 g of 2-methylnicotinamide as a colorless crystal (76%): mp 160–163° C. Anal. Calcld. For $C_7H_8N_2O$: C, 61.75, H, 5.92, N, 20.57. Found: C, 61.44, H, 6.14, N, 20.66.

Step 2: Preparation of 3-cyano-2-methylpyridine:

To a suspension of 2-methylnicotinamide from step 1 (11.1 g, 0.081 mol) in triethylamine (24.8 g, 0.243 mol) and 400 mL of methylene chloride was added trifluoroacetic anhydride (21.0 g, 0.100 mol) rapidly at 0° C. The reaction was complete after a few minutes at this temperature. Water was added and the aqueous layer was extracted with methylene chloride. The combined organic layers were washed with water, brine and dried over magnesium sulfate. After filtration, the filtrate was concentrated and the residue was purified by chromatography on silica gel (ethyl acetate/hexane, 1:1) to give 7.2 g of 3-cyano-2-methylpyridine as a pale yellow solid (75%): mp(DSC) 56–58° C.

Step 3: Preparation of 2-methyl-3-[4-hydroxy-1-[4-(methylsulfonyl)phenyl]-4- (trifluoromethyl)-4 5-dihydro-1H-imidazol-2-yl]pyridine:

To a suspension of 4-(methylsulfonyl)aniline hydrochloride (6.85 g, 0.040 mol) in dichloroethane (400 mL) was added triethylaluminum (1.9M solution in toluene, 32.0 mL, 60 mmol) over 15 minutes at 0° C. The reaction mixture was warmed to room temperature and stirred for 2 hours. A solution of 3-cyano-2-methylpyridine, from step 2, in 70 mL of dichloroethane was added over 10 minutes and the mixture was stirred at 75° C. for 16 hours. The reaction mixture was cooled to room temperature and treated with 50 g of silica gel. The mixture was stirred for 30 minutes and filtered. The filtrate and washings were concentrated under reduced pressure and the residue was washed with ether to give 7.3 g of crude 2-methyl-N-[4-(methylsulfonyl)phenyl]-3-pyridinecarboximidamide (60%). To a mixture of the above crude amidine (7.0 g, 0.024 mol) and sodium bicarbonate (4.0 g, 0.048 mol) in isopropanol (350 mL) was added 3-bromo-1,1,1-trifluoroacetone (6.9 g, 0.036 mol) rapidly at room temperature. After heating the reaction mixture at 75–80° C. for 16 hours, the solvent was removed and the residue was partitioned between water and methylene chloride. The organic layers were washed with brine, dried over anhydrous magnesium sulfate, filtered and concentrated under reduced pressure. The crude was purified by chromatography on silica gel (ethyl acetate/acetone, 98:2) to give 4.02 g of pure 2-methyl-3-[4-hydroxy-1-[4-(methylsulfonyl)phenyl]-4-(trifluoromethyl)-4,5-dihydro-1H-imidazol-2-yl]pyridine as a yellow solid (25%): mp (DSC) 237–239° C. Anal. Calc'd. for $C_{17}H_{16}F_3N_3O_3S$: C, 51.12, H, 4.04, N, 10.52, S, 8.03. Found: C, 50.92, H, 4.12, N, 10.04, S, 7.83.

Step 4: Preparation of 2-methyl-3-[1-[4-(methylsulfonyl)phenyl]-4-(trifluoromethyl)-1H-imidazol-2-yl]pyridine:

A mixture of 2-methyl-3-[4-hydroxy-1-[4-(methylsulfonyl)phenyl]-4-(trifluoromethyl)-4,5-dihydro-1H-imidazol-2-yl]pyridine from step 3 (3.97 g, 0.01 mol) and p-toluenesulfonic acid monohydrate (0.60 g, 0.0032 mol) in 250 mL of toluene was heated to reflux for 24 hours. The reaction mixture was cooled and the solvent was removed under reduced pressure. The residue was partitioned between water and methylene chloride. The organic layer was washed with water, saturated sodium bicarbonate solution and brine, dried over magnesium sulfate and filtered. The filtrate was evaporated in vacuo and the crude product was purified by recrystallization from ethyl acetate/hexane to give 2.8 g of 2-methyl-3-[1-[4-(methylsulfonyl)phenyl]-4-(trifluoromethyl)-1H-imidazol-2-yl]pyridine (73%): mp 160–161° C. Anal. Calc'd. for $C_{17}H_{14}F_3N_3O_2S$: C, 53.54, H, 3.70, N, 11.02, S, 8.41. Found: C, 53.58, Ho 3.88, N, 11.02, S, 8.51.

EXAMPLE 45

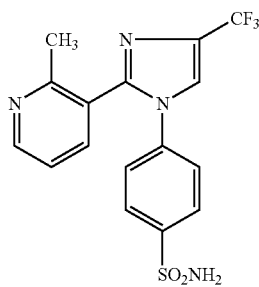

4-[2-(2-Methylpyridin-3-yl)-4-(trifluoromethyl)-1H-imidazol-1-yl]benzenesulfonamide Step 1: Preparation of 2-methyl-3-[1-]4-[[2-(trimethylsilyl)ethyl]sulfonyl]phenyl]-4-(trifluoromethyl)-1H-imidazol-2-yl]pyridine To a solution of diisopropylamine (0.7 mL, 0.005 mol) in 9 mL of dry THF was added butyllithium (BuLi) (2.83 mL of 1.62M solution in hexane, 4.6 mmol) at 0° C. The solution was stirred at this temperature for 5 minutes and cooled to −78° C. with a dry ice/isopropanol bath. A solution of 2-methyl-3-[1-[4-(methylsulfonyl)phenyl]-4-(trifluoromethyl)-1H-imidazol-2-yl]pyridine (Example 44) (1.46 g, 3.8 mmol) in 12 mL of dry THF was added over 10 minutes and the reaction mixture was stirred at −78° C. for 1 hour. (Iodomethyl)trimethylsilane (1.23 g, 57 mmol) was added dropwise and the reaction mixture was warmed to room temperature and was stirred overnight. The reaction was quenched with 50 mL of 1 N HCl and the aqueous phase was extracted with ethyl acetate (3×60 mL). The combined organic layers were washed with brine, dried over $MgSO_4$, filtered and concentrated. The crude mixture was purified by chromatography on silica gel (ethyl acetate/hexane, 65:35) to give 1.30 g of 2-methyl-3-[1-[4-[[2-(trimethylsilyl)ethyl]sulfonyl]phenyl]-4-(trifluoromethyl)-1H-imidazol-2-yl]pyridine as a white solid (74%): mp(DSC) 155–157° C. Anal. Calc'd. for $C_{21}H_{24}F_3N_3O_2SSi$: C, 53.94; H, 5.17; N, 8.99; S, 6.86. Found: C, 53.77; H, 4.94; N, 8.75; S, 6.98.

Step 2: Preparation of 4-[2-(2-methylpyridin-3-yl)-4-(trifluoromethyl)-1H-imidazol-1-yl]benzenesulfonamide:

To a solution of 2-methyl-3-[1-[4-[[2-(trimethylsilyl)ethyl]sulfonyl]phenyl]-4-(trifluoromethyl)-1H-imidazol-2-yl]pyridine from Step 1 (0.234 g, 0.5 mmol) in 1.5 mL of dry THF was added n-Bu$_4$NF (1.5 mL of 1.0M THF solution, 1.5 mmol). The mixture was heated to reflux for 1 hour and cooled to room temperature. A solution of sodium acetate (0.19 g, 2.3 mmol) in 3 mL of water and hydroxylamine-o-sulfonic acid (0.28 g, 2.5 mmol) were added sequentially and the mixture was stirred for 1 hour. Water (7 mL) and ethyl acetate (7 mL) were added. The organic phase was separated and washed with sat. $NaHCO_3$ solution, water, and brine, dried over $MgSO_4$ and filtered. The filtrate was concentrated and the residue was purified by chromatography on silica gel (ethyl acetate/acetone, 95:5) to give 0.16 g of 4-[2-(2-methylpyridin-3-yl)-4-(trifluoromethyl)-1H-imidazol-1-yl]benzenesulfonamide as a colorless solid (84%): mp 235–237° C. Anal. Calc'd. for $C_{16}H_{13}F_3N_4O_2S$: C, 50.26; H, 3.43; N, 14.65; S, 8.39. Found: C, 50.06; H, 3.29; N, 14.44; S, 8.52.

EXAMPLE 46

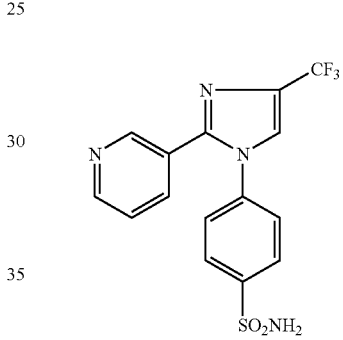

4-[2-(Pyridin-3-yl)-4-(trifluoromethyl)-1H-imidazol-1-yl]benzenesulfonamide

3-[1-[4-[[2-(Trimethylsilyl)ethyl]sulfonyl]phenyl]-4-(trifluoromethyl)-1H-imidazol-2-yl]pyridine was prepared with the product of Example 28 with a method similar to that described in Example 45, Step 1. To a solution of 3-[1-[4-[[2-(trimethylsilyl)ethyl]sulfonyl]phenyl]-4-(trifluoromethyl)-1H-imidazol-2-yl]pyridine (0.200 g, 0.46 mmol) in 1.0 mL of dry THF was added n-Bu$_4$NF (1.38 mL of 1.0 M THF solution, 1.38 mmol). The mixture was heated to reflux for 1 hour and cooled to room temperature. A solution of sodium acetate (0.17 g, 2.1 mmol) in 3 mL of water and hydroxylamine-O-sulfonic acid (0.26 g, 2.3 mmol) were added sequentially and the mixture was stirred for 1 hour. Water (7 mL) and ethyl acetate (7 mL) were added. The organic phase was separated and washed with saturated $NaHCO_3$ solution, water, brine, dried over $MgSO_4$ and filtered. The filtrate was concentrated and the residue was purified by chromatography on silica gel (ethyl acetate/acetone, 95:5) to give 0.147 g of 4-[2-(pyridin-3-yl)-4-(trifluoromethyl)-1H-imidazol-1-yl]benzenesulfonamide as a colorless solid (87%): mp(DSC) 213–215° C. Anal. Calc'd. for $C_{15}H_{11}F_3N_4O_2S$: C, 48.91; H. 3.01; N, 15.21; S, 8.71. Found: C, 48.58; H, 2.99; N, 14.87; S. 8.85.

The following imidazole derivatives could be prepared by the procedure described in Example 26 or 45:

EXAMPLE 47

4-[2-(4-chlorophenyl)-4-methyl-1H-imidazol-1-yl]benzenesulfonamide

EXAMPLE 48

4-(2-(4-chlorophenyl)-4-phenyl-1H-imidazol-1-yl]benzenesulfonamide

EXAMPLE 49

4-[2-(4-chlorophenyl)-4-(4-fluorophenyl)-1H-imidazol-1-yl]benzenesulfonamide

EXAMPLE 50

4-[2-(4-chlorophenyl)-4-(4-bromophenyl)-1H-imidazol-1-yl]benzenesulfonamide

EXAMPLE 51

4-[2-(4-chlorophenyl)-4-[2-naphthyl)-1H-imidazol-1-yl]benzenesulfonamide

EXAMPLE 52

4-[2-(4-chlorophenyl)-4-[4-(trifluoromethoxy)phenyl]-1H-imidazol-1-yl]benzenesulfonamide

EXAMPLE 53

4-[2,4-bis(4-chlorophenyl)-1H-imidazol-1-yl]benzenesulfonamide;

EXAMPLE 54

4-[2-(4-chlorophenyl)-4-(3-chlorophenyl)-1H-imidazol-1-yl]benzenesulfonamide

EXAMPLE 55

4-[2-(4-chlorophenyl)-4-[4-(methoxy)phenyl]-1H-imidazol-1-yl]benzenesulfonamide

EXAMPLE 56

4-[2-(4-chlorophenyl)-4-(3-fluorophenyl)-1H-imidazol-1-yl]benzenesulfonamide

EXAMPLE 57

4-[2-(4-chlorophenyl)-4-[(4-chlorophenoxy)methyl]-1H-imidazol-1-yl]benzenesulfonamide

EXAMPLE 58

4-[2-(3,4-methylenedioxyphenyl)-4-(trifluoromethyl)-1H-imidazol-1-yl]benzenesulfonamide

EXAMPLE 59

4-[2-(3-fluoro-4-methoxyphenyl)-4-(trifluoromethyl)-1H-imidazol-1-yl]benzenesulfonamide

EXAMPLE 60

4-[2-(4-chlorophenyl)-4-[(phenylthio)methyl]-1H-imidazol-1-yl]benzenesulfonamide

EXAMPLE 61

4-[2-(4-chlorophenyl)-4-[(N-methyl-N-phenylamine)methyl]-1H-imidazol-1-yl]benzenesulfonamide

EXAMPLE 62

4-[2-(4-chlorophenyl)-4-[(2-quinolylmethoxy)methyl]-1H-imidazol-1-yl]benzenesulfonamide

EXAMPLE 63

4-[2-(4-chlorophenyl)-4-methoxymethyl-1H-imidazol-1-yl]benzenesulfonamide

EXAMPLE 64

4-[2-(4-fluorophenyl)-4-(trifluoromethyl)-1H-imidazol-1-yl]benzenesulfonamide

EXAMPLE 65

4-[2-phenyl-4-(trifluoromethyl)-1H-imidazol-1-yl]benzenesulfonamide; and

EXAMPLE 66

4-[2-(4-trifluoromethylphenyl)-4-(trifluoromethyl)-1H-imidazol-1-yl]benzenesulfonamide The following imidazole derivative was prepared by the procedure described in Example 28:

EXAMPLE 67

1-methyl-3-[1-[4-(methylsulfonyl)phenyl]-4-trifluoromethyl-1H-imidazol-2-yl]-1H-indole The following imidazole derivatives in Tables I–IV were obtained according to procedures of Schemes I–XV. Many of these were synthesized by using the experimental conditions given in Examples 1–5, and 44. The sulfonamide derivatives were synthesized from the corresponding sulfones using experimental procedure given for Examples 26–27, and 45 and from protected nitrobenzenes as in Example 179.

TABLE I
Characterization of Compounds
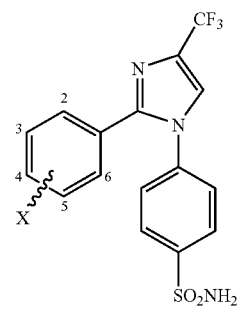
| Example | X | mp DSC (° C.) | Calc'd C | H | N | S | Found C | H | N | S |
|---|---|---|---|---|---|---|---|---|---|---|
| 68 | 4-CH₃ | 263 | 53.54 | 3.70 | 11.02 | 8.41 | 53.91 | 3.62 | 10.71 | 8.57 |
| 69 | 3-CH₃ | 222.9 | 53.54 | 3.70 | 11.02 | 8.41 | 53.81 | 3.56 | 10.89 | 8.54 |
| 70 | 3-Cl | 204.1 | 47.82 | 2.76 | 10.46 | 7.98 | 48.09 | 2.50 | 10.09 | 8.16 |
| 71 | 3,5-diF, 4-OCH₃ | 245.1 | 57.27 | 3.85 | 10.02 | 7.64 | 56.94 | 3.77 | 9.78 | 7.50 |
| 72 | H | 234–235 | 52.31 | 3.29 | 11.44 | 8.71 | 52.40 | 3.27 | 11.06 | 8.44 |
| 73 | 3,4-diF | 215.9 | 47.65 | 2.50 | 10.42 | 7.95 | 47.68 | 2.44 | 10.25 | 8.07 |
| 74 | 3-Cl, 4-OCH₃ | 212.0 | 47.29 | 3.03 | 9.73 | 7.43 | 47.41 | 2.76 | 9.49 | 7.48 |
| 75 | 3-F | 204–205 | 49.74 | 3.13 | 10.88 | 8.30 | 49.99 | 2.95 | 10.49 | 8.45 |
| 76 | 4-Cl, 5-OCH₃ | 208–209 | 47.29 | 3.03 | 9.73 | 7.43 | 47.21 | 2.95 | 9.62 | 7.73 |
| 77 | 3-F, 5-OCH₃ | 208.8 | 49.16 | 3.15 | 10.12 | 7.72 | 49.31 | 2.95 | 9.84 | 7.88 |
| 78 | 3-Br, 4-OCH₃ | 208–210 | 41.69 | 2.98 | 8.58 | 6.55 | 41.52 | 2.9 | 7.81 | 6.14 |
| 79 | 2-F | 169–171 | 49.87 | 2.88 | 10.9 | 8.32 | 49.5 | 2.83 | 10.34 | 8.61 |
| 80 | 3-Br | 203–205 | 43.07 | 2.48 | 9.42 | 7.19 | 42.71 | 2.44 | 8.94 | 6.68 |
| 81 | 3-Cl, 4-SCH₃ | 205–207 | 45.59 | 2.93 | 9.38 | 14.32 | 46.00 | 3.11 | 8.96 | 14.29 |
| 82 | 3-Cl, 5-CH₃ | 219–221 | 49.1 | 3.15 | 10.11 | 7.71 | 49.44 | 3.11 | 9.7 | 7.89 |
| 83 | 3-F, 5-CH₃ | 230–231 | 51.13 | 3.28 | 10.52 | 8.03 | 51.49 | 3.51 | 10.00 | 8.15 |
| 84 | 3-CF₃ | 208.8 | 46.90 | 2.55 | 9.65 | 7.37 | 47.30 | 2.54 | 9.47 | 7.49 |
TABLE II
Characterization of Compounds
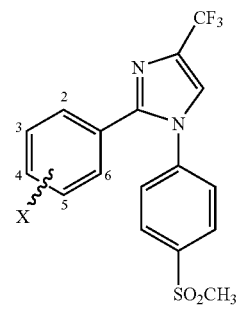
| Example | X | mp DSC (° C.) | Calc'd C | H | N | S | Found C | H | N | S |
|---|---|---|---|---|---|---|---|---|---|---|
| 85 | 3,4-diF | 159.5 | 50.75 | 2.76 | 6.96 | 8.80 | 50.66 | 2.82 | 6.87 | 8.30 |
| 86 | 3-CH₃ | 169.8 | 56.84 | 3.97 | 7.36 | 8.43 | 56.88 | 3.76 | 7.26 | 8.81 |
| 87 | 3-Cl | 175.4 | 50.94 | 3.02 | 6.99 | 8.00 | 51.06 | 3.06 | 6.93 | 8.13 |
| 88 | 3-F | 189.3 | 53.13 | 3.15 | 7.29 | 8.34 | 53.50 | 3.16 | 7.22 | 8.46 |
| 89 | 4-F, 3-CH₃ | 166.9 | 54.27 | 3.54 | 7.03 | 8.05 | 54.47 | 3.40 | 6.88 | 8.31 |
| 90 | 3-CF₃ | 168.2 | 49.77 | 2.78 | 6.45 | 7.38 | 49.91 | 2.60 | 6.34 | 7.68 |
| 91 | 3,5-diF, 4-OCH₃ | 174.7 | 50.00 | 3.03 | 6.48 | 7.42 | 50.00 | 3.03 | 6.33 | 7.44 |

TABLE II-continued
Characterization of Compounds
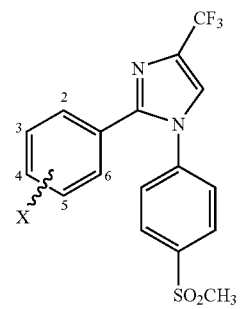
| | | | Elemental Analysis | | | | | | | |
|---|---|---|---|---|---|---|---|---|---|---|
| | | mp | Calc'd | | | | Found | | | |
| Example | X | DSC (° C.) | C | H | N | S | C | H | N | S |
| 92 | 3-CH$_2$OCH$_3$ | 101.9 | 55.60 | 4.18 | 6.83 | 7.81 | 55.50 | 4.14 | 6.72 | 8.06 |
| 93 | 3-Cl, 4-OCH$_3$ | 193.3 | 50.18 | 3.28 | 6.50 | 7.44 | 49.78 | 3.32 | 6.39 | 7.42 |
| 94 | 3,4-diCH$_3$ | 187–188 | 57.86 | 4.34 | 7.10 | 8.13 | 57.59 | 4.23 | 7.20 | 8.05 |
| 95 | 4-OCH$_3$ | 167.5 | 54.54 | 3.81 | 7.07 | 8.09 | 54.32 | 3.88 | 6.90 | 8.24 |
| 96 | 3-OCH$_3$ | 143.2 | 54.54 | 3.81 | 7.07 | 8.09 | 54.27 | 3.82 | 6.91 | 8.31 |
| 97 | 4-Cl, 5-OCH$_3$ | 215.3 | 50.18 | 3.28 | 6.50 | 7.44 | 50.20 | 3.20 | 6.23 | 7.76 |
| 98 | 3-F, 5-OCH$_3$ | 178–179 | 52.17 | 3.41 | 6.76 | 7.74 | 52.07 | 3.29 | 6.66 | 7.87 |
| 99 | 4-SCH$_3$ | 193–195 | 52.42 | 3.67 | 6.79 | 15.55 | 52.19 | 3.63 | 6.61 | 15.55 |
| 100 | 4-SO$_2$CH$_3$ | 215–216 | 48.64 | 3.4 | 6.3 | 14.43 | 48.87 | 3.47 | 6.24 | 14.36 |
| 101 | 3,5-CH$_3$, 4-OCH$_3$ | 167–169 | 56.6 | 4.51 | 6.6 | 7.55 | 56.04 | 4.61 | 6.44 | 7.72 |
| 102 | 2,5-CH$_3$, 4-OCH$_3$ | 193–194 | 56.6 | 4.51 | 6.6 | 7.55 | 56.63 | 4.65 | 6.47 | 7.99 |
| 103 | 2-F | 191–192 | 53.13 | 3.15 | 7.29 | 8.34 | 53.55 | 3.55 | 6.89 | 8.55 |
| 104 | 2-Cl | 201–203 | 50.94 | 3.02 | 6.99 | 8.00 | 50.86 | 3.06 | 6.88 | 7.83 |
| 105 | 4-N(CH$_3$)$_2$ | 219–221 | 55.74 | 4.43 | 10.26 | 7.83 | 55.19 | 4.00 | 10.06 | 7.81 |
| 106 | 3-F, 4-N(CH$_3$)$_2$ | 163–164 | 53.59 | 4.01 | 9.83 | 7.5. | 53.48 | 3.79 | 9.73 | 7.67 |
| 107 | 3-Br | 163–165 | 45.86 | 3.73 | 6.29 | 7.2 | 45.84 | 2.59 | 6.16 | 7.37 |
| 108 | 3-NO$_2$ | 207–209 | 49.64 | 2.94 | 10.21 | 7.79 | 49.48 | 3.01 | 10.07 | 7.81 |
| 109 | 4-NH(CH$_3$) | 200–202 | 54.68 | 4.08 | 10.63 | 8.11 | 54.74 | 3.98 | 10.42 | 7.96 |
| 110 | 3-NH$_2$ | 218–200 | 53.54 | 3.7 | 11.02 | 8.41 | 52.92 | 3.58 | 10.67 | 8.6 |
| 111 | 3-NH(CH$_3$) | 90–92 | 54.68 | 4.08 | 10.63 | 8.11 | 54.56 | 4.12 | 10.28 | 8.09 |
| 112 | 3-F, 4-NH(CH$_3$) | 205–206 | 52.3 | 3.66 | 10.16 | 7.76 | 51.74 | 3.51 | 9.96 | 7.99 |
| 113 | 3-SCH$_3$ | 135–137 | 52.42 | 3.67 | 6.79 | 15.55 | 52.29 | 3.57 | 6.74 | 15.22 |
| 114 | 3-Cl, 5-CH$_3$ | 171–173 | 52.12 | 3.4 | 6.75 | 7.73 | 51.95 | 3.22 | 6.69 | 7.9 |
| 115 | 3,5-Cl, 4-OCH$_3$ | 198–202 | 46.47 | 2.82 | 6.02 | 15.24 | 46.49 | 2.77 | 5.8 | 14.73 |
| 116 | 3-F, 4-CH$_3$ | 173–176 | 54.27 | 3.54 | 7.03 | 8.05 | 54.65 | 3.64 | 6.74 | 8.14 |
| 117 | 3-F, 5-CH$_3$ | 178–181 | 54.27 | 3.54 | 7.03 | 8.05 | 53.85 | 3.29 | 6.81 | 8.3 |
| 118 | 4-Cl, 3-Cl$_3$ | 182–184 | 52.12 | 3.4 | 6.25 | 7.73 | 52.36 | 3.49 | 6.78 | 7.95 |
| 119 | 3-Cl, 4-N(CH$_3$)$_2$ | 178–179 | 51.41 | 3.86 | 9.47 | 7.22 | 51.44 | 3.65 | 9.34 | 7.28 |
| 120 | 3-Cl, 4-SCH$_3$ | 181–184 | 48.38 | 3.16 | 6.27 | 14.35 | 47.9 | 3.05 | 5.97 | 13.84 |
| 121 | 2-CH$_3$ | 132–134 | 56.84 | 3.97 | 7.36 | 8.43 | 56.75 | 3.82 | 7.28 | 8.59 |
| 122 | 3-N(CH$_3$)$_2$ | 170–171 | 55.74 | 4.43 | 10.26 | 7.83 | 55.66 | 4.66 | 9.95 | 7.7 |

TABLE III

Characterization of Compounds

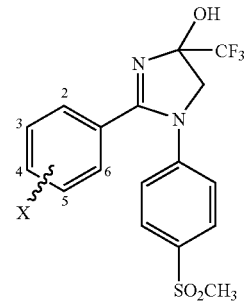

| | | | Elemental Analysis | | | | | | | |
|---|---|---|---|---|---|---|---|---|---|---|
| | | mp | Calc'd | | | | Found | | | |
| Example | X | DSC (° C.) | C | H | N | S | C | H | N | S |
| 123 | 3-Cl, 4-OCH$_3$ | 222.1 | 48.17 | 3.59 | 6.24 | 7.14 | 48.11 | 3.83 | 5.80 | 7.21 |
| 124 | 3-CH$_3$, 4-OCH$_3$ | 173.7 | 54.85 | 4.70 | 6.73 | 7.71 | 54.65 | 4.45 | 6.58 | 8.30 |
| 125 | 4-OCH$_3$ | 168.5 | 52.17 | 4.13 | 6.76 | 7.74 | 52.32 | 4.20 | 6.52 | 7.84 |
| 126 | 3-OCH$_3$ | 176.4 | 52.17 | 4.13 | 6.76 | 7.74 | 51.80 | 4.12 | 6.55 | 8.02 |
| 127 | 4-Cl, 5-OCH$_3$ | 137–138 | 46.85 | 3.80 | 6.07 | 6.95 | 46.45 | 3.72 | 5.84 | 7.25 |
| 128 | 3-F, 5-OCH$_3$ | 185–186 | 50.00 | 3.73 | 6.48 | 7.42 | 50.12 | 3.78 | 6.36 | 7.70 |
| 129 | 4-SCH$_3$ | 187–190 | 50.22 | 3.98 | 6.51 | 14.9 | 49.99 | 3.88 | 6.32 | 14.95 |
| 130 | 3-F, 4-N(CH$_3$)$_2$ | 212–214 | 51.23 | 4.3 | 9.43 | 7.2 | 50.58 | 4.38 | 9.09 | 7.23 |

TABLE IV

Characterization of Compounds

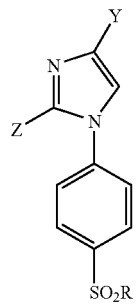

| | | | | | Elemental Anaylsis | | | | | | | |
|---|---|---|---|---|---|---|---|---|---|---|---|---|
| | | | | mp | Calc'd | | | | Found | | | |
| Ex. | R | Y | Z | DSC (° C.) | C | H | N | S | C | H | N | S |
| 131 | NH$_2$ | CF$_3$ | 3-methoxy-5-pyridyl | 262–264 | 48.24 | 3.29 | 14.06 | 8.05 | 48.49 | 3.34 | 13.55 | 8.01 |
| 132 | CH$_3$ | CF$_3$ | 3-methoxy-5-pyridyl | 207–208 | 51.38 | 3.55 | 10.57 | 8.07 | 50.98 | 3.31 | 10.38 | 8.15 |
| 133 | CH$_3$ | CF$_3$ | 2-isoquinolyl | 264.5 | 57.55 | 3.38 | 10.07 | 7.68 | 57.52 | 3.36 | 9.98 | 7.60 |
| 134 | CH$_3$ | CF$_3$ | 2-pyrazinyl | 200.6 | 48.91 | 3.01 | 15.21 | | 48.79 | 2.84 | 15.00 | |
| 135 | CH$_3$ | CF$_3$ | 2-methyl-4-thiazolyl | 197.2 | 46.51 | 3.12 | 10.85 | 16.35 | 46.53 | 3.28 | 10.62 | 16.67 |
| 136 | NH$_2$ | H | 5-methyl-2-pyridyl | 216 | 50.26 | 3.43 | 14.65 | | 50.58 | 3.49 | 14.50 | |
| 137 | CH$_3$ | CH$_3$ | 3-pyridyl | 130–131 | 57.99 | 4.56 | 12.68 | | 57.84 | 4.83 | 12.49 | |
| 138 | NH$_2$ | CF$_3$ | 6-methyl-2-pyridyl | 260 | 50.26 | 3.43 | 14.65 | | 50.33 | 3.60 | 14.39 | |
| 139 | CH$_3$ | CF$_3$ | 4-methyl-3-pyridyl | 192–193 | 53.54 | 3.70 | 11.02 | 8.41 | 53.40 | 3.62 | 10.68 | 8.60 |
| 140 | NH$_2$ | CF$_3$ | 2-methyl-4-thiazolyl | 250.8 | 43.30 | 2.85 | 14.43 | 16.51 | 43.28 | 2.79 | 14.14 | 16.48 |
| 141 | NH$_2$ | CF$_3$ | 4-methyl-3-pyridyl | 224–227 | 50.26 | 3.43 | 14.65 | 8.39 | 49.94 | 3.49 | 14.44 | 8.58 |
| 142 | CH$_3$ | CF$_3$ | 3-methyl-2-pyridyl | 178 | 53.54 | 3.70 | 11.02 | | 53.44 | 3.49 | 10.92 | |
| 143 | CH$_3$ | CF$_3$ | 1-isoquinolyl | 200–201 | 57.55 | 3.38 | 10.07 | | 57.58 | 3.38 | 10.03 | |
| 144 | NH$_2$ | CF$_3$ | 3-methyl-2-pyridyl | 235 | 50.26 | 3.43 | 14.65 | | 49.92 | 3.34 | 14.43 | |
| 145 | CH$_3$ | CF$_3$ | 3-quinolyl | 221 | 57.28 | 3.47 | 9.66 | | 57.16 | 3.39 | 9.59 | |
| 146 | NH$_2$ | CF$_3$ | 2-thienyl | 225.5–226.5 | 45.04 | 2.70 | 11.25 | 17.18 | 44.92 | 2.62 | 11.09 | 17.48 |
| 147 | CH$_3$ | CF$_3$ | 5-bromo-3-pyridyl | 235–237 | 43.07 | 2.48 | 9.42 | 7.19 | 42.64 | 2.34 | 9.22 | 7.69 |
| 148 | CH$_3$ | CF$_3$ | 2-methyl-4-oxazolyl | 234.9 | 48.52 | 3.26 | 11.32 | 8.63 | 48.51 | 3.19 | 11.22 | 8.89 |
| 149 | NH$_2$ | CF$_3$ | 5-bromo-3-pyridyl | 266–268 | 40.28 | 2.25 | 12.53 | 7.17 | 40.16 | 2.26 | 12.35 | 7.20 |

TABLE IV-continued

Characterization of Compounds

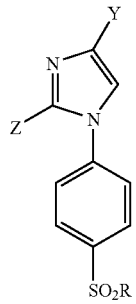

| Ex. | R | Y | Z | mp DSC (° C.) | Calc'd C | Calc'd H | Calc'd N | Calc'd S | Found C | Found H | Found N | Found S |
|---|---|---|---|---|---|---|---|---|---|---|---|---|
| 150 | $NH_2$ | $CF_3$ | 2-quinolyl | 245 | 54.54 | 3.13 | 13.39 | | 54.35 | 2.92 | 13.38 | |
| 151 | $CH_3$ | $CF_2H$ | 3-pyridyl | 212–213.5 | 55.01 | 3.75 | 12.03 | | 54.86 | 3.87 | 11.78 | |
| 152 | $CH_3$ | CN | 3-pyridyl | 193.9 | 58.44 | 3.68 | 17.04 | | 58.37 | 3.55 | 16.78 | |
| 153 | $CH_3$ | CN | 5-methyl-3-pyridyl | 184.3 | 60.34 | 4.17 | 16.56 | | 60.08 | 4.22 | 16.23 | |
| 154 | $NH_2$ | CN | 5-methyl-3-pyridyl | 280–283 | 54.46 | 3.71 | 19.85 | | 54.84 | 3.83 | 19.50 | |
| 155 | $CH_3$ | (2-ethylthio-methylphenyl) | 3-pyridyl | ND | 62.14 | 4.76 | 9.45 | | 62.11 | 4.70 | 9.25 | |

EXAMPLE 156

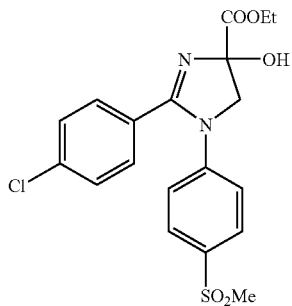

Ethyl [2-(4-chlorophenyl)-4-hydroxy-1-[4-(methylsulfonyl)phenyl]-4,5-dihydro-1H-imidazol-4-yl]carboxylate A mixture of 4-chloro-N-[4-(methylsulfonyl)phenyl]benzenecarboximidamide (Example 1, step 1) (1.00 g, 3.34 mmol), sodium bicarbonate (544 mg, 6.47 mmol), and ethyl bromopyruvate (1.40 g, 7.19 mmol) in 50 ml of isopropanol was stirred at reflux for 7 hours. After cooling, the mixture was evaporated. The residue was partitioned between dichloromethane and water, and the aqueous layer further extracted with dichloromethane. The combined organic extracts were dried over sodium sulfate, filtered, and evaporated. Chromatography of the residue over silica gel using mixtures of ethyl acetate and toluene as eluents gave the title compound as a pale yellow solid: mp (DSC) 162° C. Anal. Calc'd. for $C_{19}H_{19}ClN_2O_5S$ (MW 422.89): C, 53.96; H, 4.53; N, 6.62. Found: C, 53.99; H, 4.49; N, 6.42.

EXAMPLE 157

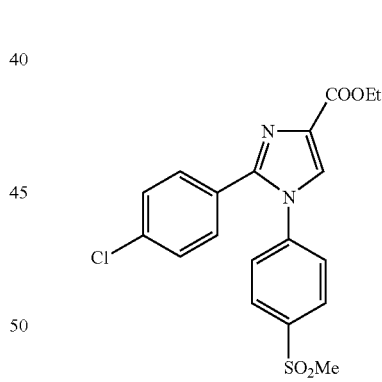

Ethyl [2-(4-chlorophenyl)-1-[4-(methylsulfonyl)phenyl]-1H-imidazol-4-yl]carboxylate A mixture of 4-chloro-N-[4-(methylsulfonyl)phenyl]benzenecarboximidamide (Example 1, step 1) (12.1 g, 39.2 mmol), sodium bicarbonate (6.58 g, 78.3 mmol), and 90% ethyl bromopyruvate (16.9 g) in 480 ml of 2-propanol was stirred at reflux overnight. After cooling, the mixture was concentrated. The residue was partitioned between dichloromethane and water and the aqueous layer further extracted with dichloromethane. The combined organic extracts were dried over sodium sulfate, filtered, and evaporated. Trituration of the residue with ethyl acetate gave the title compound as a pale beige, crystalline solid (6.61 g): mp (DSC) 218° C. Anal. Calc'd. for $C_{19}H_{17}ClN_2O_4S$ (MW 404.87): C, 56.37; H, 4.23; N, 6.92. Found: C, 56.28;.H, 4.13; N, 6.80.

EXAMPLE 158

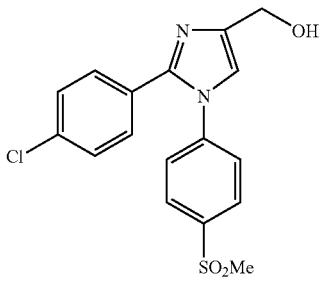

2-(4-Chlorophenyl)-1-[4-(methylsulfonyl)phenyl]-1H- imidazole-4 -methanol

To a solution of 4.00 g (9.88 mmol) of Example 157 in 125 ml of dichloromethane stirring in a dry ice/isopropanol bath was added 24.7 ml of 1M diisobutylaluminum hydride in toluene (containing 24.7 mmol). The mixture was warmed to room temperature overnight. Excess reagent was quenched with methanol, and the resulting mixture was washed with 15% aqueous acetic acid. The aqueous layer was further extracted with dichloromethane, and the combined organic extracts were dried over sodium sulfate. After filtration and evaporation, the residue was triturated with 50% ethyl acetate/hexane, and the alcohol was obtained as a white solid: m.p. 205–208° C. Anal. Calc'd. for $C_{17}H_{15}ClN_2O_3S\cdot\frac{1}{2}H_2O$ (MW 371.84): C, 54.91; H, 4.07; N, 7.53. Found: C, 54.75; H, 3.96; N, 7.17.

EXAMPLE 159

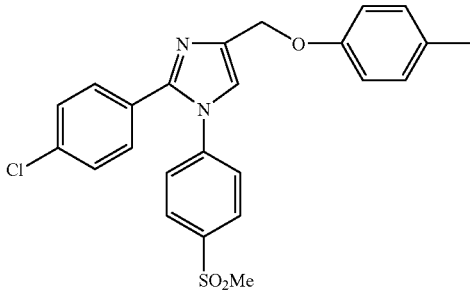

2-(4-Chlorophenyl)-4-[(4-methylphenoxy)methyl]-1-[4-(methylsulfonyl)phenyl]-1H-imidazole Step 1: Preparation of 4-chloromethyl-2-(4-chlorophenyl)-1-[4-(methylsulfonyl)phenyl]-1H-imidazole A suspension of the title product of Example 158 (1.82 g, 4.96 mmol) in 10 ml of chloroform was treated with thionyl chloride (1.18 g, 9.92 mmol), and the resulting mixture was stirred at reflux for 1 hour. Another 1.18 g of thionyl chloride was added, and reflux continued for 1 hour. After cooling, the mixture was evaporated and the residue was chromatographed over silica gel using 50% ethyl acetate/hexane as eluent to give the chloromethyl compound as a very pale yellow crystalline solid (1.26 g): m.p. 166–169° C.

Step 2: Preparation of 2-(4-Chlorophenyl)-4-[(4-methylphenoxy)methyl]-1-[4-(methylsulfonyl)phenyl]-1H-imidadzole A mixture of 122 mg (0.32 mmole) of 4-chloromethyl-2-(4-chlorophenyl)-1-[4-(methylsulfonyl)phenyl]-1H-imidazole (Step 1), p-cresol (69 mg, 0.64 mmole), and potassium carbonate (110 mg, 0.8 mmole) in 5 ml of dimethylformamide was stirred at 85–90° C. for 6 hours. After cooling, the mixture was partitioned between ethyl acetate and aqueous sodium chloride, and the aqueous layer was extracted with ethyl acetate. The combined organic extracts were washed with brine, dried over sodium sulfate, filtered, and evaporated. Chromatography of the residue over silica gel using mixtures of ethyl acetate and hexane gave 2-(4-chlorophenyl)-4-[(4-methylphenoxy)methyl]-1-[4-(methylsulfonyl)phenyl]-1H-imidazole as a pure white solid (118 mg): m.p. (DSC) 193° C. Anal. Calc'd. for $C_{24}H_{21}ClN_2O_3S$ (Mw 452.96): C, 63.64; H, 4.67; N, 6.18. Found: C, 63.42; H, 4.64; N, 5.79.

EXAMPLE 160

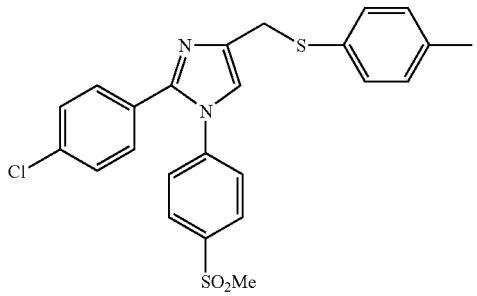

2-(4-Chlorophenyl)-4-[[(4-methylphenoxy)thio]methyl]-1-[4-(methylsulfonyl)phenyl]-1H-imidazole To a solution of 4-chloromethyl-2-(4-chlorophenyl)-1-[4-(methylsulfonyl)phenyl]-1H-imidazole (Example 159, Step 1) in 5 ml of dimethylformamide was added p-thiocresol (98 mg, 0.79 mmole) and anhydrous potassium carbonate (136 mg, 0.985 mmole), and the mixture was stirred rapidly overnight. The mixture was partitioned between ethyl acetate and water, and the aqueous layer was extracted with ethyl acetate The combined organic extracts were dried over sodium sulfate, filtered and evaporated. Chromatography of the residue over silica gel using mixtures of ethyl acetate and hexane as eluent gave the title compound as a glassy solid: m.p. (DSC) 51° C. Anal. Calc'd. for $C_{24}H_{21}ClN_2O_2S_2$ (MW 469.03): C, 61.46; H, 4.51; N, 5.97. Found: C, 61.38; H, 4.68; N. 5.81.

EXAMPLE 161

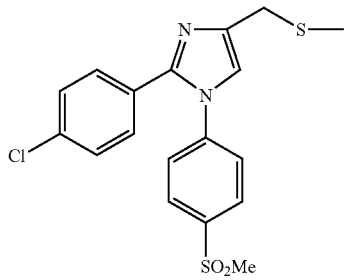

2-(4-Chlorophenyl)-1-[4-(methyloulfonyl)phenyl]-4-[(4-methylthio)methyl]-1H-imidazole To a solution of 4-chloromethyl-2-(4-chlorophenyl)-1-[4-(methylsulfonyl)phenyl]-1H-imidazole (Example 159, Step 1) (150 mg, 0.394 mmole) in 5 ml of dimethylformamide was added sodium thiomethoxide (55 mg, 0.79 mmole) and the mixture was stirred for three days. The mixture was partitioned between ethyl acetate and water, and the aqueous layer was extracted with ethyl acetate. The combined organic extracts were washed with brine, dried over sodium sulfate, filtered, and evaporated. Chromatography of the residue over silica gel using mixtures of ethyl acetate and hexane as eluents gave the title compound as a pale yellow oil (64 mg): Anal. Calc'd. for $C_{18}H_{17}ClN_2O_2S_2 \cdot \frac{1}{2}H_2O$ (MW 401.93): C, 53.79; H, 4.26; N, 6.97. Found: C, 53.97; H, 4.43; N, 6.84.

EXAMPLE 162

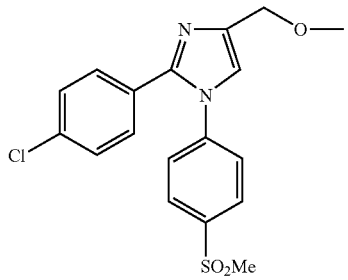

2-(4-Chlorophenyl)-4-(4-methoxymethyl)-1-[4-(methylsulfonyl)phenyl]-1H-imidazole To a solution of 46 mg (2.0 mmol) of sodium metal in 2 ml of methanol was added a solution of 4-chloromethyl-2-(4-chlorophenyl)-1-[4-(methylsulfonyl)phenyl]-1H-imidazole (Example 159, Step 1) (167 mg, 0.438 mmole) and the mixture was stirred overnight. The mixture was partitioned between ethyl acetate and water, and the aqueous layer was extracted with ethyl acetaze. The combined organic extracts were washed with brine, dried over sodium sulfate, filtered, and evaporated. Chromatography of the residue over silica gel using ethyl acetate as the eluent gave the title compound as a white crystalline solid (72%): mp 171–172° C. Anal. Calc'd. for $C_{15}H_{17}ClN_2O_3S$ (MW 376.86): C, 57.37; H, 4.55; N, 7.43. Found: C, 57.29; H, 4.42; N, 7.33.

EXAMPLE 163

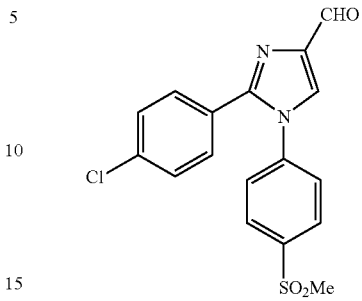

2-(4-Chlorophenyl)-1-[4-(methylsulfonyl)phenyl]-1H-imidazole-4-carboxaldehyde

To 8 ml of a 1:1 mixture of dimethyl sulfoxide and dichloromethane stirring in a dry ice/isopropanol bath under nitrogen was added dropwise oxalyl chloride (321 µl, 3.69 mmol). After stirring for 10 minutes, a solution of 2-(4-chlorophenyl)-1-[4-(methylsulfonyl)phenyl]-1H-imidazole-4-methanol (Example 158) (670 mg, 1.85 mmol) in 25 ml of a 1:1 mixture of dimethyl sulfoxide and dichloromethane. Stirring was continued while warming to 0° C., where it was maintained for 15 minutes. Triethylamine (1.87 g, 18.5 mmol) was added, and the mixture was stirred overnight while warming to room temperature. The mixture was partitioned between dichloromethane and water, the organic layer was washed with water and then brine, dried over sodium sulfate, filtered, and evaporated. Chromatography of the residue. over silica gel using mixtures of ethyl acetate and hexane gave the title compound as an off-white solid (330 mg): mp (DSC) 203° C. Anal. Calc'd. for $C_{17}H_{13}ClN_2O_3S$ (MW 360.82): C, 56.59; H, 3.63; N, 7.76. Found: C, 56.24; H, 3.62; N, 7.50.

EXAMPLE 164

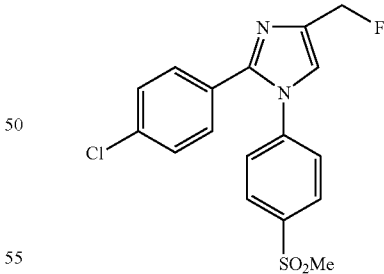

2-(4-Chlorophenyl)-4-fluoromethyl-1-[4-(methylsulfonyl)phenyl]-1H-imidazole

To a suspension of 2-(4-chlorophenyl)-1-[4-(methylsulfonyl)phenyl]-1H-imidazole-4-methanol (Example 158) (250 mg, 0.689 mmole) in 5 ml of dichloromethane was added dropwise a solution of diethylamino sulfur trifluoride (DAST) (166 mg, 1.03 mmole) in 1 ml of dichloromethane. As the addition proceeded, the mixture became homogeneous. After stirring for two hours, water was added, the layers separated and the aqueous layer was extracted with dichloromethane. The combined organic extracts were dried over sodium sulfate, filtered and evaporated. Chromatography of the residue over silica gel using 60% ethyl acetate in hexane gave the title compound as a very slightly yellow solid (106 mg): mp (DSC) 165° C. Anal. Calc'd. for $C_{17}H_{14}ClFN_2O_2S \cdot \frac{1}{4}H_2O$ (MW 369.33): C, 55.29; H, 3.82; N, 7.59. Found: C, 55.15; H, 3.82; N, 7.42.

EXAMPLE 165

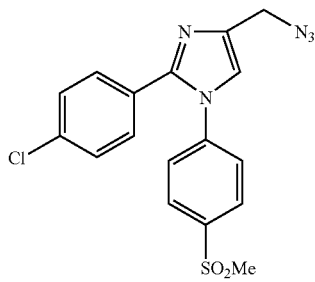

4-Azidomethyl-2-(4-chlorophenyl)-1-[4-(methylsulfonyl)phenyl]-1H-imidazole

A mixture of 4-chloromethyl-2-(4-chlorophenyl)-1-(4-(methylsulfonyl)phenyl]-1H-imidazole (Example 159, Step 1) (500 mg, 1.31 mmol) and sodium azide (256 mg, 3.94 mmol) in 5 ml of dimethylformamide was stirred overnight at room temperature. The mixture was warmed to 80° C. for one hour and then cooled. The mixture was partitioned between ethyl acetate and water, and the aqueous layer was extracted with ethyl acetate. The combined organic extracts were washed with brine, dried over sodium sulfate, filtered, and evaporated. Chromatography of the residue over silica gel using 50% ethyl acetate in hexane as the eluent gave the title compound as a pure white crystalline solid (496 mg): mp (DSC) 186° C. Anal. Calc'd. for $C_{17}H_{14}ClN_5O_2S$ (MW 387.85): C, 52.64; H, 3.64; N, 18.06. Found: C, 52.46; H, 3.77; N, 17.84.

EXAMPLE 166

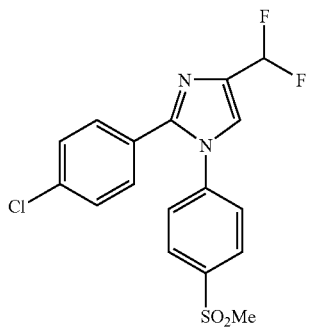

2-(4-Chlorophenyl)-4-difluoromethyl-1-[4-(methylsulfonyl)phenyl]-1H-imidazole To a suspension of 2-(4-chlorophenyl)-1-[4-(methylsulfonyl)phenyl]-1H-imidazole-4-carboxaldehyde (Example 163) (150 mg, 0.416 mmole) in 5 ml of dichloromethane was added dropwise a solution of DAST (201 mg, 1.25 mmol) of in 1 ml of dichloromethane, producing a homogeneous solution. After stirring at room temperature for 30 minutes, the mixture was partitioned between dichloromethane and water, and the aqueous layer was extracted with dichloromethane. The combined organic extracts were dried over sodium sulfate, filtered, and evaporated. Chromatography of the residue over silica gel using 50% ethyl acetate in hexane as the eluent, followed by crystallization from ethyl acetate and hexane gave the title compound as very small pale beige plates (21 mg): m.p. 179–180° C. Anal. Calc'd. for $C_{17}H_{13}ClF_2N_2O_2S$ (MW 382.82): C, 53.34; H, 3.42; N, 7.32. Found: C, 53.42; H, 3.26; N, 7.08.

EXAMPLE 167

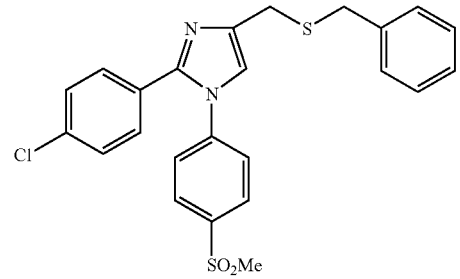

2-(4-Chlorophenyl)-1-[4-(methylsulfonyl)phenyl]-4-[[(4-phenylmethyl)thio]methyl]-1H-imidazole To a solution of benzyl mercaptan (195 mg, 1.6 mmol) in 5 ml of dimethylformamide was added 63 mg of a 60% dispersion of sodium hydride in mineral oil. After gas evolution ceased, 4-chloromethyl-2-(4-chlorophenyl)-1-[4-(methylsulfonyl)phenyl]-1H-imidazole (Example 159, Step 1) (300 mg, 0.787 mmole) was added as a solid and stirring continued overnight. The mixture was partitioned between ethyl acetate and water, and the aqueous layer was extracted with ethyl acetate. The combined organic extracts were washed with brine, dried over sodium sulfate, filtered, and evaporated. Radial chromatography of the residue over a 2 mm layer of silica gel using 50% ethyl acetate in hexane as the eluent gave the title compound as a pale yellow solid (343 mg): mp(DSC) 41° C. Anal. Calc'd. for $C_{24}H_{21}ClN_2O_2S_2$ (MW 469.03): C, 61.46; H, 4.51; N, 5.97. Found: C, 61.06; H, 4.34; N, 5.80.

EXAMPLE 168

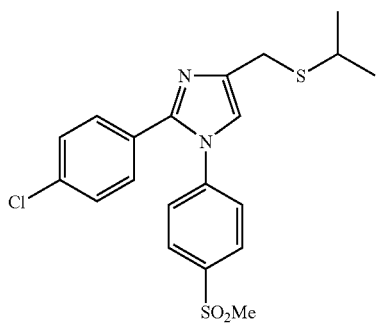

2-(4-Chlorophenyl)-4-[[(1-methylethyl)thio]methyl]-1-[4-(methylsulfonyl)phenyl]-1H-imidazole The title compound was prepared as a white solid by the method of Example 167 except that 2-mercaptopropane was used in place of benzyl mercaptan: mp (DSC) 118° C. Anal. Calc'd. for $C_{20}H_{21}ClN_2O_2S_2$ (MW 420.98): C, 57.06; H, 5.03; N, 6.65. Found: C, 56.72; H, 4.89; N, 6.42.

EXAMPLE 169

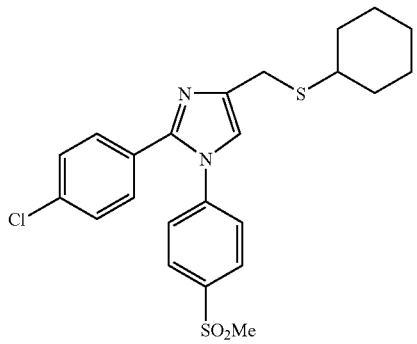

2-(4-Chlorophenyl)-4-[[(cyclohexyl)thio]methyl]-1-[4-(methylsulfonyl)phenyl]-1H-imidazole The title compound was prepared as a white solid by the method of Example 167 except that cyclohexyl mercaptan was used in place of benzyl mercaptan, and that 40% ethyl acetate in hexane was used as the chromatography eluent: mp (DSC) 48° C. Anal. Calc d. for $C_{23}H_{25}ClN_2O_2S_2$ (MW 461.05): C, 59.92; H. 5.47; N, 6.08. Found: C, 59.63; H, 5.52; N, 5.96.

EXAMPLE 170

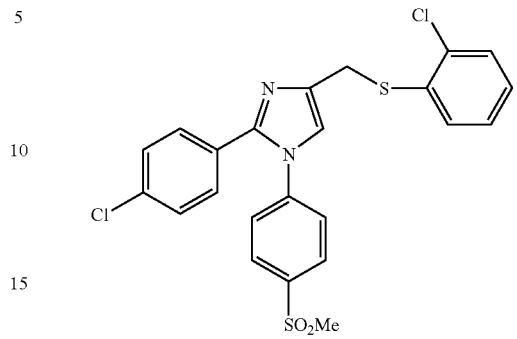

2-(4-Chlorophenyl)-4-[[(2-chlorophenyl)thio)methyl]-1-[4-(methylsulfonyl)phenyl]-1H-imidazole To a solution of 4-chloromethyl-2-(4-chlorophenyl)-1-[4-(methylsulfonyl)phenyl]-1H-imidazole (Example 159, Step 1) (250 mg, 0.656 mmol) and 2-chlorothiophenol (190 mg, 1.31 mmol) in 5 ml of dimethylformamide was added potassium carbonate (226 mg, 1.64 mmol). The mixture was stirred rapidly overnight at room temperature and partitioned between ethyl acetate and water. The aqueous layer was extracted with ethyl acetate, the combined organic extracts were washed with brine, and dried-over sodium sulfate. The solution was filtered and then concentrated. Chromatography of the residue over silica gel using 50% ethyl acetate in hexane as the eluent followed by crystallization gave the title compound as a pure white crystalline solid (147 mg): mp (DSC) 153° C. Anal. Calc'd. for $C_{23}H_{18}Cl_2N_2O_2S_2$ (MW 489.44): C, 56.44; H, 3.71; N, 5.72. Found: C, 56.51; H, 3.54; N, 5.57.

EXAMPLE 171

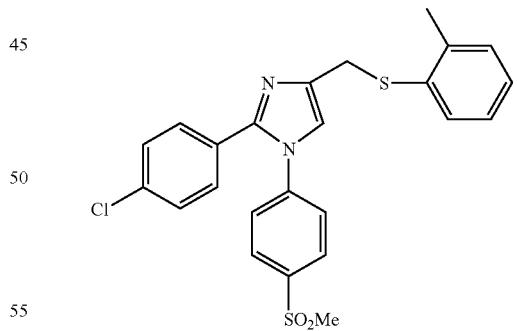

2-(4-Chlorophenyl)-4-[[(2-methylphenyl)thio]methyl]-1-[4-(methylsulfonyl)phenyl]-1H-imidazole To a solution of 4-chloromethyl-2-(4-chlorophenyl)-1-(4-(methylsulfonyl)phenyl]-1H-imidazole (Example 159, Step 1) (250 mg, 0.656 mmol) and o-thiocresol (163 mg, 1.31 mmol) in 5 ml of dry dimethylformamide was added anhydrous potassium carbonate (226 mg, 1.64 mmol). The mixture was stirred rapidly overnight at room temperature. The mixture was then partitioned between ethyl acetate and water. The aqueous layer was further extracted with ethyl acetate, the combined organic extracts washed with brine, and dried over sodium sulfate. The solution was filtered and concentrated. Chromatography of the residue over silica gel using 40% ethyl acetate in hexane gave the title compound as a very pale yellow solid (210 mg): mp (DSC) 51° C. Anal. Calc'd. for $C_{24}H_{21}ClN_2O_2S_2$ (MW 469.03): C, 61.46; H, 4.51; N, 5.97. Found: C, 61.16; H, 4.50; N, 5.86.

EXAMPLE 172

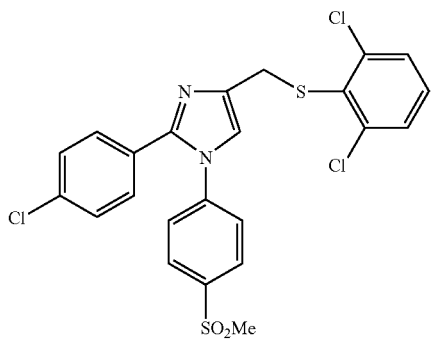

2-(4-Chlorophenyl)-4-[[(2,6-dichlorophenyl)thiolm-ethyl]-1-[4-(methyloulfonyl)phenyl]-1H-imidazole To a solution of 4-chloromethyl-2-(4-chlorophenyl)-1-[4-(methylsulfonyl)phenyl]-1H-imidazole (Example 159, Step 1) (250 mg, 0.656. mmole) and 2,6-dichlorothiophenol in 5 ml of dimethylformamide (235 mg, 1.31 mmol) was added 226 mg (1.64 mmol) of potassium carbonate. The resulting mixture was stirred rapidly at room temperature for two days. The mixture was partitioned between ethyl acetate and water and the aqueous layer was further extracted with ethyl acetate. The combined organic extracts were washed with brine, dried over sodium sulfate, filtered, and evaporated. Chromatography of the residue over silica gel using 50% ethyl acetate in hexane gave the title compound, 282 mg, as a pure white solid: mp (DSC) 202° C. Anal. Calc'd. for $C_{23}H_{17}C_{13}N_2O_2S_2$ (MW 523.89): C, 52.73; H, 3.27; N, 5.35. Found: C, 52.55; H, 2.98; N, 5.19.

EXAMPLE 173

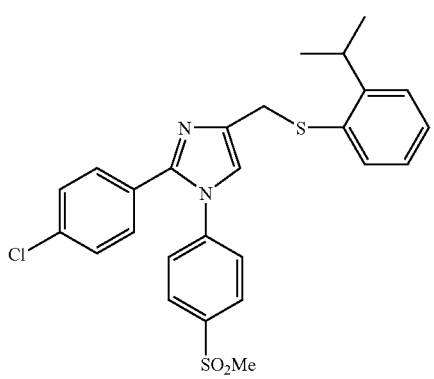

2-(4-Chlorophenyl)-4-[[2-(1-methylethyl)phenyl]thio]methyl]-1-[4-(methylsulfonyl)phenyl]-1H-imidazole The title compound was prepared as a white solid by the method of Example 172 except that 2-isopropylthiophenol was used in place of 2,6-dichlorothiophenol and that 40% ethyl acetate in hexane was used as chromatography eluent: m.p. 68–73° C. Anal. Calc'd. for $C_{26}H_{25}ClN_2O_2S_2·¼H_2O$ (MW 501.58): C, 62.26; H, 5.02; N, 5.59. Found: C, 62.36; H, 5.11; N, 5.45.

EXAMPLE 174

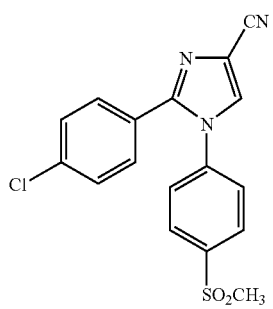

2-(4-Chlorophenyl)-1-[4-(methylsulfonyl)phenyl]-1H-imidazole-4-carbonitrile

A solution of 82 mg (0.23 mmole) of 2-(4-chlorophenyl)-1-[4-(methylsulfonyl)phenyl]-1H-imidazole-4-carboxaldehyde (Example 163) and 51 mg (0.45 mmole) of hydroxylamine O-sulfonic acid in 10 ml of absolute ethanol and 1 ml of pyridine was stirred at reflux overnight. After cooling, the mixture was evaporated, and the residue was taken up in dichloromethane. The solution was washed with aqueous sodium bicarbonate, dried over sodium sulfate, filtered, and evaporated. Chromatography of the residue over silica gel using 50% ethyl acetate in hexane as the eluent gave the title compound; 71 mg, as a pure white crystalline solid: mp (DSC) 205° C. Anal. Calc'd. for $C_{17}H_{12}ClN_3O_2S·¼H_2O$ (MW 362.32): C, 56.36; H, 3.34; N, 11.60. Found: C, 56.49; H, 3.27; N, 11.45.

EXAMPLE 175

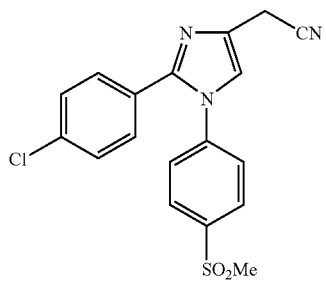

2-(4-Chlorophenyl)-1-[4-(methylsulfonyl)phenyl]-1H-imidazole-4-acetanitrile

A mixture of 250 mg (0.656 mmole) of 4-chloromethyl-2-(4-chlorophenyl)-1-[4-(methylsulfonyl)phenyl]-1H-imidazole (Example 159, Step 1) and 86 mg (1.3 mmol) of potassium cyanide in 4 ml of dimethylformamide was stirred at 85° C. for 24 hours. An additional 86 mg of potassium cyanide was added, and stirring continued for 8 hours. After cooling, the mixture was partitioned between dichloromethane and water and the aqueous layer further extracted with dichloromethane. The combined organic extracts were washed with brine, dried over sodium sulfate, filtered, and evaporated. Chromatography of the residue over silica gel using 60% ethyl acetate in toluene, followed by trituration with ethyl acetate gave the title compound, 59 mg, as a very pale yellow crystalline solid: mp (DSC) 197° C. Anal. Calc'd. for $C_{18}H_{14}ClN_3O_2S$ (MW 371.85): C, 58.14; H, 3.80; N, 11.30. Found: C, 57.92; H, 3.57; N, 11.01.

EXAMPLE 176

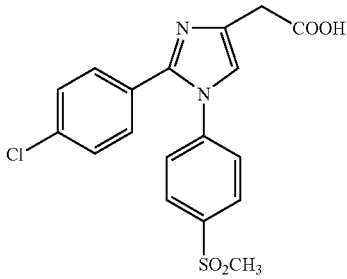

2-(4-Chlorophenyl)-1-[4-(methylsulfonyl)phenyl]-1H-imidazole-4-acetic acid

A mixture of 50 mg (0.13 mmole) of the title product of Example 175 and 5 ml of concentrated hydrochloric acid was stirred at reflux for one hour. After cooling, the mixture was evaporated and the residue taken up in water. The mixture was basified with aqueous sodium bicarbonate solution, and the pH then adjusted to 4 with acetic acid. The mixture was extracted with dichloromethane and the combined organic extracts dried over sodium sulfate. After filtration, the solution was evaporated and the residue azeotropically distilled with toluene. Trituration of the residue with ethyl acetate gave the title compound, 31 mg, as a white solid: m.p. 263–264° C. Anal. Calc'd. for $C_{18}H_{15}ClN_2O_4S \cdot \frac{1}{4}H_2O$ (MW 395.35): C, 54.69; H, 3.82; N, 7.09. Found: C, 54.39; H, 3.88; N, 6.72.

EXAMPLE 177

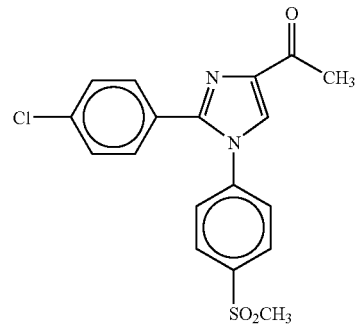

1-[2-(4-Chlorophenyl)-1-[4-(methyloulfonyl)phenyl]-1H-imidazol-4-yl]-1-ethanone

Step 1—Preparation of 2-(4-chlororhenyl)-1-[4-(methylsulfonyl)phenyl]-1H-imidazole-4-carboxylic acid A suspension of ethyl [2-(4-chlorophenyl)-1-[4-(methylsulfonyl)phenyl]-1H-imidazol-4-yl]carboxylate (Example 159) (929 mg, 2.29 mmol) in 16 ml of methanol and 16 ml of 1N aqueous sodium hydroxide was stirred at reflux for one hour. After cooling, the mixture was concentrated, water was added, and the resulting mixture was acidified with acetic acid. The mixture was extracted with dichloromethane, and the combined organic extracts were dried over sodium sulfate, filtered, and evaporated. Acetic acid was removed by azeotropic distillation with toluene to give the title compound, 520 mg, as a white crystalline solid: mp (DSC) 121° C. Anal. Calc'd. for $C_{17}H_{13}ClN_2O_4S \cdot H_2O$ (MW 394.83): C, 51.71; H, 3.32; N, 7.10. Found: C, 51.89; H, 3.29; N, 6.97.

Step 2—Preparation of 2-(4-chlorophenyl)-N-methoxy-N-methyl-1-[4-(methylsulfonyl)phenyl]-1H-imidazole-4-carboxamide Oxalyl chloride (0.34 g, 2.65 mmole) in 5 ml acetonitrile was added to 16 ml acetonitrile containing dimethylformamide (0.25 g, 3.46 mmole) cooled to 0° C. After 15 minutes, 2-(4-chlorophenyl)-1-[4-(methylsulfonyl)phenyl]-1H-imidazole-4-carboxylic acid from step 1 (1.0 g, 2.65 mmole) was added with 20 ml acetonitrile. After warming to room temperature N,0-dimethylhydroxylamine HCl (0.28 g, 2.92 mmole) and pyridine (0.42 g, 5.31 mmole) were added and the mixture was stirred at room temperature for three days. The reaction mixture was concentrated to give an oily solid. The amide was purified by silica gel chromatography: Anal. Calc'd. $C_{19}H_{15}N_3O_4SCl$ (419.89); C, 54.35; H. 4.32; N, 10 10.01. Found: C, 53.96; H, 4.30; N, 9.68.

Step 3—Preparation of 1-[2-(4-chlorophenyl)-1-[4-(methylsulfonyl)phenyl]-1H-imidazol-4-yl]-1-ethanone Methyl lithium-LiBr complex (1.5 M in ethyl ether) (0.47 ml, 0.7 mmol) was added by syringe to a cold (−70° C.) solution of 2-(4-chlorophenyl)-N-methoxy-N-methyl-1-[4-(methylsulfonyl)phenyl]-1H-imidazole-4-carboxamide from step 2 (250 mg, 0.6 mmol) in 50 ml tetrahydrofuran. The reaction was warmed to 0° C. and re-cooled to −60° C. before additional methyl lithium (0.47 ml) was added. The reaction was warmed to room temperature. After stirring for two days, 50 ml of 10% acetic acid was added and the mixture was concentrated to a gum. The gum was dissolved in 50 ml ethyl acetate, washed with water (2×50 ml), dried over Na$_2$SO$_4$, filtered and concentrated. The product was purified by silica gel chromatography: Anal. Calc'd. C$_{18}$H$_{15}$N$_2$O$_3$SCl.¼H$_2$O: C, 56.99; H, 4.12; N, 7.38. Found: C, 56.88; H, 4.05; N, 7.6838

EXAMPLE 178

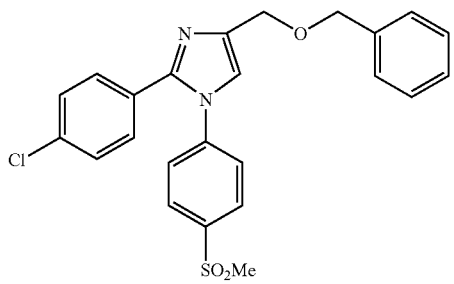

2-(4-Chlorophenyl)-1-[4-(methyloulfonyl)phenyl]-4-(phenylmethoxymethyl)-1H-imidazole To a suspension of 58 mg of 60% sodium hydride in mineral oil (containing 35 mg, 1.4 mmol) in 2 ml of dimethylformamide was added a solution of 142 mg (1.31 mmol) of benzyl alcohol in 0.5 ml of dimethyl formamide. The mixture was stirred while heating to 40° C. After 15 minutes, 250 mg (0.656 mmole) of the title product of Example 158 was added as a solid and stirred while heating to 85° C. The temperature was maintained for 6 hours and then the mixture was cooled. The mixture was partitioned between ethyl acetate and water and the aqueous layer further extracted with ethyl acetate. The combined organic extracts were washed with brine, dried over sodium sulfate, filtered, and evaporated. Chromatography of the residue over silica gel using 50% ethyl acetate in hexane as the eluent gave the title compound, 60 mg, as pure white crystalline solid, m.p. 64–65° C. Anal. Calc'd. for C$_{24}$H$_{21}$ClN$_2$O$_3$S.¼H$_2$O (MW 457.56): C, 63.01; H, 4.63; N, 6.12. Found: C, 62.76; H, 4.43; N, 6.20.

EXAMPLE 179

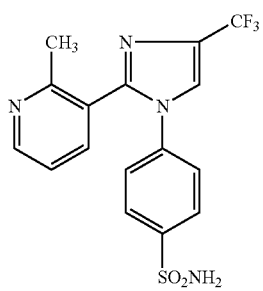

4-[2-(2-Methylpyridin-3-yl)-4-(trifluoromethyl)-1H-imidazol-1-yl]benzenesulfonamide Step 1: Preparation of 4-[(2,5-dimethyl-1H-pyrrol-1-yl)sulfonyl]nitrobenzene A mixture of 4-nitrobenzenesulfonamide (30.3 g, 0.15 mol), acetonylacetone (34.2 g, 0.30 mol) and 4-toluene-sulfonic acid (3.0 g, catalyst) in 200 mL of toluene was heated at reflux under nitrogen using a Dean-Stark trap for 18 hours. The reaction was cooled and filtered through silica gel (700 g), eluting with mixtures of ethyl acetate and hexane. Removal of solvent in vacuo gave a crude brown solid. The crude product in ethyl acetate was treated with activated charcoal, and recrystallized from ethyl acetate and hexane to afford 4-[(2,5-dimethyl-1H-pyrrol-1-yl)sulfonyl]nitrobenzene (32.5 g, 77%) as a light yellow solid: mp (DSC): 101–103° C. Anal. Calc'd. for C$_{12}$H$_{12}$N$_2$O$_4$S: C, 51.42; H, 4.32; N, 9.99; S, 11.44. Found: C, 51.62; H, 4.18; N, 9.96; S, 11.31.

Step 2: Preparation of 4-[(2,5-dimethyl-1H-pyrrol-1-yl)sulfonyl]benzenamine

A mixture of 4-[(2,5-dimethyl-1H-pyrrol-1-yl)sulfonyl]nitrobenzene (Step 1) (7.3 g, 26 mmol) and Raney Nickel (0.7 g) in 70 mL of methanol was hydrogenated in a Parr apparatus at a pressure of 50 psi. After 3 hours, the catalyst was filtered and the filtrate was concentrated to give 4-[(2,5-dimethyl-1H-pyrrol-1-yl)sulfonyl]benzenamine (6.4 g) as a pale yellow solid: mp (DSC): 110–111° C. Anal. Calc'd. for C$_{12}$H$_{14}$N$_2$O$_2$S: C, 57.58; H, 5.64; N, 11.16; S, 12.81. Found: C, 57.44; H, 5.78; N, 11.11; S. 12.30.

Step 3: Preparation of 1-[4-[(2,5-dimethyl-1H-pyrrol-1-yl)sulfonyl]phenyl-4,5-dihydro-2-(2-methylpyridin-3-yl)-4-(trifluoromethyl)-1H-imidazol-4-ol To a solution of sodium bis(trimethylsilyl)amide (120 mL of 1.0 M in tetrahydrofuran, 0.12 mol) was added dropwise a solution of 4-[(2,5-dimethyl-1H-pyrrol-1-yl)sulfonyl]benzenamine (Step 2) (28.43 g, 0.114 mol) in 35 mL of tetrahydrofuran at room temperature. The dark solution was stirred for 10 minutes. A solution of 3-cyano-2-methylpyridine in 20 mL of tetrahydrofuran was added rapidly. The reaction mixture was stirred for 16 hours, poured into 1 L of water and extracted with ethyl acetate (500 mL). The organic layer was washed with brine, dried over magnesium sulfate and filtered. The filtrate was concentrated to give 22.0 g of crude amidine as a pale yellow solid which was used in next step without purification. To a suspension of the crude amidine (21.9 g, 0.065 mol) and sodium bicarbonate (8.20 g, 0.098 mol) in 600 mL of isopropanol at 50° C., was added a solution of 3-bromo-1,1,1-trifluoroacetone (18.6 g, 0.098 mol) in 30 mL of isopropanol over 30 minutes. The mixture was stirred at 80° C. for 4 hours, cooled and filtered. The filtrate was concentrated and the residue was treated with ethyl acetate/hexane to give 28.6 g of 1-(4-[(2,5-dimethyl-1H-pyrrol-1-yl)sulfonyl]phenyl]-4,5-dihydro-2-(2-methylpyridin-3-yl)-4-(trifluoromethyl)-1H-imidazol-4-ol as a yellowish solid (53%): mp (DSC) 213–216° C. Anal. Calc'd. for C$_{22}$H$_{19}$F$_3$N$_4$O$_3$S: C, 55.46, H, 4.02, N, 11.76, S, 6.73. Found: C, 54.71, H, 4.40, N, 11.21, S, 6.78.

Step 4: Preparation of 3-[1-[4-[(2,5-dimethyl-1H-pyrrol-1-yl)sulfonyl]phenyl]-4-(trifluoromethyl)-1H-imidazol-2-yl]-2-methylpyridine A mixture of 1-(4-[(2,5-dimethyl-1H-pyrrol-1-yl)sulfonyl]phenyl]-4,5-dihydro-2-(2-methylpyridin-3-yl)-4-(trifluoromethyl)-1H-imidazol-4-ol (Step 3) (18.0 g, 38 mmol) and p-toluenesulfonic acid (1.8 g) in 400 mL of toluene was heated at reflux with a Dean-Stark trap under a nitrogen atmosphere for 36 hours. The mixture was cooled to room temperature and filtered. The filtrate was basified with ammonium hydroxide and extracted with ethyl acetate (400 mL). The organic layer was washed with brine, dried over magnesium sulfate and filtered. The filtrate was concentrated and purified by chromatography on silica gel (ethyl acetate/hexane, 95:5) to give 3-[1-[4-[2,5-dimethyl-1H-pyrrol-1-yl)sulfonyl]phenyl]-4-(trifluoromethyl)-1H-imidazol-2-yl]-2-methylpyridine as a white solid (11.86 g, 72%): mp (DSC): 141–143° C. Anal. Calc'd. for $C_{22}H_{19}F_3N_4O_2S$: C, 57.64; H, 3.74; N, 12.22; S, 6.99. Found: C, 57.27; H, 4.03; N, 11.79; S, 7.05.

Step 5: Preparation of 4-[2-(2-methylpyridin-3-yl)-4-(trifluoromethyl)-1H-imidazol-yl]benzenesulfonamide A mixture of 3-[1-[4-[(2,5-dimethyl-1H-pyrrol-1-yl)sulfonyl]phenyl]-4,5-dihydro-4-(trifluoromethyl)-1H-imidazol-2-yl]-2-methylpyridine (Step 4) (4.6 g, 0.01 mol) in 75 mL of TFA and 25 mL of water was heated at reflux for 2 hours. The solution was cooled, treated with 400 nL of water and basified with sodium bicarbonate to pH 8. The aqueous phase was extracted with ethyl acetate (400 mL). The organic layer was washed with brine, dried over magnesium sulfate and filtered. The filtrate was concentrated and the crude was purified by chromatography on silica gel (ethyl acetate/acetone, 95:5) to afford 4-[2-(2-methylpyridin-3-yl)-4-(trifluoromethyl)-1H-imidazol-1-yl]benzenesulfonamide as a white solid (3.0 g, 78%): mp (DSC): 235–237° C. Anal. Calc'd. for $C_{16}H_{13}F_3N_3O_2S$: C, 50.26; H, 3.43; N, 14.65; S, 8.39. Found: C, 50.06; H,3.29; N. 14.4; S, 8.52.

Biological Evaluation

Rat Carrageenan Foot Pad Edema Test

The carrageenan foot edema test was performed with materials, reagents and procedures essentially as described by Winter, et al., (*Proc. Soc. Exp. Biol. Med.,* 111, 544 (1962)). Male Sprague-Dawley rats were selected in each group so that the average body weight was as close as possible. Rats were fasted with free access to water for over sixteen hours prior to the test. The rats were dosed orally (1 ml) with compounds suspended in vehicle containing 0.5% methylcellulose and 0.025% surfactant, or with vehicle alone. One hour later a subplantar injection of 0.1 ml of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDS,* in *Non-steroidal Anti-Inflammatory Drugs,* (J. Lombardino, ed. 1985)). The % inhibition shows the % decrease from control paw volume determined in this procedure and the data for selected compounds in this invention are summarized in Table V.

Rat Carrageenan-induced Analgesia Test

The rat carrageenan analgesia test was performed with materials, reagents and procedures essentially as described by Hargreaves, et al., (*Pain,* 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table V.

TABLE V

| Example | RAT PAW EDEMA % Inhibition @ 30 mg/kg body weight | ANALGESIA % Inhibition @ 10 mg/kg body weight |
|---|---|---|
| 2 | 9 | |
| 5 | 21 | |
| 6 | 23.5 | |
| 7 | 27 | |
| 18 | 36 | 13 |
| 23 | 38 | 25 |
| 24 | 24 | 19 |
| 26 | 51 | 47 |
| 27 | 40 | 21 |
| 28 | 57 | 51 |
| 29 | 37 | |
| 31 | 28 | 36 |
| 32 | 30 | |
| 36 | 68 | |
| 40 | 42 | |
| 43 | 45* | 18 |
| 45 | 49 | 47 |
| 59 | 34 | 27 |
| 69 | 43 | 32 |
| 70 | 34* | 35 |
| 72 | 55 | 28 |
| 74 | 48 | |
| 83 | 25 | |
| 84a | 36 | 8 |
| 86 | 36 | 7 |
| 87 | 28* | 5 |
| 91 | 16 | |
| 93 | 16 | 4 |
| 117 | 51 | |

*10 mg/kg

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of Recombinant COX Baculoviruses

Recombinant COX-1 and COX-2 were prepared as described by Gierse et al, [*J. Biochem.,* 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures,* Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-((3-cholamidopropyl)dimethylammonio)-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 Activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table VI.

TABLE VI

| Example | Human COX-2 $ID_{50}$ μM | Human COX-1 $ID_{50}$ μM |
|---|---|---|
| 1 | 4 | >100 |
| 2 | 0.1 | 23 |
| 3 | 40 | >100 |
| 4 | 4.7 | >100 |
| 5 | 0.2 | >100 |
| 6 | 0.3 | >100 |
| 7 | 0.1 | >100 |
| 9 | 0.3 | >100 |
| 10 | 0.5 | >100 |
| 12 | 0.2 | >100 |
| 13 | 1.6 | >100 |
| 14 | 0.2 | >100 |
| 16 | <0.1 | >100 |
| 17 | 0.2 | 1.0 |
| 18 | 0.2 | 49 |
| 23 | 0.1 | >100 |
| 24 | 0.2 | 26 |
| 26 | <0.1 | 1.6 |
| 27 | <0.1 | 0.6 |
| 28 | 1.8 | >100 |
| 29 | 1.5 | >100 |
| 30 | >100 | >100 |
| 31 | 1.8 | >100 |
| 32 | 2.9 | >100 |
| 34 | 0.5 | >100 |
| 35 | 1.2 | 49 |
| 36 | 0.3 | 88.5 |
| 40 | 0.4 | >100 |
| 41 | 0.5 | >100 |
| 43 | 0.5 | >100 |
| 45 | 9.6 | >100 |
| 56 | 0.1 | 3.6 |
| 57 | <0.1 | 0.9 |
| 59 | <0.1 | 3.6 |
| 67 | 1.1 | >100 |
| 68 | 0.2 | 4.6 |
| 69 | <0.1 | 2.8 |
| 70 | <0.1 | 6.2 |
| 72 | <0.1 | 19.3 |
| 73 | <0.1 | 29.8 |
| 74 | <0.1 | 5.8 |
| 75 | <0.1 | 67.7 |
| 76 | <0.1 | 8.6 |
| 78 | <0.1 | 2.7 |
| 79 | 0.1 | 31.2 |
| 80 | <0.1 | 7.0 |
| 81 | <0.1 | 3.6 |
| 82 | <0.1 | >100 |
| 83 | <0.1 | 82.0 |
| 85 | 0.1 | >100 |
| 86 | <0.1 | 78.1 |
| 87 | <0.1 | >100 |
| 88 | <0.1 | >100 |
| 89 | 0.2 | 24.1 |
| 90 | 0.2 | >100 |
| 91 | 0.2 | >100 |
| 93 | 0.1 | >100 |
| 94 | 0.2 | 29.9 |
| 95 | 0.6 | 3.0 |
| 96 | 0.4 | >100 |
| 97 | 0.3 | >100 |
| 98 | 1.0 | >100 |
| 99 | 0.2 | 2.1 |
| 101 | 0.7 | >100 |
| 103 | 0.5 | >100 |
| 104 | 0.9 | >100 |
| 105 | 0.8 | 4.5 |
| 106 | 0.3 | 17.1 |
| 107 | <0.1 | >100 |
| 108 | 0.6 | >100 |
| 109 | 1.48 | 53.5 |
| 112 | 0.7 | >100 |
| 113 | 0.3 | >100 |
| 114 | <0.1 | >100 |
| 115 | 0.1 | >100 |
| 116 | 0.1 | >100 |
| 117 | 0.1 | >100 |
| 118 | <0.1 | 7.9 |
| 119 | 0.3 | 1.6 |
| 120 | <0.1 | >100 |
| 122 | 3.0 | 42.2 |
| 129 | 9.7 | >100 |
| 130 | 49.4 | >100 |
| 132 | 37.6 | >100 |
| 133 | 1.2 | 32 |
| 135 | 1.0 | >100 |
| 136 | 0.7 | >100 |
| 137 | 79 | >100 |
| 138 | 0.4 | >100 |
| 139 | 54 | >100 |
| 140 | 0.5 | >100 |
| 141 | 51 | >100 |
| 142 | 5.8 | >100 |
| 143 | 1.71 | >100 |
| 144 | 1.5 | >100 |
| 145 | 0.6 | 82 |
| 146 | <0.1 | 47 |
| 147 | 1.0 | >100 |
| 149 | <0.3 | >100 |
| 151 | 33 | >100 |
| 152 | 24.4 | >100 |
| 153 | 45 | >100 |
| 155 | 10.7 | >100 |
| 161 | <0.1 | >100 |
| 162 | <0.1 | >100 |
| 163 | 0.6 | >100 |
| 165 | 1.6 | >100 |
| 166 | 0.4 | >100 |
| 168 | 0.6 | >100 |
| 169 | 0.1 | >100 |
| 170 | 0.6 | >100 |
| 171 | 0.1 | >100 |
| 172 | <0.1 | >100 |
| 173 | <0.1 | >100 |
| 174 | <0.1 | 13.7 |
| 175 | <0.1 | >100 |
| 176 | 0.3 | >100 |
| 177 | 1.5 | >100 |
| 180 | 0.5 | 100 |

Biological paradigms for testing the cytokine-inhibiting activity of these compounds are found in WO95/13067, published 18 May 1995.

Also embraced within this invention is a class of pharmaceutical compositions comprising the active compounds of this combination therapy in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The active compounds and composition may, for example, be administered orally, intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compounds that are administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredients in the range of about 0.1 to 2000 mg, preferably in the range of about 0.5 to 500 mg and most preferably between about 1 and 100 mg. A daily dose of about 0.01 to 100 mg/kg body weight, preferably between about 0.5 and about 20 mg/kg body weight and most preferably between about 0.1 to 10 mg/kg body weight, may be appropriate. The daily dose can be administered in one to four doses per day.

In the case of psoriasis and other skin conditions, it may be preferable to apply a topical preparation of compounds of this invention to the affected area two to four times a day.

For inflammations of the eye or other external tissues, e.g., mouth and skin, the formulations are preferably applied as a topical ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti inflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

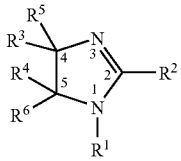

wherein $R^1$ and $R^2$ are independently selected from aryl, cycloalkyl, cycloalkenyl and heterocyclo, wherein $R^1$ and $R^2$ are optionally substituted at a substitutable position with one or more radicals independently selected from alkylsulfonyl, aminosulfonyl, haloalkylsulfonyl, halo, alkylthio, alkyl, cyano, carboxyl, alkoxycarbonyl, haloalkyl, hydroxyl, alkoxy, hydroxyalkyl, alkoxyalkyl, haloalicoxy, amino, alkylarnino, arylamino and nitro;

wherein $R^3$ is a radical selected from hydrido, alkyl, haloalkyl, aralkyl, heterocycloalkyl, acyl, cyano, alkoxy, alkylthio, alkylthioalkyl, alkylsulfonyl, cycloalkylthio, cycloalkylthioalkyl, cycloalkylsulfonyl, cycloalsufonylalkyl, cycloalkyloxy, cycloalkyloxyalkyl, haloalkylsulfonyl, arylsulfonyl, halo, hydroxyalkyl, alkoxyalkyl, alkylcarbonyl, arylcarbonyl, aralkylcarbonyl, heterocycloalkylcarbonyl, cyanoalkyl, azidoalkyl, aminoalkyl, alkylaminoalkyl, Narylaminoalkyl, N-alkyl-N-arylaminoalkyl, carboxyalkyl, alkoxycarbonylalkyl, alkoxycarbonyl, haloalkylcarbonyl, carboxyl, aminocarbonyl, alkylaminocarbonyl, alkylaminocarbonylalkyl, heteroarylalkoxyalkyl, heteroaryloxyalkyl, heteroarylthioalkyl, aralkoxy, aralkylthio, heteroaralkoxy, heteroaralkylthio, heteroarylalkylthioalkyl, heteroaryloxy, heteroarylthio, arylthioalkyl, aryloxyalkyl, axylthio, aryloxy, aralkylthioalkyl, aralkoxyalkyl, aryl and heterocyclo;

wherein $R^4$ is a radical selected from hydrido, alkyl and fluoro;

wherein $R^5$ is selected from hydroxyl and ailkoxy; and wherein $R^6$ is hydrido; or wherein $R^5$ and $R^6$ together form a double bond;

provided at least one of $R^1$ and $R^2$ is aryl substituted with alkylsulfonyl, haloalkylsulfonyl or aminosulfonyl;

or a pharmaceutically-acceptable salt thereof.

2. Compound of claim I wherein 1 and $R^2$ are independently selected from phenyl, naphthyl, biphenyl, lower cycloalkyl, lower cycloalkenyl and heteroaryl, wherein $R^1$ and $R^2$ are optionally substituted at a substitutable position with one or more radicals independently selected from lower alkylsulfonyl, aminosulfonyl, lower haloalkylsulfonyl, halo, lower alkylthio, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; wherein $R^3$ is a radical selected from hydrido, lower alkyl, lower haloalkyl, lower aralkyl, lower heterocycloalkyl, acyl, cyano, lower alkoxy, lower alkylthio, lower alkylsulfonyl, lower cycloalkyloxy, lower cycloalkyloxyalkyl, lower cycloalkylthio, lower cycloalkylthioalkyl, lower cycloalkylsulfonyl, tower cycloalkylsulfonylalkyl, phenysulfonyl, lower haloalkylsulfonyl, halo, lower hydroxyalkyl, lower alkoxyalkyl, lower alkylcarbonyl, lower azidoalkyl, lower haloalkylcarbonyl, phenylcarbonyl, lower aralkylcarbonyl, lower heterocycloalkylcarbonyl, lower cyanoalkyl, lower aminoalkyl, lower alkylaiminoalkyl, lower N-arylaminoalkyl, lower N-alkyl-N-arylaminoalkyl, lower carboxyalkyl, lower alkoxycarbonylalkyl, lower alkoxycarbonyl, lower alkylthioalkyl, aminocarbonyl, lower alkylaminocarbonyl, lower alkylaminocarbonylalkyl, lower aralkoxy, lower aralkylthio, lower heteroaralkoxy, lower heteroaralkylthio, lower heteroarylalkoxyalkyl, lower heteroarylalkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, and heteroaryl, wherein the aryl and heteroaryl radicals are optionally substituted at a substitutable position with one or more radicals selected from halo, lower alkylthio, lower alkylsulfmyl, lower alkyl, cyano. lower haloalkyl, hydroxyl, lower atkoxy, lower hydroxyalkyl and lower haloalkoxy; wherein $R^4$ is a radical selected from hydrido, lower alkyl and fluoro; and wherein $R^5$ is selected from hydroxyl and lower alikoxy; wherein $R^6$ is hydrido; or wherein $R^5$ and $R^6$ together form a double bond; or a pharmaceutically-acceptable salt thereof.

3. Compound of claim 2 wherein $R^1$ and $R^2$ are independently selected from phenyl, naphthyl, biphenyl, cyclohexyl, cyclohexenyl, benzofuryl, benzodioxolyl, furyl, imidazolyl, thienyl, thiazolyl, pyrrolyl, oxazolyl, isoxazolyl, triazolyl, pyrimidinyl, isoquinolyl, quinolinyl, benzimidazolyl, indolyl, pyrazolyl and pyridyl, wherein $R^1$ and $R^2$ are optionally substituted at a substitutable position with one or more radicals independently selected from methylsulfonyl, aminosulfonyl, fluoromethylsulfonyl, difluoromethylsulfonyl, fluoro, chioro, bromo, methylthio, methyl, ethyl, isopropyl, tert-butyl, isobutyl, pentyl, hexyl, cyano, carboxyl, methoxycarbonyl, ethoxycarbonyl, isopropoxycarbonyl, tertbutoxycarbonyl, propoxycarbonyl, butoxycarbonyl, isobutoxycarhonyl, pentoxycarbonyl, fluoromethyl, difluoromethyl, trifluoromethyl, chloromethyl, dichioromethyl, trichlotnmethyl, pentafluoroethyl, heptafluoropropyl, difluorochloromethyl, dichlorofluorornethyl, difluoroethyl, difluoropropyl, dichloroethyl, dichloropropyl, hydroxyl, methoxy, methylenedioxy, ethoxy, propoxy, n-butoxy, hydroxymethyl, hydroxyethyl, methoxymethyl, ethoxymethyl, trifluoromethoxy, amino, methylamino, N,N-dimethylamino, phenylamino and nitro; wherein $R^3$ is a radical selected from hydrido, methyl, ethyl, isopropyl, renbutyl, isoburyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinomethyl, pyrrolidinylmethyl, piperazinylmethyl, piperidinylmethyl, pyridylmethyl, thienylmethyl, formyl, cyano, methoxy, ethoxy, propoxy, n-butoxy, methylthio, ethylthio, isopropylthio, methlylsulfonyl, phenylsulfonyl, trifluoromethylsul fonyl, fluoro, chloro, bromo, hydroxymethyl, hydroxyethyl, methoxymethyl, ethoxymethyl, methylthiomethyl, isopropylthiomethyl, cyclohexylthiomethyl, benzyloxy, benzylthio, methlylcarbonyl, ethylcarbonyl, phenylcarbonyl, azidomethyl, trifluoro methylcarbonyl, difluoromethylcarbonyl, fluoromethylcarbonyl, benzylcarbonyl, cyanomethyl, cyanobutyl, aminomethyl, niethylaminomethyl, N-phenylaminomethyl. N-methyl-N-phenylaminomethyl, acetyl, propanoyl, butanoyl, methoxycarbonylmethyl, ethoxycarbonylethyl, methoxycatbonyl, ethoxycarbonyl, isopropoxycarbonyl, tertbutoxycarbonyl, propoxycarbonyl, isobutoxycarbonyl, carboxymethyl, carboxypropyl, aminocarbonyl, methylaminocarbonyl, N,N-diethylarrdnocarbonyl, N-methylaminocarbonylmethyl, pyridyloxy, pyridylthio, phenyloxy, 4-chlorophenoxy, furylmethoxy, furylmethylthio, 5-phenylpyridyl-2-methoxy, thienylmethoxy, quinolylmethoxy, pyridylmethoxy, thienylmethylthia, pyridylmethylthia, benzylthiomethyL, quinolylmethoxymethyl, furylbutaxyethyl, pyridyloxymethyl, pyridylmethoxyniethyl, thienyloxyhexyl, thienylthiomethyl, pyridylthiohexyl, furyloxymethyl, furylmethylthiometbyl. quinolylmethylthioethyl, phenylthioniethyl, 2-chlorophenylthiomethyl, 2,6-dichlorophenylthiomethyl, 4-methylphenylthiomethyl, 2-isopropylphenyltbiomethyl, 2-methylphenylthiomethyl, phenyloxymethyl, 4-chlorophenyloxyniethyl, 4-methylphenyloxymethyl, benzyloxymethyl, 4-methoxybenzyloxymethyl, naphthyl, phenyl, thienyl, furyl, pyridyl, wherein the thienyl, furyl, pyridyl and phenyl radicals are optionally substituted at a substitutable position with one or more radicals selected from fluoro, chloro, bromo, xnethylthio, methylsulfmyl, methyl, ethyl, isopropyl, tert-butyl, isobutyl, pentyl, hexyl, cyano, fluoromethyl, difluoromethyl, trifluoromethyl, chloromethyL dichloromethyl, trichloromethyl, pentafluoroethyl, heptafluoropropyl, difluorochloromethyl, dichlorofluoromethyl, difluoroethyl, clifluoropropyl, dichloroethyl, dichloropropyl, hydroxyl, methoxy, methylenedioxy, ethoxy, propoxy, n-butoxy, hydroxymethyl, hydroxyethyl and trifluoromethoxy; wherein $R^4$ is a radical selected from hydrido, methyl, ethyl, and fluoro; and wherein $R^5$ is selected from hydroxyl, methoxy, ethoxy, propoxy and n-butoxy; wherein $R^5$ is hydrido; or wherein $R^5$ and $R^6$ together form a double bond; or a pharmaceuticafly-acceptable salt thereof.

4. A compound of Formula

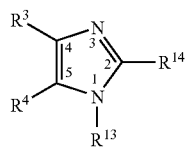

(V)

wherein $R^3$ is a radical selected from hydrido, alkyl, haloalkyl, aralkyl, heterocycloalkyl, heteroaralkyl, acyl, cyano, alkoxy, alkylthio, alkylthioalkyl, alkylsulfonyl, cycloalkylthio, cycloalkylthioalkyl, cyoloalkylsulfonyl, cycloalkylsulfonylalkyl, haloalkyl sulfonyl, arylsulfonyl, halo, hydroxyalkyl, alkoxyalkyl, alkylcarbonyl, arylcarbonyl, aralkylcarbonyl, heterocyclocarbonyl, cyanoalkyl, aminoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl, carboxyl, aminocarbonyl, alkylaminocarbonyl, alkylaminocarbonylalkyl, heteroaralkoxyalkyl, heteroaryloxyalkyl, heteroarylthioalkyl, aralkoxy, aralkylthio, heteroaralkoxy, heteroaralkylthia, heteroarylalkylthioalkyl, heteroaryloxy, heteroarylthio, arylthioalkyl, aryloxyalkyl, arylthio, aryloxy, aralkylthioalkyl, aralkoxyalkyl, aryl and heteroaryl; wherein $R^4$ is a radical selected from hydrido, alkyl and halo; and wherein $R^{13}$ and $R^{14}$ are independently selected from aryl and heterocyclo, wherein $R^{13}$ and $R^4$ are optionally substituted at a substitutable position with one or more radicals independently selected from alkylsulfonyl, aminosulfonyl, halo, alkylthio, alkyl, cyano, carboxyl, alkoxycarbonyl, haloalkyl, hydroxyl, alkoxy, hydroxyalkyl, alkoxyalkyl, haloalkoxy, amino, alicylamino, arylamino and nitro; provided at least one of $R^{13}$ and $R^{14}$ is aryl substituted with alkylsulfonyl or aininosulfonyl, or a pharmaceutically-acceptable salt thereof.

5. Compound of claim 4 wherein 3 is a radical selected from hydrido, lower alkyl, lower haloalkyl, lower aralkyl, lower heterocycloalkyl, lower heteroaralkyl, acyl, cyano, lower alkoxy, lower alkylthio, lower alkylsulfonyl, phenylsulfonyl, lower haloalkylsulfonyl, halo, lower hydroxyalkyl, lower alkoxyalkyl, lower alkylcarbonyl, lower haloalkylcarbonyl, phenylcarbonyl, lower aralkylcarbonyl, lower cyanoalkyl, lower aminoalkyl, lower alkylaminoalkyl, lower N-arylaniinoalkyl, lower N-alkyl-N-arylaminoalkyl, lower carboxyalkyl, lower alkoxycaibonylalkyl, lower alkoxycarbonyl, carboxyl, lower alkylthioalkyl, aminocarbonyl, lower alkylaminocarbonyl, lower alkylaminocarbonylalkyl, lower aralkoxy, lower aralkylthio, lower heteroaralkoxy, lower heteroaralkylthio, lower heteroarylalkoxyalkyl, lower heteroarylalkylthioalkyl, lower heteroaryloxyalkyl, lower heteroarylthioalkyl, lower heteroaryloxy, lower heteroarylthio, lower arylthioalkyl, lower aryloxyalkyl, lower arylthio, lower aryloxy, lower aralkylthioalkyl, lower aralkoxyalkyl, aryl selected from phenyl and naphthyl, 5 or 6 membered heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, hydroxyl, lower alkoxy, lower hydroxyaillcyl and lower haloalkoxy; wherein $R^4$ is a radical selected from hydride, lower alkyl and halo; and wherein $R^{13}$ and $R^{14}$ are independently selected from phenyl and heteroaryl, wherein $R^{13}$ and $R^{14}$ are optionally substituted at a substitutable position with one or more radicals independently selected from lower methylsulfonyl, aminosulfonyl, lower alkylthio, lower alkyl, lower haloalkyl, lower alkoxy, lower hydroxyalkyl, lower alkoxyalkyl, and lower haloalkoxy; or a pharmaceutically-acceptable salt thereof.

6. Compound of claim 5 wherein $R^3$ is a radical selected from hydrido, methyl, ethyl, isopropyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, phenylpropyl, furylmethyl, morpholinotnethyl, pyrrolidinylmethyl, piperazinylmethyl, piperidinylmethyl, pyridylnaethyl, thienylmethyl, formyl, cyano, methoxy, ethoxy, propoxy, n-butoxy, methylthio, ethyltbio, isopropylthio, methylsulfonyl, phenylsulfonyl, trifluoromethylsulfonyl, fluoro, chloro, bromo, hydraxymethyl. hydroxyethyl, methoxymethyl, ethoxymethyl, methyl thiomethyl, isopropylthiomeLhyl, cyclohexylthiomethyl, benzyloxy, benzylthio, methylcarbonyl, ethylcarbonyl, phenylcarbonyl, tTifluoromethylcarbonyl, difluoromethylcarbonyl, fluoromethylcaifbonyl, benzylcarbonyl, pyrrolidinylcarbonyl, cyanomethyl, cyanabutyl, aminomethyl, methylaminomethyl, N-phenylaminomethyl, N-methyl-N-phenylaminomethyl, acetyl, propanoyl, butanoyl, methoxycarbonylmethyl, ethoxycarbonylethyl, methoxycarbonyl, ethoxycarbonyl, isopropoxycarbonyl, tert-butoxycarbonyL propoxycarbonyl, butoxycarbonyl, isobutoxycarbortyl, pentoxycaxbonyl, carboxyl, carboxymethyl, carboxypropyl, aminocarbonyl, methylaminacarbonyl, N,N-diethylaminocarbonyl, N-methoxy-N-methylaminocarbonyl, methylaminocarbonyhnethyl, pyridyloxy, pyridylthio, phenyloxy, 4-chlorophenoxy, furylmethoxy, furylmethylthia, thienylmethoxy, quinolyhnethoxy, pyridylmethoxy, 5-phenylpyridyl-2-methoxy, thienylmethylthio, pyridylmethylthia, quinolylmethoxymethyl, furylbutoxyethyl, pyridyloxymethyl, pyridylmethoxymethyl, thienyloxyhexyl, thienylthiomethyl, pyridylthiohexyl, furyloxymethlyl, fuzylmethylthiomethyl, quinolylmethylthioethyl, phenylthiomethyl, 2-chlorophenylthiomethyl, 2,6-dichlorophenylthiomethyl, 4-methylpbenylthiomethyl, 2-isopropylphenylthiomethyl, 2-methylphenylthiomethyl, phenyloxymethyl, 4-chlorophenyloxymethyl, 4-methylphenyloxymethyl, benzyloxymethyl, 4-methoxybenzyloxymethyl, naphthyl, phenyl, thienyl, fuiyl, pyridyl, wherein the thienyl, furyl, pyridyl and phenyl radicals are optionally substituted at a substitutable position with one or more radicals selected from fluoro, chloro, bromo, methylthia, methylsulfinyl, methyl, ethyl, isopropyl, tert-butyl, isobutyl, pentyl, hexyl, cyano, fluoromethyl, difluoromethyl, trifluoromethyl, chloromethyl, dichloromethyl, trichloromethyl. pentafluoroethyl, heptafluoropropyl, difluorochloromethyl, dichlorofluoromethyl, difluoroethyl, difluoropropyl, dichloroethyl, dichloropropyl, hydroxyl, methoxy, niethylenedioxy, ethoxy, propoxy, n-butoxy, hydroxymethyl, hydroxyethyl and trifluoromethoxy; wherein $R^4$ is a radical selected from hydrido, methyl, ethyl, fluoro, chloro and bromo; and wherein $R^{13}$ and $R^{14}$ are independently selected from phenyl, imidazolyl, thienyl, thiazolyl, pyrrolyl, oxazolyl, isoxazolyl, triazolyl, pyrazinyl, pyriimidinyl, isoquinolyl, quinolyl, indolyl, benzimidazolyl, pyrazolyl and pylidyl, wherein $R^{13}$ and $R^{14}$ are optionally substituted at a substitutable position with one or more radicals independently selected from methylsulfonyl, aininosulfonyl, fluoromethylsulfonyl, difluoromethylsulfonyl, fluoro, chloro, bromo, methylthio, methylsulfinyl, methyl, ethyl, isopropyl, tert-butyl, isobutyl, pentyl, hexyl, cyano, carboxyl, methoxycarbonyl, ethoxycarbonyl, isopropoxycarbonyl, tert-butoxycarbonyl. propoxycarbonyl. butoxycarbonyl, isobutoxycarbonyl, pentoxycarbonyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl. hydroxyl, niethoxy, methylenedioxy, ethoxy, propoxy, n-butoxy, hydroxyniethyl, hydroxyethyl, methoxymethyl, ethoxymethyl, trifluoromethoxy, amino, methylamino, N,N-diethylamnino, phenylamino and nitro; or a pharmaceutically-acceptable salt thereof.

7. Compound of claim 6 wherein $R^3$ is a radical selected from hydrido, methyl, ethyl, isopropyl, tert-butyl, isobutyl, pentyl, hexyl, cyano, fluoromethyl, difluoromethyl, trifluoromethyl, chloromethyl, dichloromethlyl, trichloromethyl, pentafluoroethyl, heptafluoropropyl, difluorochloromethyl, dichlorofluoromethyl, difluoroetbyl, difluoropropyl, dichloroethyl, dichloropropyl and 2-methylphenylthiomediyl; wherein $R^4$ is hydrido; wherein $R^{13}$ is phenyl optionally substituted with methylsulfonyl or aniinosulfonyl; and wherein $R^{14}$ is selected from imidazolyl, rhienyl, thiazolyl, pyrrolyl, oxazolyl, isoxazolyl, tuazolyl, pyrimidinyl, quinolinyl, isoquinolyl, indolyl, benzimidazolyl, pyrazolyl and pyridyl, wherein $R^{14}$ isoptionally substituted at a substitutable position with one or more radicals independently selected from methylthio, methyl, ethyl, isopropyl, tert-butyl, isobutyl, pentyl. hexyl, fluoromethyl, difluoromethyl, trifluoroniethyl, chloromethyl, dichloromethyl, trichloromethyl, pentafluoroethyl, heptafluoropropyl, difluorochloromethlyl, dichlorofluoromethyl, difluoroethyl, difluoropropyl, dichloroethyl, dichloropropyl, methoxy, methylenedioxy, ethoxy, propoxy, n-butoxy, hydroxymethyl, hydroxyethyl, methoxymethyl, ethoxymethyl, and tnfluoromethoxy; or a pharmaceutically-acceptable salt thereof.

8. A pharmaceutical composition comprising a therapeutically-effective amount of a compound, said compound selected from a family of compounds of claim 1; or a pharmaceutically-acceptable salt thereof.

9. A pharmaceutical composition comprising a therapeutically-effective amount of a compound, said compound selected from a family of compounds of claim 4; or a pharmaceutically-acceptable salt thereof.

10. A pharmaceutical composition comprising a therapeutically-effective amount of a compound, said compound selected from a family of compounds of claim 5; or a pharmaceutically-acceptable salt thereof.

11. A pharmaceutical composition comprising a therapeutically-effective amount of a compound, said compound selected from a family of compounds of claim 6; or a pharmaceutically-acceptable salt thereof.

12. A pharmaceu.tical composition comprising a therapeutically-effective amount of a compound, said compound selected from a family of compounds of claim 7; or a pharmaceutically-acceptable salt thereof.

13. A method of treating inflammation in a subject, said method comprising:
    treating the subject with a therapeutically-effective amount of a compound
    of claim I or a pharmaceutically-acceptable salt thereof.

14. A method of treating inflammation in a subject, said method comprising:
    treating the subject with a therapeutically-effective amount of a compound of claim 4 or a pharmaceutically-acceptable salt thereof.

15. A method of treating arthritis, pain, or fever in a subject, said method comprising:
    treating the subject with a therapeutically-effective amount of a compound of claim 4 or a pharmaceutically-acceptable salt thereof.

16. A method of treating inflammation in a subject, said method comprising:
    treating the subject with a therapeutically-effective amount of a. compound of claim 5 or a pharmaceutically-acceptable salt thereof.

17. A method of treating inflammation in a subject, said method comprising:
    treating the subject with a therapeutically-effective amount of a compound of claim 6 or a pharmaceutically-acceptable salt thereof.

18. A method of treating inflammation in a subject, said method comprising:
    treating the subject with a therapeutically-effective amount of a compound of claim 7 or a pharmaceutically-acceptable salt thereof.

* * * * *